(12) United States Patent
Leroyer et al.

(10) Patent No.: US 12,411,143 B2
(45) Date of Patent: Sep. 9, 2025

(54) CD146 AND USES THEREOF AS A BIOMARKER AND AS A THERAPEUTIC TARGET IN THE DIAGNOSIS AND TREATMENT OF FIBROSIS

(71) Applicants: ASSISTANCE PUBLIQUE HÔPITAUX DE MARSEILLE, Marseilles (FR); INSERM (INSTITUT NATIONAL DE LA SANTÉ ET DE LA RECHERCHE MÉDICALE), Paris (FR); UNIVERSITE D'AIX-MARSEILLE, Marseilles (FR); QUEEN MARY UNIVERSITY OF LONDON, London (GB); SORBONNE UNIVERSITÉ, Paris (FR)

(72) Inventors: Aurélie Leroyer, Marseilles (FR); Marcel Blot-Chabaud, Fuveau (FR); Christos Chadjichristos, Villers Sous Saint Leu (FR); Nathalie Bardin, Marseilles (FR); Françoise Dignat-George, Marseilles (FR); Alexandrine Bertaud, Marseilles (FR); Benjamin Guillet, Aix En Provence (FR); Christoph Thiemermann, Woodford Green (GB); Guillaume Hache, Marseilles (FR)

(73) Assignees: UNIVERSITE D'AIX-MARSEILLE, Marseilles (FR); ASSISTANCE PUBLIQUE HÔPITAUX DE MARSEILLE, Marseilles (FR); INSERM (INSTITUT NATIONAL DE LA SANTÉ ET DE LA RECHERCHE MÉDICALE), Paris (FR); QUEEN MARY UNIVERSITY OF LONDON, London (GB)

( * ) Notice: Subject to any disclaimer, the term of this patent is extended or adjusted under 35 U.S.C. 154(b) by 1072 days.

(21) Appl. No.: 17/280,202

(22) PCT Filed: Sep. 26, 2019

(86) PCT No.: PCT/EP2019/075966
§ 371 (c)(1),
(2) Date: Mar. 26, 2021

(87) PCT Pub. No.: WO2020/064897
PCT Pub. Date: Apr. 2, 2020

(65) Prior Publication Data
US 2022/0003784 A1  Jan. 6, 2022

(30) Foreign Application Priority Data
Sep. 26, 2018 (EP) .................. 18306253

(51) Int. Cl.
G01N 33/68 (2006.01)
A61K 38/17 (2006.01)
A61K 39/00 (2006.01)
A61P 19/04 (2006.01)
C07K 16/30 (2006.01)

(52) U.S. Cl.
CPC ..... *G01N 33/6893* (2013.01); *A61K 38/1774* (2013.01); *A61P 19/04* (2018.01); *C07K 16/3092* (2013.01); *A61K 2039/505* (2013.01); *C07K 2317/56* (2013.01); *C07K 2317/565* (2013.01); *G01N 2333/70596* (2013.01); *G01N 2800/32* (2013.01); *G01N 2800/347* (2013.01); *G01N 2800/50* (2013.01); *G01N 2800/7052* (2013.01)

(58) Field of Classification Search
None
See application file for complete search history.

(56) References Cited

U.S. PATENT DOCUMENTS

| | | | |
|---|---|---|---|
| 9,605,048 B2 | 3/2017 | Blot-Chabaud et al. | |
| 10,774,153 B2 | 9/2020 | Blot-Chabaud et al. | |
| 2004/0197328 A1* | 10/2004 | Young | A61K 51/1045 424/155.1 |

(Continued)

FOREIGN PATENT DOCUMENTS

| | | |
|---|---|---|
| EP | 2 216 399 | 8/2010 |
| WO | WO 2004/112565 | 12/2004 |
| WO | WO 2012/098256 | 7/2012 |

OTHER PUBLICATIONS

Ito et al. (Clin. Rheumatol (2017, 36: 119-124) (Year: 2017).*

(Continued)

*Primary Examiner* — Peter J Reddig
(74) *Attorney, Agent, or Firm* — SALIWANCHIK, LLOYD & EISENSCHENK

(57) ABSTRACT

The present invention relates to the field of medicine and in particular to the diagnostic and treatment of fibrosis. More particularly, the invention relates to CD146 and uses thereof as a biomarker in the diagnosis of fibrosis and as a therapeutic target in the treatment of fibrosis. The invention also relates to compositions and methods of detecting predisposition to, of diagnosing, prognosing and/or monitoring fibrosis in a subject. It further relates to CD146 inhibitors, and to compositions comprising a CD146 inhibitor, for use in prevention or treatment of fibrosis in a subject, as well as to compositions, kits and uses thereof in a diagnostic or therapeutic context.

6 Claims, 62 Drawing Sheets
Specification includes a Sequence Listing.

(56) References Cited

U.S. PATENT DOCUMENTS

2011/0286963 A1* 11/2011 Blot-Chabaud ......... A61P 17/02
530/387.2

OTHER PUBLICATIONS

Ito et al. (Clin. Rheumatology 2017 36: 119-124) (Year: 2017).*
Gura (Science, 1997, 278:1041-1042) (Year: 1997).*
Kaiser (Science, 2006, 313: 1370) (Year: 2006).*
Chames et al (British J. of Pharmacology, 2009, 157, 220-233) (Year: 2009).*
Khan et al. (Expert Opinion on Drug Delivery, 2023 20 (9): 1167-1187) (Year: 2023).*
Abed, et al. "Abstracts of the 30$^{th}$ Meeting of the European Renal Cell Study Group (ERCSG)" *Nephron Journals*, 2018, pp. 83-111, vol. 139, No. 1.
Kaspi, E. et al. "Identification of CD146 as a novel molecular actor involved in systemic sclerosis" *J Allergy Clin Immunol*, 2017, pp. 1448-1451 and pp. 1451.e1-1451e6, vol. 140, No. 5.
Zhang, L. et al. "CD146: a potential therapeutic target for systemic sclerosis" *Protein Cell*, 2018, pp. 1050-1054, vol. 9, No. 12.
Written Opinion in International Application No. PCT/EP2019/075966, Nov. 8, 2019, pp. 1-7.

* cited by examiner

Figure 1:
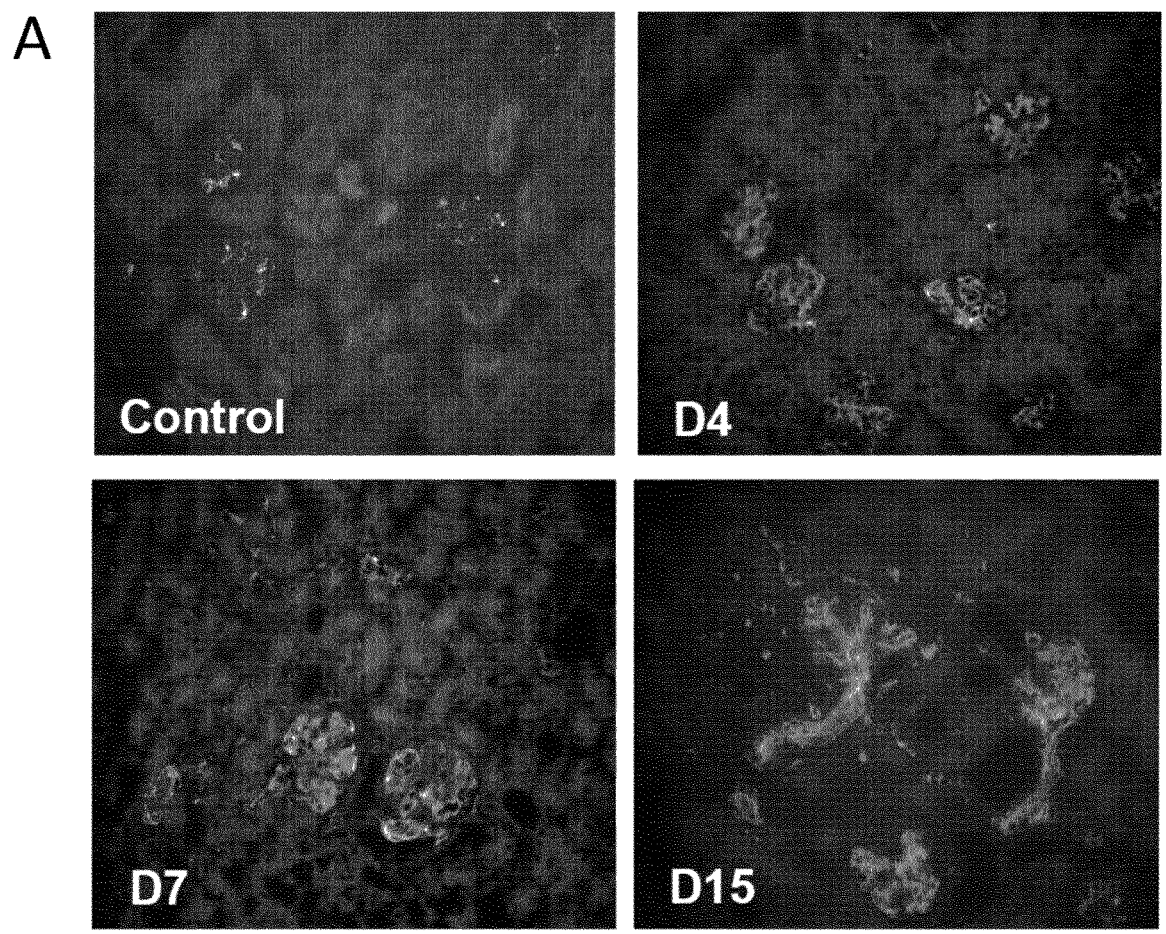
Figure 1:
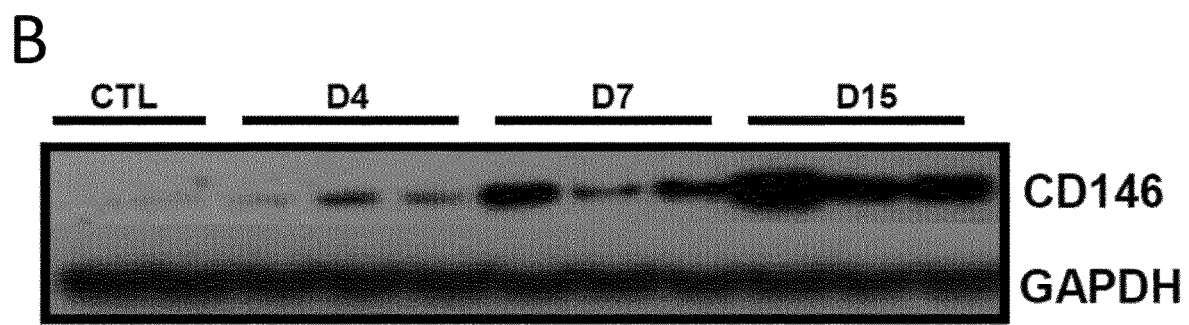

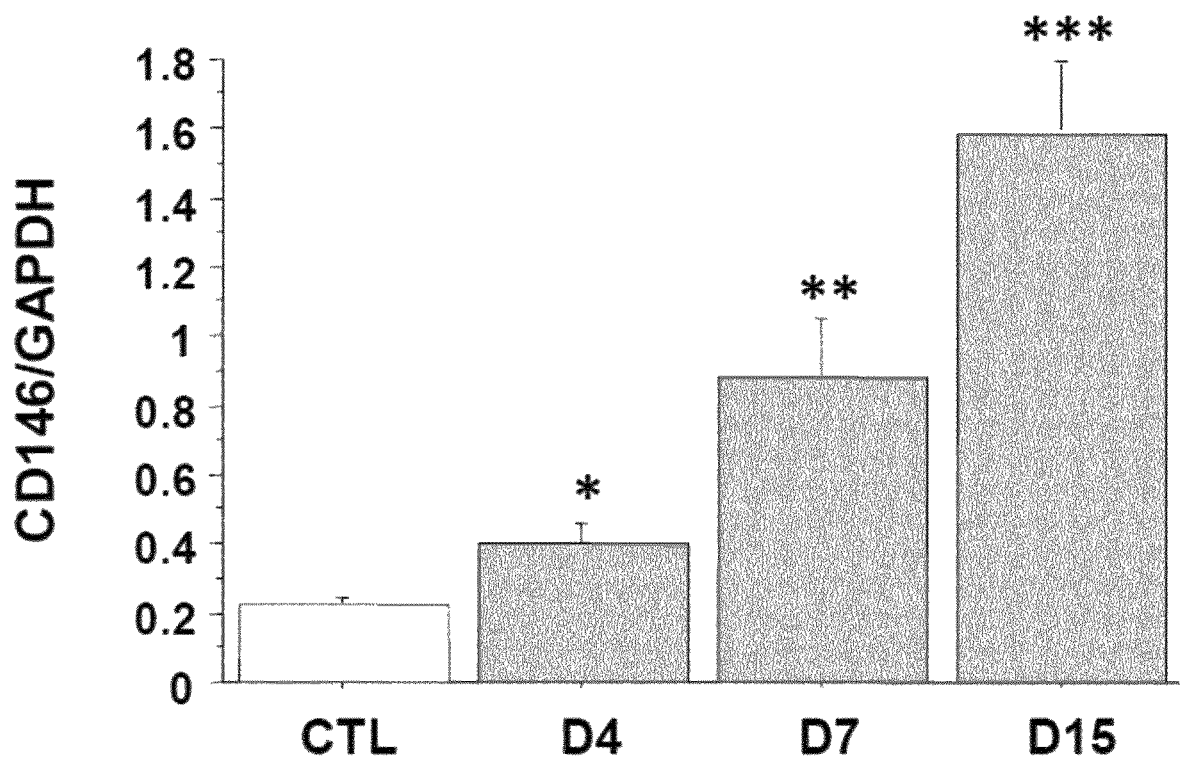
FIGURE 1 (Following)

Figure 2:
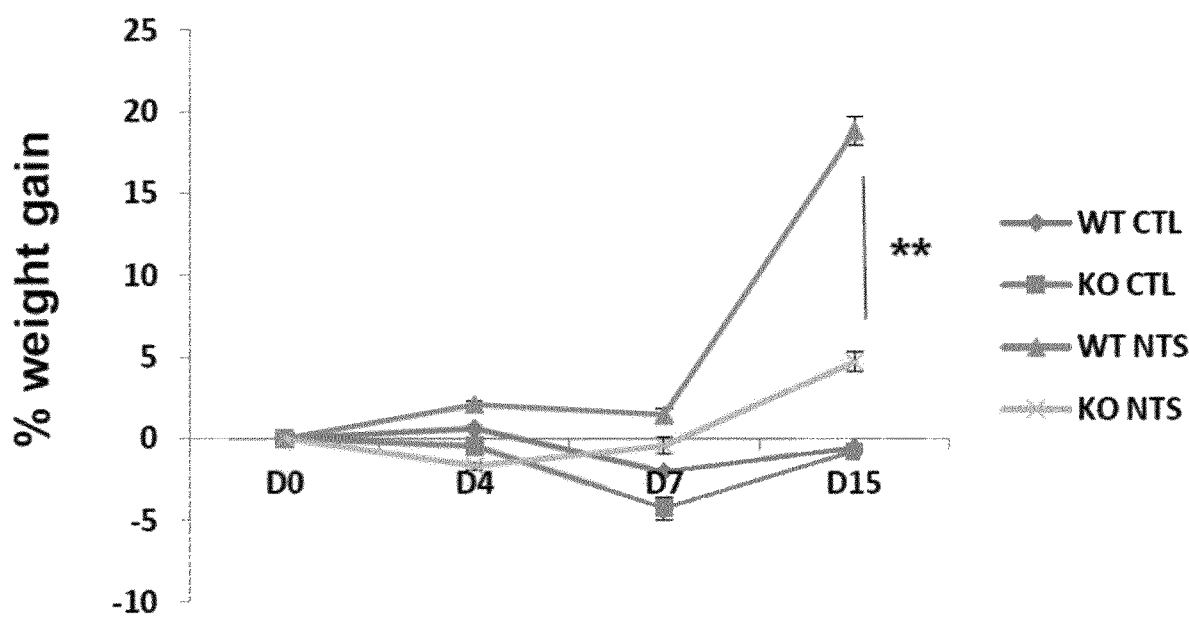
Figure 2:
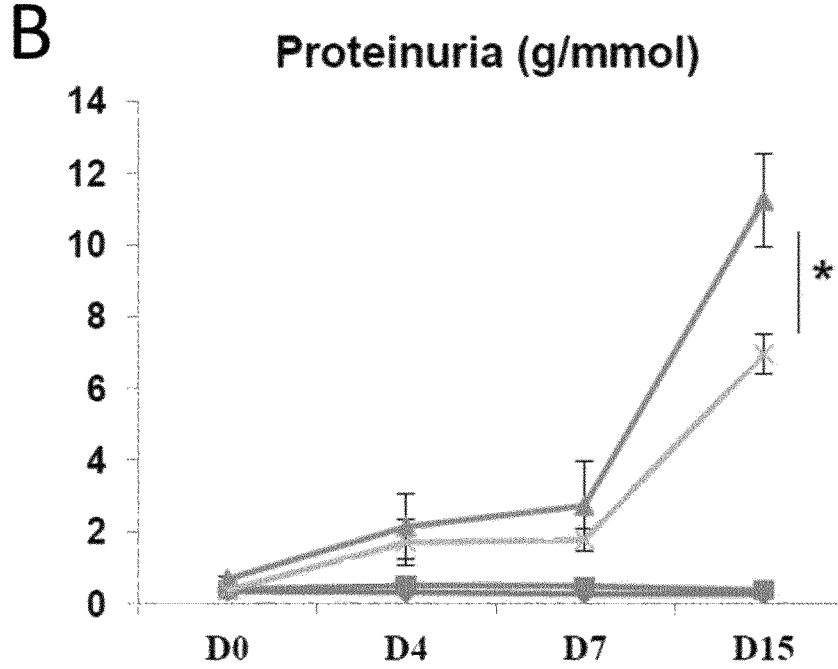

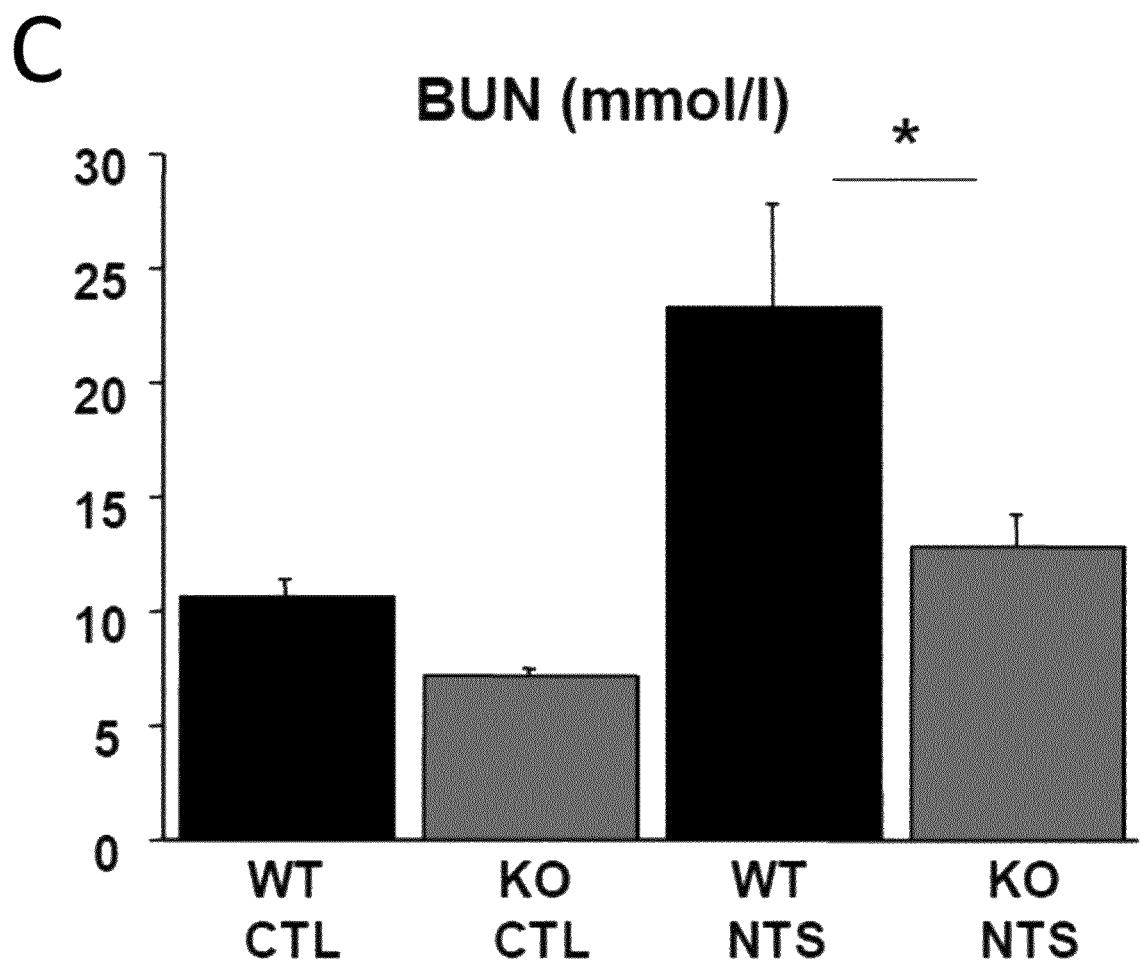
FIGURE 2 (Following)

D
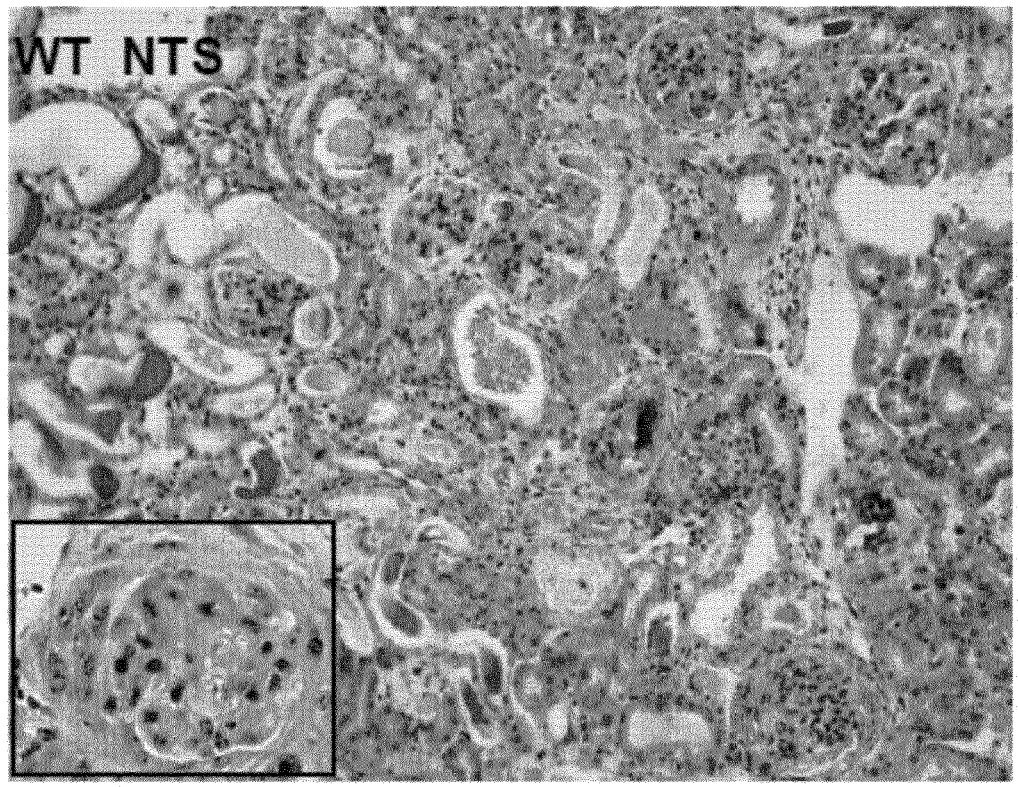
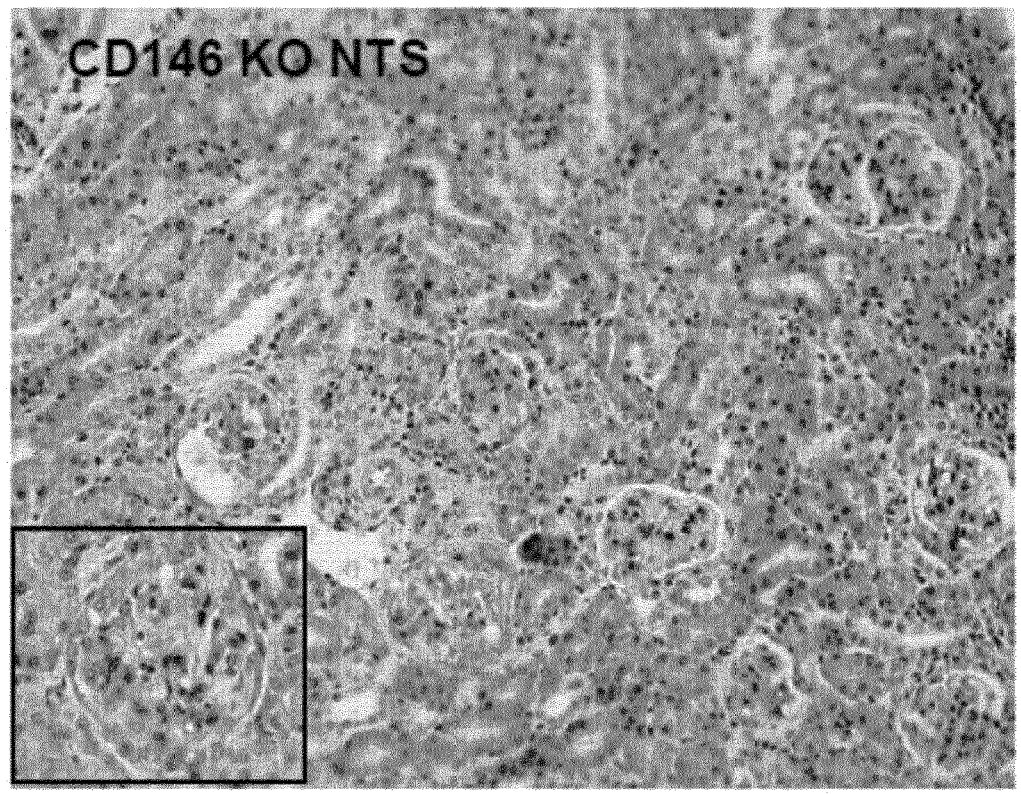
FIGURE 2 (Following)

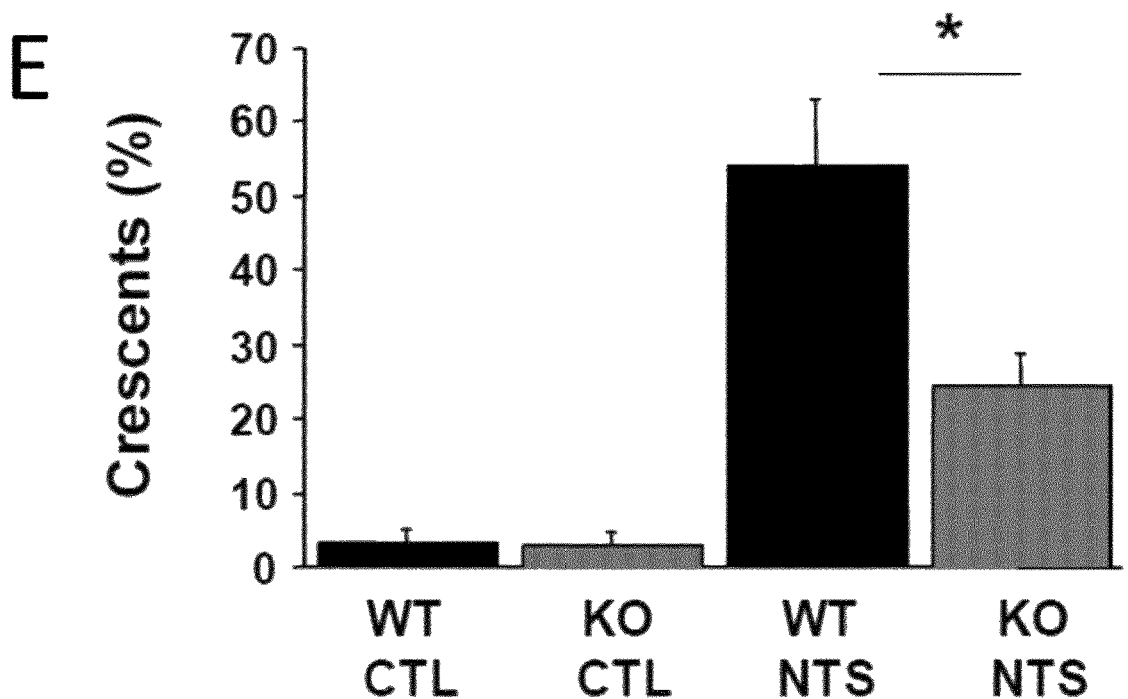
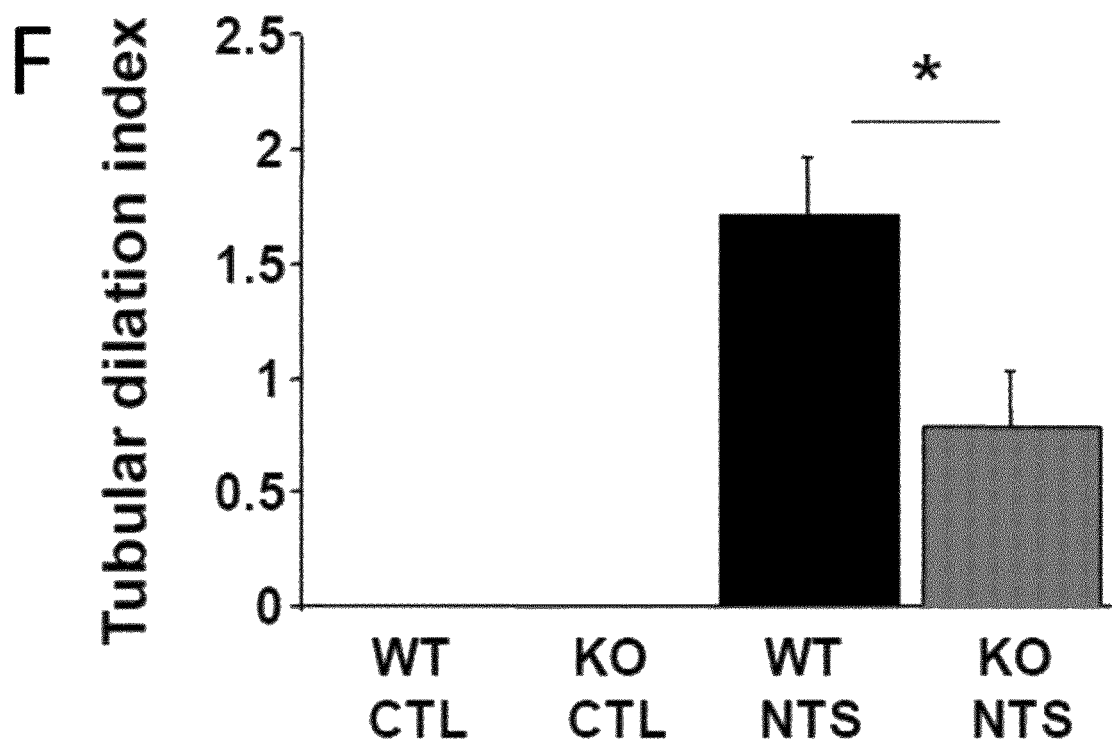
FIGURE 2 (Following)

Figure 3:
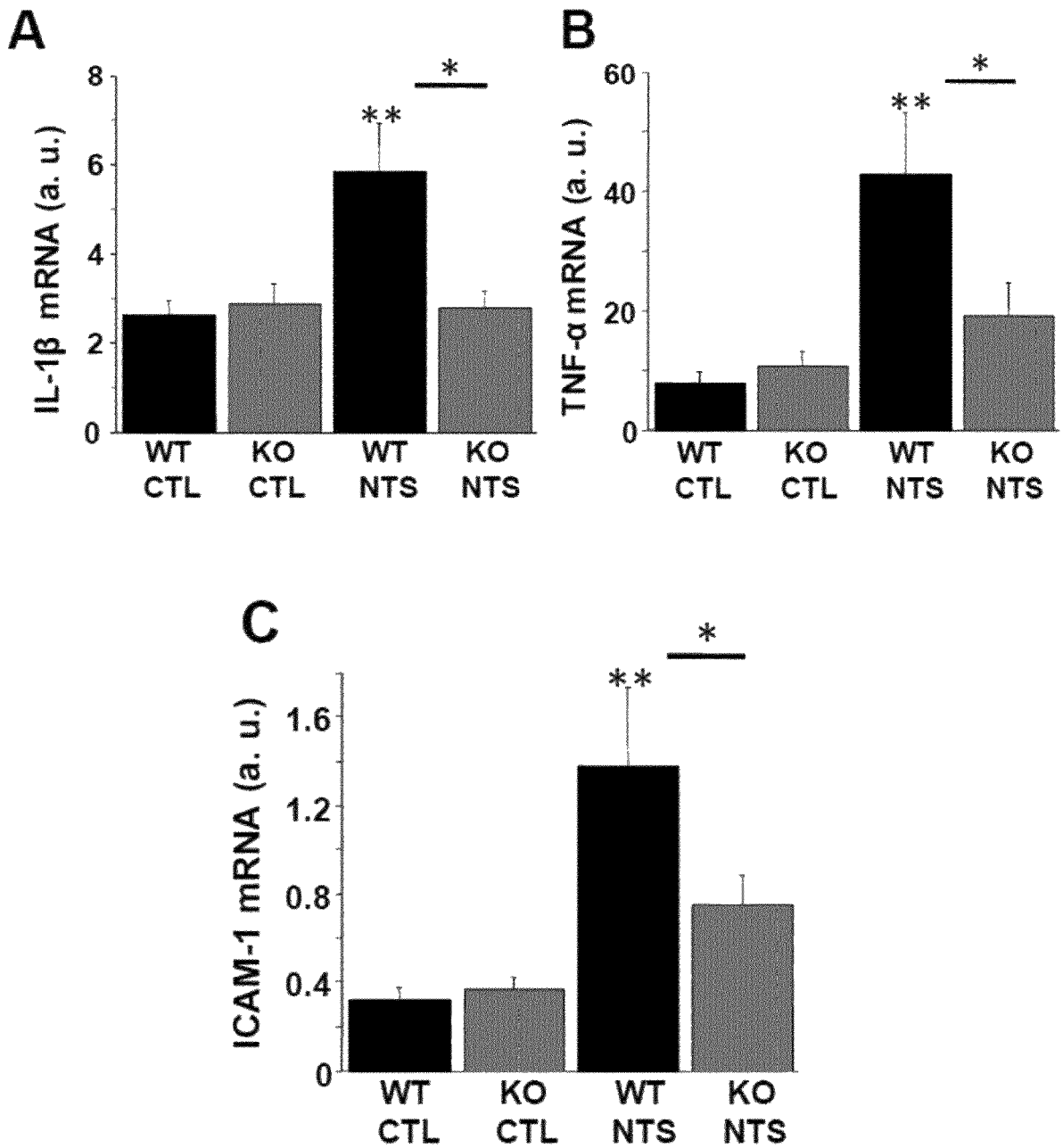

D
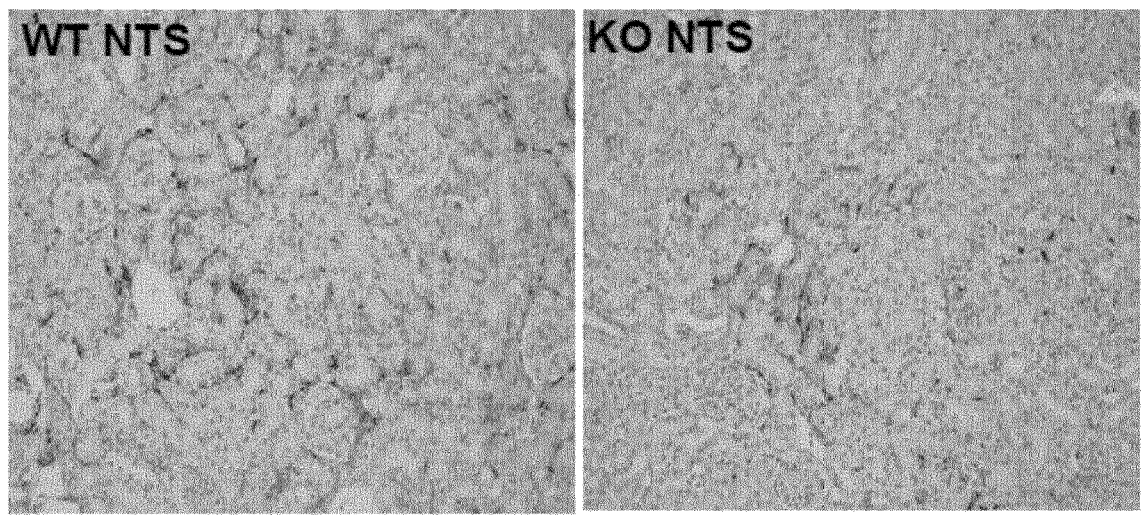
E
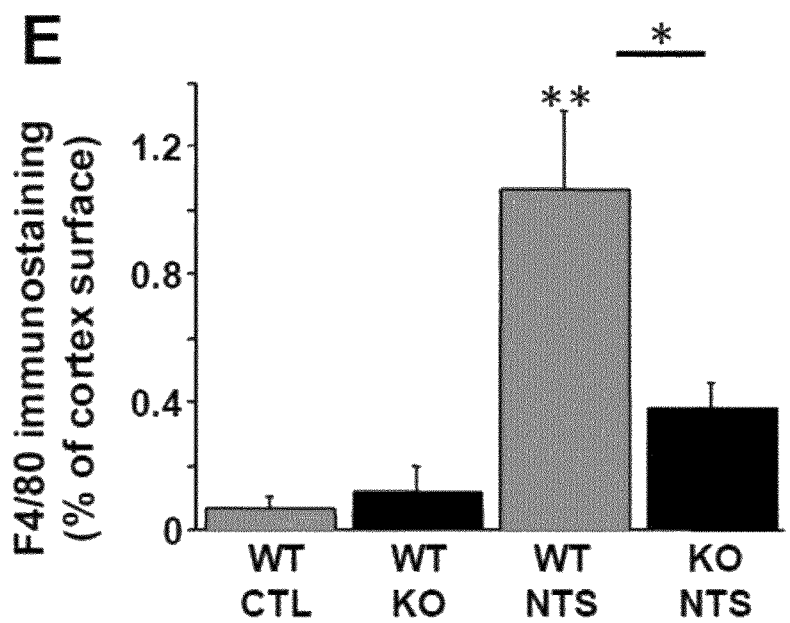
FIGURE 3 (Following)

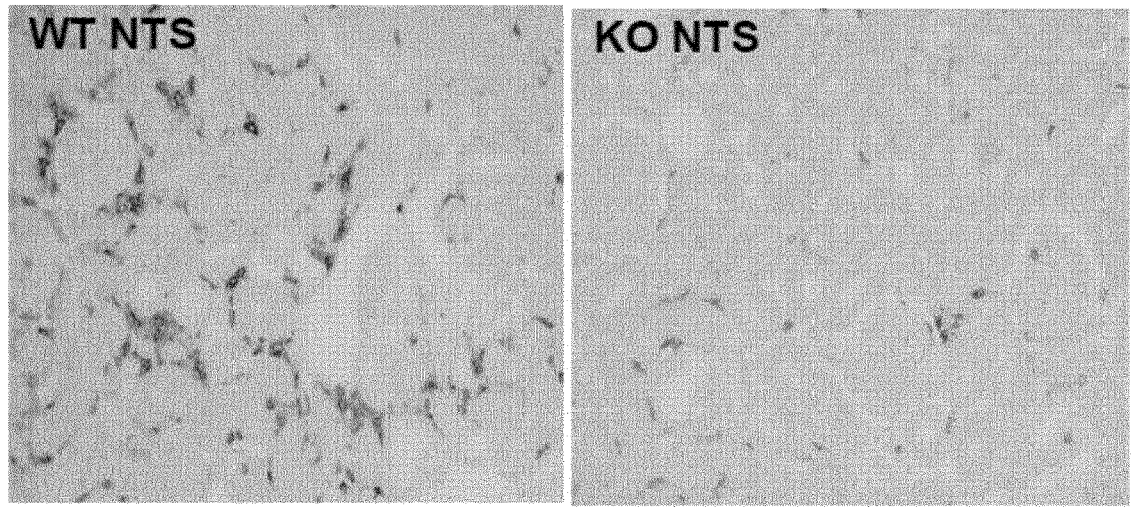
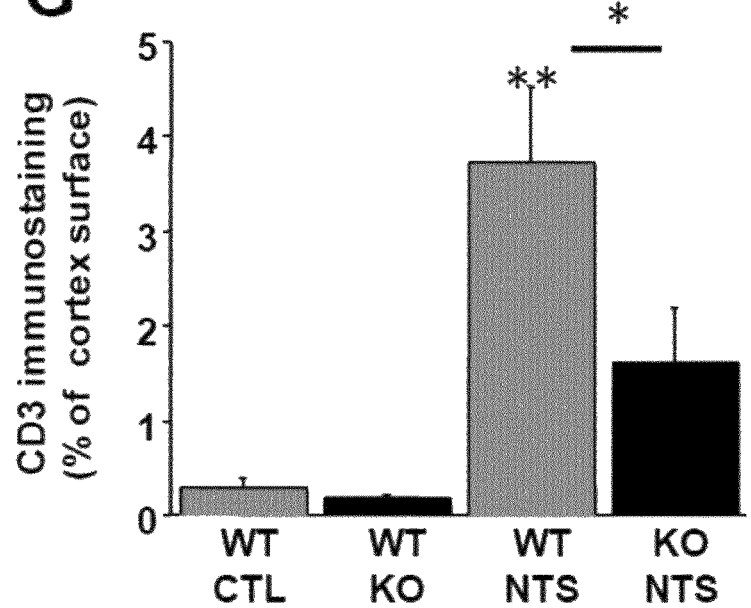
FIGURE 3 (Following)

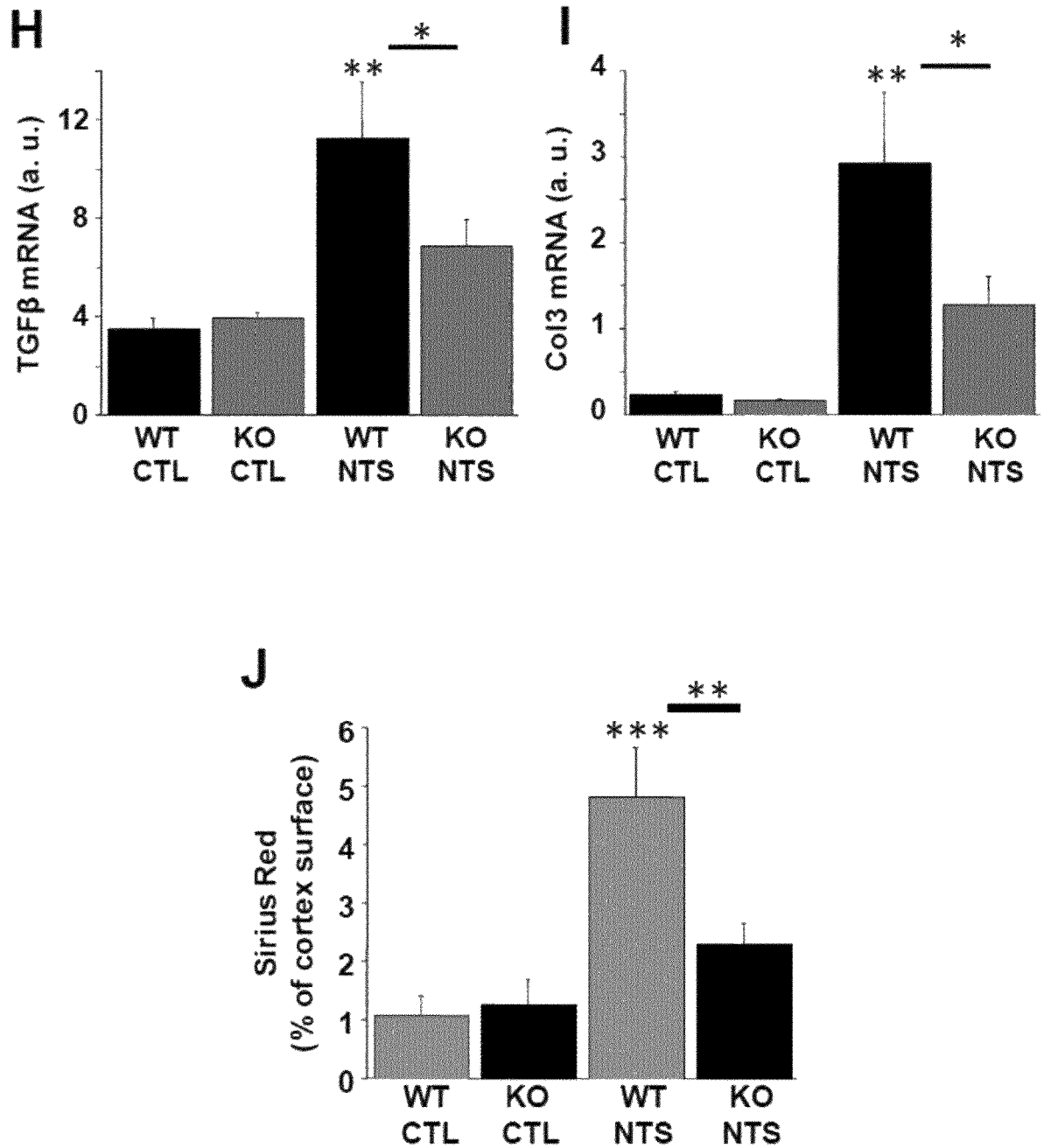
FIGURE 3 (Following)

Figure 5:
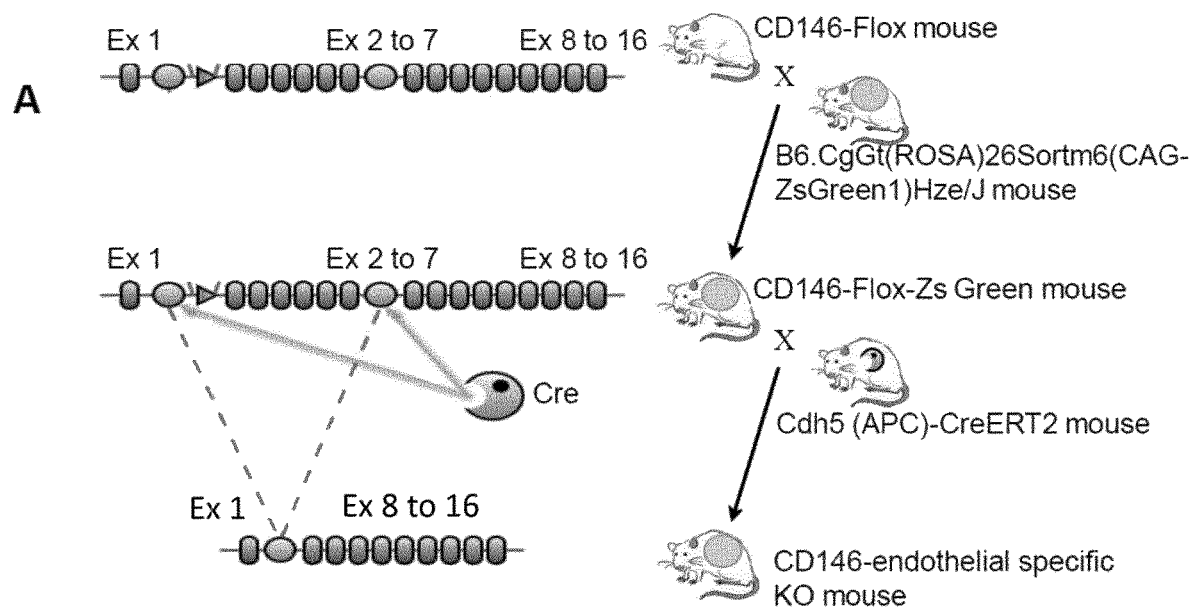
Figure 5:
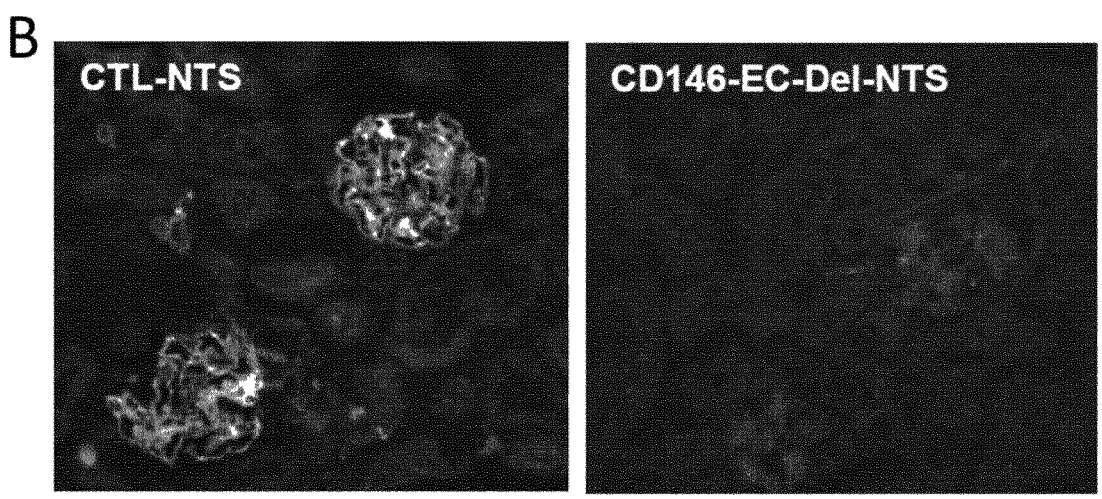

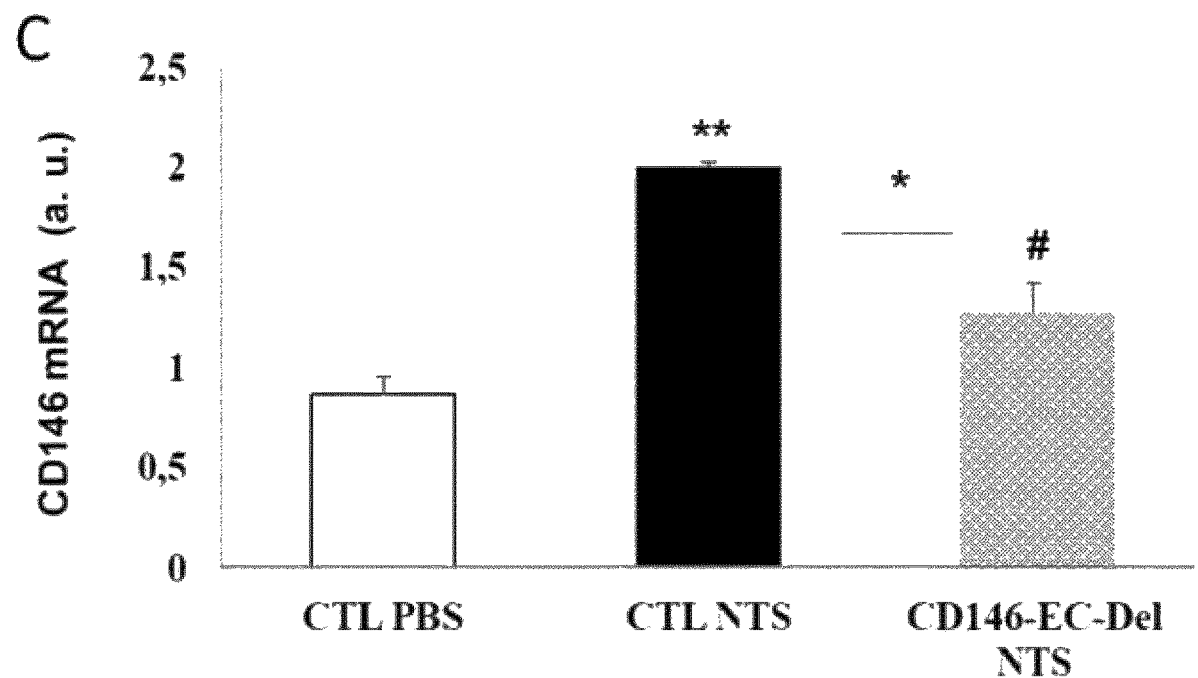
FIGURE 5 (Following)

Figure 6:
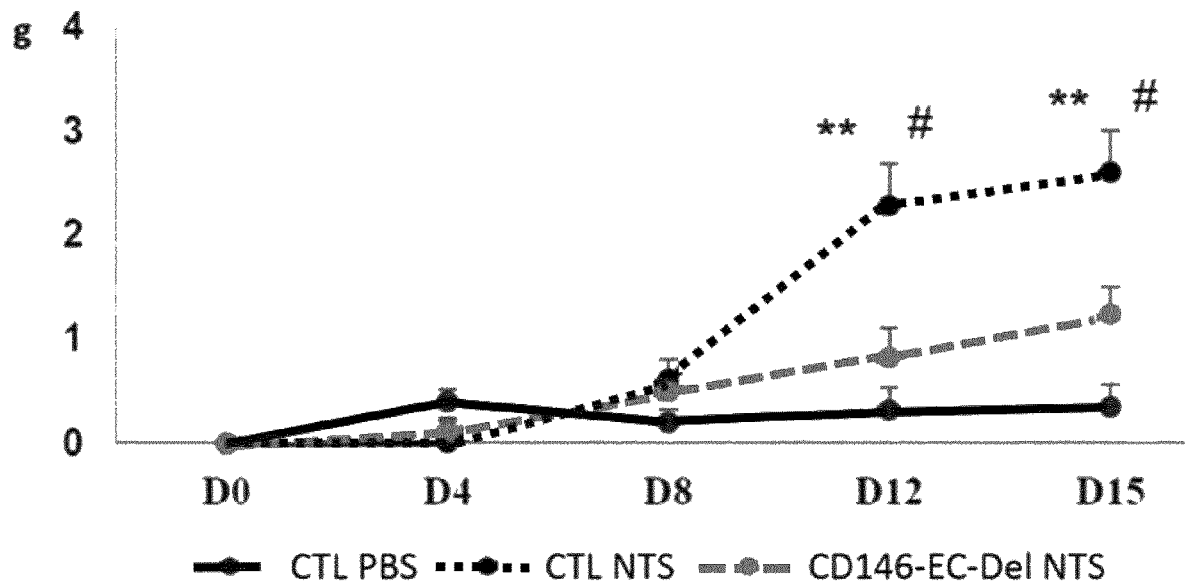
Figure 6:
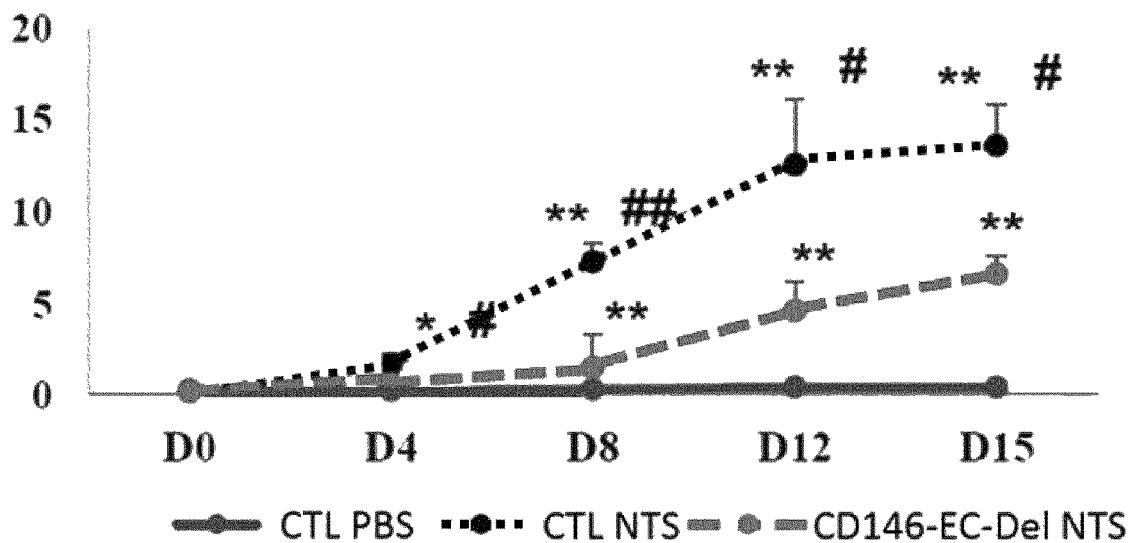

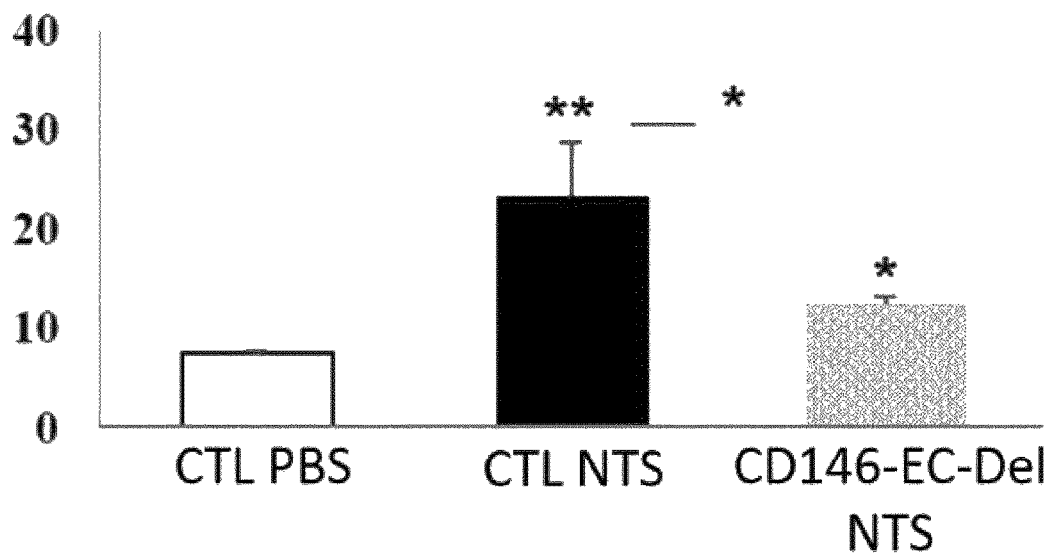
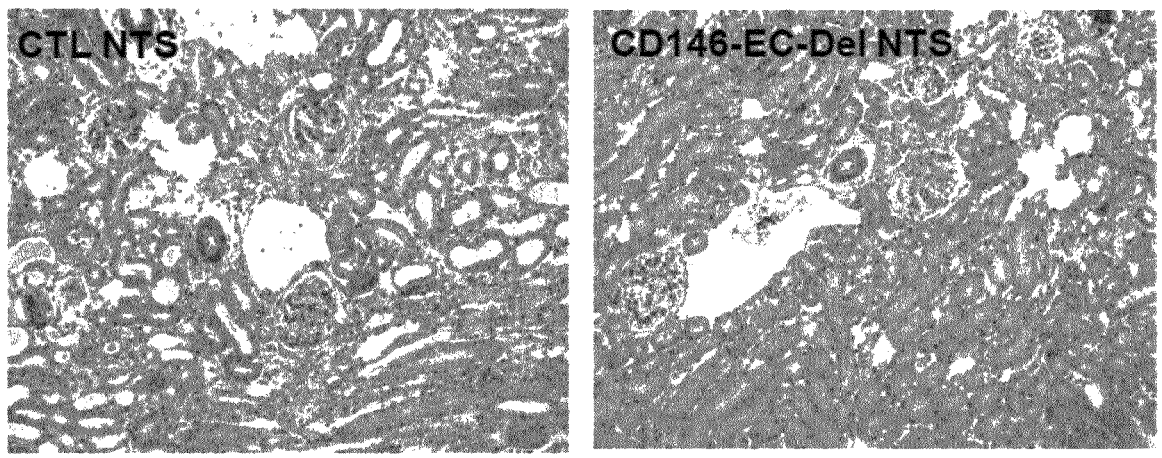
FIGURE 6 (Following)

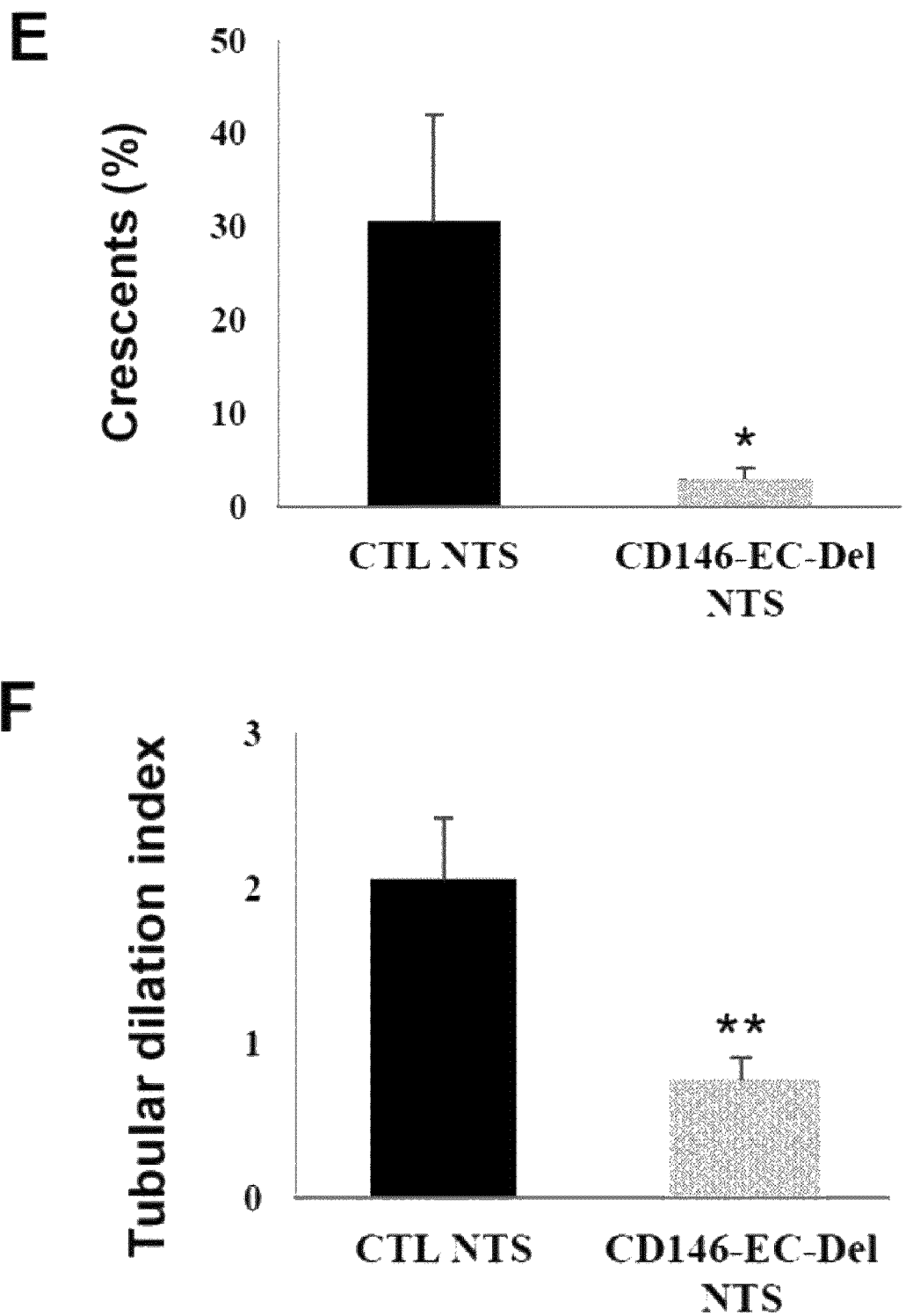
FIGURE 6 (Following)

A

B

Figure 7:
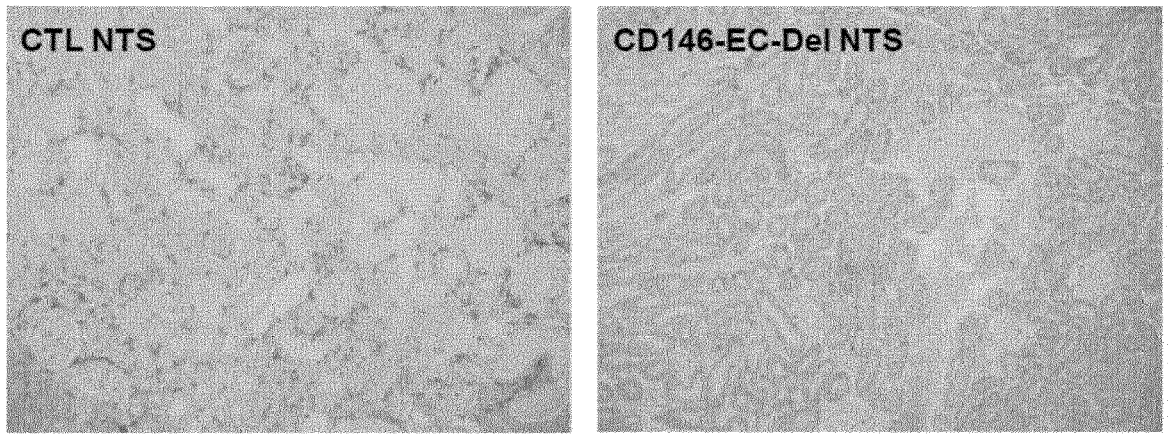
Figure 7:
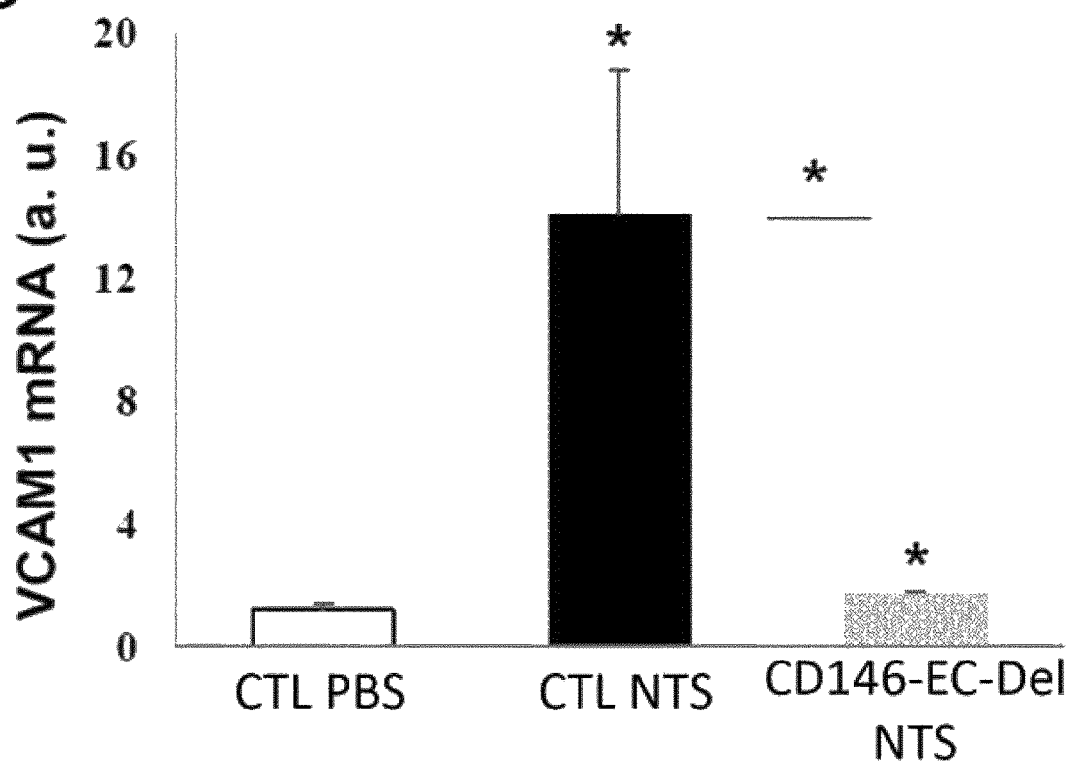

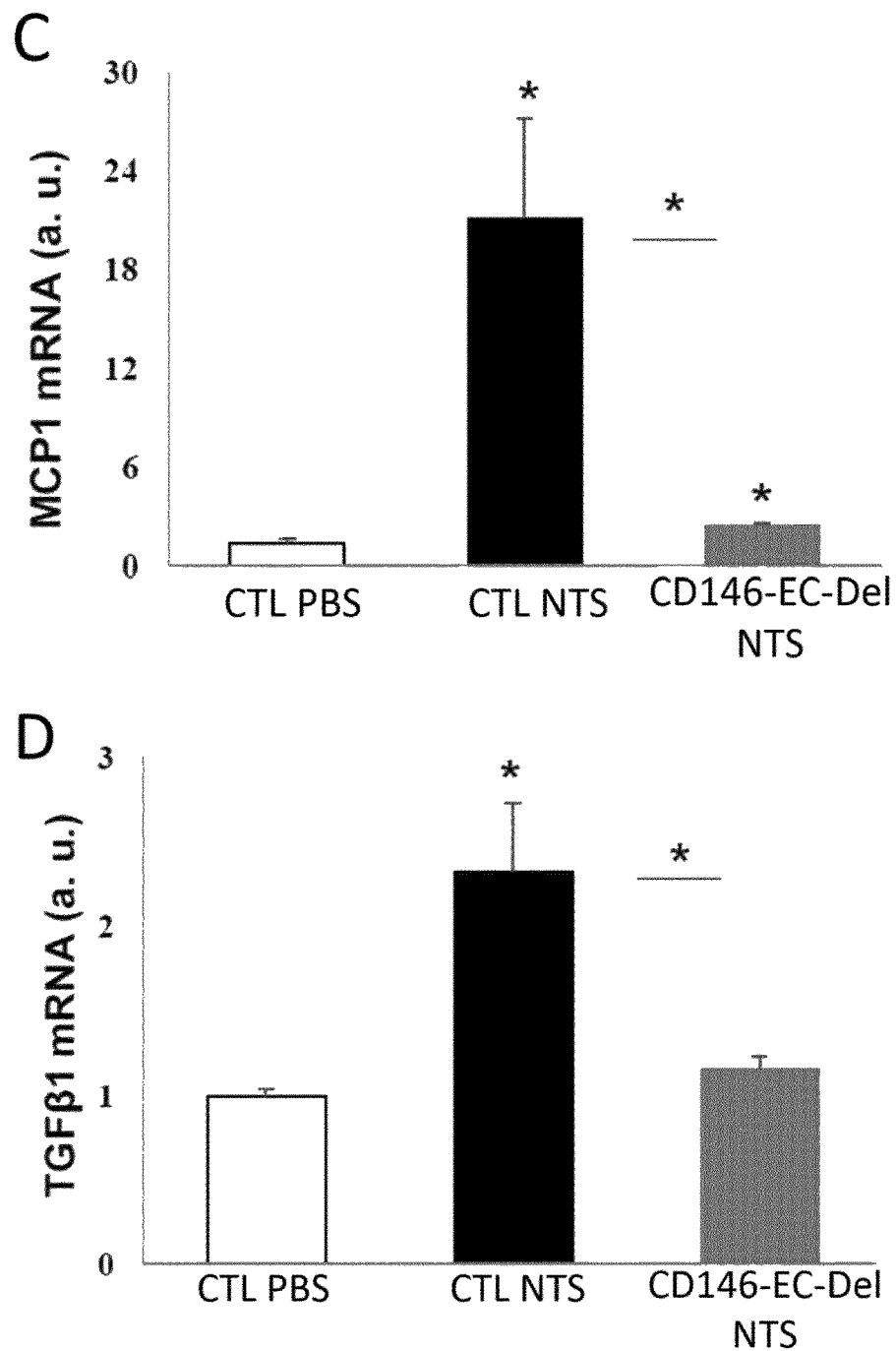
FIGURE 7 (Following)

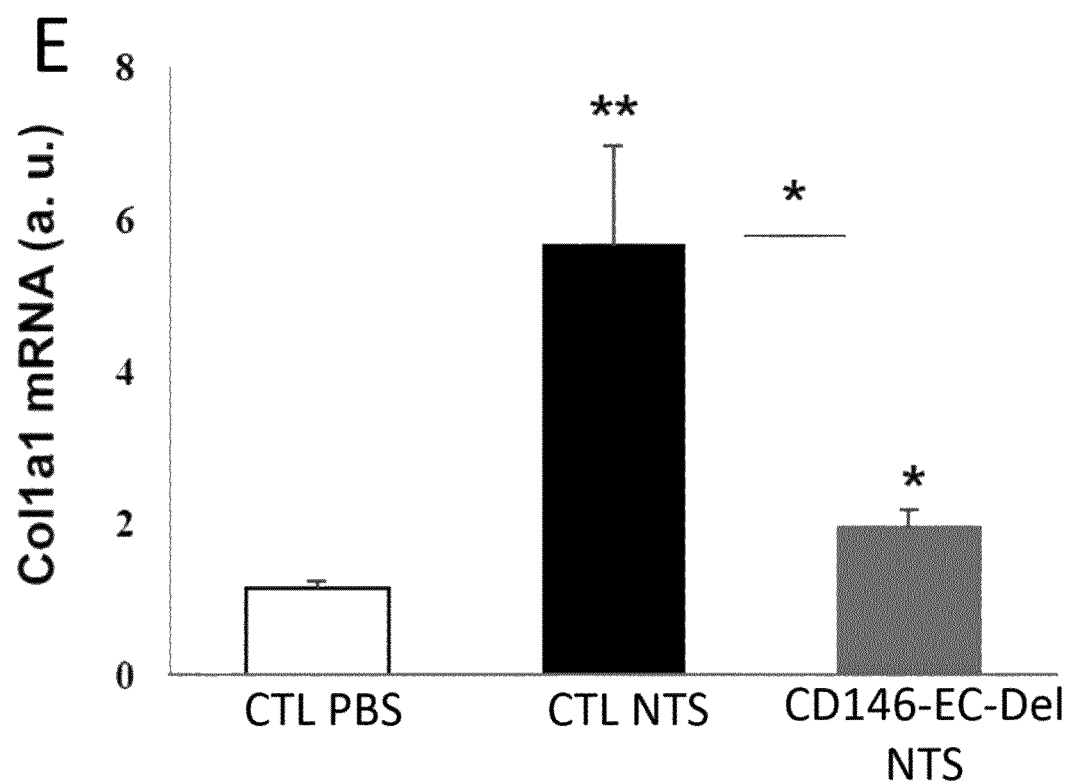
FIGURE 7 (Following)

| Disease | DN | MCD | IgA | FSGS | MGN | SLE | RPGN |
|---|---|---|---|---|---|---|---|
| Average fold increase | 1,91 | 1,28 | 1,29 | 1,64 | 1,31 | 1,37 | 1,45 |

FIGURE 8

Figure 9:
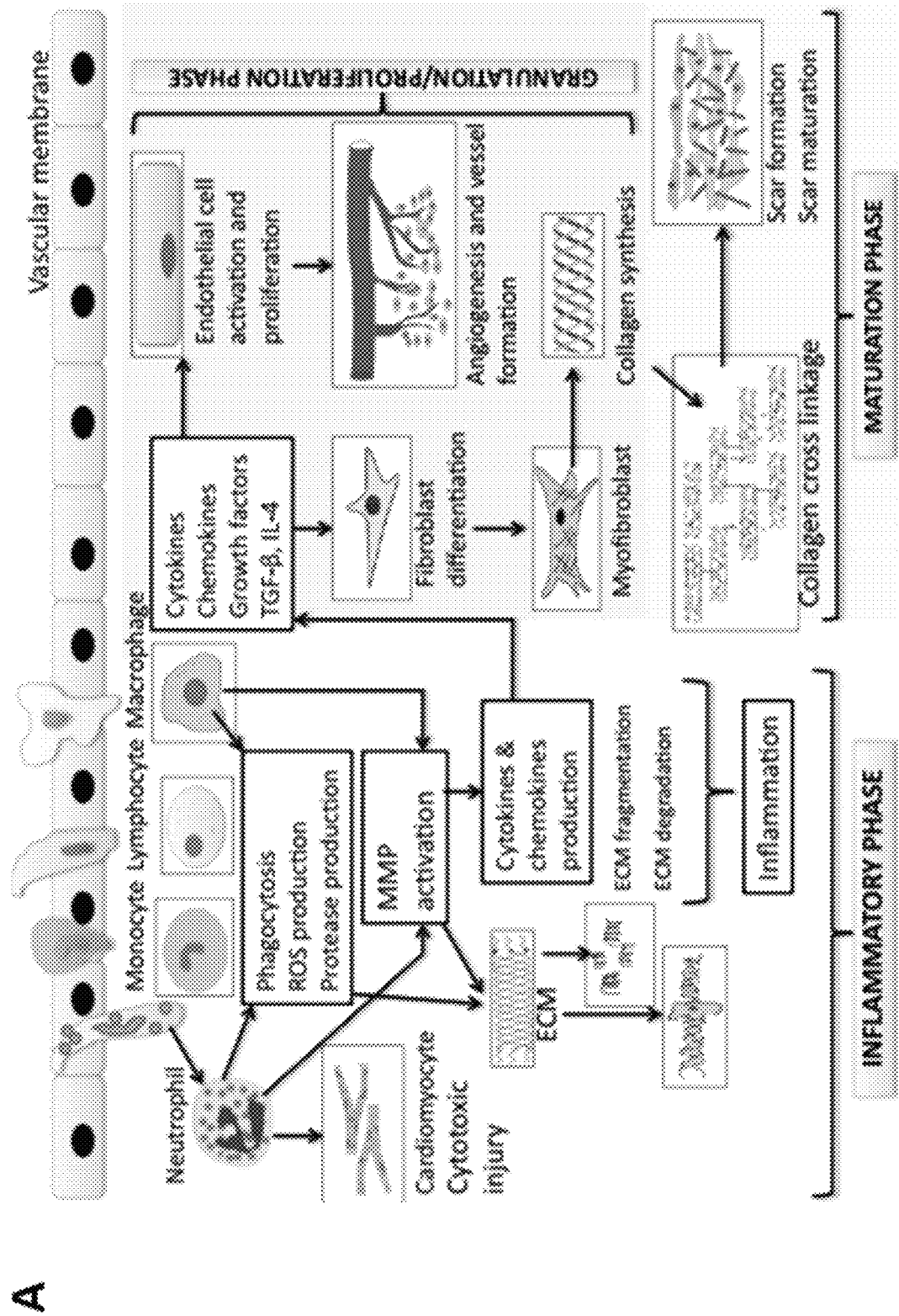

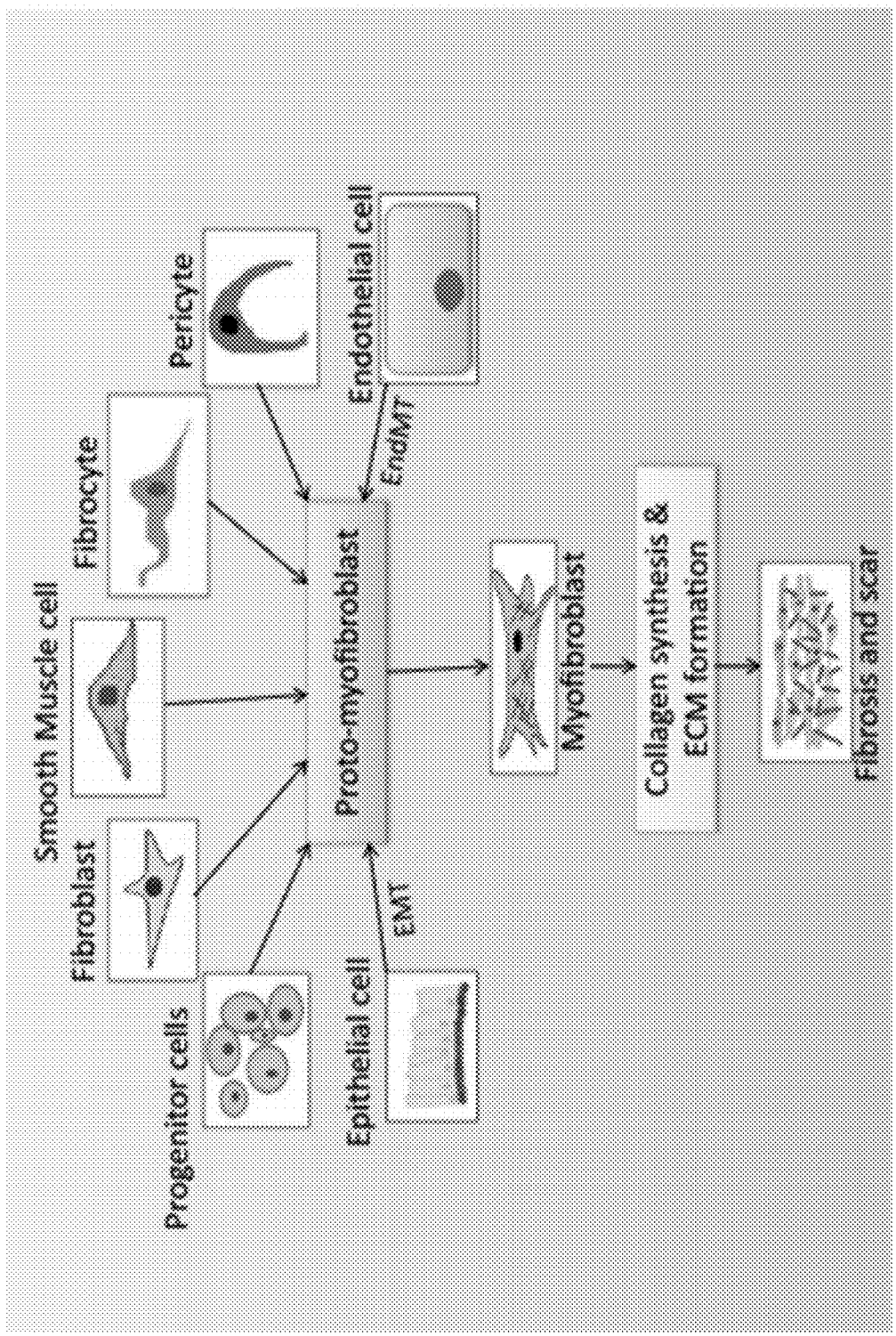
FIGURE 9 (Following)

Figure 10:
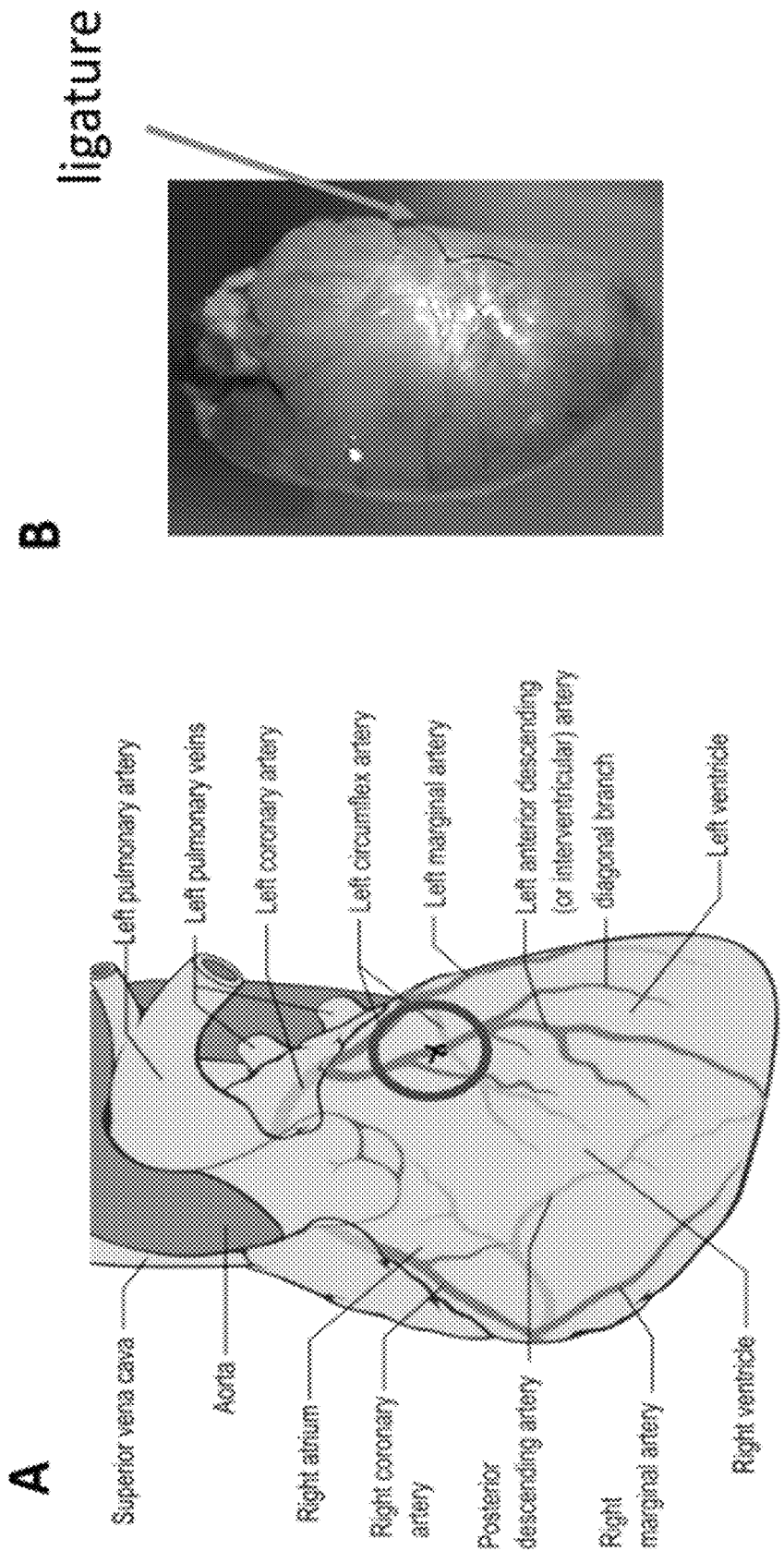

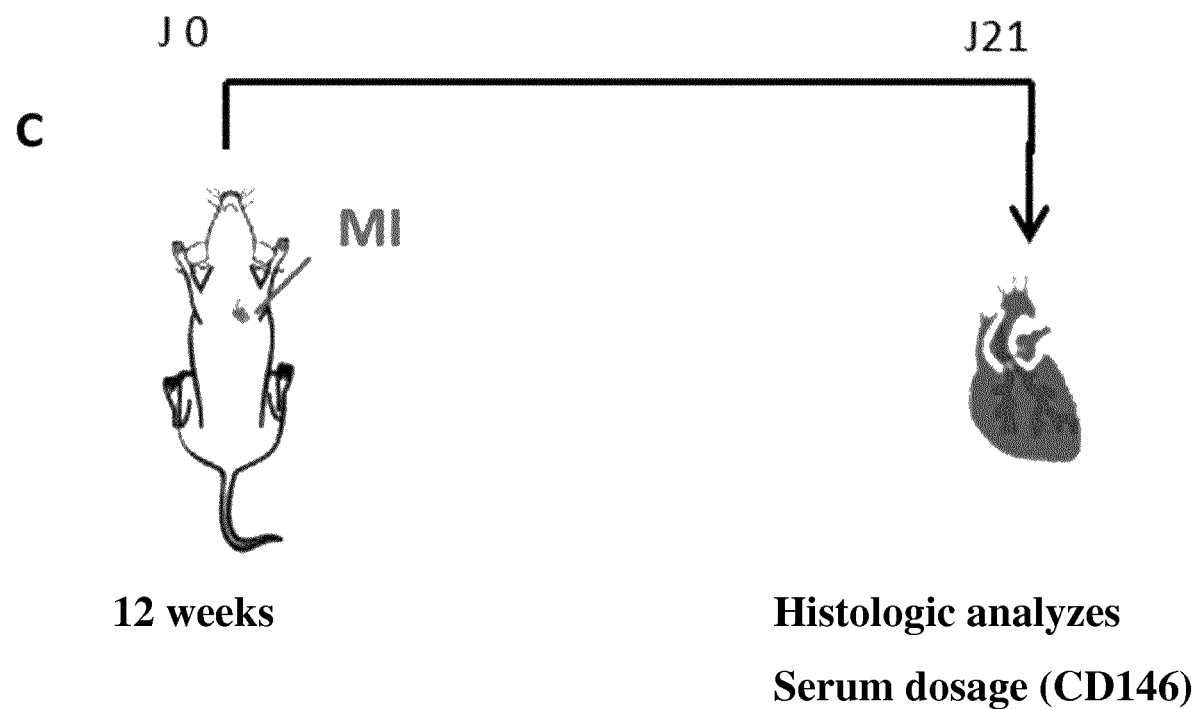
FIGURE 10 (Following)

A

Toluidine blue

B

SHAM

MI

Sirius red

Figure 13:
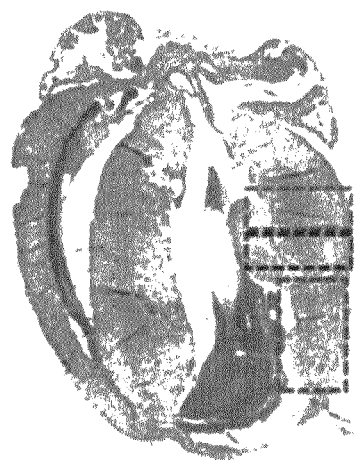
Figure 13:
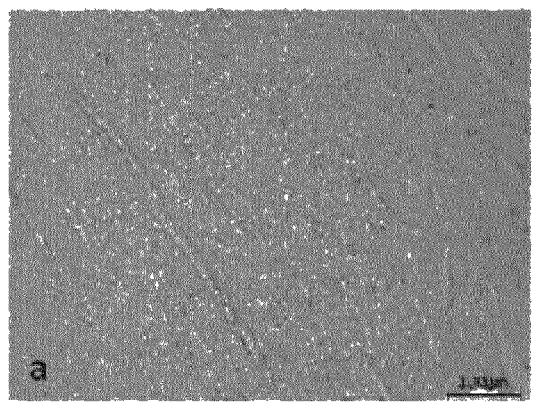
Figure 13:
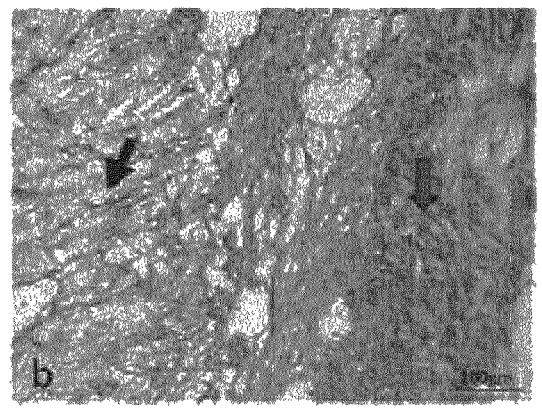

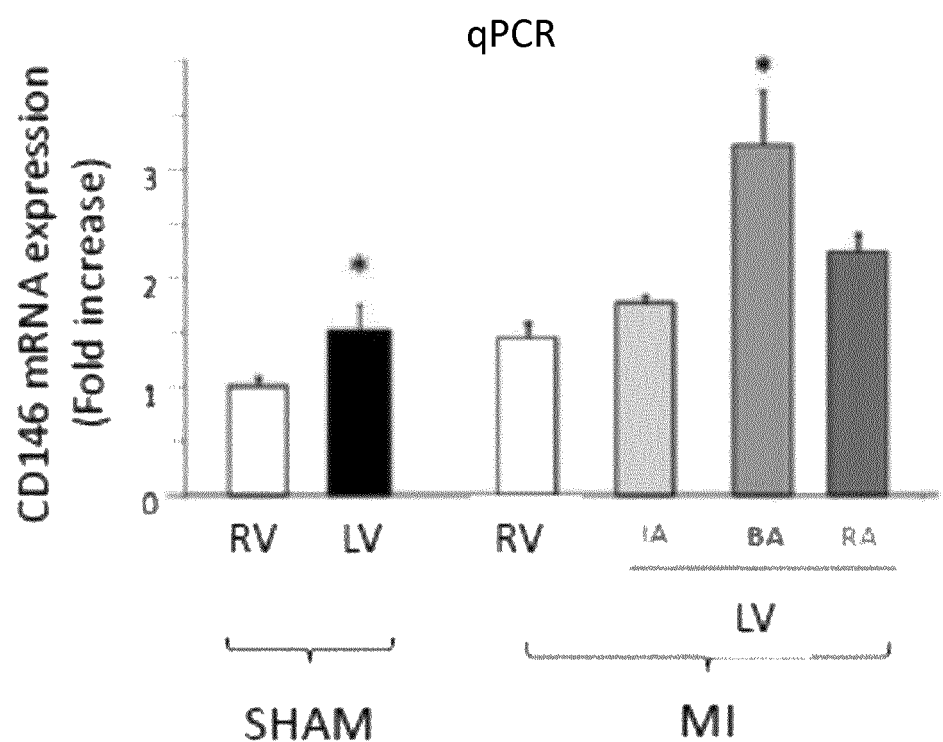
FIGURE 13 (Following)

A

Figure 14:
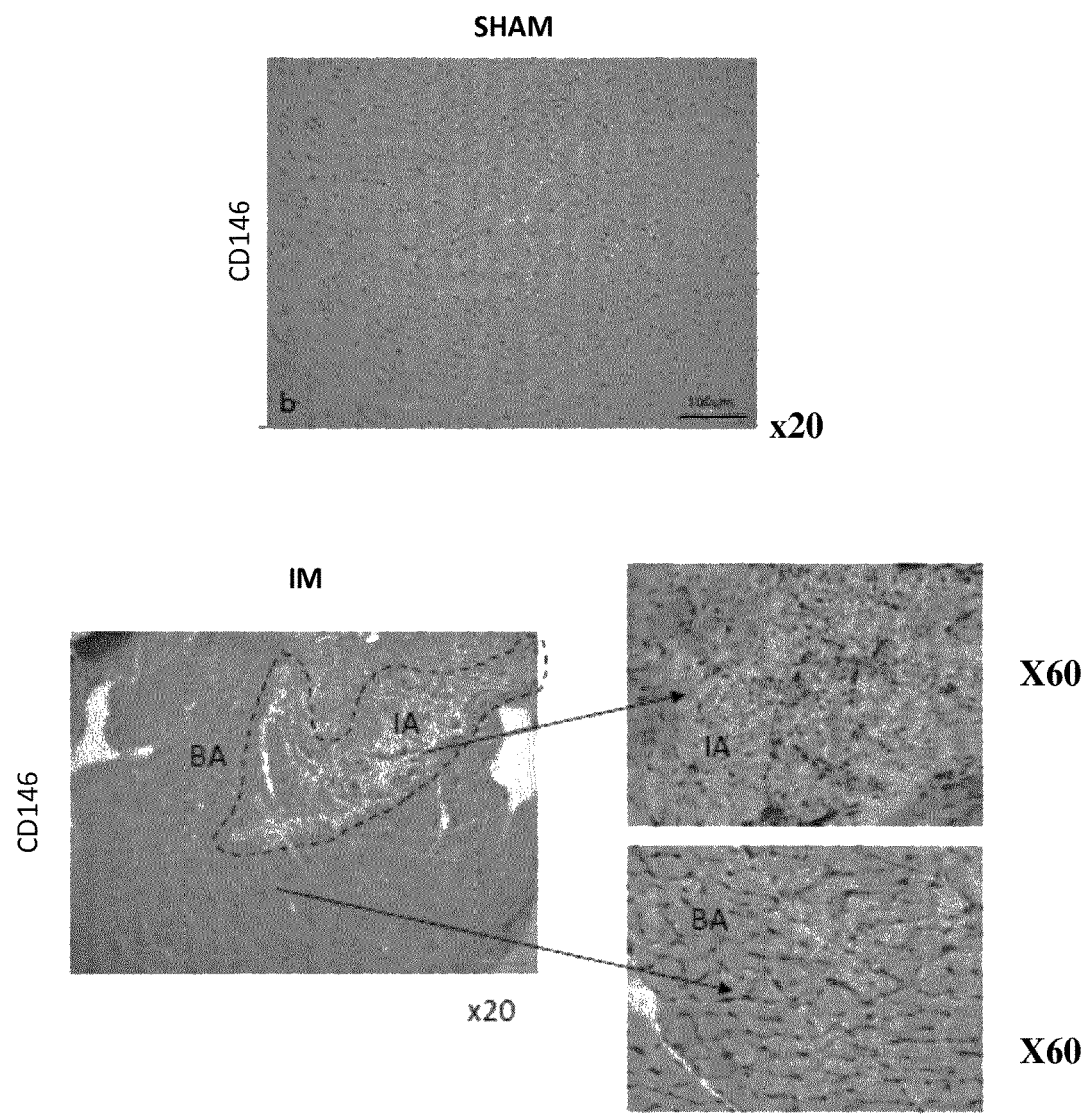

B
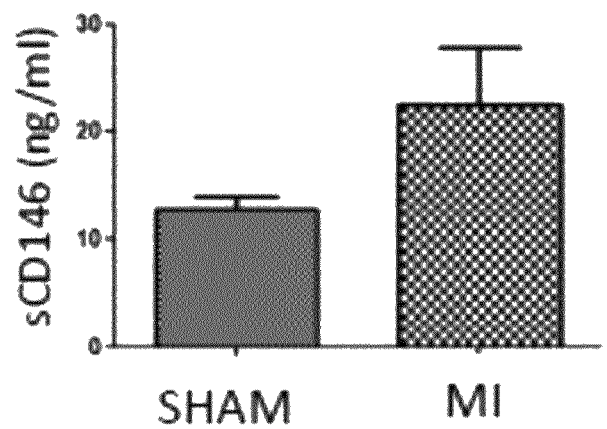
FIGURE 14 (Following)

A

Sirius red (n=3)

Figure 16:
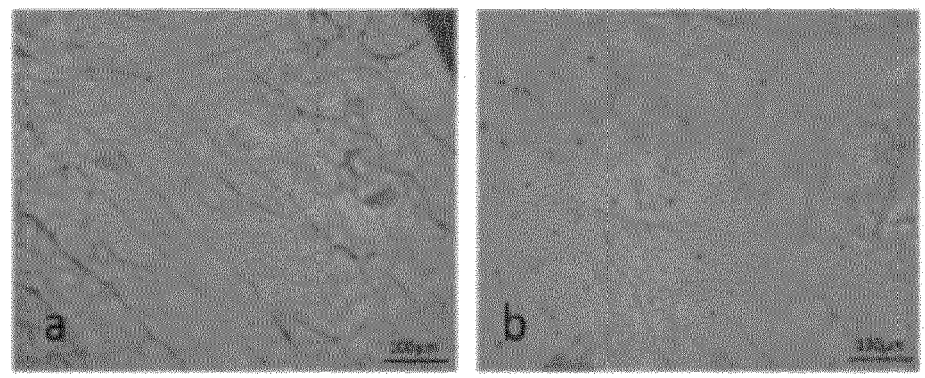
Figure 16:
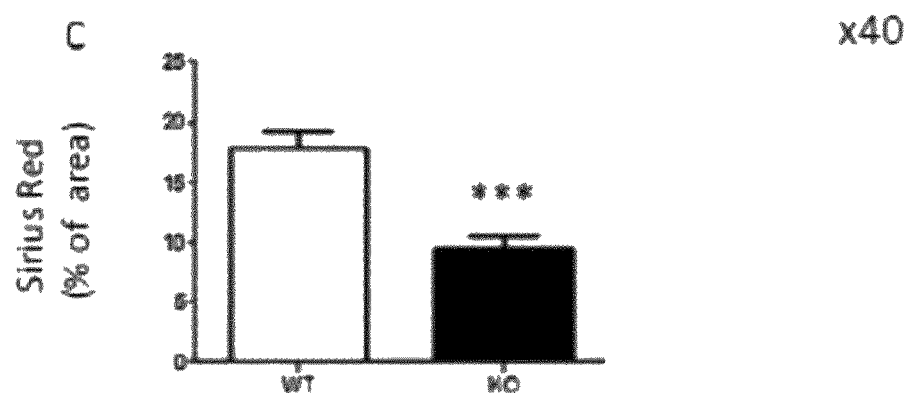

B
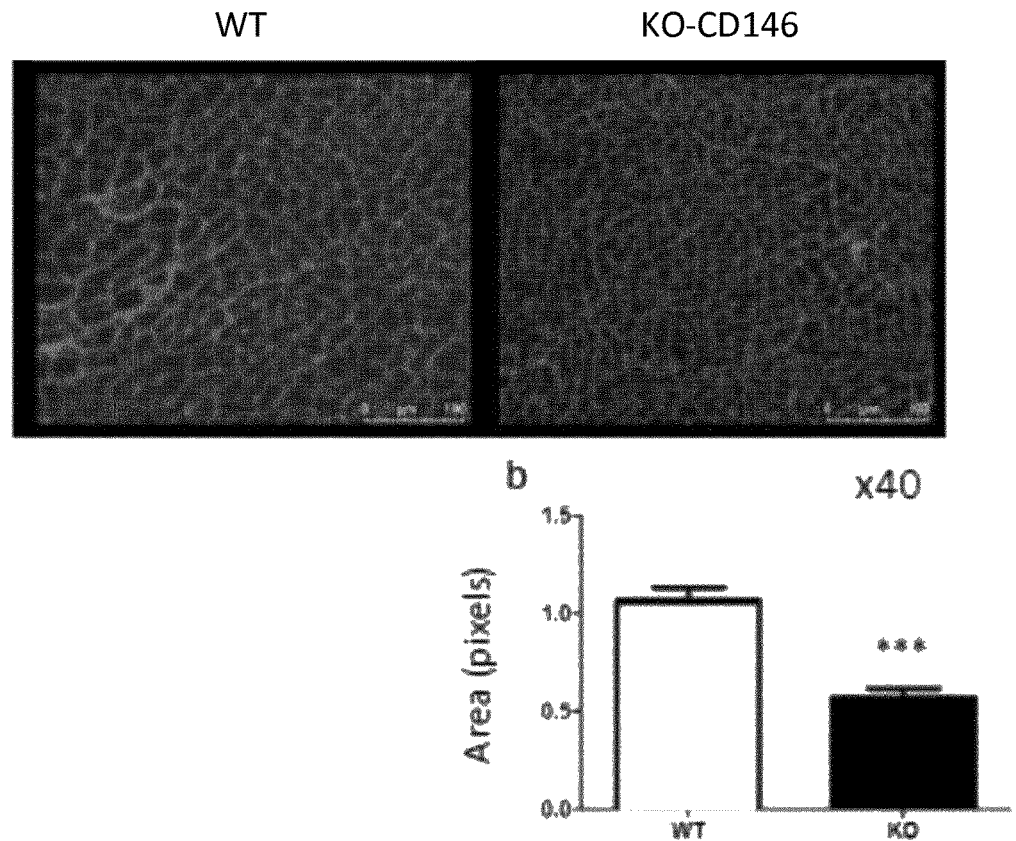
FIGURE 16 (Following)

A

B

Figure 17:
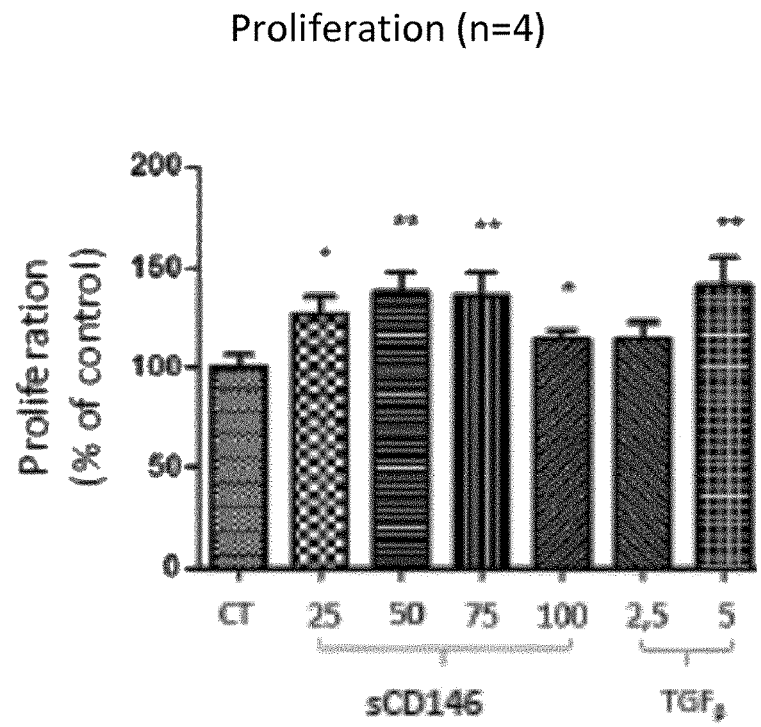
Figure 17:
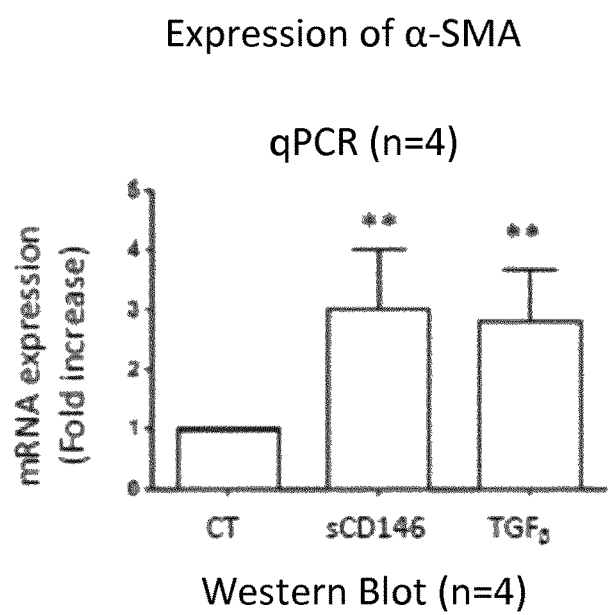

C
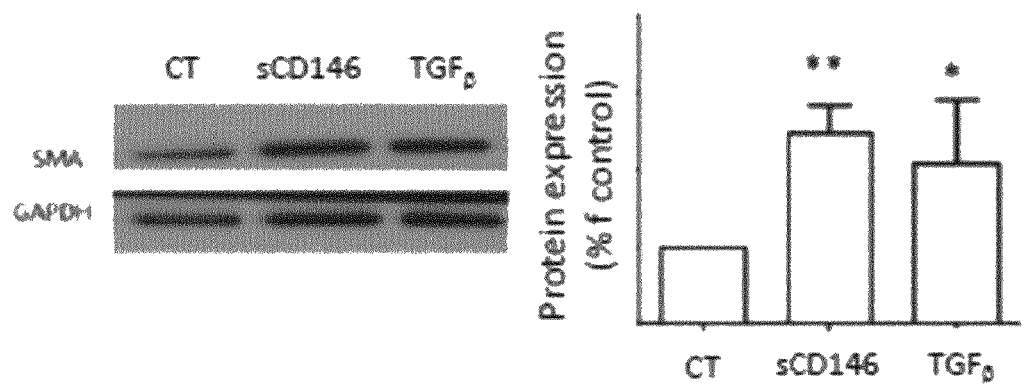
Immunofluorescence (n=3)
D
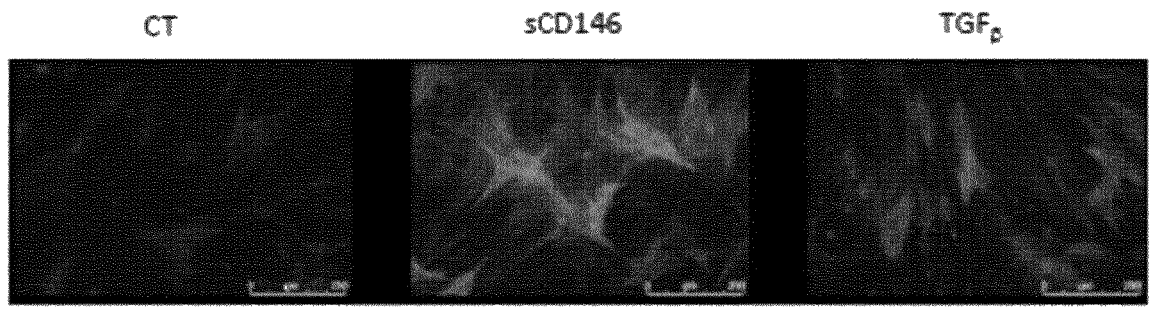
FIGURE 17 (Following)

E
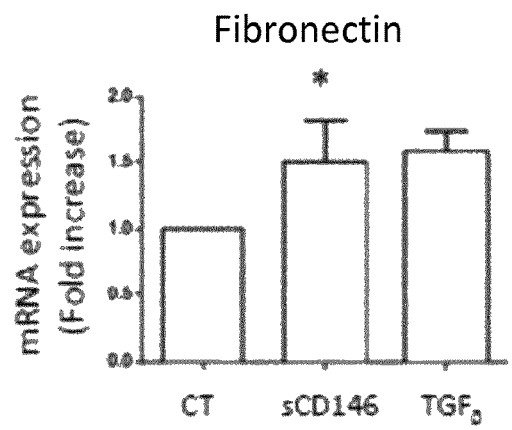
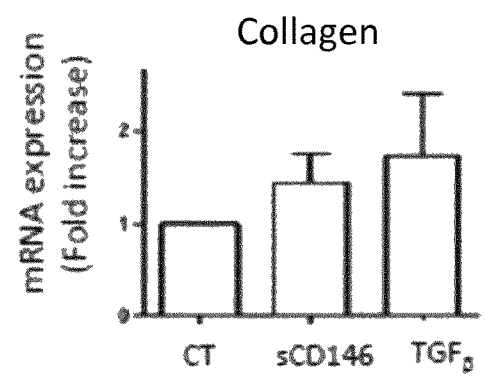
F
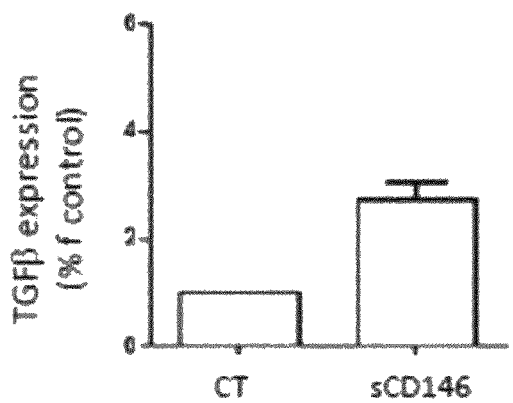
FIGURE 17 (Following)

Figure 21:
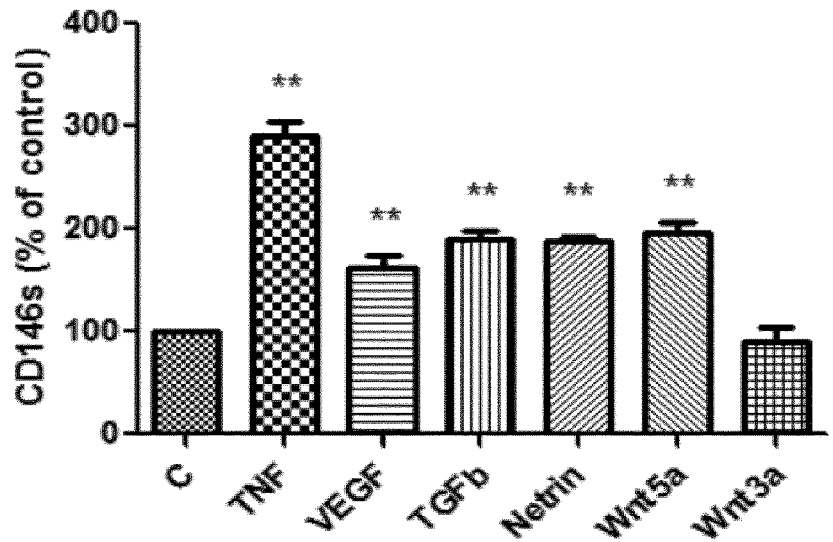
Figure 21:
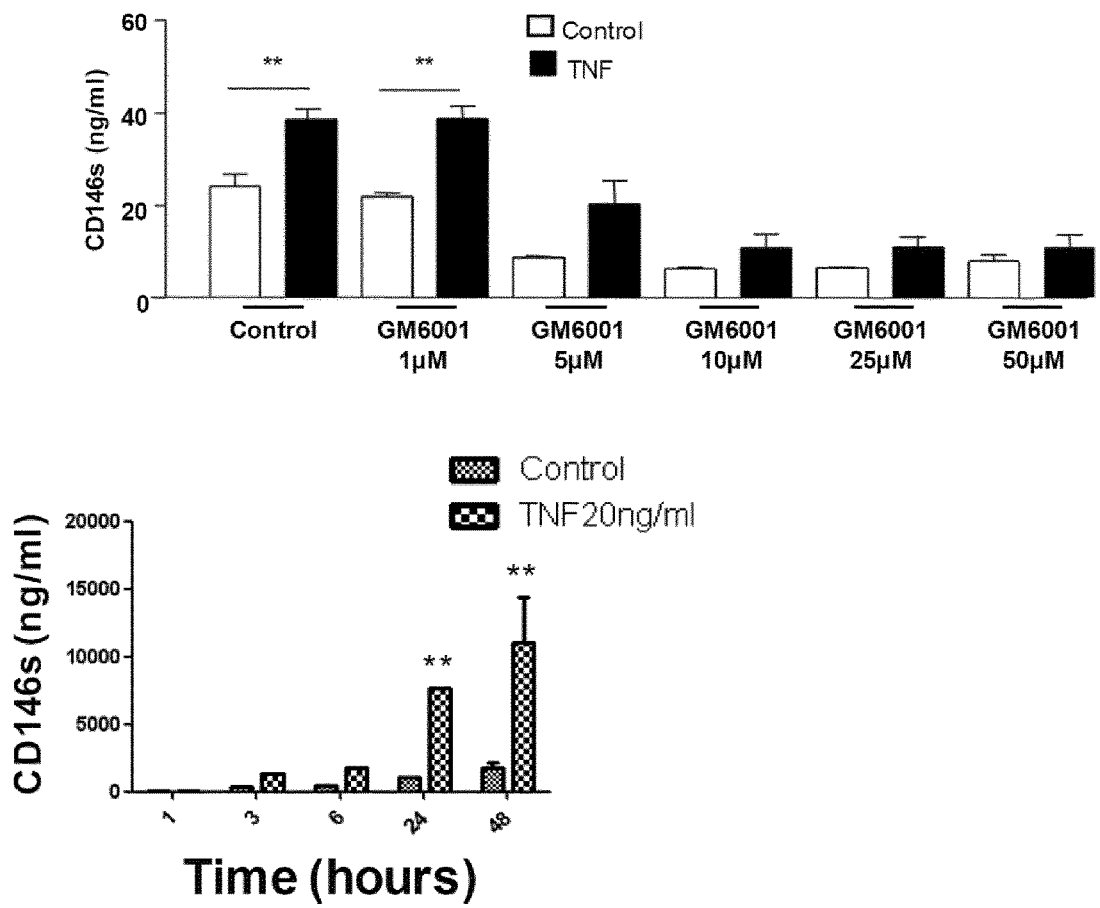

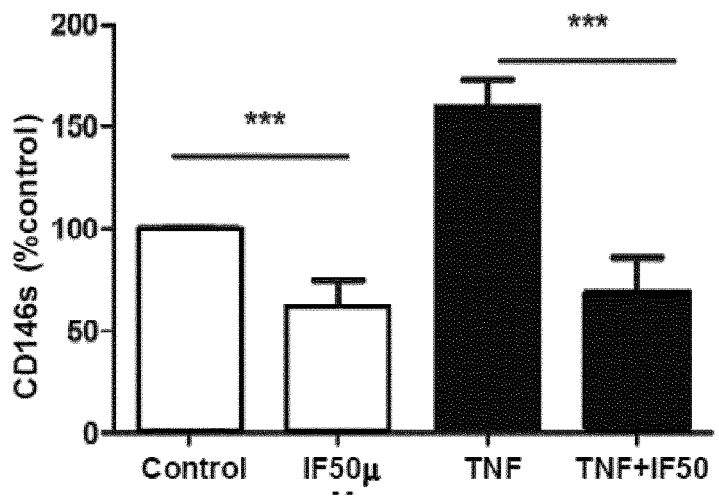
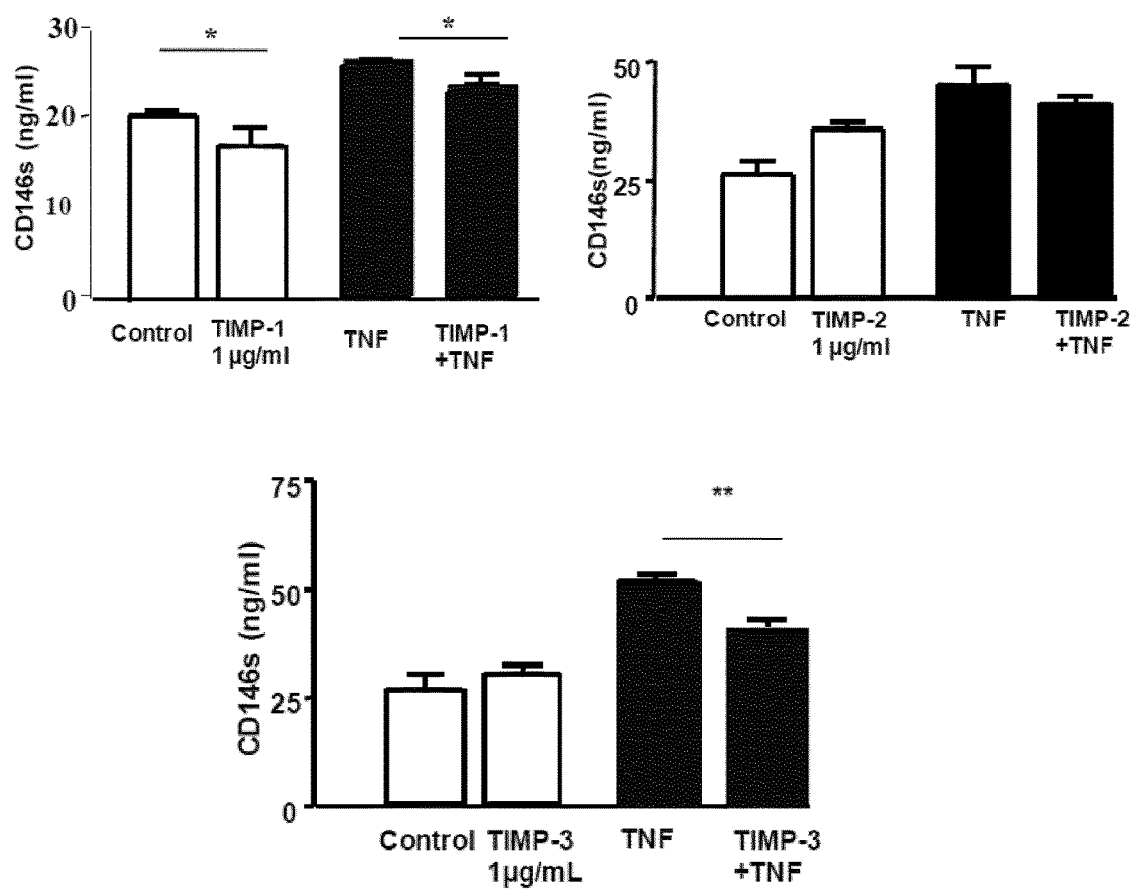
FIGURE 21 (following)

Figure 22:
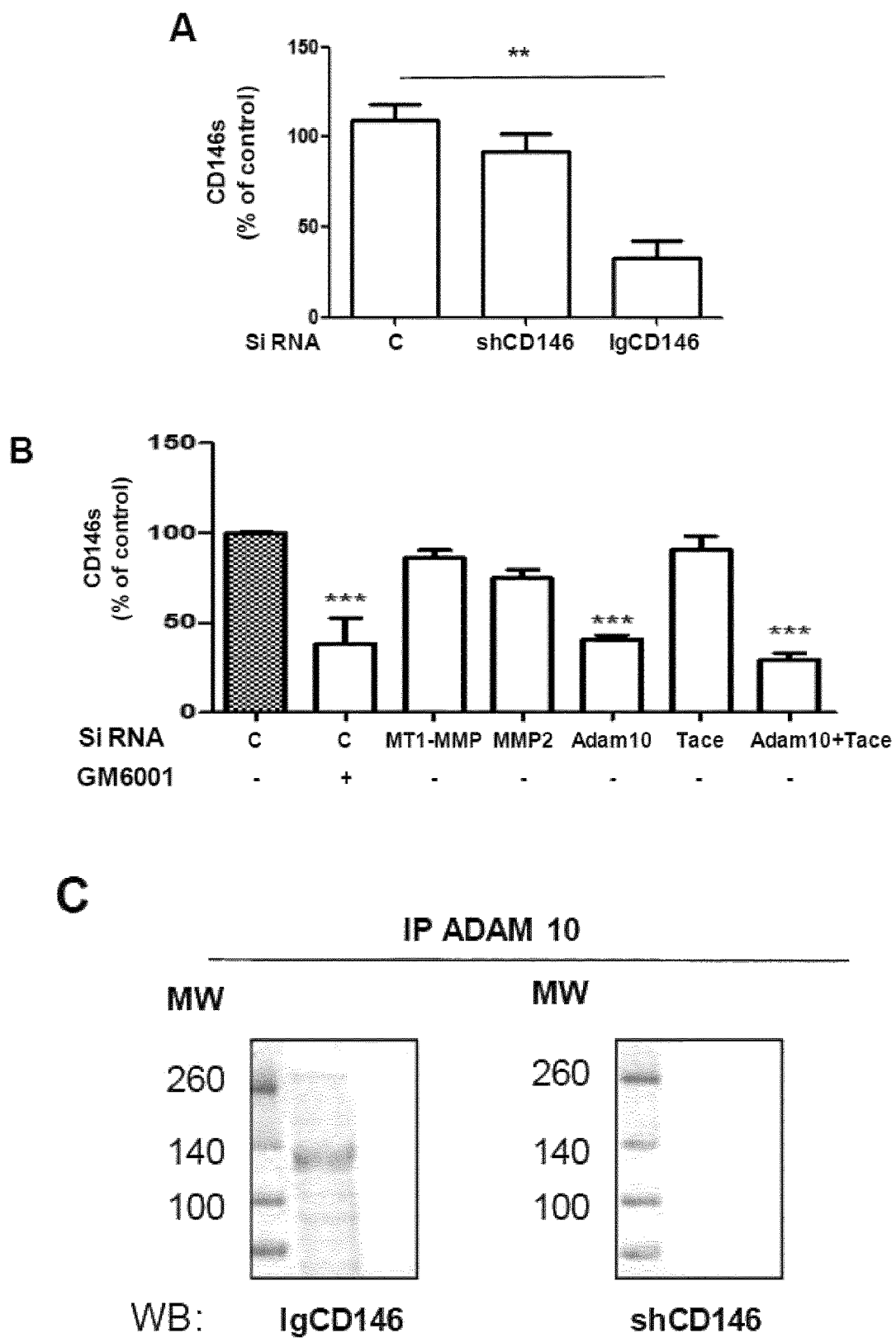

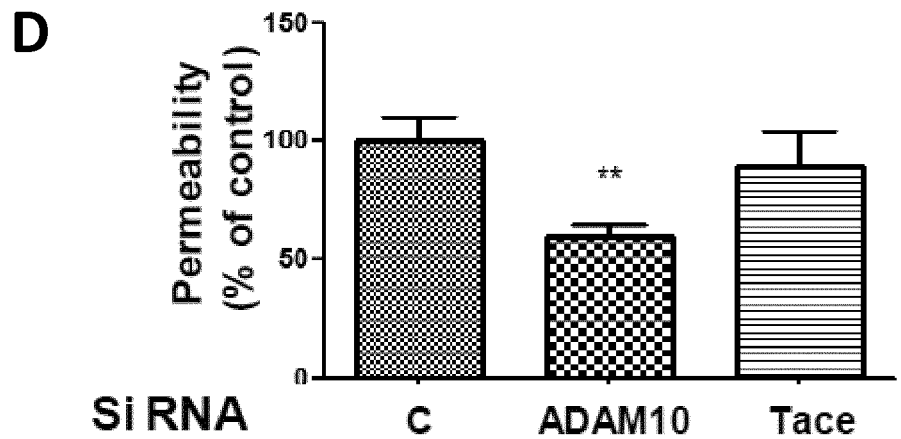
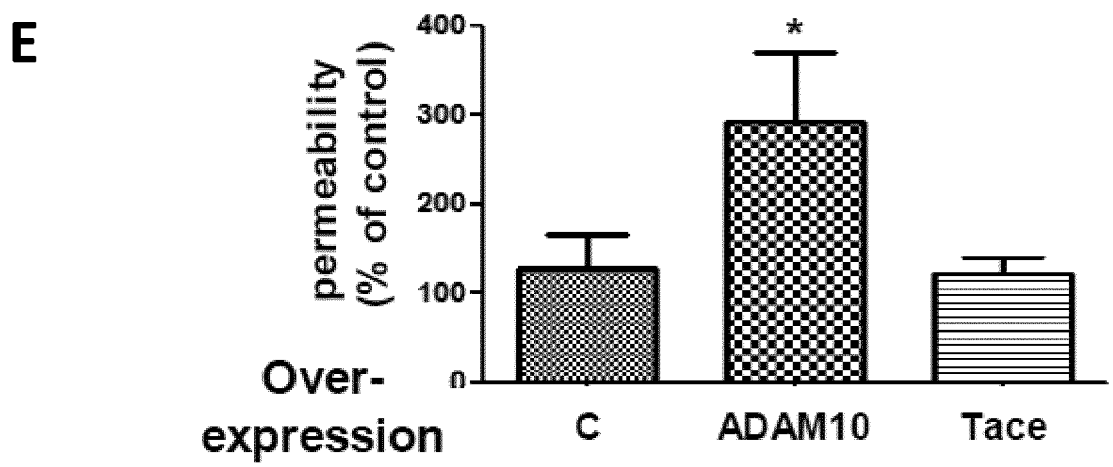
FIGURE 22 (following)

Figure 24:
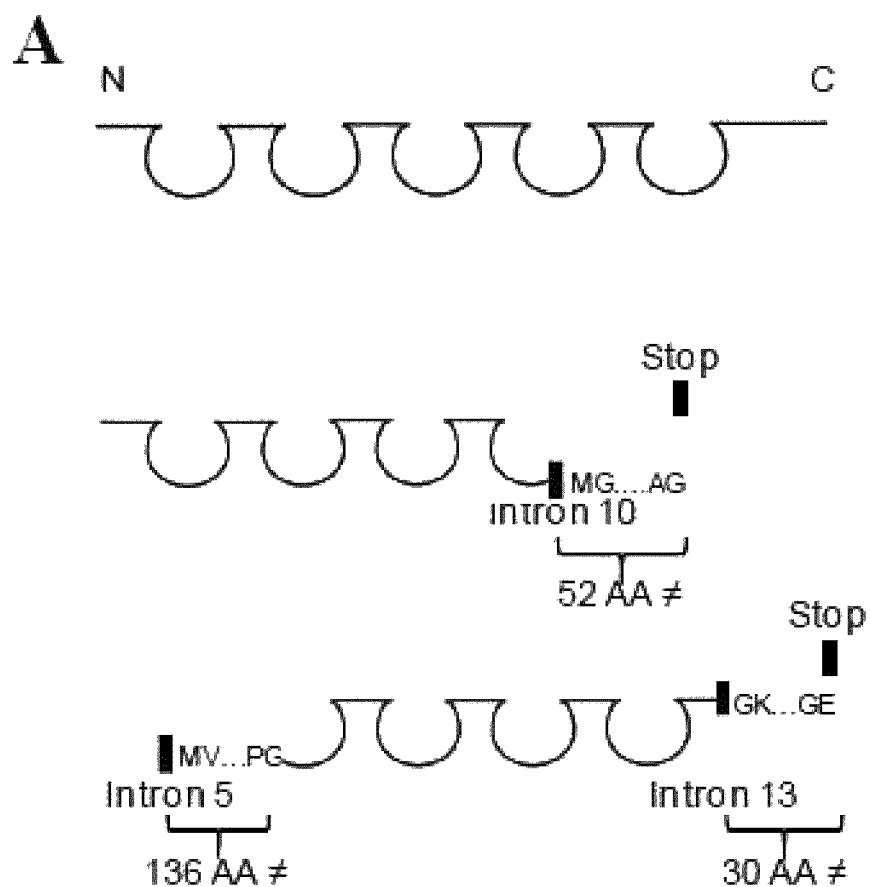

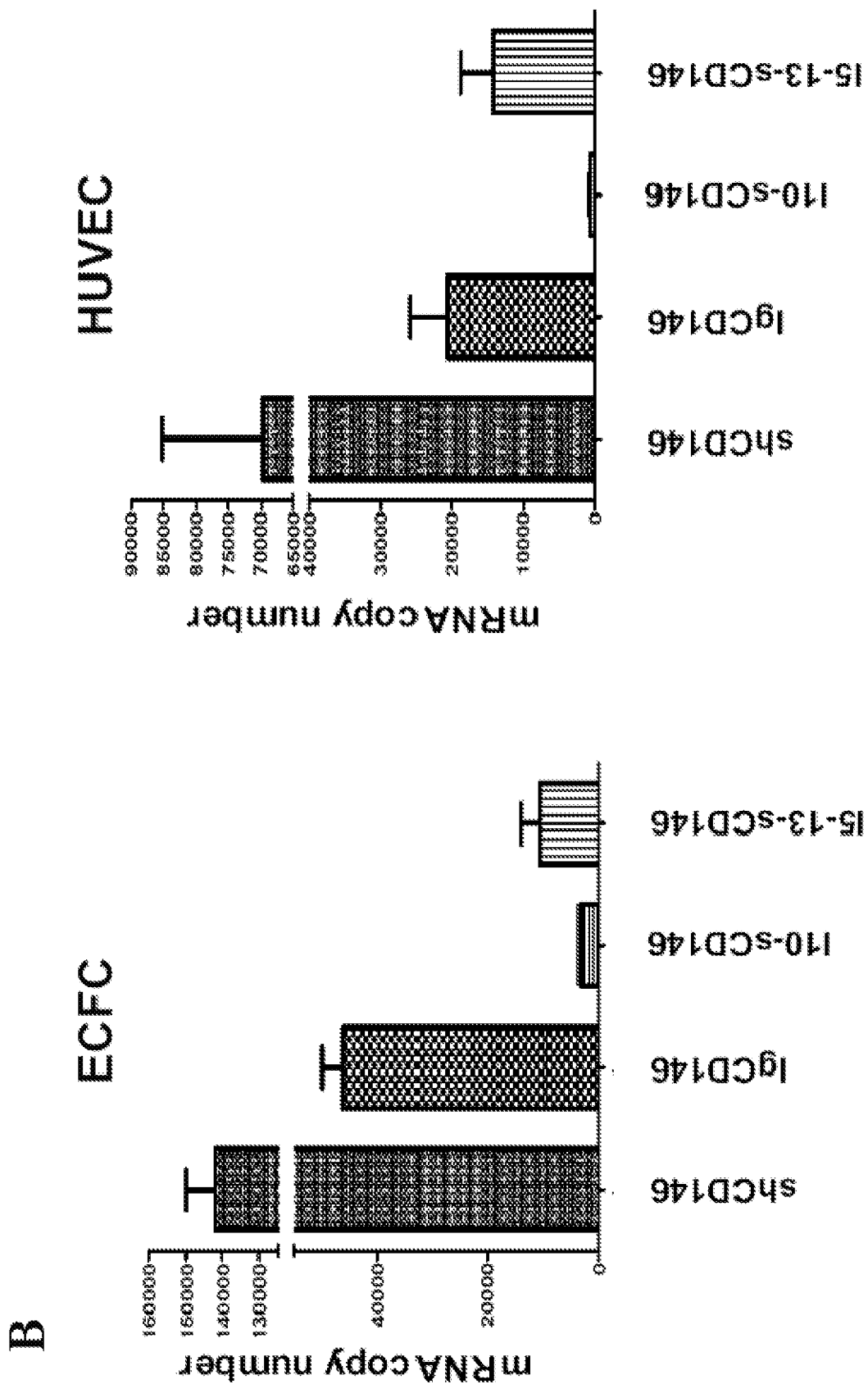
FIGURE 24 (Following)

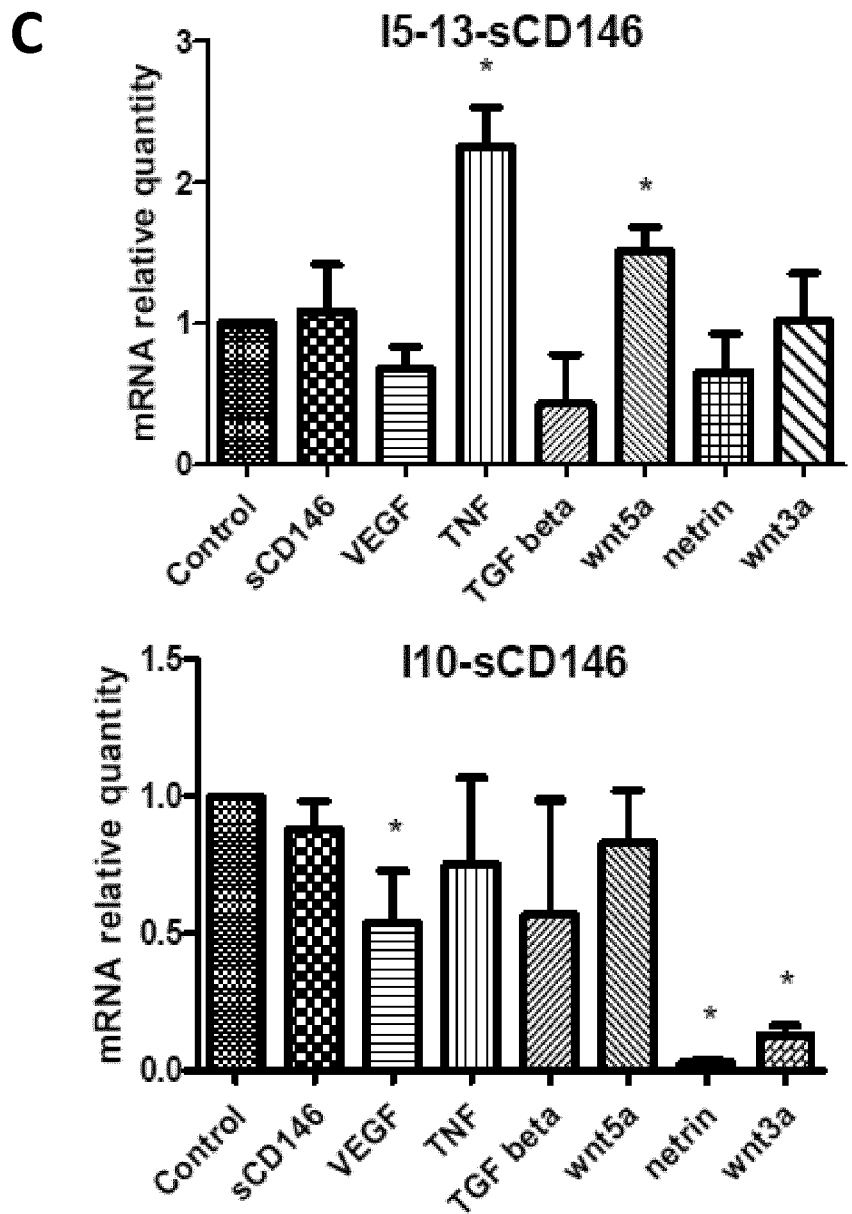
FIGURE 24 (following)

Figure 25:
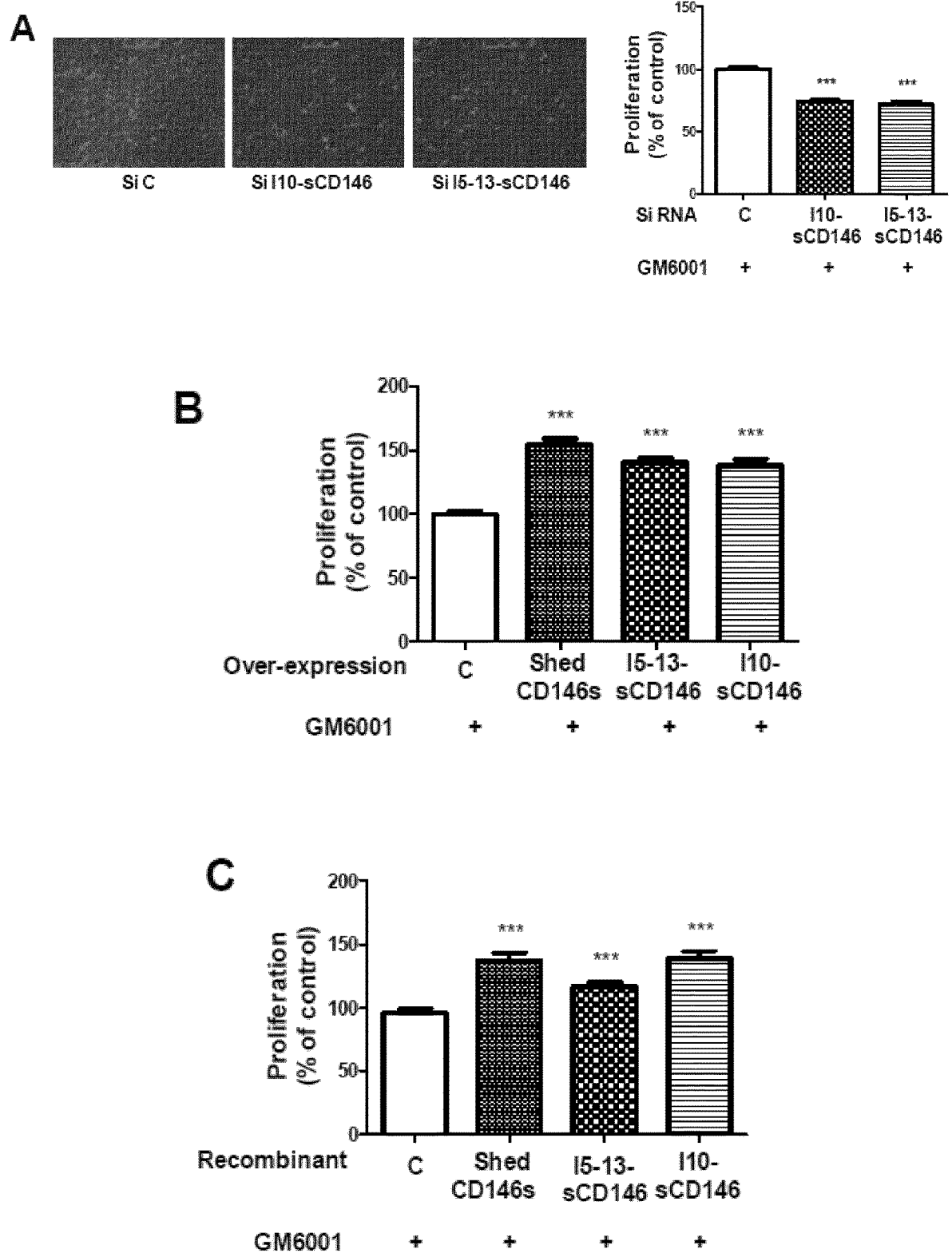

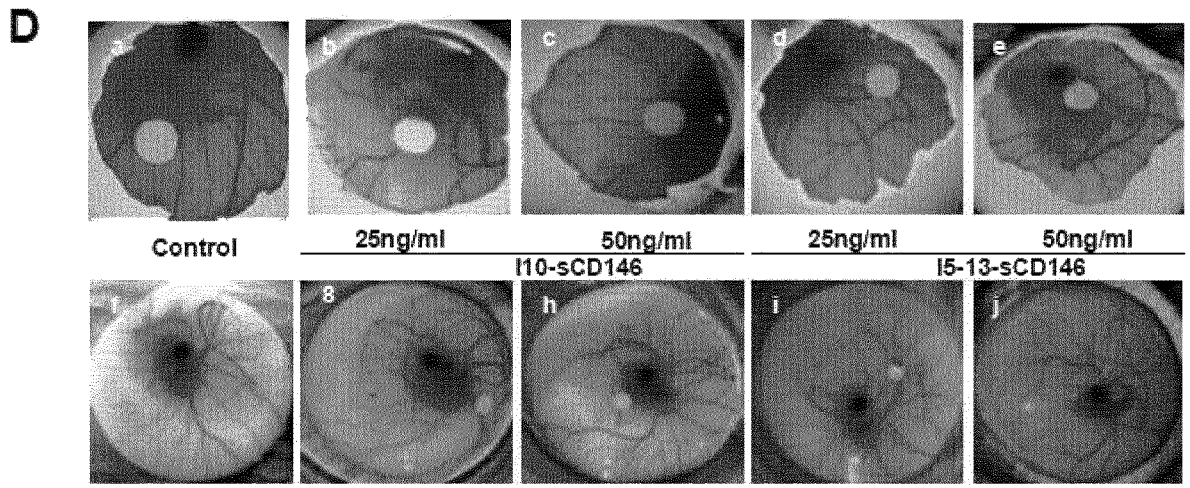
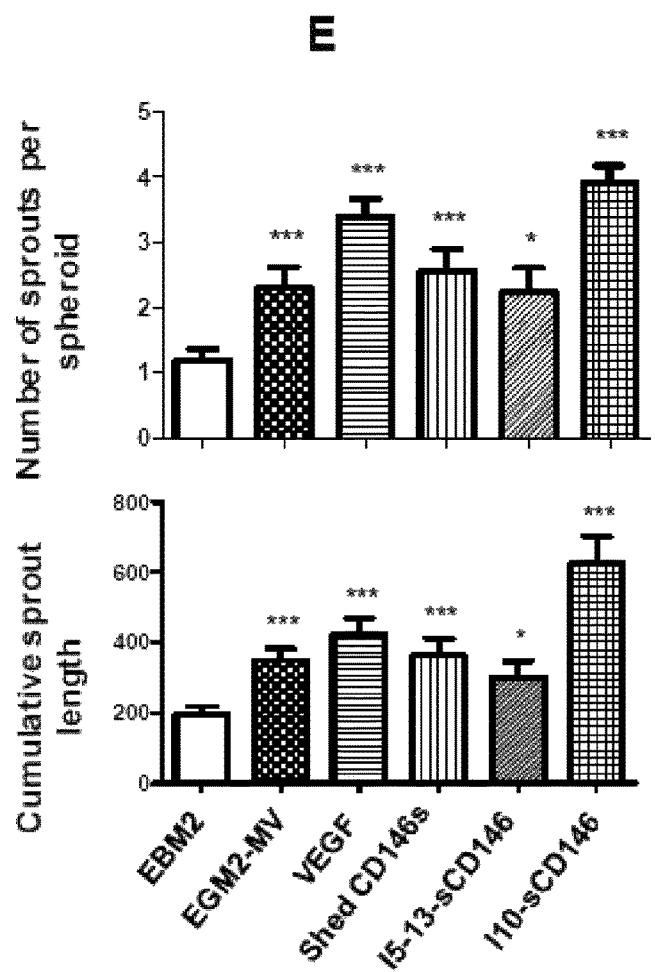
FIGURE 25 (following)

Figure 26:
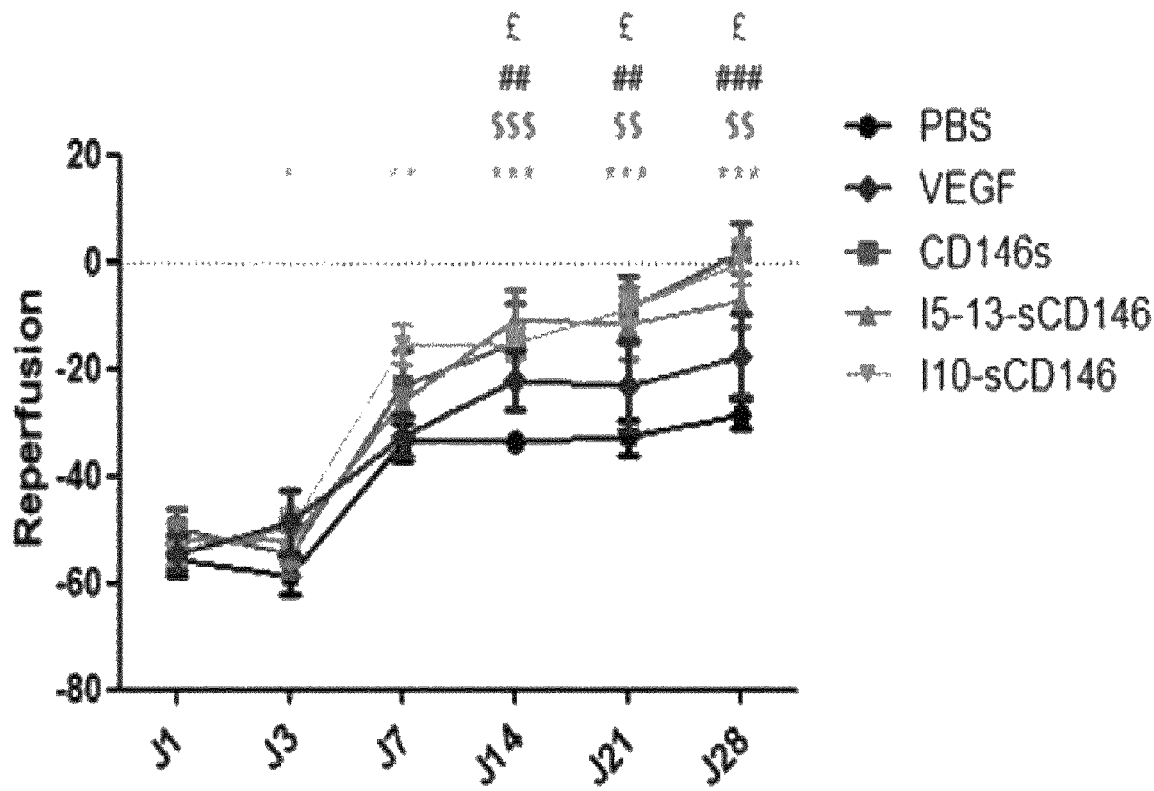
Figure 26:
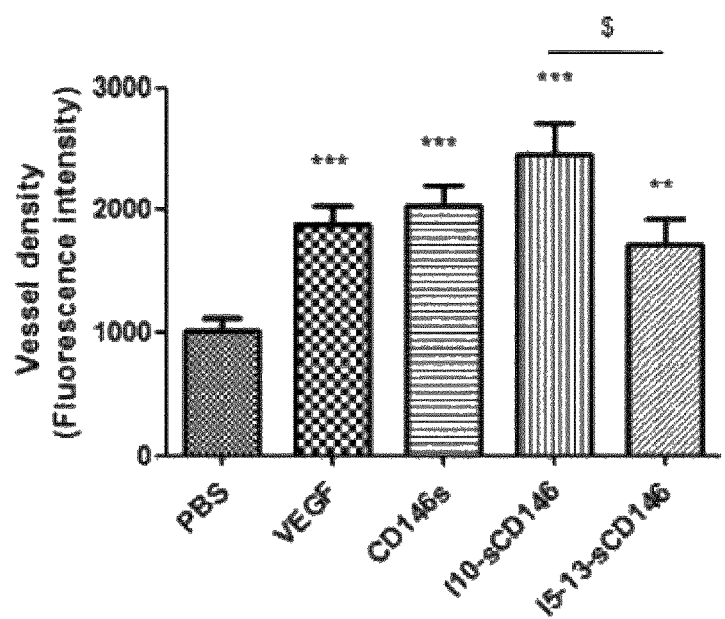

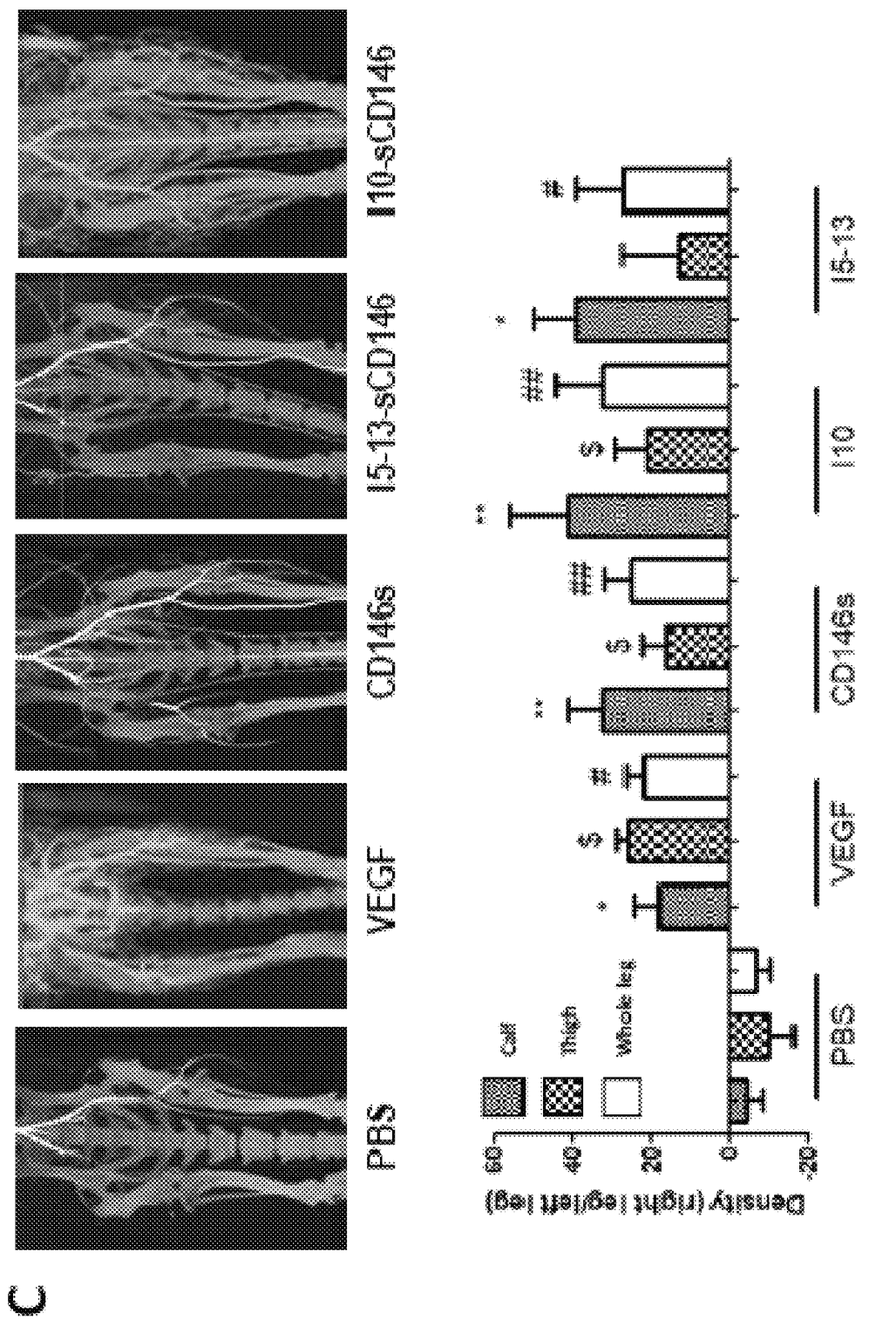
FIGURE 26 (following)

Figure 27:
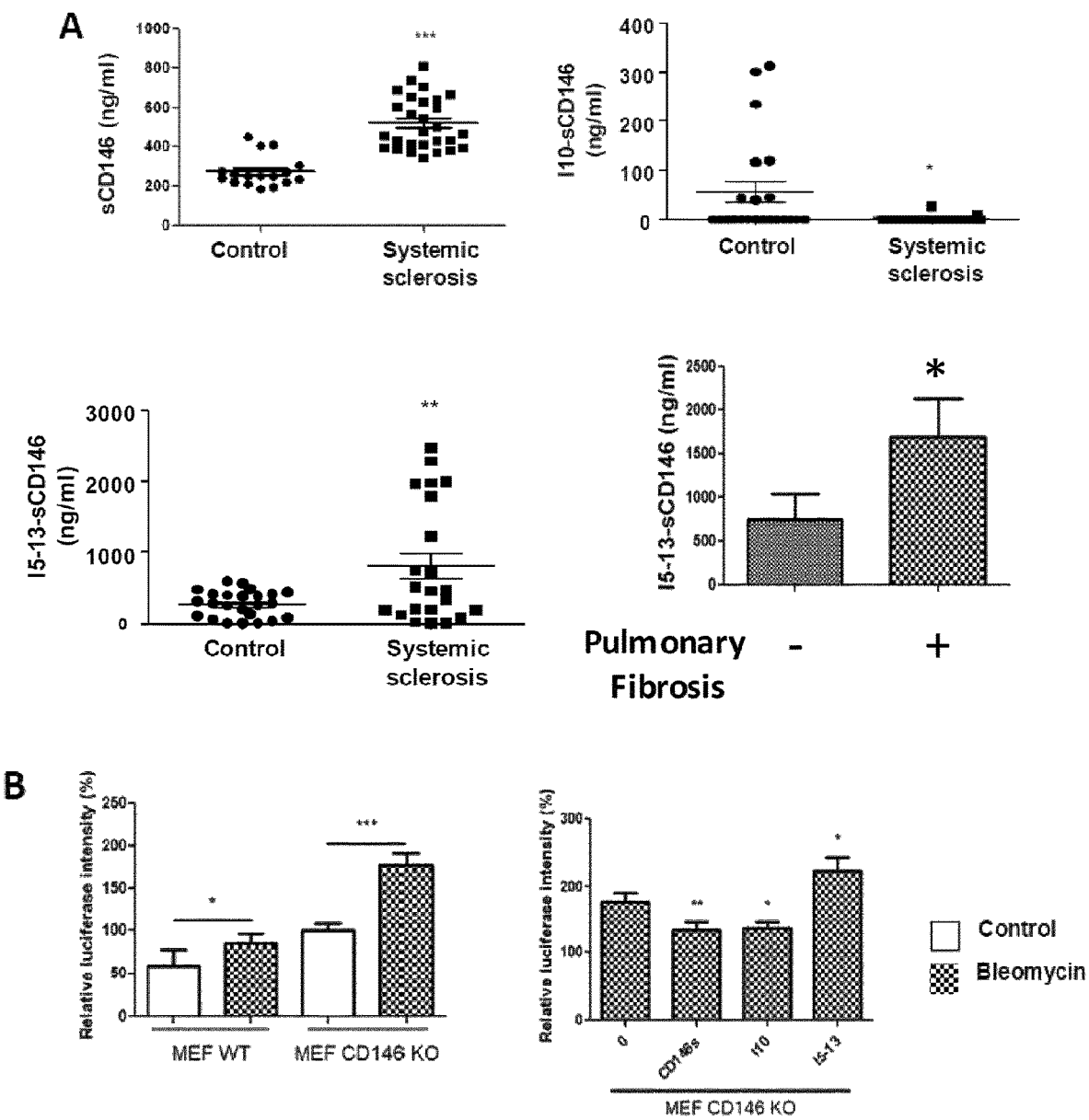

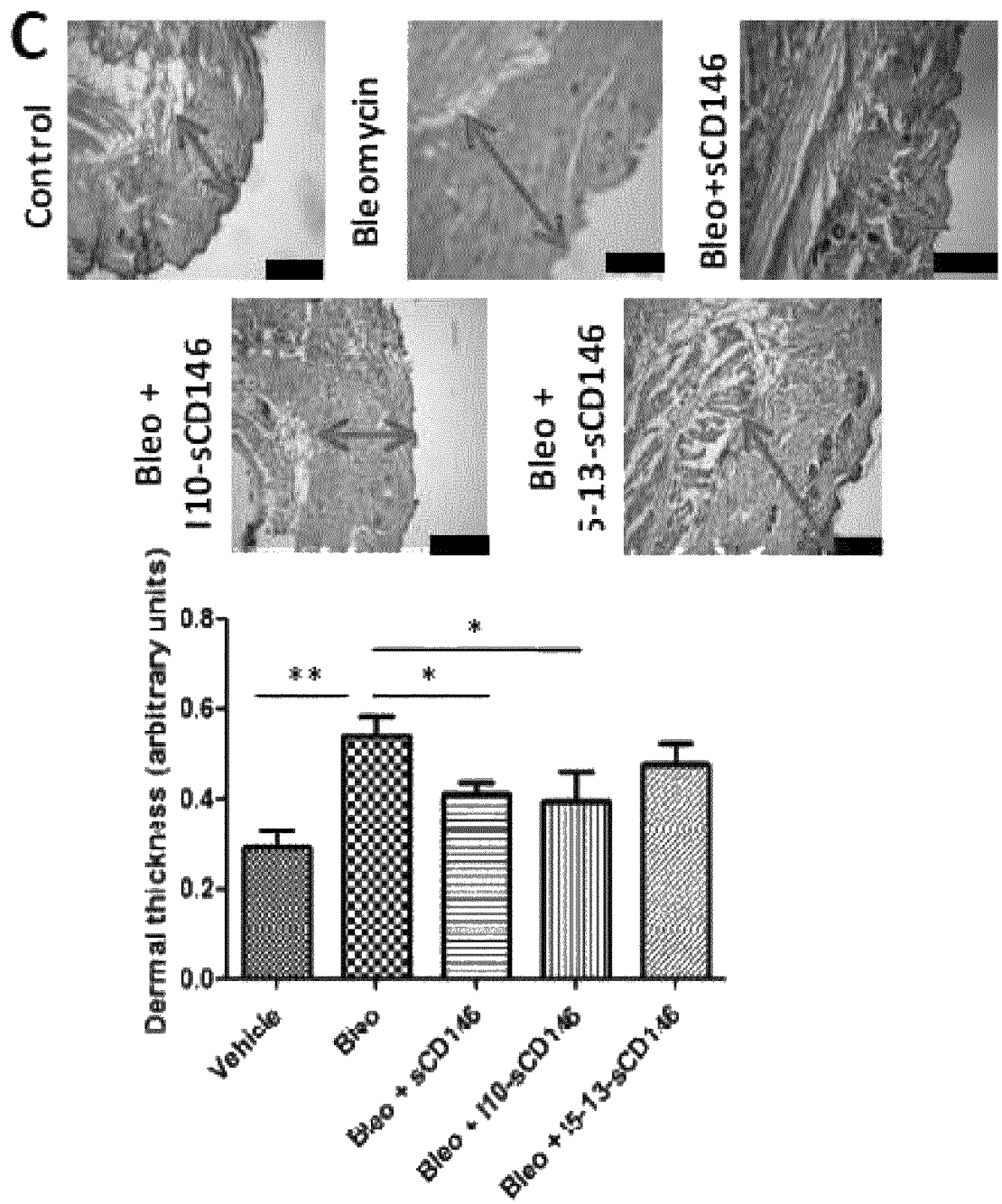
FIGURE 27 (following)

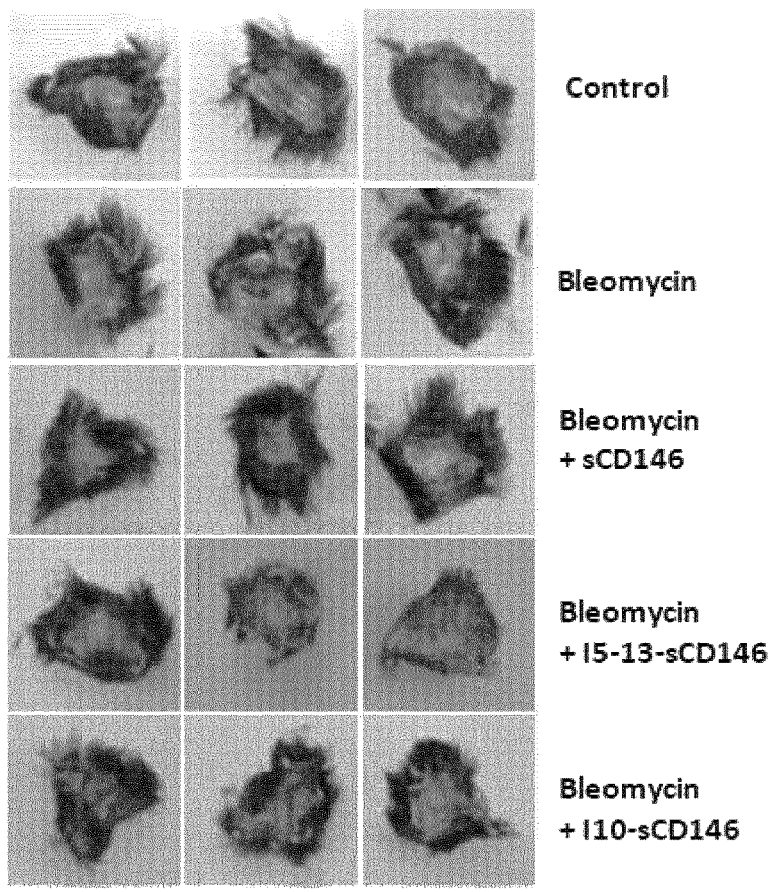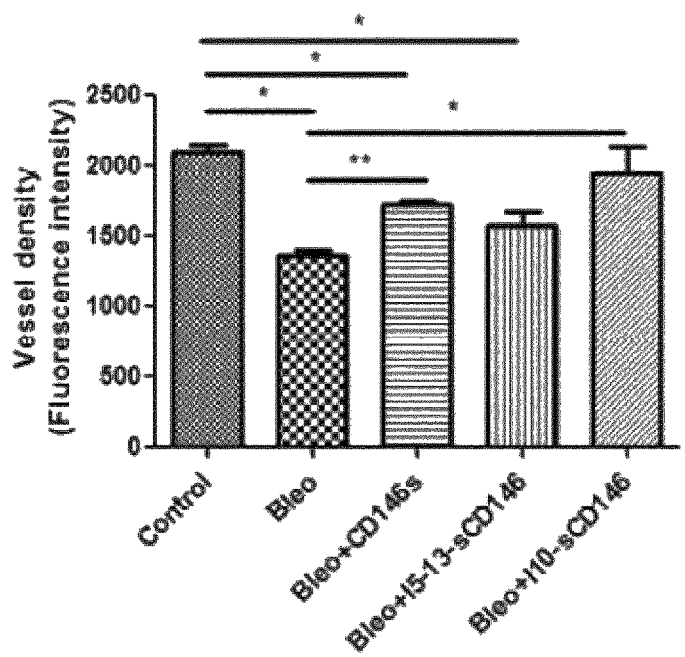
FIGURE 27 (following)

CD146 AND USES THEREOF AS A BIOMARKER AND AS A THERAPEUTIC TARGET IN THE DIAGNOSIS AND TREATMENT OF FIBROSIS

CROSS-REFERENCE TO RELATED APPLICATION

This application is the U.S. national stage application of International Patent Application No. PCT/EP2019/075966, filed Sep. 26, 2019.

The Sequence Listing for this application is labeled "Seq-List.txt" which was created on Feb. 23, 2021 and is 93 KB. The entire content of the sequence listing is incorporated herein by reference in its entirety.

FIELD OF THE INVENTION

The present invention relates to the field of medicine and in particular to the diagnostic and treatment of fibrosis. More particularly, the invention relates to CD146 and uses thereof as a biomarker in the diagnosis of fibrosis and as a therapeutic target in the treatment of fibrosis. The invention also relates to compositions and methods of detecting predisposition to, of diagnosing, prognosing and/or monitoring fibrosis in a subject. It further relates to CD146 inhibitors, and to compositions comprising a CD146 inhibitor, for use in prevention or treatment of fibrosis in a subject, as well as to compositions, kits and uses thereof in a diagnostic or therapeutic context.

BACKGROUND

Fibrosis is the formation of excessive fibrous connective tissue in an organ or tissue in a reparative or reactive process. Physiologically, fibrosis acts to deposit connective tissue, which can obliterate the architecture and function of the underlying organ or tissue. Defined by the pathological accumulation of extracellular matrix (ECM) proteins, fibrosis results in scarring and thickening of the affected tissue. It is in essence an exaggerated wound healing response which interferes with normal organ function. The tissue becomes more rigid and loses its functionality.

Fibrosis is similar to the process of scarring, in that both involve stimulated fibroblasts laying down connective tissue, including collagen and glycosaminoglycans. The process is initiated when immune cells such as macrophages release soluble factors that stimulate fibroblasts. The best characterized pro-fibrotic mediator is TGF beta, which is released by macrophages as well as any damaged tissue between surfaces called interstitium. Other known soluble mediators of fibrosis include CTGF, platelet-derived growth factor (PDGF), and Interleukin 4 (IL-4). Autoimmune diseases can also lead to fibrosis. This process of tissue repair is complex, with tight regulation of ECM synthesis and degradation ensuring maintenance of normal tissue architecture. However, the entire process, although necessary, can lead to a progressive irreversible fibrotic response if tissue injury is severe or repetitive, or if the wound healing response itself becomes deregulated.

Fibrosis can occur in the organs and in many tissues within the body, typically as a result of inflammation or damage, and examples include heart (atrial fibrosis, endomyocardial fibrosis, infarction, in particular old myocardial infarction), kidneys (renal fibrosis), liver (cirrhosis, biliary atresia), lungs (progressive massive fibrosis), brain (glial scar), arteries (arterial stiffness), joints (arthrofibrosis) such as knee or shoulder, intestine (Crohn's disease), hands, fingers (Dupuytren's contracture), skin (keloid, nephrogenic systemic fibrosis), soft tissue of the mediastinum (mediastinal fibrosis), soft tissue of the retroperitoneum (retroperitoneal fibrosis), bone marrow (myelofibrosis), etc.

Glomerular diseases can lead to renal fibrosis and chronic kidney disease (CKD), either progressively or rapidly. Rapidly progressive or crescentic glomerulonephritis (GN) are a group of rare kidney diseases that may rapidly progress to end stage renal failure as a consequence of pronounced inflammation with glomerular damage and development of crescents (Mathieson, P, 2007). Other kidney compartments are affected, including tubulo-interstitium which shows an inflammation leading to renal interstitial fibrosis. The functional outcome of such structural lesions is a rapid deterioration of renal function (Moeller, M. J 2013). Even though several studies, mostly on preclinical models of experimental GN, provided pathophysiological advances, both on the inflammatory process and in the consequent fibrosis, molecular insights in the regulation and the progression of the disease are still limited and current treatments remain only partially effective.

Cardiac fibrosis is a wound healing process which develops spontaneously in response to certain forms of heart disease such as myocardial infarction, certain cardiomyopathies, or hypertension. It is characterized by an increased deposition of extracellular matrix proteins (fibronectin, collagens I and III) associated with decreased expression of metalloproteinases (MMPs) involved in degradation of the matrix (Talman and Ruskoaho, 2016). This accumulation of tissue is responsible for an increase in the rigidity and a decrease in the compliance of the injured heart which loses not only its ability to contract and to relax but also its ability to drive intrinsic cardiac electrical activity. All these changes end in the patient developing cardiac insufficiency, leading, in the long term, to cardiac arrest. (Chaturvedi et al., 2010).

Cardiac fibrosis is classified into two categories according its location within the myocardium:

"Reactive/interstitial" fibrosis which corresponds to expansion of the fibrosis into the interstitial space between cardiomyocytes. This type of fibrosis is more particularly described in the context of ageing (Chen and Frangogiannis, 2010; Mays et al., 1991). Indeed, much work has shown that cardiac ageing is associated with the decrease in the total number of cardiomyocytes, which becomes hypertrophic, as well as a significant increase in myocardial collagen deposition. These changes are responsible for a decrease in the compliance of the heart which results in the establishment of diastolic dysfunction with preserved systolic function (Biernacka and Frangogiannis, 2011), and "Reparative fibrosis" refers to the formation of scar tissue in response to heart disease such as myocardial infarction (Weber, 1989).

At present there are few effective therapies to control the deleterious process of cardiac fibrosis. Thus, the search of new therapies to inhibit or reverse this process is a major public health issue.

The frequency of pathologies with fibrosis increases significantly due to the aging of the population and the exacerbation of cardiovascular risk factors (diabetes, obesity and hypertension).

So far, no specific biomarker is available to detect fibrosis. The only way to quantify fibrosis is biopsy. Likewise, no treatment is available to treat fibrosis, in particular no treatment can reverse the fibrotic process.

A simple, reliable and specific test of diagnosing and monitoring fibrosis or of determining whether a patient is at risk of developing fibrosis is still lacking, and would be of high value to set up quickly prophylactic and therapeutic strategies intended to preserve or improve patient's health. This is the aim of the present invention.

SUMMARY OF THE INVENTION

Inventors herein identify for the first time CD146 as a particularly interesting biomarker in the diagnosis of fibrosis and as an advantageous therapeutic target, or therapeutic tool, in the treatment of fibrosis.

A CD146 protein, in particular a soluble CD146 (sCD146) protein selected from SEQ ID NO:1, SEQ ID NO:2, SEQ ID NO:3, SEQ ID NO:4, SEQ ID NO:5, SEQ ID NO:6 and SEQ ID NO:7 or the I5-13 soluble CD146 protein of SEQ ID NO: 8 or the I10 soluble CD146 protein of SEQ ID NO: 9, for use, typically as a biomarker, in the detection of a predisposition to, in the diagnosis and/or prognosis of, or in the monitoring of fibrosis, in particular cardiac, renal, skin and/or pulmonary fibrosis, in a subject, is thus herein described.

Also herein described is an in vitro, ex vivo or in vivo method of detecting predisposition to or of diagnosing and/or prognosing fibrosis, in particular cardiac, renal, skin or pulmonary fibrosis, in a subject. This method typically comprises a step of determining in a biological sample of the subject the CD146 protein level of expression, typically the soluble CD146 protein level of expression, in particular the level of expression of the soluble CD146 protein selected from SEQ ID NO:1, SEQ ID NO:2, SEQ ID NO:3, SEQ ID NO:4, SEQ ID NO:5, SEQ ID NO:6 and SEQ ID NO:7 level of expression; the I5-13 soluble CD146 protein of SEQ ID NO: 8 level of expression; or the I10 soluble CD146 protein of SEQ ID NO: 9 level of expression.

Also herein described is an in vitro, ex vivo or in vivo method of monitoring fibrosis, preferably cardiac or renal fibrosis, in a subject is also herein described. The method typically comprises determining in a biological sample of the subject at two or more time points the CD146 protein level of expression, in particular the soluble CD146 protein level of expression, said soluble CD146 protein being selected from SEQ ID NO:1, SEQ ID NO:2, SEQ ID NO:3, SEQ ID NO:4, SEQ ID NO:5, SEQ ID NO:6 and SEQ ID NO:7, wherein a higher soluble CD146 protein level of expression in a biological sample of the subject at a later time point, compared to a reference value obtained in a biological sample of the subject at an earlier time point, is indicative of fibrosis increase in the subject whereas a lower soluble CD146 protein level is indicative of a fibrosis decrease and an equal soluble CD146 protein level indicates that fibrosis does not progress in the subject.

Also herein described is an in vitro, in vivo, or ex vivo method of monitoring fibrosis, in particular skin or pulmonary fibrosis, in a subject comprising determining the I5-13 soluble CD146 protein of SEQ ID NO: 8 level of expression in a biological sample of the subject at two or more time points, wherein a higher soluble CD146 protein level of expression in a biological sample of the subject at a later time point, compared to a reference value obtained in a biological sample of the subject at an earlier time point, is indicative of fibrosis increase in the subject whereas a lower human soluble CD146 protein level is indicative of a fibrosis decrease and an equal human soluble CD146 protein level indicates that fibrosis does not progress in the subject.

Also herein described is an in vitro, in vivo, or ex vivo method of monitoring fibrosis, in particular skin or pulmonary fibrosis, in a subject comprising determining the I10 soluble CD146 protein of SEQ ID NO: 9 level of expression in a biological sample of the subject at two or more time points, wherein a lower soluble CD146 protein level of expression in a biological sample of the subject at a later time point, compared to a reference value obtained in a biological sample of the subject at an earlier time point, is indicative of fibrosis increase in the subject whereas a higher human soluble CD146 protein level is indicative of a fibrosis decrease and an equal human soluble CD146 protein level indicates that fibrosis does not progress in the subject.

Further herein described is a CD146 inhibitor, in particular an inhibitor of a soluble CD146 protein selected from SEQ ID NO:1, SEQ ID NO:2, SEQ ID NO:3, SEQ ID NO:4, SEQ ID NO:5, SEQ ID NO:6 and SEQ ID NO:7, for use in prevention or treatment of fibrosis, in particular cardiac and/or renal fibrosis, in a subject, typically in a subject who has been identified by a herein described method as having predisposition to fibrosis, as being affected by fibrosis, as having a fibrosis which does not progress, as having a fibrosis increase or as having a poor prognosis fibrosis.

Further herein described is a CD146 inhibitor, in particular an inhibitor of the I5-13 soluble CD146 protein of SEQ ID NO: 8, for use in prevention or treatment of fibrosis, in particular skin or pulmonary fibrosis, in a subject, typically in a subject who has been identified by a herein described method as having predisposition to fibrosis, as being affected by fibrosis, as having a fibrosis which does not progress, as having a fibrosis increase or as having a poor prognosis fibrosis.

Also herein disclosed is the use of a CD146 inhibitor, in particular an inhibitor of a soluble CD146 protein selected from SEQ ID NO:1, SEQ ID NO:2, SEQ ID NO:3, SEQ ID NO:4, SEQ ID NO:5, SEQ ID NO:6 and SEQ ID NO:7 or an inhibitor of the I5-13 soluble CD146 protein of SEQ ID NO: 8, to prepare, in vitro or ex vivo, a composition for (use for) preventing or treating fibrosis, in particular cardiac and/or renal fibrosis, in a subject in need thereof.

Inventors also herein provide a composition comprising a CD146 inhibitor, in particular an inhibitor of a soluble CD146 inhibitor protein selected from SEQ ID NO:1, SEQ ID NO:2, SEQ ID NO:3, SEQ ID NO:4, SEQ ID NO:5, SEQ ID NO:6 and SEQ ID NO:7, or an inhibitor of the I5-13 soluble CD146 protein of SEQ ID NO: 8, and a pharmaceutically acceptable carrier for use in prevention or treatment of fibrosis, in particular of cardiac, renal, skin and/or pulmonary fibrosis, in a subject.

Also herein described is a composition comprising a CD146 protein, in particular a soluble CD146 protein selected from SEQ ID NO:1, SEQ ID NO:2, SEQ ID NO:3, SEQ ID NO:4, SEQ ID NO:5, SEQ ID NO:6 and SEQ ID NO:7, or the I10 soluble CD146 protein of SEQ ID NO: 9, and a pharmaceutically acceptable carrier for use in prevention or treatment of skin fibrosis and/or pulmonary fibrosis in a subject, preferably a human being.

Inventors also herein describe an antibody as well as fragments thereof, directed against a CD146 protein, in particular a soluble CD146 protein selected from SEQ ID NO:1, SEQ ID NO:2, SEQ ID NO:3, SEQ ID NO:4, SEQ ID NO:5, SEQ ID NO:6 and SEQ ID NO:7, the I5-13 soluble CD146 protein of SEQ ID NO: 8, or the I10 soluble CD146 protein of SEQ ID NO: 9. A preferred antibody, herein newly described, or fragment thereof, comprises the heavy chain variable region (VH) CDR polypeptide sequence of SEQ ID NO: 94, SEQ ID NO: 95 and SEQ ID NO: 96, and the light chain variable region (VL) CDR polypeptide sequence of SEQ ID NO: 97, sequence FAS, and SEQ ID NO: 98. Another herein newly described antibody is an antibody or fragment thereof comprising the heavy chain variable region (VH) CDR polypeptide sequence of SEQ ID NO: 87, SEQ ID NO: 88 and SEQ ID NO: 89, and the light chain variable region (VL) CDR polypeptide sequence of SEQ ID NO: 90, sequence QVS and SEQ ID NO: 91.

Inventors further herein describe a method of diagnosing fibrosis, in particular cardiac or renal fibrosis, in a subject. This method typically comprises a step of detecting and preferably dosing, in the subject's biological sample, typically in the subject's serum, the amount of CD146, preferably of sCD146protein selected from SEQ ID NO:1, SEQ ID NO:2, SEQ ID NO:3, SEQ ID NO:4, SEQ ID NO:5, SEQ ID NO:6 and SEQ ID NO:7. Such a method typically involves the use of an antibody binding a CD146 protein, preferably a sCD146 protein, as herein described.

Inventors also herein describe a method of treating fibrosis, in particular cardiac, renal, skin and/or pulmonary fibrosis, in a subject in need thereof, typically in a subject who has been identified by a herein described method as having predisposition to fibrosis, as being affected by fibrosis, as having a fibrosis which does not progress, as having a fibrosis increase or as having a poor prognosis fibrosis. This method typically comprises a step of administering a CD146 inhibitor, in particular an inhibitor of a soluble CD146 inhibitor protein selected from SEQ ID NO:1, SEQ ID NO:2, SEQ ID NO:3, SEQ ID NO:4, SEQ ID NO:5, SEQ ID NO:6 and SEQ ID NO:7, or an inhibitor of the I5-13 soluble CD146 inhibitor protein of SEQ ID NO: 8, or composition comprising such a CD146 inhibitor, typically an effective amount thereof, to said subject.

A method of monitoring in vitro, ex vivo or in vivo the efficacy of a drug, typically of a CD146 inhibitor, in particular of an inhibitor of a soluble CD146 inhibitor protein selected from SEQ ID NO:1, SEQ ID NO:2, SEQ ID NO:3, SEQ ID NO:4, SEQ ID NO:5, SEQ ID NO:6 and SEQ ID NO:7, or of an inhibitor of the I5-13 soluble CD146 inhibitor protein of SEQ ID NO: 8, or of a composition for treating fibrosis, in particular cardiac, renal, skin and/or pulmonary fibrosis, is also described. This method typically comprises a step of comparing the expression of CD146, typically soluble CD146, in a first biological sample from a subject before any treatment of fibrosis to the expression of CD146, typically soluble CD146, in a second biological sample of the same subject who has been exposed to a drug or composition for treating fibrosis.

In another aspect, the present disclosure provides kits comprising any one or more of the herein described products, typically proteins, inhibitors of (soluble) CD146 or compositions. Typically, the kit also comprises instructions for using the protein(s), inhibitor(s) or composition(s) according to the disclosed methods.

DETAILED DESCRIPTION OF THE INVENTION

CD146 is a glycoprotein that belongs to the immunoglobulin superfamily. It is known to be involved in endothelial permeability, inflammation and angiogenesis.

Membranous CD146 is an adhesive protein detected in all endothelial cells of the vascular tree, regardless of the vessel caliber or anatomical region (Bardin, N. 2001; Georges F 1991). It mainly localizes at the intercellular junctions and controls inter-endothelial cell cohesion and paracellular permeability (Anfosso, F., 2001; Solovey, A. N., 2001; Jouve, N., 2015) but also monocyte transmigration (Bardin, N., 2009) and angiogenesis (Chan, B., 2005; Harhouri, K., 2010; Yan, X., 2003; Halt J K I, 2016). CD146 exists as different isoforms: a short isoform with a putative PDZ binding motif (Kebir, A., S. 2001; Taira, E., 1995; Vainio, O., 1996), which may mediate its anchoring to the cytoskeleton, a long isoform with a putative endocytosis motif (Guezguez, B., 2007), and a soluble form (sCD146) as the result of metalloprotease-dependent shedding of membrane CD146 (Bardin, N., 2003; Boneberg, E. M., 2009). sCD146 is detectable in the human serum and its level is modulated in different pathologies such as inflammatory bowel diseases (Bardin, N., 2006), abnormal pregnancies (Pasquier, E., 2005) or chronic renal failure (Bardin, N., 2003).

Inventors herein demonstrate for the first time that the short and long membrane isoforms of CD146 are shed through the Tace and ADAM10 proteinases, respectively. In addition, RNA sequencing experiments revealed the existence of two alternative sCD146 spliced variants, herein identified as "I5-13-sCD146" (or I5-13 soluble CD146) and "I10-sCD146" (or I10 soluble CD146).

Additionally, inventors have discovered, and now herein describe for the first time, that CD146, typically sCD146, can advantageously be used as a biomarker in the diagnosis of fibrosis and as a therapeutic target or as a therapeutic tool in the treatment of fibrosis.

CD146 is particularly advantageous for use in the detection of a predisposition to, in the diagnosis and/or prognosis of, or in the monitoring of fibrosis, in particular cardiac, renal, skin and/or pulmonary fibrosis, in a subject.

In the context of the invention, CD146 is typically a CD146 protein, for example a membranous CD146 or a soluble CD146 (sCD146), preferably a sCD146protein selected from SEQ ID NO:1, SEQ ID NO:2, SEQ ID NO:3, SEQ ID NO:4, SEQ ID NO:5, SEQ ID NO:6 and SEQ ID NO:7, the I5-13 soluble CD146 protein of SEQ ID NO: 8 or the I10 soluble CD146 protein of SEQ ID NO: 9, as further described herein below.

More precisely, the inventors demonstrated for the first time that soluble CD146, in particular sCD146 protein selected from SEQ ID NO:1, SEQ ID NO:2, SEQ ID NO:3, SEQ ID NO:4, SEQ ID NO:5, SEQ ID NO:6 and SEQ ID NO:7 is involved in the establishment of cardiac and renal fibrosis and is therefore a biomarker of cardiac and renal fibrosis. As a matter of fact, inventors showed that sCD146 stimulates cells responsible for fibrosis, i.e. fibroblasts and endothelial cells. Inventors' experiments demonstrate in particular that in two models of severe renal fibrosis induction (model induced by glomerular basement membrane serum and model of unilateral obstruction of the ureter), CD146 is greatly increased and the concentration of sCD146 rises in the circulating blood; the effect on fibrosis is greatly reduced when using KO mice for CD146. They also demonstrated a CD146 and sCD146 increase in a model of myocardial infarction in mice; a reduced amount of fibrosis in KO animals for CD146 after myocardial infarction compared to control animals, as well as a reduction in elderly mice of the development of cardiac fibrosis in KO CD146 mice in comparison with wild-type (WT) mice.

They also demonstrated that soluble CD146, in particular a sCD146 protein selected from SEQ ID NO:1, SEQ ID NO:2, SEQ ID NO:3, SEQ ID NO:4, SEQ ID NO:5, SEQ ID NO:6 and SEQ ID NO:7 has a pro-fibrotic activity in heart and kidney and is therefore a therapeutic target for treating cardiac fibrosis and/or renal fibrosis. Fibrosis phenomenon can thus be prevented or reversed in the presence of an inhibitor of a soluble CD146protein selected from SEQ ID NO:1, SEQ ID NO:2, SEQ ID NO:3, SEQ ID NO:4, SEQ ID NO:5, SEQ ID NO:6 and SEQ ID NO:7, in particular a monoclonal antibody directed against such a sCD146 protein.

On the other hand, inventors demonstrated that soluble CD146, in particular a sCD146 protein selected from SEQ ID NO:1, SEQ ID NO:2, SEQ ID NO:3, SEQ ID NO:4, SEQ ID NO:5, SEQ ID NO:6 and SEQ ID NO:7 has an antifibrotic activity in skin and lung and can therefore be used for the prevention or treatment of skin fibrosis and/or pulmonary fibrosis in a subject.

Inventors also demonstrated that the newly identified isoforms I5-13 soluble CD146 protein of SEQ ID NO: 8 and the I10 soluble CD146 protein of SEQ ID NO: 9 are both biomarkers of fibrosis, in particular of skin fibrosis and/or pulmonary fibrosis. However, these two isoforms don't vary in the same manner Whereas, I5-13 soluble CD146 is upregulated in fibrosis, I10 soluble CD146 is down-regulated. I5-13 is a therapeutic target for treating fibrosis, in particular skin fibrosis and/or pulmonary fibrosis, whereas I10 can be used as a therapeutic tool for the prevention or treatment of fibrosis, in particular of skin fibrosis and/or pulmonary fibrosis, in a subject.

As indicated herein above, fibrosis may occur after ischemic events such as myocardial infarction, in the context of an immune disease, and also during aging.

The term "subject" refers to any testable subject and typically designates a patient. Preferably the subject is a mammal, even more preferably a human being. The invention may be used both for an individual and for an entire population. The subject may be tested whatever his/her age or sex.

"Human long CD146 protein" or "long CD146" refers to a human protein, peptide or amino acid molecule, mainly present in the membrane of endothelial cells and having an amino acid sequence corresponding to herein described SEQ ID NO:10.

"Human short CD146 protein" or "short CD146" refers to a human protein, peptide or amino acid molecule mainly present in the membrane of endothelial cells and having an amino acid sequence corresponding to herein described SEQ ID NO: 11.

"Human soluble CD146 protein" or "soluble CD146" or "sCD146" typically refers to a human protein, peptide or amino acid molecule. Such a sCD146 protein is typically present in the human serum. Particular human soluble CD146 proteins according to the present invention comprises or consists in an amino acid sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 9.

Among SEQ ID NO: 1, SEQ ID NO: 2, SEQ ID NO: 3, SEQ ID NO: 4, SEQ ID NO: 5, SEQ ID NO: 6 and SEQ ID NO: 7, SEQ ID NO: 7 is a preferred human soluble CD146 protein usable in the context of the present invention where the subject is a mammal, in particular a human being.

A typical sCD146 protein according to the present invention is, as explained previously, a protein usable as a biomarker in the context of diagnostic and as a therapeutic target as a therapeutic tool in the context of a therapeutic or prophylactic/preventive treatment.

The present description further describes nucleic acid molecules which respectively encode the herein described proteins of the invention.

Such nucleic acid molecules are RNA or DNA that typically encode biologically active human CD146 proteins, in particular human soluble CD146 proteins, or may be used to prepare recombinant forms thereof.

The terms "Treatment" or "therapy" refer to both therapeutic and prophylactic or preventive treatments or measures able to alleviate, slow progression or cure (reverse) fibrosis or any pathology, disease, disorder or dysfunctional state leading to, resulting from or associated with fibrosis, typically any fibrotic human disease. Examples of such diseases include atrial fibrosis, endomyocardial fibrosis, infarction, in particular old myocardial infarction; renal fibrosis; cirrhosis, biliary atresia; progressive massive fibrosis, glial scar; arterial stiffness; arthrofibrosis; Crohn's disease; Dupuytren's contracture; nephrogenic systemic fibrosis; mediastinal fibrosis; retroperitoneal fibrosis; myelofibrosis, systemic sclerosis, etc.

Such a "treatment" is typically intended for a subject as herein above defined in need thereof, typically a mammal subject, preferably a human subject. Are considered as such, the subjects suffering from a pathology, disease, disorder or dysfunctional state leading to, resulting from or associated with fibrosis, or those considered "at risk of developing", or suspected to be at risk of developing, such a pathology, disease, disorder or dysfunctional state, in which this has to be prevented.

For example the patient can be a subject predisposed to (or suspected to be predisposed to) develop fibrosis or one of the herein described pathology, disease, disorder or dysfunctional state leading to, resulting from or associated with fibrosis. The subject is for example a subject suffering from, or considered "at risk of developing", cardiac fibrosis (for example atrial fibrosis, endomyocardial fibrosis or infarction, in particular old myocardial infarction) or renal fibrosis.

The subject can be asymptomatic, or present early or advanced signs of such a pathology, disease, disorder or dysfunctional state.

A typical subject is a subject who has been identified thanks to a herein described method as having predisposition to fibrosis, as being affected by fibrosis, as having a fibrosis which does not progress, as having a fibrosis increase or as having a poor prognosis fibrosis.

Another particular object herein described is a soluble CD146 protein selected from SEQ ID NO:1, SEQ ID NO:2, SEQ ID NO:3, SEQ ID NO:4, SEQ ID NO:5, SEQ ID NO:6 and SEQ ID NO:7 for use, typically as a biomarker, in the detection of (for detecting) a predisposition to, in the diagnosis and/or prognosis of (for diagnosing and/or prognosing), or in the monitoring of (for monitoring) fibrosis, in particular cardiac and/or renal fibrosis, in a subject, typically in a mammal, preferably in a human being.

A preferred human soluble CD146 protein comprises or consists in SEQ ID NO: 7.

A further particular object herein described is the I5-13 soluble CD146 protein of SEQ ID NO: 8 for use as a biomarker in the detection of a predisposition to, in the diagnosis and/or prognosis of, or in the monitoring of fibrosis, in particular of skin fibrosis and/or pulmonary fibrosis, in a subject. Another particular object herein described is the I10 soluble CD146 protein of SEQ ID NO: 9 for use as a biomarker in the detection of a predisposition to, in the diagnosis and/or prognosis of, or in the monitoring of fibrosis, in particular of skin fibrosis and/or pulmonary fibrosis, in a subject.

An in vitro, ex vivo or in vivo method of detecting predisposition to or of diagnosing and/or prognosing fibrosis, in particular cardiac, renal, skin and/or pulmonary fibrosis, in a subject, typically in a mammal, preferably in a human being, is in particular herein described. In a preferred aspect in relation with cardiac and/or renal fibrosis, the sCD146 used in a such a method is selected from SEQ ID NO:1, SEQ ID NO:2, SEQ ID NO:3, SEQ ID NO:4, SEQ ID NO:5, SEQ ID NO:6 and SEQ ID NO:7.

In another preferred aspect in relation with skin and/or pulmonary fibrosis, the sCD146 used in the I5-13 soluble CD146 protein of SEQ ID NO: 8 or is the I10 soluble CD146 protein of SEQ ID NO: 9.

The terms "diagnostic" or "diagnosing" refer to the detection or identification of a pathology, disease, disorder or dysfunctional state as herein defined, typically fibrosis, or to the evaluation (dosing, comparison) of the severity or of the stage of such a pathology, disease, disorder or dysfunctional state in a subject.

In particular aspect, a diagnostic method of the invention comprises the determination of the presence and/or the measure of the quantity of CD146, typically sCD146 protein, present in a biological sample of a subject, and preferably the comparison of the quantity to a reference value.

The terms "prediction" or "predicting" refer to the assessment of a predisposition of the subject to develop a pathology, disease, disorder or dysfunctional state as herein defined, typically fibrosis. The terms "prognostic" or "prognosing" refer to the assessment or monitoring of the progression (course) of a pathology, disease, disorder or dysfunctional state as herein defined in a subject, treated or not, typically the prediction of the worsening of such a disease or disorder and associated harmful effects or, on the contrary, the prediction of an improvement of the subject's health.

A prognostic method of the invention can comprise one or several steps of monitoring, dosing, comparing the measured quantity(ies) or level(s) of CD146, typically CD146 protein, etc., at various stages, including early, pre-symptomatic stages, and late stages, in a biological sample or in biological samples from the subject.

Prognosis typically includes the assessment (prediction) of the progression of fibrosis, and the characterization of a subject to define the most appropriate treatment.

The herein described methods typically comprise a step of verifying the presence of CD146, in particular sCD146, or in other words of determining the CD146 protein expression, and preferably a step of determining the CD146 level of expression (measure of CD146 quantity), in a biological sample of the subject.

In particular, any of the herein described human CD146 proteins, typically human soluble CD146 proteins, may be used as a biomarker providing an indication of the presence of a fibrosis or fibrosis-associated disease in a subject, typically in a mammal, preferably in a human being, in particular of a cardiac, renal, skin and/or pulmonary fibrosis.

In a particular aspect, the method of detecting predisposition to or of diagnosing and/or prognosing fibrosis in a subject comprises the steps of i) determining the soluble CD146 protein expression level in a biological sample of the subject, said soluble CD146 protein being selected from SEQ ID NO:1, SEQ ID NO:2, SEQ ID NO:3, SEQ ID NO:4, SEQ ID NO:5, SEQ ID NO:6 and SEQ ID NO:7, ii) comparing the expression level determined at step i) with a reference value, for example a predetermined reference value, and iii) concluding that the subject has predisposition to, is affected by or has a poor prognosis, when the level determined at step i) is higher than the reference value or concluding that the patient has no predisposition to, is not affected by or has a good prognosis when the level determined at step i) is lower than the reference value.

In another particular aspect, the method of detecting predisposition to or of diagnosing and/or prognosing fibrosis in a subject comprises a step of determining the level of expression of the I5-13 soluble CD146 protein of SEQ ID NO: 8 or the I10 soluble CD146 protein of SEQ ID NO: 9 in a biological sample of the subject.

More precisely in one aspect, the method comprises the steps of i) determining the I5-13 soluble CD146 protein expression level in a biological sample of the subject, ii) comparing the expression level determined at step i) with a reference value and iii) concluding that the subject has predisposition to, is affected by or has a poor prognosis, when the level determined at step i) is higher than the reference value or concluding that the patient has no predisposition to, is not affected by or has a good prognosis when the level determined at step i) is lower than the reference value.

In another aspect, the method comprises the steps of i) determining the I10 soluble CD146 protein expression level in a biological sample of the subject, ii) comparing the expression level determined at step i) with a reference value and iii) concluding that the subject has predisposition to, is affected by or has a poor prognosis, when the level determined at step i) is lower than the reference value or concluding that the patient has no predisposition to, is not affected by or has a good prognosis when the level determined at step i) is higher than the reference value.

The terms "reference value", "control value" or "cut-off value" can refer to a basal value corresponding to the mean of values (measured levels, quantities or concentrations) obtained with the biological samples of a reference population, typically of a population or cohort of healthy subjects, i.e., of subjects who do not suffer from a pathology, disease, disorder or dysfunctional state as herein defined.

The reference value can also be a statistic or discriminating value, i.e., a value which has been determined by measuring the parameter in both a healthy control population and a population with a known pathology, disease, disorder or dysfunctional state as herein defined. The discriminating value identifies the diseased population with a predetermined specificity and/or a predetermined sensitivity based on an analysis of the relation between the parameter values and the known clinical data of the healthy control population and of the diseased patient population. The discriminating value determined in this manner is valid for the same experimental setup in future individual tests. For example, the reference value can be 300 ng/ml regarding the I5-13 soluble CD146 protein and 50 ng/ml regarding I10 soluble CD146 protein.

A particular method herein described is an in vitro, ex vivo or in vivo method of monitoring fibrosis, in particular cardiac or renal fibrosis, in a subject. The method typically comprises determining the presence of and/or measuring the soluble CD146 protein level of expression or soluble CD146 protein quantity in a biological sample of the subject at two or more time points, said soluble CD146 protein being selected from SEQ ID NO:1, SEQ ID NO:2, SEQ ID NO:3, SEQ ID NO:4, SEQ ID NO:5, SEQ ID NO:6 and SEQ ID NO:7, the presence (following the absence) or a higher CD146 protein level of expression in a biological sample of the subject at a later time point compared to a reference value obtained in a biological sample of the subject at an earlier time point, being indicative of fibrosis increase or fibrosis worsening in the subject whereas a lower soluble CD146 protein level is indicative of a fibrosis decrease and an equal soluble CD146 protein level indicates that fibrosis is stabilized, or in other words does not progress, in the subject.

Another particular method herein described is an in vitro, in vivo or ex vivo method of monitoring fibrosis in a subject comprising determining the I5-13 soluble CD146 protein of SEQ ID NO: 8 level of expression in a biological sample of the subject at two or more time points, wherein a higher soluble CD146 protein level of expression in a biological sample of the subject at a later time point, compared to a reference value obtained in a biological sample of the subject at an earlier time point, is indicative of fibrosis increase in the subject whereas a lower human soluble CD146 protein level is indicative of a fibrosis decrease and an equal human soluble CD146 protein level indicates that fibrosis does not progress in the subject.

Another particular method herein described is an in vitro, in vivo or ex vivo method of monitoring fibrosis in a subject comprising determining the I10 soluble CD146 protein of SEQ ID NO: 9 level of expression in a biological sample of the subject at two or more time points, wherein a lower soluble CD146 protein level of expression in a biological sample of the subject at a later time point, compared to a reference value obtained in a biological sample of the subject at an earlier time point, is indicative of fibrosis increase in the subject whereas a higher human soluble CD146 protein level is indicative of a fibrosis decrease and an equal human soluble CD146 protein level indicates that fibrosis does not progress in the subject.

In order to assess the evolution of fibrosis or control the efficiency of the treatment, testing a patient, under treatment or before any treatment, and testing the same patient under treatment (typically in the absence of any interruption of the treatment) several days, weeks or months later can be of help. In such a situation, the results (measured value(s)) of the second test are compared with the results of the first test.

A CD146 quantity/level of expression "above the reference value" or "higher than the reference value" may mean a significant statistical increase, for example of at least 2 standard deviations.

The term "biological sample" includes any biological sample from a subject, in particular a mammalian subject, typically a human being. The biological sample may be a tissue biopsy, for example a heart biopsy, or a biological fluid sample.

Typical examples of biological samples usable in the context of the present invention may be selected from a plasma, a blood, a serum, a urinary, a cerebrospinal fluid, and a saliva sample. Preferably, the biological sample is a plasma, a blood or a serum sample, even more preferably a serum sample. The biological sample is preferably a diluted sample, the dilution being typically of 1/25, 1/50, 1/100, 1/200 or 1/400, preferably 1/25.

In particular, the serum concentration of the considered CD146 protein may be an indication of high value in a method of detecting predisposition to, of diagnosing, prognosing or monitoring fibrosis. Indeed, the measured value may be compared to standard values associated to a healthy status of a subject. In particular, an overexpression of the considered form of CD146, typically of a sCD146 selected from SEQ ID NO:1, SEQ ID NO:2, SEQ ID NO:3, SEQ ID NO:4, SEQ ID NO:5, SEQ ID NO:6 and SEQ ID NO:7, or of the I5-13 soluble CD146 protein of SEQ ID NO: 9, may be indicative of the presence of a fibrosis.

Preferably, the determination of the presence as well as the measure of the quantities of CD146, in particular of sCD146, is determined in an immunoassay through a one-step method wherein the subject's biological sample is directly contacted with the appropriate anti-CD146 antibody or through a method implying a preliminary treatment of the biological sample.

Antibodies binding to CD146, in particular sCD146, and capable of identifying/dosing it in a biological sample of a subject are known in the art. A preferred antibody is a monoclonal antibody, preferably a monoclonal antibody which selectively binds to CD146, in particular which selectively binds to sCD146 (versus membrane CD146).

A particular antibody selectively binding to sCD146 may be selected from an antibody selectively binding to a protein comprising or consisting in SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 9 (versus membrane CD146), preferably SEQ ID NO: 7, SEQ ID NO: 8 or SEQ ID NO: 9.

Advantageously, the antibody selectively binding sCD146 (versus membrane CD146) according to the invention comprises the heavy chain variable region (VH) CDR polypeptide sequences of SEQ ID NO: 87, SEQ ID NO: 88 and SEQ ID NO: 89, and the light chain variable region (VL) CDR polypeptide sequences of SEQ ID NO: 90, sequence QVS and SEQ ID NO: 91.

SEQ ID NO:87 correspond to the following amino acid sequence: GYTFTSHF

SEQ ID NO:88 correspond to the following amino acid sequence: IFPGSGDT

SEQ ID NO:89 correspond to the following amino acid sequence: ARTWAY

SEQ ID NO:90 correspond to the following amino acid sequence: QSLLYSDGKTY

SEQ ID NO:91 correspond to the following amino acid sequence: AQTTHFPLT

In a particular aspect, the antibody or fragment thereof according to the invention comprises a light chain variable region (VL) comprising SEQ ID NO: 93 and a heavy chain variable region (VH) comprising SEQ ID NO: 92.

Advantageously, the antibody selectively binding sCD146 (versus membrane CD146) according to the invention comprises the heavy chain variable region (VH) CDR polypeptide sequence of SEQ ID NO: 94, SEQ ID NO: 95 and SEQ ID NO: 96, and the light chain variable region (VL) CDR polypeptide sequence of SEQ ID NO: 97, sequence FAS and SEQ ID NO 98.

SEQ ID NO:94 correspond to the following amino acid sequence: GFTFSDYG

SEQ ID NO:95 correspond to the following amino acid sequence: IYYDSSKM

SEQ ID NO:96 correspond to the following amino acid sequence: AAFQFDY

SEQ ID NO:97 correspond to the following amino acid sequence: QGISTS

SEQ ID NO:98 correspond to the following amino acid sequence: QQSYNLPYT

In a particular aspect, the antibody or fragment thereof according to the invention comprises a light chain variable region (VL) comprising SEQ ID NO: 100 and a heavy chain variable region (VH) comprising SEQ ID NO: 99.

Any of the herein described antibody(ies) may be incorporated into a composition, typically in a diagnostic composition, further comprising a pharmaceutically acceptable carrier or support, in respective appropriate dosages easily determined by the skilled person in the art.

The antibody binding to CD146 is typically used, or present in the composition, in an effective amount.

The expression "effective amount" designates an amount or concentration of anti-CD146 antibody sufficient to detect and/or measure CD146, in particular sCD146, in a subject or in a biological sample of a subject.

A typical effective amount of anti-CD146 antibody for use in a diagnostic context in a mammal, typically in a human being, is between about 1 µg/ml and 5 µg/ml, preferably between about 1 µg/ml and 2.5 µg/ml, or between about 2.5 µg/ml and 5 µg/ml.

The immunoassay can be performed through well-known methods of the art: in solid phase or homogeneous phase, in one or two steps, through competitive method, etc.

More preferably, said immunoassay is selected from the group consisting of ELISA, FEIA, western blot, dot blot, bead-based assay, antigen array and Radio Immuno Assay.

In an ELISA, an antigen must be immobilized to a solid surface and then complexed with an antibody that is linked to an enzyme. Detection is accomplished by assessing the conjugated enzyme activity via incubation with a substrate to produce a colored product.

In FEIA, the colored product is fluorescent.

In Radio Immuno Assay, the final product is radioactive.

Protein detection using the dot blot protocol is similar to western blotting in that both methods allow for the identification and analysis of proteins of interest. Dot blot methodology differs from traditional western blot techniques by not separating protein samples using electrophoresis. Sample proteins are instead spotted onto membranes and hybridized with an antibody probe. Bead-based assay or antigen array are new approaches for investigators to simultaneously measure multiple analytes in biological and environmental samples.

Semi-quantitative measurements can be obtained with each of the previously described methods using for example normal controls to normalize the value and then establish a ratio, or using a positive control as a calibrator (expressed in arbitrary units).

The detection may be performed on a solid support, for example a microplaque, on which are laid out in a definite and ordered way a plurality of antibodies in order to detect and/or quantify one or different forms of CD146, or solid particles, test tubes, etc.

In a particular aspect where the antibody is an antibody binding a soluble CD146 protein, for example an antibody selectively binding a soluble CD146 protein (versus membranous CD146), in particular a soluble CD146 protein comprising or consisting of SEQ ID NO: 7, an increased level of said soluble CD146 protein in the serum of the tested subject when compared to a reference level is indicative of fibrosis or fibrosis increase, in particular of cardiac and/or renal fibrosis or fibrosis increase.

In another particular aspect where the antibody is an antibody binding a I5-13 soluble CD146 protein comprising or consisting of SEQ ID NO: 8, an increased level of said I5-13 soluble CD146 protein in the biological sample, typically in the serum, of the tested subject when compared to a reference level is indicative of fibrosis or fibrosis increase, in particular of skin fibrosis and/or pulmonary fibrosis or fibrosis increase.

In another particular aspect where the antibody is an antibody binding a I10 soluble CD146 protein comprising or consisting in SEQ ID NO: 9, an increased level of said I10 soluble CD146 protein in the biological sample, typically in the serum, of the tested subject when compared to a reference level is indicative of fibrosis decrease, in particular of skin fibrosis and/or pulmonary fibrosis decrease.

Inventors also herein describe a method of diagnosing fibrosis, in particular cardiac or renal fibrosis, in a subject. This method typically comprises a step of detecting and preferably measuring/dosing, in the subject's serum, the amount of CD146, preferably of sCD146. Such a method typically involves the use of an antibody binding a CD146 protein, preferably a sCD146 protein, as herein described.

Inventors also herein describe a CD146 inhibitor, in particular an inhibitor of a soluble CD146 protein selected from SEQ ID NO:1, SEQ ID NO:2, SEQ ID NO:3, SEQ ID NO:4, SEQ ID NO:5, SEQ ID NO:6 and SEQ ID NO: 7, or a composition comprising such a CD146 inhibitor, for use in the prevention or in the treatment of fibrosis, in particular cardiac and/or renal fibrosis, or of any pathology, disease, disorder or dysfunctional state leading to, resulting from or associated with fibrosis, in a subject, typically in a subject who has been identified by a herein described method as having predisposition to fibrosis, as being affected by fibrosis, as having a fibrosis which does not progress, as having a fibrosis increase or as having a poor prognosis fibrosis.

Inventors also herein describe an inhibitor of the I5-13 soluble CD146 protein of SEQ ID NO:8, or a composition comprising such a CD146 inhibitor, for use in the prevention or in the treatment of fibrosis, in particular skin fibrosis and/or pulmonary fibrosis, in particular pulmonary fibrosis associated to systemic sclerosis, or of any pathology, disease, disorder or dysfunctional state leading to, resulting from or associated with fibrosis, in a subject, typically in a subject who has been identified by a herein described method as having predisposition to fibrosis, as being affected by fibrosis, as having a fibrosis which does not progress, as having a fibrosis increase or as having a poor prognosis fibrosis.

Herein described pathology, disease, disorder or dysfunctional states leading to, resulting from or associated with fibrosis characterized by an excessive expression of at least one particular form of CD146, typically sCD146, or of a receptor for CD146, are advantageously treated by a CD146 inhibitor, preferably by an antibody directed against CD146, preferably against a human CD146, in particular a human sCD146, or any other CD146 antagonist directed against such a CD146, as herein described. Inventors have indeed discovered that such a CD146 inhibitor is able, once administered to a subject, to prevent, stop or even reverse fibrosis.

In particular, the description relates to the use of a CD146 inhibitor, preferably an inhibitor of a soluble CD146 protein selected from SEQ ID NO:1, SEQ ID NO:2, SEQ ID NO:3, SEQ ID NO:4, SEQ ID NO:5, SEQ ID NO:6 and SEQ ID NO:7, an inhibitor of I5-13 soluble CD146 protein of SEQ ID NO: 8, or of a composition comprising such a CD146 inhibitor, for preparing, in vitro or ex vivo, a composition, typically a pharmaceutical composition, for preventing or treating fibrosis, in particular cardiac, renal, skin and/or pulmonary fibrosis, or any pathology, disease, disorder or dysfunctional state leading to, resulting from or associated with fibrosis, in a subject in need thereof.

In a typical aspect, the CD146 inhibitor is selected from an antibody, an aptamer, a polypeptide, a small organic molecule and a nucleic acid.

In a preferred aspect, the CD146 inhibitor is an anti-CD146 antibody or a CD146 antigen-binding molecule, preferably an anti-sCD146 antibody or a sCD146 antigen-binding molecule, a functional fragment thereof (i.e. a fragment capable of binding to CD146) or derivative thereof.

The term "antibody" is used in the broadest sense, and covers monoclonal antibodies (including full-length monoclonal antibodies), polyclonal antibodies, multispecific antibodies, chimeric antibodies, humanized antibodies, and antibody fragment so long as they exhibit the desired biological activity (e.g., inhibiting fibrosis). Antibody fragments comprise a portion of a full length antibody, generally an antigen binding or variable region thereof. Examples of antibody fragments include Fab, Fab', F(ab')2, and Fv fragments, diabodies, linear antibodies, single-chain antibody molecules, single domain antibodies (e.g., from camelids), shark NAR single domain antibodies, and multispecific antibodies formed from antibody fragments. Antibody fragments can also refer to binding moieties comprising CDRs or antigen binding domains including, but not limited to, V H regions (V H, V H-V H), anticalins, PepBodies, antibody-T-cell epitope fusions (Troybodies) or Peptibodies. Antibodies according to the present invention can be of any class, such as IgG, IgA, IgD1 IgE1 IgM1 or IgY1 although IgG antibodies are typically preferred. Antibodies can be of any mammalian or avian origin, including human, murine (mouse or rat), donkey, sheep, goat, rabbit, camel, horse, or chicken. The antibodies can be modified by the covalent attachment of any type of molecule to the antibody. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, or other modifications known in the art.

In general, techniques for preparing antibodies (including polyclonal antibodies, monoclonal antibodies and hybridomas) and for detecting antigens using antibodies are well known in the art, e.g., Harlow & Lane, Using Antibodies, A Laboratory Manual, Cold Spring Harbor Laboratory Press, Cold Spring Harbor, N.Y., 1998; Kohler & Milstein, Nature 256:495-497 (1975); Kozbor et al, Immunology Today 4:72 (1983); and Cole et al., pp. 77-96 in Monoclonal Antibodies and Cancer Therapy, 1985. Additionally, antibodies according to the present invention can be fused to marker sequences, such as a peptide tag to facilitate purification; a suitable tag is a hexahistidine tag. The antibodies can also be conjugated to a diagnostic or therapeutic agent by methods known in the art. Techniques for preparing such conjugates are well known in the art. Other methods of preparing these monoclonal antibodies, as well as chimeric antibodies, humanized antibodies, and single-chain antibodies, are known in the art.

In a particular aspect, the anti-CD146 antibody specifically/selectively recognizes/binds to a human soluble CD146 protein, preferably to the protein comprising or consisting in an amino acid sequence of SEQ ID NO: 7 or SEQ NO: 8 or to an epitope thereof involved in the fibrotic process.

This antibody preferably also neutralizes a biological activity of the targeted CD146 protein, in particular of the targeted soluble CD146 protein selected from SEQ ID NO:1, SEQ ID NO:2, SEQ ID NO:3, SEQ ID NO:4, SEQ ID NO:5, SEQ ID NO:6 and SEQ ID NO:7, and/or of the I5-13 soluble CD146 protein of SEQ ID NO: 8, preferably of the targeted human soluble CD146 protein. Preferably, the monoclonal antibody decreases or inhibits fibrosis in a subject as herein defined, typically a mammal, preferably a human being.

A particular monoclonal antibody is also preferably able to reduce or suppress an excessive expression (compared to a standard expression) of a soluble CD146 receptor or of a CD146 protein receptor subunit. Antibodies binding both a human CD146 protein, typically a human soluble CD146 protein, and a CD146 or soluble CD146 protein receptor (or a CD146 protein receptor subunit) are also usable in the context of the present invention. Methods of making such antibodies are known in the art (See for example Despoix N, Walzer T, Jouve N, Blot-Chabaud M, Bardin N, Paul P, Lyonnet L, Vivier E, Dignat-George F, Vely F. Mouse CD146/MCAM is a marker of natural killer cell maturation. Eur J Immunol 2008; 38: 2855-64).

Preferred antibodies selected by inventors usable in the context of the present invention, capable of selectively binding soluble CD146 (versus membrane CD146), can be an antibody comprising the heavy chain variable region (VH) CDR polypeptide sequences of SEQ ID NO: 87, SEQ ID NO: 88 and SEQ ID NO: 89, and the light chain variable region (VL) CDR polypeptide sequence of SEQ ID NO: 90, sequence QVS and SEQ ID NO: 91, or a distinct antibody comprising the heavy chain variable region (VH) CDR polypeptide sequences of SEQ ID NO: 94, SEQ ID NO: 95 and SEQ ID NO: 96, and the light chain variable region (VL) CDR polypeptide sequences of SEQ ID NO: 97, sequence FAS and SEQ ID NO: 98.

In a particular aspect, the antibody comprises a light chain variable region (VL) comprising SEQ ID NO: 93 and a heavy chain variable region (VH) comprising SEQ ID NO: 92.

In another particular aspect, the antibody comprises a light chain variable region (VL) comprising SEQ ID NO: 100 and a heavy chain variable region (VH) comprising SEQ ID NO: 99.

The CD146 inhibitor can also be an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as *E. coli* Thioredoxin A that are selected from combinatorial libraries by two hybrid methods (Colas et al., 1996).

In another aspect, the CD146 inhibitor is a peptide or polypeptide molecule comprising amino acid residues.

As used herein the term "amino acid residue" refers to any natural/standard and non-natural/non-standard amino acid residue in (L) or (D) configuration, and includes alpha or alpha-disubstituted amino acids. It refers to isoleucine, leucine, lysine, methionine, phenylalanine, threonine, tryptophan, valine, arginine, alanine, asparagine, aspartic acid, cysteine, glutamic acid, glutamine, glycine, histidine, proline, serine, tyrosine. It also includes beta-alanine, 3-aminopropionic acid, 2,3-diamino propionic acid, alpha-aminoisobutyric acid (Aib), 4-amino-butyric acid, N-methylglycine (sarcosine), hydroxyproline, ornithine (e.g., L-ornithine), citrulline, t-butylalanine, t-butylglycine, N-methylisoleucine, phenylglycine, cyclohexylalanine, cyclopentylalanine, cyclobutylalanine, cyclopropylalanine, cyclohexylglycine, cyclopentylglycine, cyclobutylglycine, cyclopropylglycine, norleucine (Nle), norvaline, 2-napthylalanine, pyridylalanine, 3-benzothienyl alanine, 4-chlorophenylalanine, 2-fluorophenylalanine, 3-fluorophenylalanine, 4-fluorophenylalanine, penicillamine, 1,2,3,4- tetrahydro-isoquinoline-3-carboxylix acid, beta-2-thienylalanine, methionine sulfoxide, L-homoarginine (hArg), N-acetyl lysine, 2-amino butyric acid, 2-amino butyric acid, 2,4,-diaminobutyric acid (D- or L-), p-aminophenylalanine, N-methylvaline, selenocysteine, homocysteine, homoserine (HoSer), cysteic acid, epsilon-amino hexanoic acid, delta-amino valeric acid, or 2,3-diaminobutyric acid (D- or L-), etc. These amino acids are well known in the art of biochemistry/peptide chemistry.

Compounds used in the context of the present invention which include peptides may comprise replacement of at least one of the peptide bonds with an isosteric modification. Compounds of the present invention which include peptides may be peptidomimetics. A peptidomimetic is typically characterised by retaining the polarity, three dimensional size and functionality (bioactivity) of its peptide equivalent, but wherein one or more of the peptide bonds/linkages have been replaced, often by proteolytically more stable linkages. Generally, the bond which replaces the amide bond (amide bond surrogate) conserves many or all of the properties of the amide bond, e.g. conformation, steric bulk, electrostatic character, potential for hydrogen bonding, etc. Typical peptide bond replacements include esters, polyamines and derivatives thereof as well as substituted alkanes and alkenes, such as aminomethyl and ketomethylene. For example, the peptide may have one or more peptide linkages replaced by linkages such as —$CH_2NH$—, —$CH_2S$—, —$CH_2$—$CH_2$—, —CH═CH— (cis or trans), —CH(OH)$CH_2$—, or —$COCH_2$—, —N—NH—, —$CH_2NHNH$—, or peptoid linkages in which the side chain is connected to the nitrogen atom instead of the carbon atom. Such peptidomimetics may have greater chemical stability, enhanced biological/pharmacological properties (e.g., half-life, absorption, potency, efficiency, etc.) and/or reduced antigenicity relative its peptide equivalent.

In another aspect, the CD146 inhibitor is a small organic molecule.

The term "small organic molecule" refers to a molecule of a size comparable to those organic molecules generally used in pharmaceuticals. The term excludes biological macromolecules (e.g., proteins, nucleic acids, etc.). Preferred small organic molecules range in size up to about 5000 Da, more preferably up to 2000 Da, and most preferably up to about 1000 Da.

In another aspect, the CD146 inhibitor is a nucleic acid.

The CD146 inhibitor can typically be a polynucleotide or an oligonucleotide, typically an inhibitory nucleotide. These include short interfering RNA (siRNA), microRNA (miRNA), and synthetic hairpin RNA (shRNA), anti-sense nucleic acids, complementary DNA (cDNA) or guide RNA (gRNA usable in the context of a CRISPR/Cas system). In some preferred embodiments, a siRNA targeting CD146 expression is used. Interference with the function and expression of endogenous genes by double-stranded RNA such as siRNA has been shown in various organisms. See, e.g., A. Fire et al., "Potent and Specific Genetic Interference by Double-Stranded RNA in *Caenorhabditis elegans*" Nature 391:806-811 (1998); J. R. Kennerdell & R. W. Carthew, "Use of dsDNA-Mediated Genetic Interference to Demonstrate that frizzled and frizzled 2 Act in the Wingless Pathway," CeJ 95:1017-1026 (1998); F. Wianni & M. Zernicka-Goetz, "Specific Interference with Gene Function by Double-Stranded RNA in Early Mouse Development," Nat. Cell Biol. 2:70-75 (2000). siRNAs can include hairpin loops comprising self-complementary sequences or double stranded sequences. siRNAs typically have fewer than 100 base pairs and can be, e.g., about 30 bps or shorter, and can be made by approaches known in the art, including the use of complementary DNA strands or synthetic approaches. Such double-stranded RNA can be synthesized by in vitro transcription of single-stranded RNA read from both directions of a template and in vitro annealing of sense and antisense RNA strands. Double-stranded RNA targeting CD146 can also be synthesized from a cDNA vector construct in which a CD146 gene (e.g., human CD146 gene) is cloned in opposing orientations separated by an inverted repeat. Following cell transfection, the RNA is transcribed and the complementary strands reanneal. Double-stranded RNA targeting the CD146 gene can be introduced into a cell by transfection of an appropriate construct. Typically, RNA interference mediated by siRNA, miRNA, or shRNA is mediated at the level of translation; in other words, these interfering RNA molecules prevent translation of the corresponding mRNA molecules and lead to their degradation. It is also possible that RNA interference may also operate at the level of transcription, blocking transcription of the regions of the genome corresponding to these interfering RNA molecules.

The structure and function of these interfering RNA molecules are well known in the art and are described, for example, in R. F. Gesteland et al., eds, "The RNA World" (3rd, Cold Spring Harbor Laboratory Press, Cold Spring Harbor, N.Y., 2006), pp. 535-565, incorporated herein by this reference. For these approaches, cloning into vectors and transfection methods are also well known in the art and are described, for example, in J. Sambrook & D. R. Russell, "Molecular Cloning: A Laboratory Manual" (3rd, Cold Spring Harbor Laboratory Press, Cold Spring Harbor, 2001), incorporated herein by this reference.

In addition to double stranded RNAs, other nucleic acid agents targeting CD146 can also be employed in the practice of the present invention, e.g., antisense nucleic acids. Antisense nucleic acids are DNA or RNA molecules that are complementary to at least a portion of a specific target mRNA molecule. In the cell, the single stranded antisense molecule hybridizes to that mRNA, forming a double stranded molecule. The cell does not translate an mRNA in this double-stranded form. Therefore, antisense nucleic acids interfere with the translation of mRNA into protein, and, thus, with the expression of a gene that is transcribed into that mRNA. Antisense methods have been used to inhibit the expression of many genes in vitro. See, e.g., C J. Marcus-Sekura, "Techniques for Using Antisense Oligodeoxyribonucleotides to Study Gene Expression," Anal. Biochem. 172:289-295 (1988); J. E. Hambor et al., "Use of an Epstein-Ban Virus Episomal Replicon for Anti-Sense RNA-Mediated Gene Inhibition in a Human Cytotoxic T-Cell Clone," Proc. Natl. Acad. Sci. U.S.A. 85:4010-4014 (1988); H Arima et al., "Specific inhibition of Interleukin-10 Production in Murine Macrophage-Like Cells by Phosphorothioate Antisense Oligonucleotides," Antisense Nucl. Acid Drug Dev. 8:319-327 (1998); and W.-F. Hou et al., "Effect of Antisense Oligodeoxynucleotides Directed to Individual Calmodulin Gene Transcripts on the Proliferation and Differentiation of PC12 Cells," Antisense Nucl. Acid Drug Dev. 8:295-308 (1998), all incorporated herein by this reference. Antisense technology is described further in C. Lichtenstein & W. Nellen, eds., "Antisense Technology: A Practical Approach" (IRL Press, Oxford, 1997), incorporated herein by this reference. CD146 polynucleotide sequences from human and many other animals in particular mammals have been in the art. Based on the known sequences, inhibitory nucleotides (e.g., siRNA, miRNA, or shRNA) targeting CD146 can be readily synthesized using methods well known in the art.

Exemplary siRNAs according to the invention could have up to 29 bps, 25 bps, 22 bps, 21 bps, 20 bps, 15 bps, 10 bps, 5 bps or any integral number of base pairs between these numbers. Tools for designing optimal inhibitory siRNAs include that available from DNAengine Inc. (Seattle, Wash.) and Ambion, Inc. (Austin, Tex).

The amino acid molecules of the present invention can be designed to improve their performance and/or biocompatibility with a diagnostic, therapeutic or prophylactic use in a subject, typically in a mammal, preferably in a human being. They can be, for example, glycosylated, methylated, acetylated, phosphorylated or fused to another polypeptide, preferably methylated, acetylated, phosphorylated or fused to another polypeptide, for targeting different types of tissues, in particular a pathological tissue such as, typically, a cardiac or renal tissue, preferably in a human being.

Inventors also herein provide a composition comprising a CD146 inhibitor, typically in a therapeutically effective amount, and a pharmaceutically acceptable excipient, support, vehicle or carrier.

The composition may comprise several distinct CD146 inhibitors, for example an anti-CD146 antibody directed against a particular form of CD146 such as a soluble CD146 protein selected from SEQ ID NO:1, SEQ ID NO:2, SEQ ID NO:3, SEQ ID NO:4, SEQ ID NO:5, SEQ ID NO:6 and SEQ ID NO:7, and the I5-13 soluble CD146 protein of SEQ ID NO:8; and a distinct anti-CD146 antibody directed against an identical or distinct form of CD146.

Any of the herein described antibody(ies) may be incorporated into a composition further comprising a pharmaceutically acceptable carrier or support, in respective appropriate dosages easily determined by the skilled person in the art.

The composition may further comprise an additional distinct therapeutic compound intended to prevent or treat fibrosis which is not a CD146 inhibitor.

In a particular aspect, the herein described compositions comprising an antibody, in particular an antibody specifically directed against a human soluble CD146 as herein described, may further comprise at least one other anti-fibrosis factor. In the context of the present invention an anti-fibrosis factor is a factor which inhibits or interferes with fibroblast development or which inhibits or interferes with extracellular matrix deposition.

Anti-fibrosis factors usable in the context of the present invention may be selected from Bone Morphogenetic protein 7 (BMP7), relaxin, Glitazars, and a miRNA (for example mir-29 or miR-101).

A "therapeutically affective amount" of a CD146 inhibitor is an amount allowing the prevention or treatment of fibrosis in a subject, typically a mammal, preferably a human being, in need thereof. Typical therapeutically effective amounts for use in a mammal, typically in a human being, are between about 5 mg/kg and 15 mg/kg, for example between about 5 mg/kg and 10 mg/kg or between about 10 and 15 mg/kg.

A pharmaceutically acceptable excipient, support, vehicle or carrier, usable in the context of the present invention, is for example a saline, isotonic, buffered solution such as Mannitol 20%, optionally combined with stabilizing agents such as isogenic albumin or any other stabilizing protein, glycerol, etc., and also adjuvants such as polybrene or DEAE dextrans, etc.

The composition is typically for use in prevention or treatment of fibrosis, in particular cardiac and/or renal fibrosis, in a subject.

A particular composition herein described comprising an inhibitor of the I5-13 soluble CD146 protein of SEQ ID NO:8, and a pharmaceutically acceptable carrier is for use in prevention or treatment of pulmonary fibrosis in a subject, in particular of pulmonary fibrosis associated to systemic sclerosis.

A particular composition herein described comprises a soluble CD146 protein selected from SEQ ID NO:1, SEQ ID NO:2, SEQ ID NO:3, SEQ ID NO:4, SEQ ID NO:5, SEQ ID NO:6 and SEQ ID NO:7, or the I10 soluble CD146 protein of SEQ ID NO:9, and a pharmaceutically acceptable carrier for use in prevention or treatment of skin fibrosis and/or pulmonary fibrosis, in particular of pulmonary fibrosis associated to systemic sclerosis, in a subject, preferably a human being.

Inventors further herein describe a method of preventing or treating fibrosis, in particular cardiac, skin, pulmonary and/or renal fibrosis, in a subject in need thereof, typically in a subject who has been identified by a herein described method as having predisposition to fibrosis, as being affected by fibrosis, as having a fibrosis which does not progress, as having a fibrosis increase or as having a poor prognosis fibrosis. This method typically comprises a step of administering a CD146 inhibitor, in particular a sCD146 inhibitor, or a particular sCD146, or a composition comprising such a CD146 inhibitor or particular sCD146, typically an effective amount thereof, to said subject.

In a particular aspect, the method comprises a step of administering to the subject (an effective amount of) an antibody, typically an anti-CD146 antibody as herein described, or (of) a composition (typically a pharmaceutical composition) comprising such an antibody.

The doses of the diagnostic or pharmaceutical compositions herein described may be adjusted by the skilled person depending on the treated subject, the route of administration, the targeted tissue, the biologically active compound (as herein disclosed), etc.

Various protocols may be used for the administration, such as simultaneous or sequential administration of an anti-CD146 antibody, of a CD146 inhibitor or of any other compound as described previously, single or repeated administration, etc., which may be adjusted by the skilled person.

The diagnostic or pharmaceutical composition containing a product according to the invention may be administered to a patient for example systemically, subcutaneously, intraspinally, intracerebrally or intradermally, given the targeted pathological tissue or area. Preferred modes of injection are systemic injections, in particular intra-venous or intra-arterial injections, or subcutaneous injections.

Also herein described is a method of monitoring in vitro, ex vivo or in vivo the efficacy of a drug, typically of a CD146 inhibitor, or of a composition for treating fibrosis, in particular cardiac, skin, pulmonary and/or renal fibrosis. This method typically comprises a step of comparing the expression of CD146 in a first biological sample from a subject before any treatment of fibrosis to the expression of CD146 in a second biological sample of the same subject who has been exposed to a drug or composition for treating fibrosis.

Also herein provided is a kit comprising any one or more of the herein described products, typically in an effective or therapeutic amount, typically protein(s), antibodie(s), inhibitor(s) of (soluble) CD146 or composition(s) such product(s), optionally a means or device for administering the product(s) to a subject in need thereof, and optionally a leaflet providing instructions for using the products in the context of a method as herein described.

An antibody preferably present in the kit is typically directed against one of the herein described CD146 protein, preferably against one of the herein described sCD146 protein. It is preferably a monoclonal antibody.

Typically, the kit also comprises instructions for using the protein(s), antibody(ies), inhibitor(s) or composition(s) according to the disclosed methods.

Further aspects and advantages of the present invention will be described in the following experimental section, which should be regarded as illustrative and not limiting the scope of the present application. All references cited in the present application are herein incorporated by reference.

LEGENDS TO THE FIGURES

FIG. 1. CD146 is induced in experimental GN in mice

CD146 is highly upregulated within damaged kidneys progressively from day 4 to day 15 postNTS (decomplemented nephrotoxic serum) administration in mice and mainly localized within the injured glomerulus (A). This upregulation was confirmed by western blot (B, C). *, P<0.05; , P<0.01, *, P<0.001. Magnification of microphotographs: ×200.

FIG. 2. CD146 knock-out mice are protected against NTS-induced glomerulonephritis.

Body weight increase in mice after the induction of the disease (A). Renal function was evaluated by proteinuria, expressed as grams of protein/mmol of creatinine (B) and BUN (C). All three parameters reveal a slower progression of the disease in CD146 knock-out animals. Mason trichrome staining of kidney slices (D) shows that renal structure was preserved in CD146 knock-out since they developed less glomerular crescents (E) and tubular dilation (F). Crescents are expressed as the percentage (%) of glomeruli presenting cellular crescents. *, P<0.05; **, P<0.01. Magnification of microphotographs: ×200.

FIG. 3. CD146 knock-out mice develop less renal inflammation and fibrosis.

QPCR for Il-1β (A), TNF-α (B) and ICAM-1 (C) showed restricted inflammatory response in kidneys of CD146 KO mice 15 days after the induction of NTS-GN Immunohistochemistry for F4/80 (D, E) and CD3 (F, G), confirmed respectively limited monocyte and lymphocyte adhesion in CD146 KO mice. At the same time point QPCR for TGFβ (H), collagen III (I) and quantification of Sirius red staining (J) showed restriction of the fibrotic response in CD146 KO mice.*, P<0.05; , P<0.01; *, P<0.001. Magnification of microphotographs: ×200.

Figure 4:
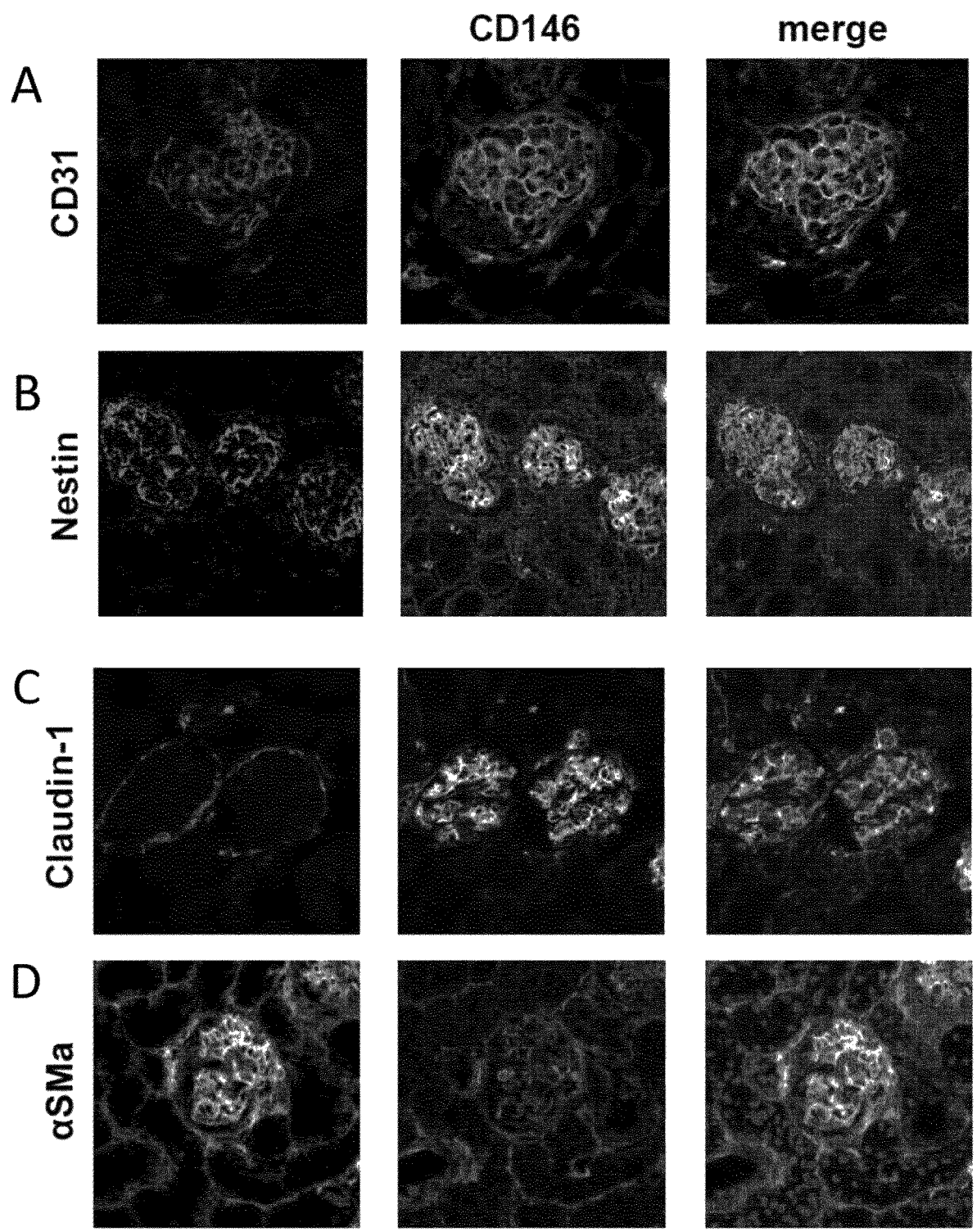

FIG. 4. CD146 is strongly induced in glomerular endothelial cells after NTS administration.

Double immunofluorescein renal cortical slices for CD146 and various markers of glomerular components such as endothelial cells (CD31/PECAM1) (A), podocytes (Nestin) (B), parietal (Claudin-1) (C) and mesangial cells (α-SMA) (D), showed that CD146 expression was induced mainly in glomerular endothelial cells, 7 days post NTS-GN. Magnification of microphotographs: ×400.

FIG. 5. Generation of CD146-EC-del mice.

CD146-floxed mice were first crossed with the B6. Cg-Gt (ROSA)26Sortm6 (CAG-ZsGreenl)Hze/J mice (Jackson laboratories) which express the fluorescent protein ZsGreenl as a reporter for CRE-recombinase activity. Then, mice with endothelial cell-specific deletion of the CD146 gene were generated by further crossing CD146 flox-Zs Green animals with the Cdh5 (PAC)-CreERT2 mouse strain established by Ralf Adams(A). The deletion of the CD146 gene was induced by I. P. injections of tamoxifen diluted in corn oil (10 mg/ml solution, 1 mg tamoxifen/injection) and administered on 3 consecutive days. Immunofluorescence for CD146 confirmed its deletion from the vascular endothelium (B). In accordance, CD146 mRNA expression was also decreased in the kidneys of the CD146-EC-del mice (C). *, P<0.05; **, P<0.01; #, P=0.05 (NTS versus CTL). Magnification of microphotographs: ×200.

FIG. 6. Endothelial-specific deletion of CD146 protected renal function and structure after the induction of NTS-GN In CD146-EC-del mice the NTS-induced increase of body weight (A), proteinuria (B) and BUN (C) were all blunted. Furthermore, Mason's trichrome staining in renal cortical slices (D) reveals that glomerular crescents (E) and tubular dilation (F) were highly reduced 15 days post NTS injection. *, P<0.05; **, P<0.01 (NTS versus CD146-EC-del); #, P<0.05; ##, P<0.01 (NTS versus CTL-PBS). Magnification of microphotographs: ×200.

FIG. 7. CD146 endothelial-specific deletion protected mice against both inflammation and renal interstitial fibrosis F4/80 staining showed that monocyte infiltration was blunted in CD146-EC-del mice 15 days post NTS injection (A). In accordance, QPCR for VCAM-1 (B) and MCP-1 (C) showed that upregulation of those inflammatory markers was blunted. Furthermore, QPCR for TGF-β1 (D) and Colla1 (E) showed similar results. *, P<0.05; **, P<0.01. Magnification of microphotographs: ×200.

FIG. 8. Expression of CD146 transcripts in glomerular diseases in humans

Gene expression data obtained from isolated glomeruli of patients with diabetic nephropathies (DN), minimal change disease (MCD), IgA nephropathy (IgA), focal segmental glomerulosclerosis (FSGS), membranous glomerulonephritis (MGN), lupus nephritis (SLE), rapidly progressive glomerulonephritis (RPGN) and controls (pre-transplant allograft biopsies). CD146 expression was significantly and differentially regulated in glomerulopathies compared with controls.

FIG. 9. Phases of cardiac fibrosis induced by myocardial infarction (A) and cell populations giving rise to myofibroblasts (B) (V. Rai, Mol. Cell Biochem., 2017).

FIG. 10. Model of myocardial infarction.

The left descending coronary artery undergoes permanent ligation (A and B). The animals are sacrificed 21 days postoperative in order to carry out the various examinations (C).

Figure 11:
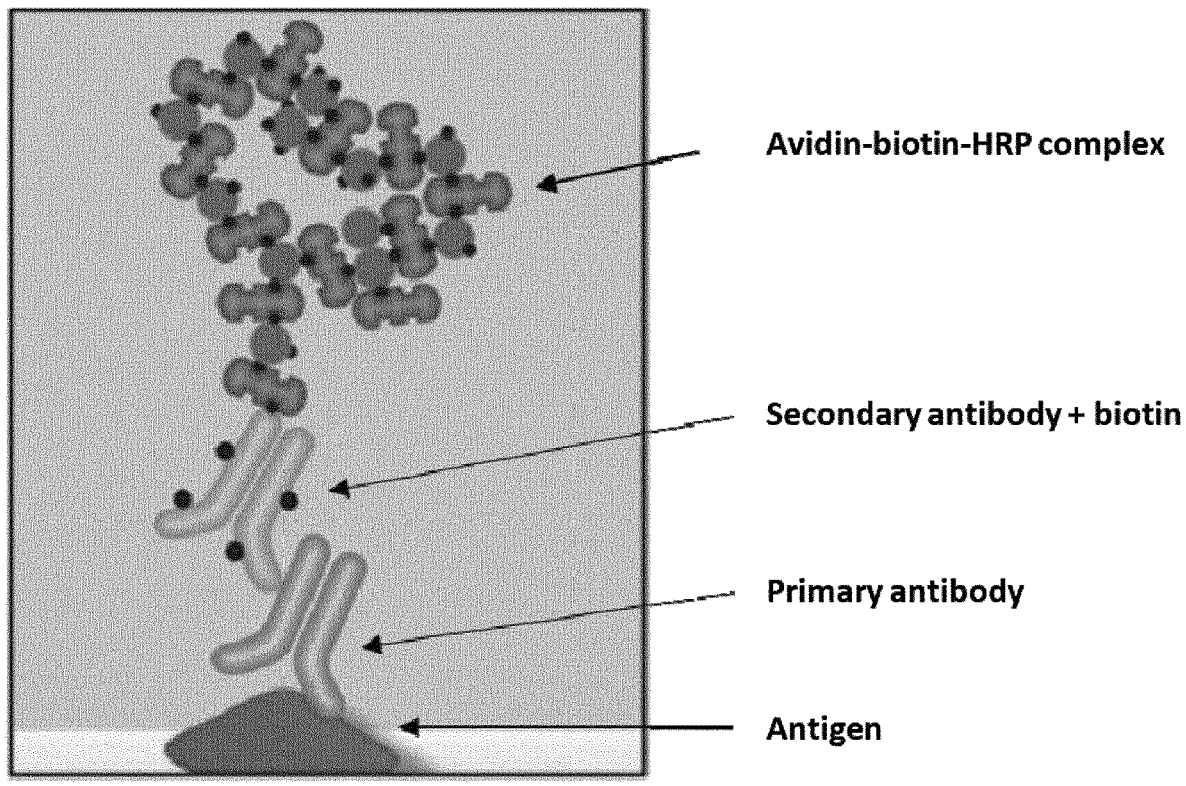

FIG. 11. Immunohistology principle and method.

Indirect immunodetection of proteins of interest is performed using a signal amplification system. In this method, the protein of interest present on a tissue is detected with a primary antibody. Hybridization of this antibody is detected by a secondary antibody conjugated to biotin molecules. Addition of an avidin-biotin complex linked to an enzyme, horseradish peroxidase (HRP), makes it possible to detect the target antigens after deposition of the specific substrate (diaminobenzidine). The reaction produces a stable brown precipitate which can be observed by optical microscopy. (Tables I and II).

Figure 12:
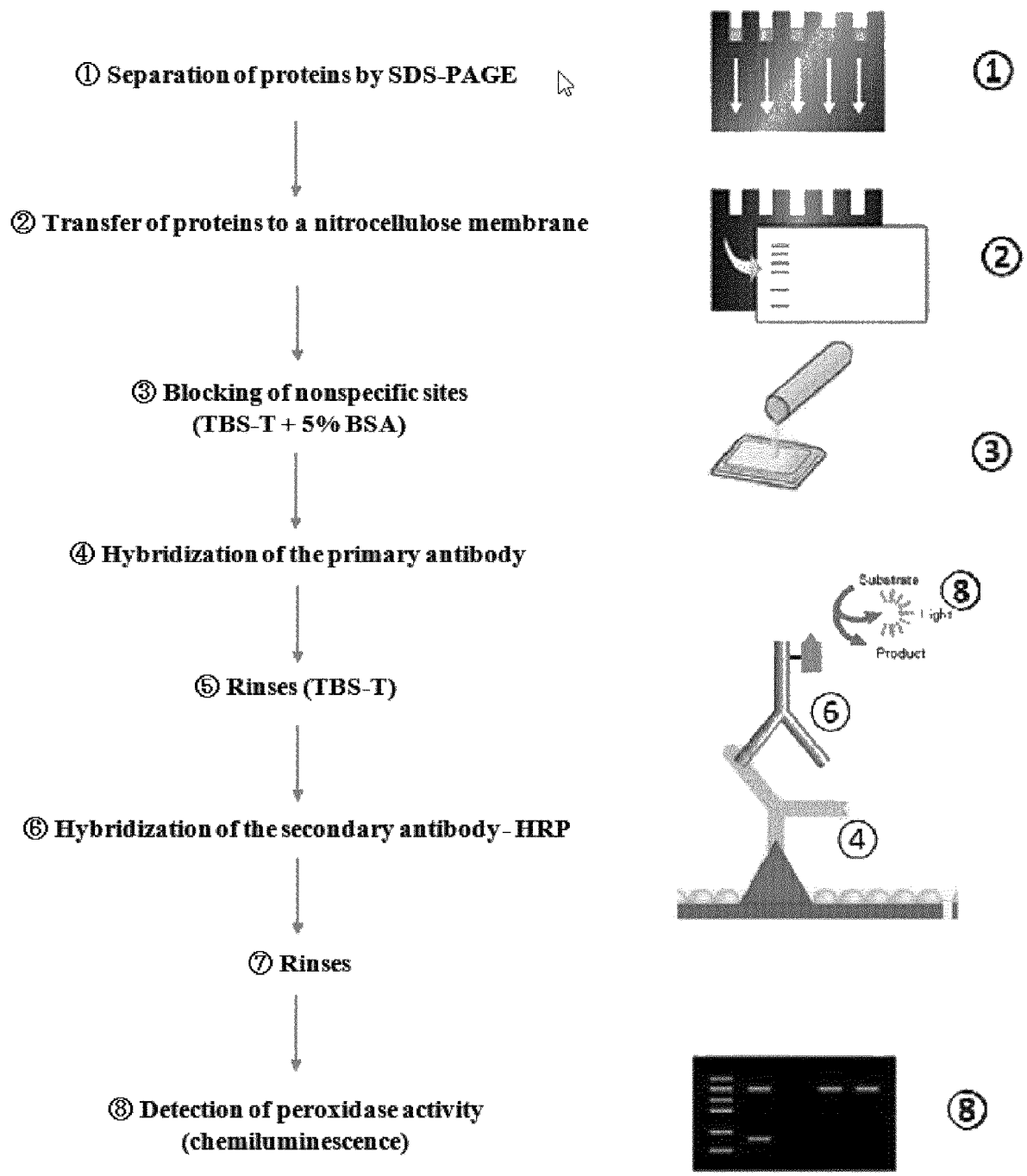

FIG. 12. Principle of the western blot.

FIG. 13. Location of the cardiac fibrosis zone (A and B) in "MI" (or "IM") animals and CD146 RNA expression (C) (n=3).

The infarcted/fibrotic zone or area ("IZ" or "IA" or "FZ" or "FA") is located at the left ventricular apex, under the ligature. The border zone or area ("BZ" or "BA") is located immediately proximal to the infarcted zone, and the distal/remote zone or area ("DZ" or "DA" or "RZ" or "RA") is located above the ligation zone. Cardiac fibrosis (B, 60× objective) is located at the infarcted zone (red arrow) and propagates in the border zone (blue arrow).

FIG. 14. Expression of CD146/sCD146 in the Myocardial Infarction model (N=3).

(A) Immunodetection of CD146 Immunodetection of CD146 shows greater labeling in the ventricle wall of MI animals compared to sham animals. The zone of fibrosis is not marked ("IA") while the peripheral cardiomyocytes are marked ("BA"). Some images are taken at the 20× objective while others are taken at 60×.

(B) CD146 ELISA(n=2). CD146 concentration was determined in the sera of 2 sham and 2 MI mice. Results are given in ng/ml.

Figure 15:
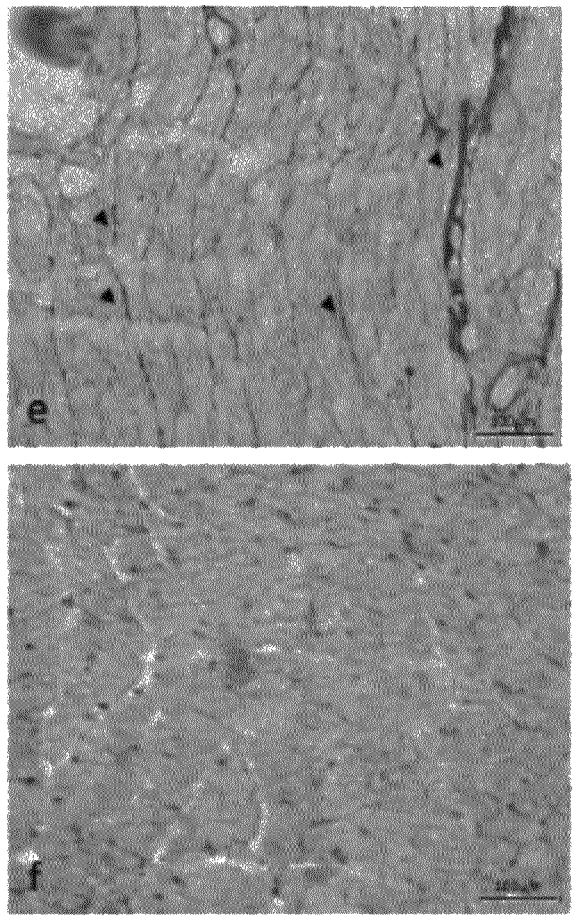

FIG. 15. CD146 expression in the model of age-related fibrosis (n=3).

Sirius red staining (e) and CD146 immunodetection (f) of myocardium sections of 24-month-old animals (e, f).

FIG. 16. Role of CD146 in cardiac fibrosis during ageing.

A— Sirius red staining of cardiac fibrosis (a, b: 40× objective) and quantification of the area fraction occupied by collagens (c) (n=3) (p=0.0001) of 24-month-old females. RT-PCR quantification of collagen RNA expression (d) (n=1).

B— Staining of cell membranes and quantification of cardiomyocyte size (n=3) (p<0.0001).

FIG. 17. Role of CD146s in acquisition of the myofibroblast phenotype.

Study of cell proliferation showing an increase during stimulation with CD146s comparable to that observed with TGF-β. (A) (p<0.05). Expression of the myofibroblast marker SMA is increased after stimulation for 48 hours with CD146s (50 ng/mL) during RNA (B) and protein (C) analysis and the actin fibres are larger (D) in a manner equivalent to simulation with TGF-β (20× objective). Expression of fibronectin and of type I collagen (E) are also increased after stimulation with CD146s in an equivalent manner after stimulation with TGF-β. CD146s induces an increase in TGF-β expression at the RNA level (F).

Figure 18:
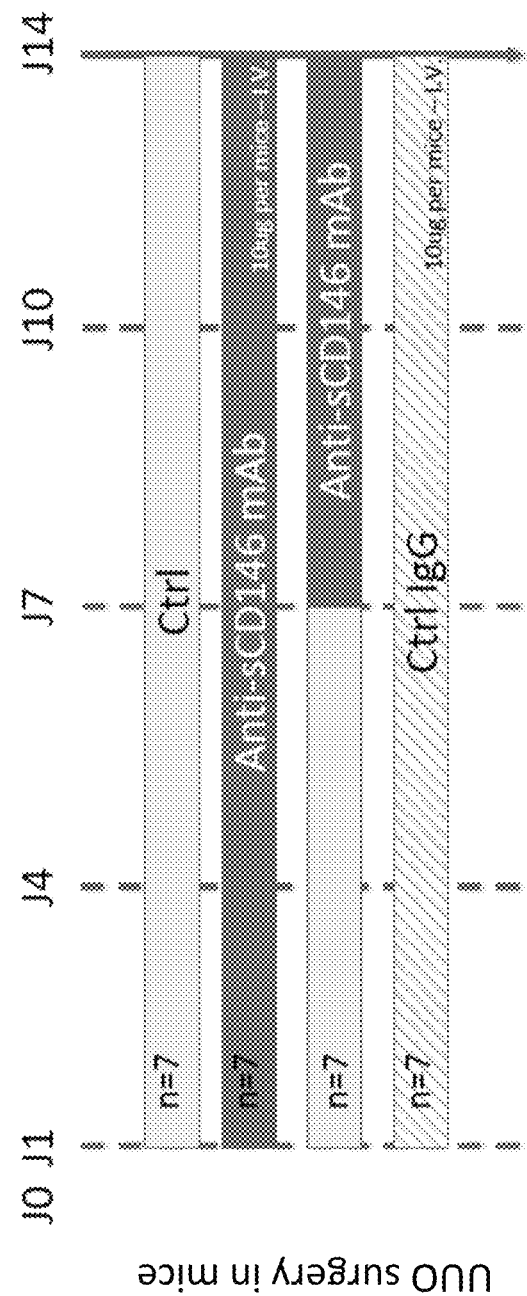

FIG. 18. Treatment of a UUO (Unilateral Ureteral Obstruction) mouse model with renal failure and fibrosis with anti-sCD146 antibody used at different times.

Eight- to 12-week-old male C57BL/6 mice underwent ligation of the right ureter. The right ureter was exposed through a midline abdominal incision and was either completely obstructed 1 cm below the renal pelvis with 5.0 silk ligature (ligated animals). After surgery, four groups of 7 animals were made. One group of animals was used as control and treated at days 1, 4, 7 and 10 IV with vehicle. One group of animals was treated with anti-sCD146 antibody IV at 10 microgrammes per mouse at days 1, 4 and 10 after surgery. Another group of animals was treated with the same protocol but only at days 7 and 10 after surgery. Finally the last group of animals was treated IV at 10 microgrammes par animal with control IgG at days 1, 4, 7 and 10 after surgery.

Figure 19:
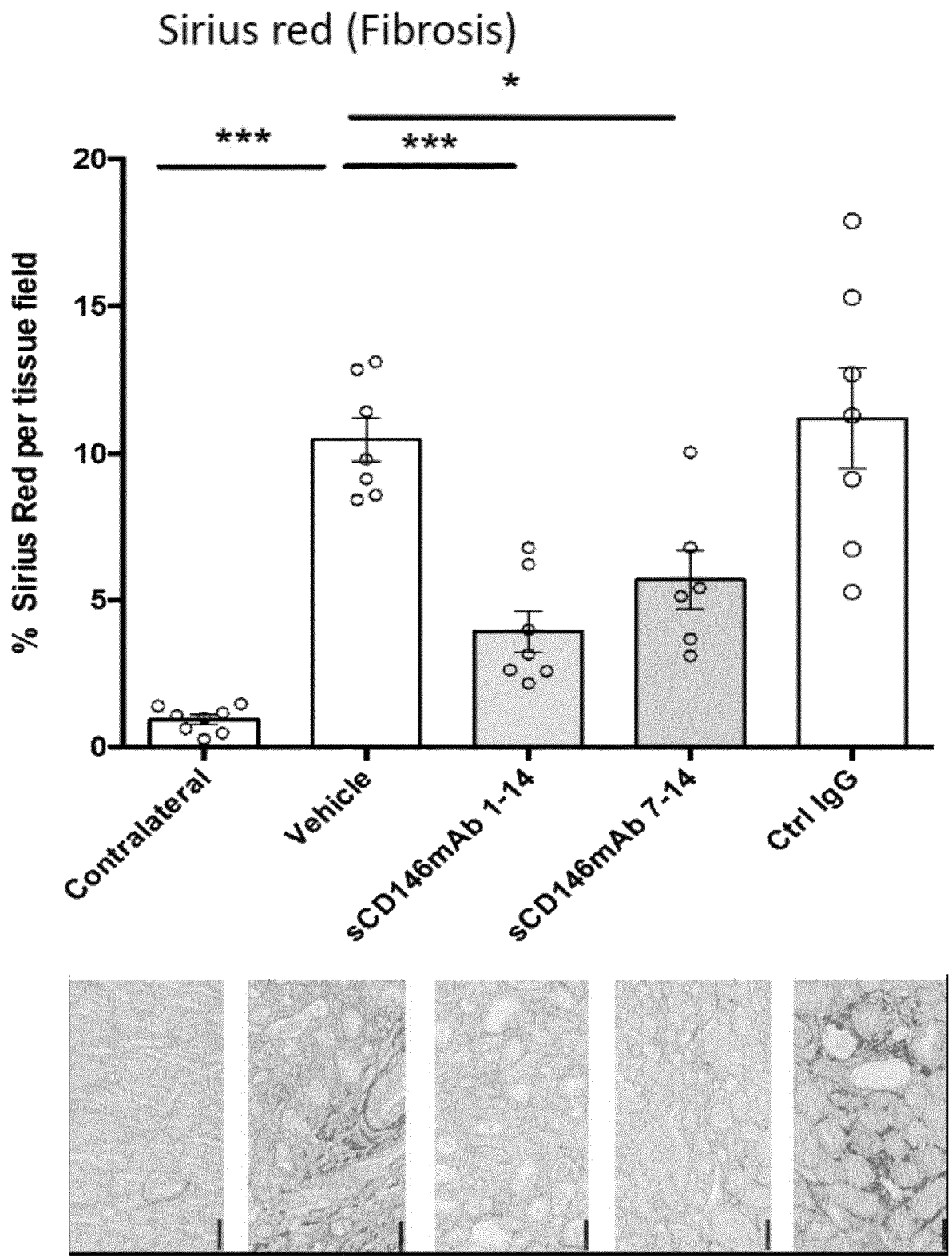

FIG. 19. Effect of anti-sCD146 treatment on renal fibrosis.

At day 14 after surgery, animals were sacrificed and kidneys were removed for immunohistochemistry. Fibrosis was estimated with sirius red on experimental kidney or contralateral kidney. Results show that fibrosis was increased in experimental kidney as compared to contralateral kidney. Treatment with IgG did not modify fibrosis. In contrast, treatment with the anti-sCD146 antibody from day 1 to 14 or from day 7 to 14 significantly decreased fibrosis.

Figure 20:
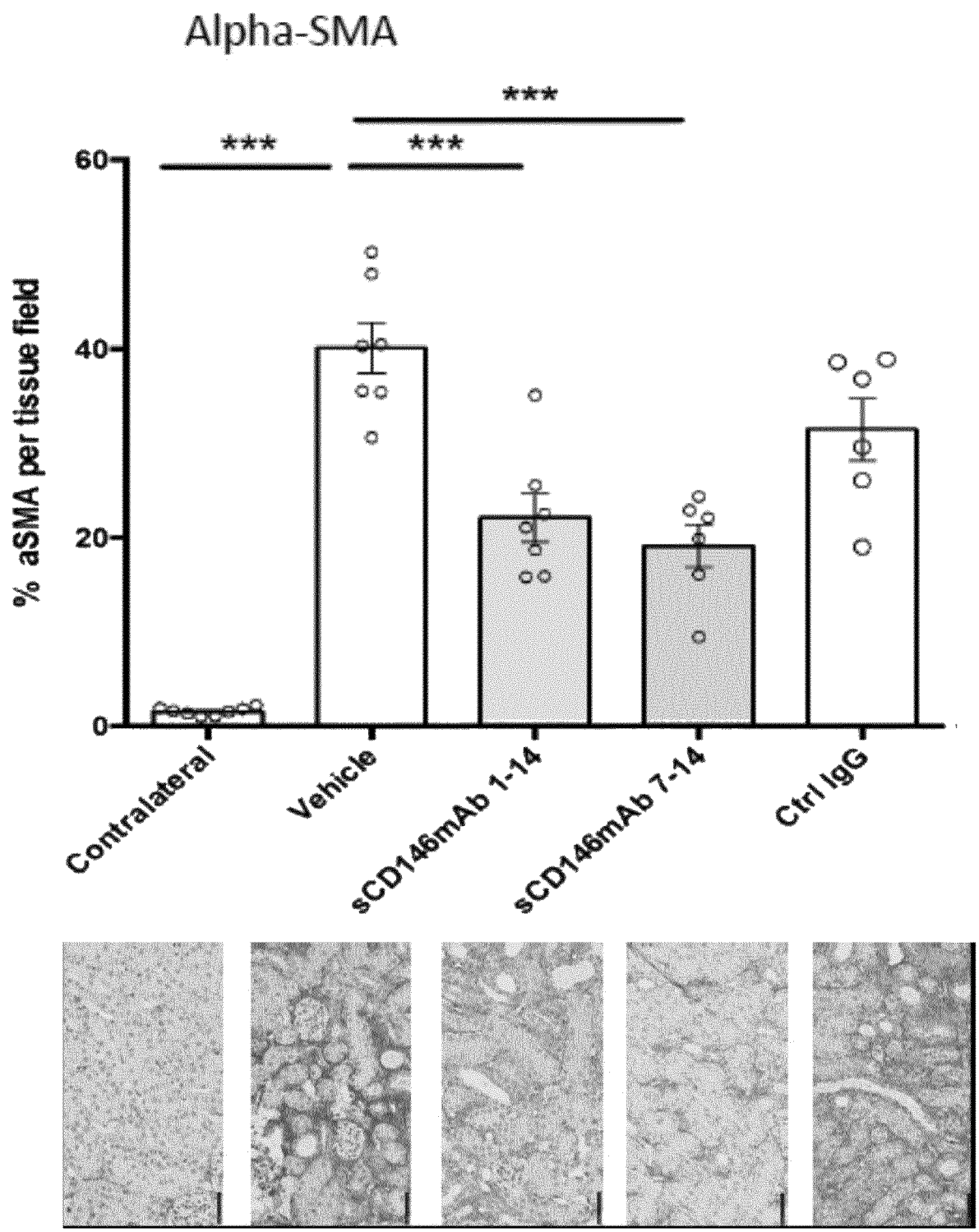

FIG. 20. Effect of anti-sCD146 treatment on alpha-SMA expression.

At day 14 after surgery, animals were sacrificed and kidneys were removed. Alpha-SMA expression was determined by immunohistochemistry with specific antibody on experimental kidney or contralateral kidney. Results show that alpha-SMA was increased in experimental kidney as compared to contralateral kidney. Treatment with IgG did not modify alpha-SMA expression. In contrast, treatment with the anti-sCD146 antibody from day 1 to 14 or from day 7 to 14 significantly decreased alpha-SMA expression.

FIG. 21. Effect of proteinases inhibitors on soluble CD146 secretion in endothelial cells A: Secretion of soluble CD146 (CD146s) was determined in ECFC in response to 24 h of treatment with 20 ng/ml TNF, 20 ng/ml VEGF, 5 ng/ml TGFb, 50 ng/ml netrin, 50 ng/ml Wnt5a and 50 ng/ml Wnt3a.

B: The effect of the pan-inhibitor GM6001 was tested on CD146s secretion in ECFC cells by ELISA. Experiments were performed in control conditions and after treatment with 20 ng/ml TNF for 24 h. Insert shows that TNF treatment significantly increases CD146s from 24 h of treatment. A dose-dependence of GM6001 effect was performed between 1 and 50 μM. Results are the mean values+/−SEM of 5 experiments.

C: The effect of furin convertase inhibitor (IF) was tested at 50 μMon CD146s secretion in control condition and after treatment with TNF 20 ng/ml for 24 h. Results are the mean values+/−SEM of 3 experiments.

D: Effect of TIMP-1, -2 and -3 (1 μg/ml) was tested on CD146s secretion in control condition and after treatment with 20 ng/ml TNF. Results are the mean values+/−SEM of 3 experiments. *: $P<0.05$, : $P<0.01$, *: $P<0.001$, experimental vs Control FIG. 22: ADAM10 is involved in the shedding of the long isoform of CD146 in ECFC A: ECFC were transfected with siRNA targeting the short (shCD146) or the long (IgCD146) isoforms of CD146 and with a control siRNA (C). Soluble CD146 (sCD146) secretion was determined. Results are the mean values+/−SEM of 4 different experiments.

B: ECFC were transfected with siRNA targeting MT1-MMP, MMP2, ADAM10 or Tace and with a control siRNA (C). Soluble CD146 (sCD146) secretion was determined. In one condition, cells were treated with GM6001 10 μM. Results are the mean values+/−SEM of 5 different experiments.

C: ADAM10 was immunoprecipitated in ECFC cultured in basal condition (EBM2). The long (IgCD146) and short (shCD146) isoforms of CD146 were then detected by western blot using specific antibodies. Results are representative of 3 different experiments.

D: ECFC were transfected with siRNA targeting ADAM10 or Tace and with a control siRNA (C). The permeability of the ECFC monolayer grown on semi-permeable filters was determined using dextran-FITC. Results are the mean values+/−SEM of 3 experiments.

E: ECFC were transfected with plasmid vectors encoding ADAM10 (p-ADAM10) or Tace (p-Tace) and with a control plasmid vector (C). The permeability of the ECFC monolayer grown on semi-permeable filters was determined using dextran-FITC. Results are the mean values+/−SEM of 3 experiments. *: $P<0.05$, : $P<0.01$, *: $P<0.001$, experimental vs Control.

Figure 23:
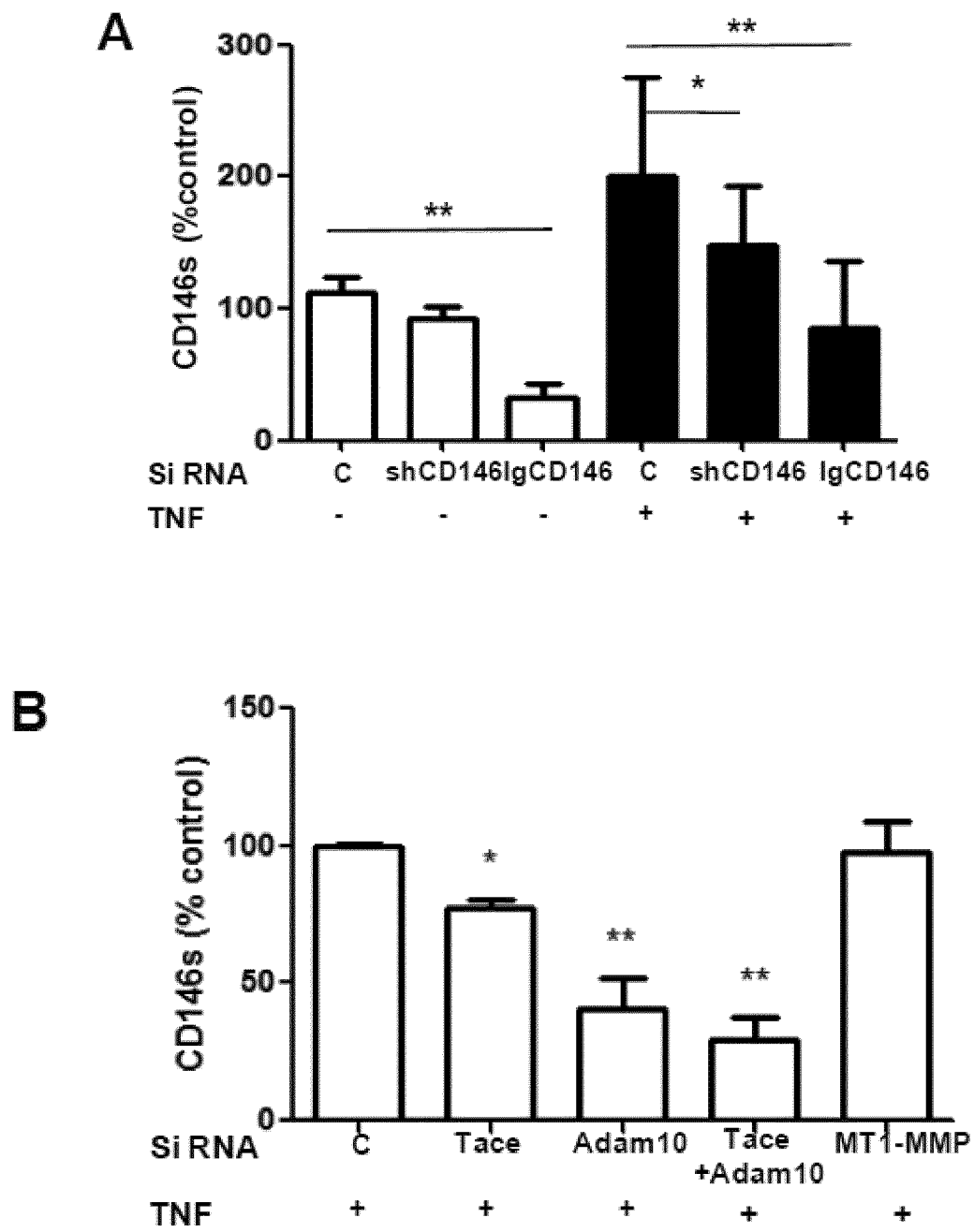

FIG. 23: Tace is involved in the shedding of the short isoform of CD146 in ECFC

A: ECFC were transfected with siRNA targeting the short (shCD146) or the long (lgCD146) isoforms of CD146 and with a control siRNA (C) and soluble CD146 (sCD146) secretion was determined in basal condition and in cells treated for 24 h with TNF 20 ng/ml. Results are the mean values +/−SEM of 5 different experiments.

B: ECFC treated for 24 h with 20 ng/ml TNF were transfected with siRNA targeting Tace, ADAM10, MT1-MMP and with a control siRNA (C) and soluble CD146 (sCD146) secretion was determined. Results are the mean values +/−SEM of 3 different experiments.

FIG. 24: Characterization of I10-sCD146 and I5-13-sCD146 isoforms

A: Schematic representation of the I10-sCD146 and I5-13-sCD146 isoforms as compared to the shed form. The differences in amino acids are indicated.

B: The mRNA expression of I10-sCD146 and I5-13-sCD146 isoforms was analyzed in ECFC and HUVEC and compared to mRNA expression of the short and long isoforms of CD146. Results are the mean values +/−SEM of 3 experiments.

C: The mRNA expression of I10-sCD146 and I5-13-sCD146 isoforms was analyzed by qPCR in ECFC after treatment of the cells for 24 h with the recombinant shed soluble CD146 50 ng/ml, VEGF 20 ng/ml, TNF 20 ng/ml, TGF beta 5 ng/ml, and netrin 50 ng/ml. Cells were also treated for 15 min with WNT5a 200 ng/ml and 1 h with WNT3a 50 ng/ml. Results are the mean values +/−SEM of 3 experiments. *: P<0.05, experimental vs Control.

FIG. 25: Effect of I5-13-sCD146 and I10-sCD146 on angiogenesis

A: Effect of siRNA targeting I10-sCD146 and I5-13-sCD146 on proliferation of ECFC. Experiments were performed in the presence of GM6001 10 µM. Results are mean values of 4 different experiments and representative pictures of the cells in one experiment are given.

B: Effect of over-expression of I10-sCD146 (p-I10-sCD146), I5-13-sCD146 (p-I5-13-sCD146) and shed sCD146 (p-shed sCD146) realized by plasmid transfection on proliferation of ECFC. Experiments were performed in the presence of GM6001 10 µM.

C: Effect of recombinant proteins I10-sCD146, I5-13-sCD146 and shed sCD146 50 ng/ml on the proliferation of ECFC. Experiments were performed in the presence of GM6001 10 µM. Results are mean values of 4 different experiments.

D: Yolk sac membrane assays were performed in the presence of 25 ng/ml or 50 ng/ml I5-13-sCD146 and I10-sCD146 for 48 h and compared to control. Representative pictures of 4 different experiments are given.

E: Effect of recombinant proteins I10-sCD146, I5-13-sCD146 and shed sCD146 50 ng/ml on the number of sprouts, branched points and cumulative sprout length in spheroid experiments realized with ECFC. Results were compared to VEGF 20 ng/ml and complete EGM2-MV medium.

Average of the experiments and representative pictures are given. Results are mean values of 4 different experiments. *: P<0.05, ***: P<0.001, experimental vs Control.

FIG. 26: Effect of local injection of recombinant I5-13-sCD146 and I10-sCD146 in a mouse ischemic hind limb model A: Ischemic mice were treated with PBS or 2 µg of rh-sCD146/rh-I10-sCD146/rh-I5-13-sCD146 or VEGF. Blood perfusion rate was monitored by laser-Doppler. Results are mean values of 6 different animals in each group and expressed as % of the control leg. *, , *: P<0.05, P<0.01, P<0.001, I10-sCD146 vs. PBS; $$, $$$: P<0.01, P<0.001, I5-13-sCD146 vs. PBS; ##, ###: P<0.01, P<0.001, shed sCD146 vs. PBS; £: P<0.05, VEGF vs. PBS.

B: Blood vessels examination in hind limb muscle sections from control (PBS) and shed rh-sCD146/rh-I10-sCD146/rh-I5-13-sCD146 treated animals 28 days after surgery. Vessels are labelled with isolectin B4., *: P<0.01, P<0.001, experimental vs control. $: P<0.05, I10-sCD146 vs I5-13-sCD146.

C: Angiographic pictures of control (PBS) and shed sCD146/I10-sCD146/I5-13-sCD146 treated animals at D28. Pictures are representative of the 6 animals in each group. Average of the density of the vessels was expressed as right versus left leg in the different parts of the legs (calf, thigh) and in the whole leg. *, **: P<0.01, P<0.001 experimental vs PBS in calf; $: P<0.05, experimental vs PBS in thigh; #, ##: P<0.05, P<0.01, experimental vs PBS in whole leg.

FIG. 27: Expression and effect of I5-13-sCD146 and I10-sCD146 isoforms in Systemic Sclerosis A: Shed sCD146, I5-13-sCD146 and I10-sCD146 concentrations were determined in 22 patients with Systemic Sclerosis as compared to matched control. I5-13-sCD146 was also compared in SSc patients with and without pulmonary fibrosis (Inset; n=10 and n=12, respectively).

B: Activation of canonical Wnt signalling (b-catenin/TCF transcription activity; Luciferase assay) was estimated in Mouse Embryonic Fibroblasts (MEF) from CD146 KO and WT mice. MEF were treated or not with bleomycin in the presence or absence of shed sCD146, I5-13-sCD146 or I10-sCD146. Results are the mean values +/−SEM of 5 independent experiments.

C: Dermal thickness was evaluated in a CD146 KO mouse model of Systemic Sclerosis induced by subcutaneous injection of bleomycin. The effect of shed sCD146, I5-13-sCD146 and I10-sCD146 was estimated and the average of 4-5 different animals was given. Representative pictures are also shown.

D: The aspect of the skin is shown in the different CD146 KO mice treated with bleomycin and injected or not with shed sCD146, I10-sCD146 and I5-13-sCD146.

E: Blood vessels examination in skin of animals treated or not with shed sCD146/I10-sCD146/I5-13-sCD146. Vessels are labelled with isolectin B4. Results are representative of 3 different experiments in the 4-5 animals.

*: P<0.05, : P<0.01, *: P<0.001, experimental vs Control.

Figure 28:
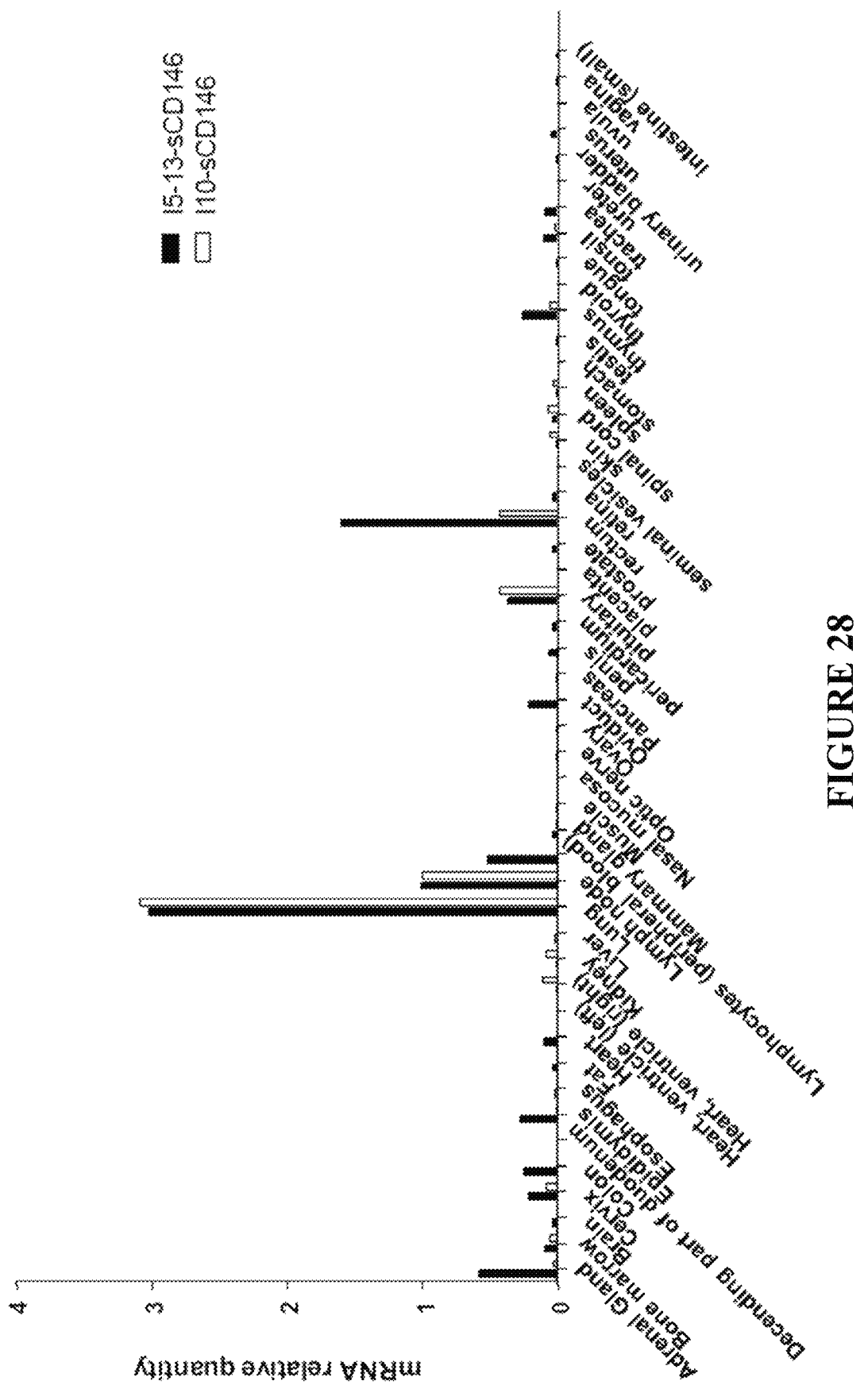

FIG. 28: Expression of I5-13-sCD146 and I10-sCD146 isoforms in normal tissues mRNA expression of I10-sCD146 and I5-13-sCD146 was examined in various organs by tissue array. Results were normalized as a function of the expression in lymph node.

Figure 29:
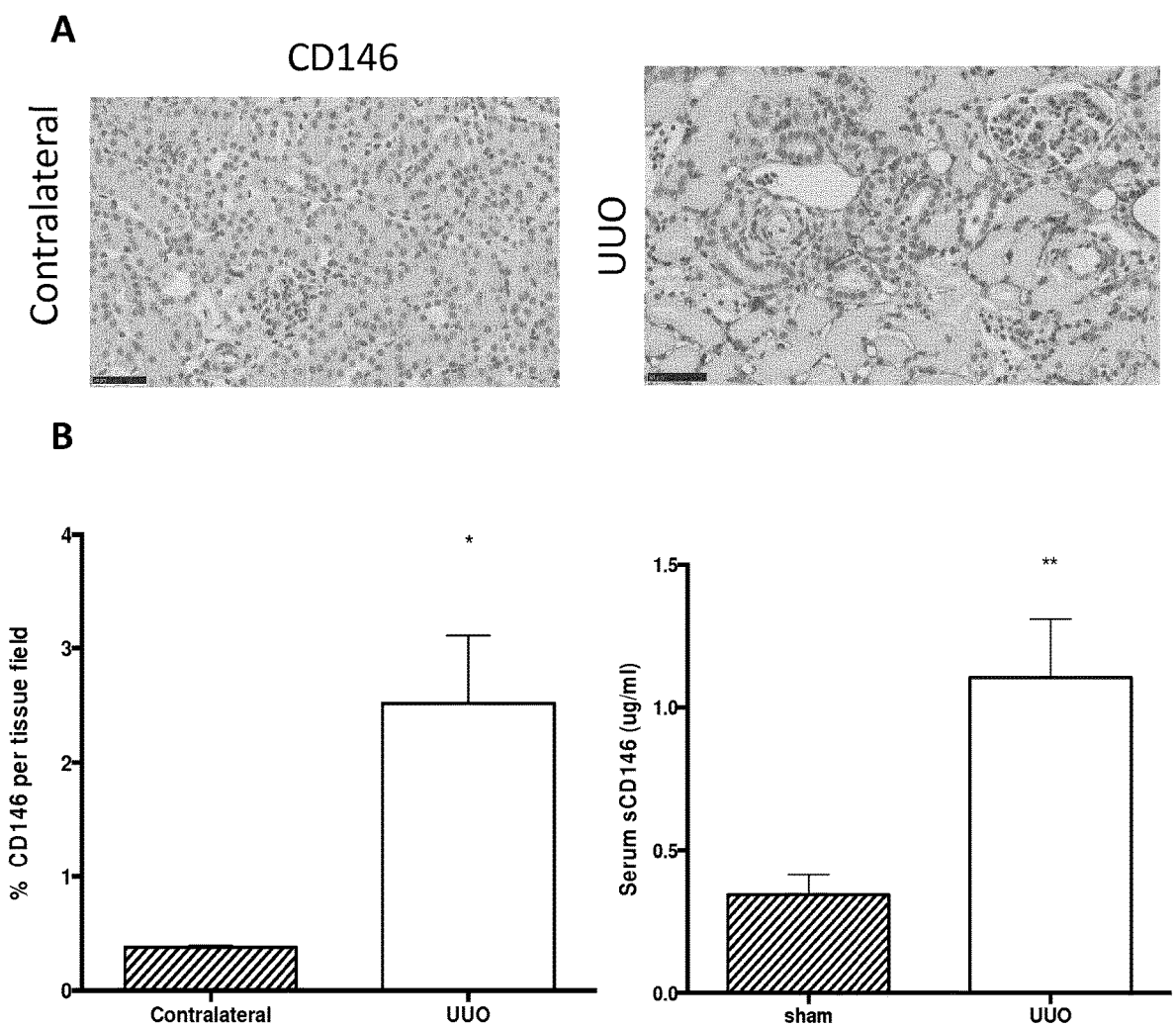

FIG. 29: Effect of UUO on the expression of CD146 and secretion of soluble CD146

A: Expression of CD146 was observed on kidney sections and quantified in kidney with UUO and in the contralateral kidney. Quantification is shown.

B: Soluble CD146 was quantified with ELISA in sham operated and UUO animals. Results are the average of 7 animals.

*: P<0.05; **: P<0.01 UUO vs contralateral

Figure 30:
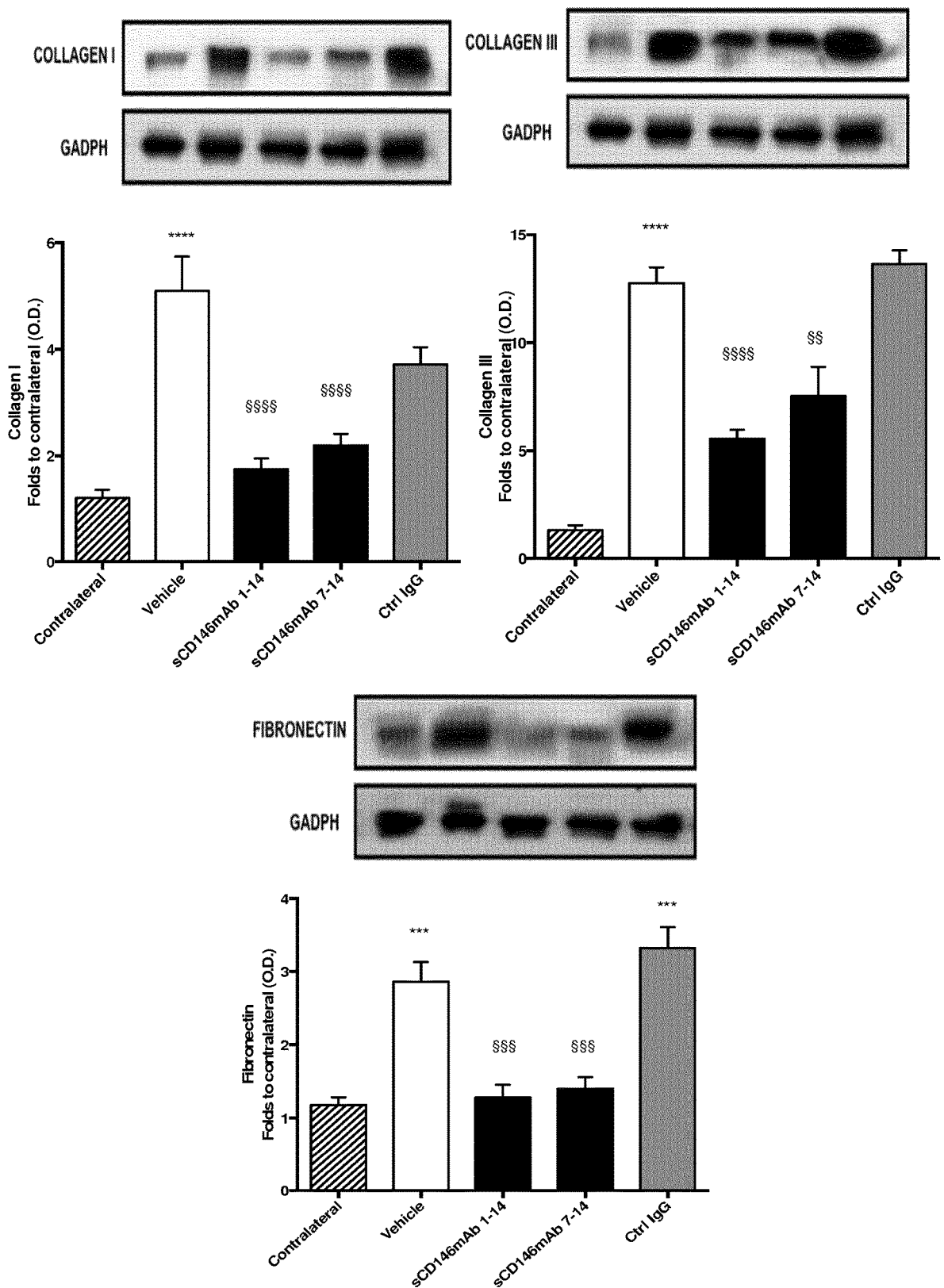

FIG. 30: Effect of antibody treatment on collagen and fibronectin expression The effect of UUO was observed on the protein expression of collagen I, collagen III and fibronectin. Effect of treatment with antibodies was also observed as compared to treatment with control IgG.

Figure 31A:
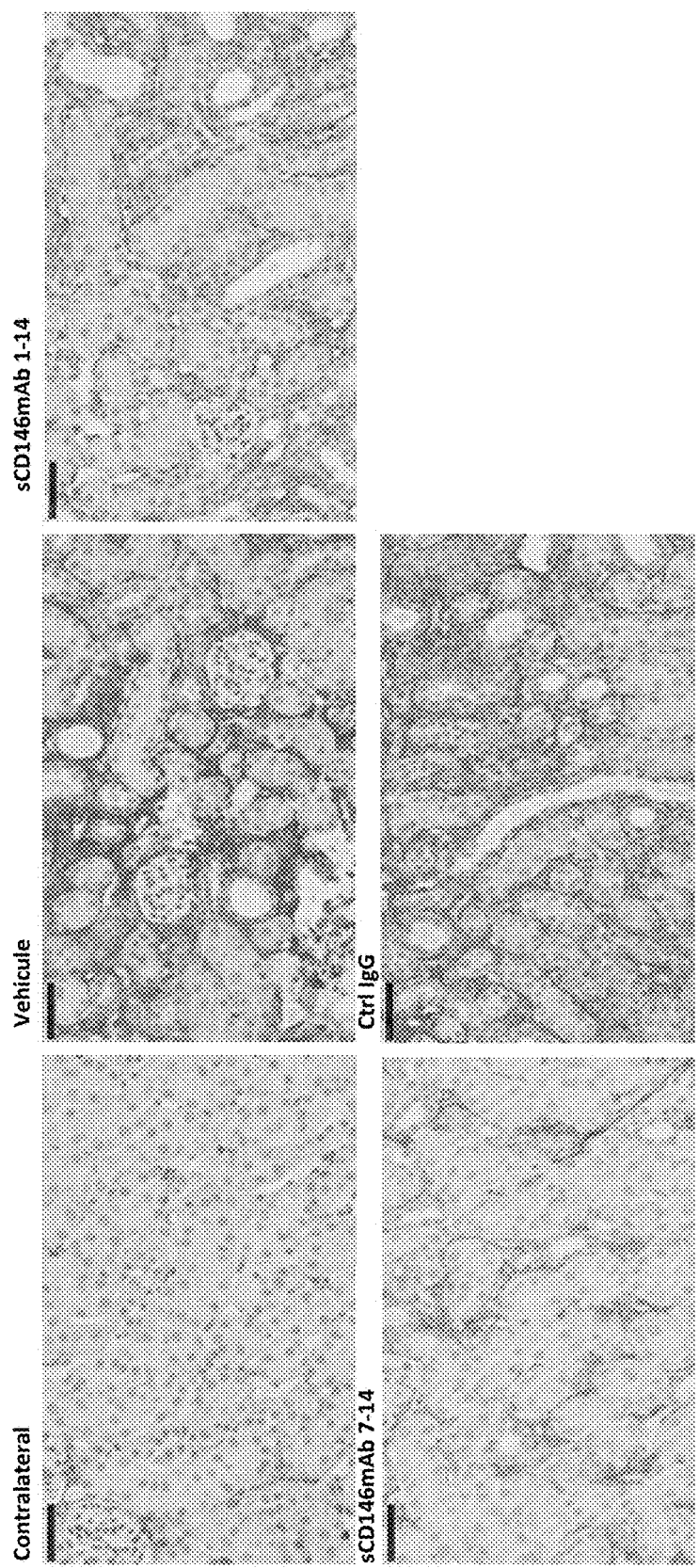
Figure 31B:
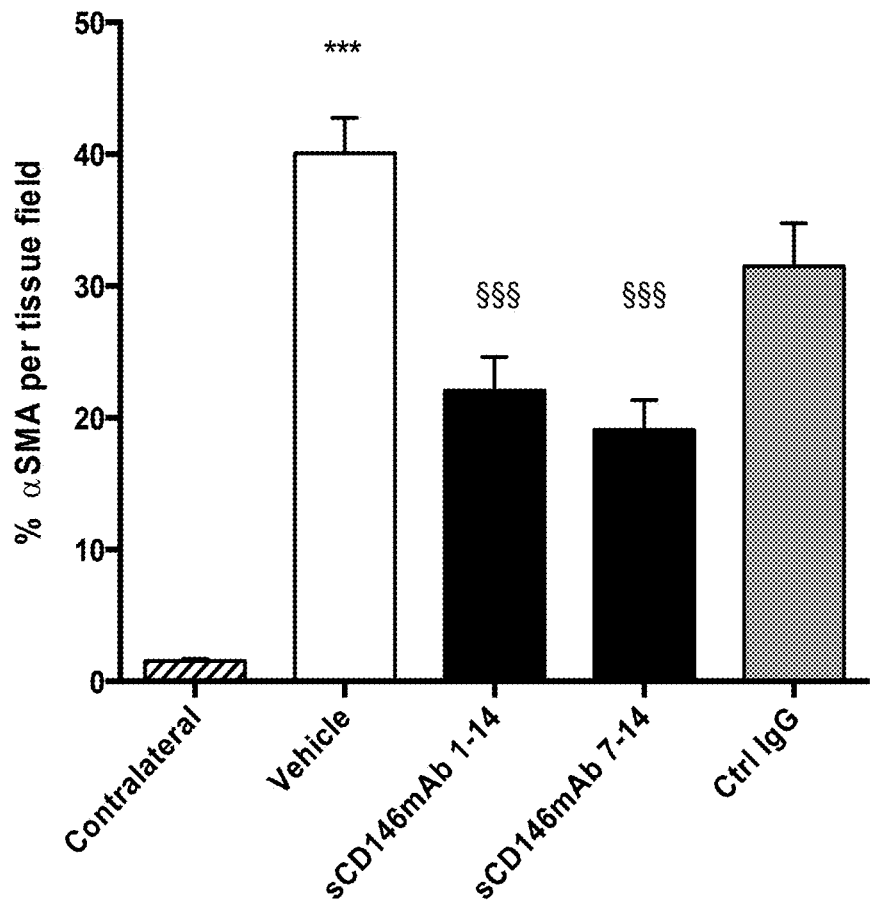

Results are mean values of 7 animals in each group.
\*\*\*\*: P<0.001, vehicle vs contralateral
§ § § §: P<0.001, mAb vs vehicle
\*\*\*: P<0.01 vehicle or Control IgG vs contralateral
§ § §: P<0.01 mAb vs vehicle FIGS. 31A-31B: effect of antibody treatment on α-SMA expression The effect of UUO was observed on the expression of α-SMA by immunohistochemistry (FIG. 31A). Effect of treatment with antibodies was also observed as compared to treatment with control IgG (FIG. 31B).

Figure 32:
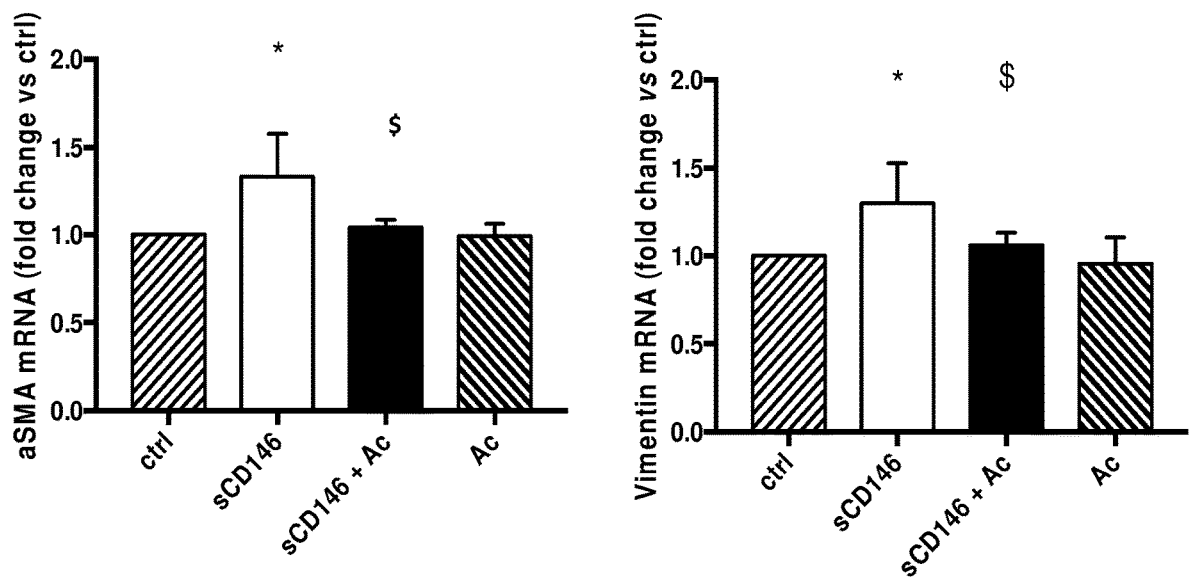

Results are mean values of 7 animals in each group.
\*\*\*: P<0.01 vehicle vs contralateral
§ § §: P<0.01 mAb vs vehicle FIG. 32: Effect of anti-sCD146 mAb on expression of α-SMA and vimentin mRNA expression in primary culture of human renal fibroblasts The effect of sCD146 (50 ng/ml) was examined on primary culture from human fibroblasts. The effect of 500 ng/ml anti-sCD146 mAb administrated either alone (Ac) or with sCD146.

Results are mean values +/−SE of 3 experiments and expressed as fold change versus control condition without treatment.
\*: P<0.05; sCD146 vs control
S: P<0.05; sCD146+Ac vs sCD146

Figure 33:
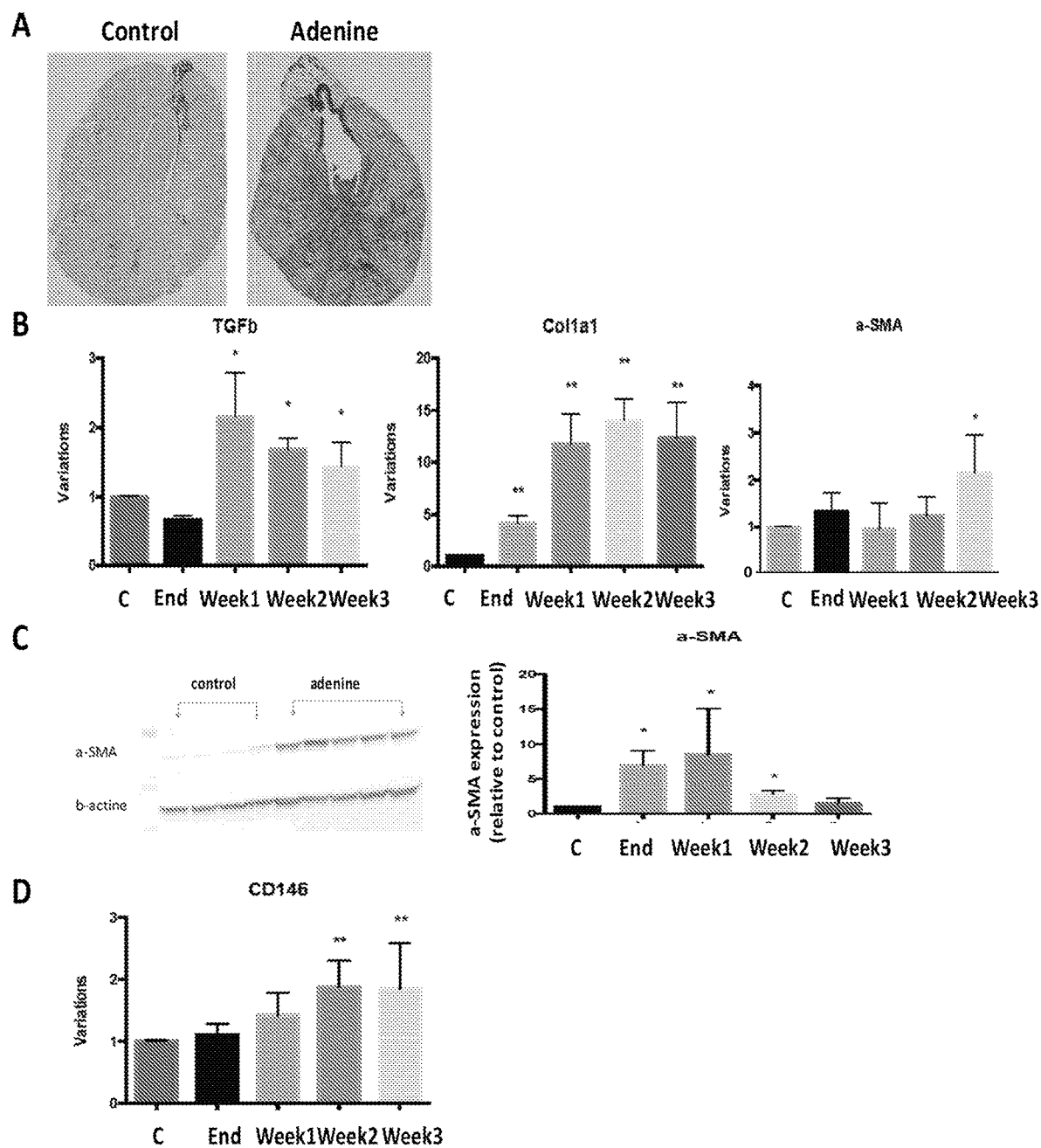

FIG. 33: Effect of the adenine diet on kidney features

A: Animals were treated (adenine) or not (control) with adenine and sacrificed 2 weeks after the end of the adenine diet. Fibrosis was detected in kidneys after coloration with Sirius red. Representative pictures are shown.

B: mRNA expressions of TGFb, Collagen a1 and alpha SMA were analyzed on control kidneys and in kidney just after the adenine diet (End), 1 week after the end of the adenine diet (week1), 2 weeks after the end of the adenine diet (week2) and 3 weeks after the end of the adenine diet (week3). Results are expressed as variations from the control group.

C: Protein expressions of alpha SMA were analyzed on control kidneys and in kidney just after the adenine diet (End), 1 week after the end of the adenine diet (week1), 2 weeks after the end of the adenine diet (week2) and 3 weeks after the end of the adenine diet (week3). Results are expressed as relative to the control group.

D: mRNA expressions of CD146 was analyzed on control kidneys and in kidney just after the adenine diet (End), 1 week after the end of the adenine diet (week1), 2 weeks after the end of the adenine diet (week2) and 3 weeks after the end of the adenine diet (week3). Results are expressed as variations from the control group.

Figure 34:
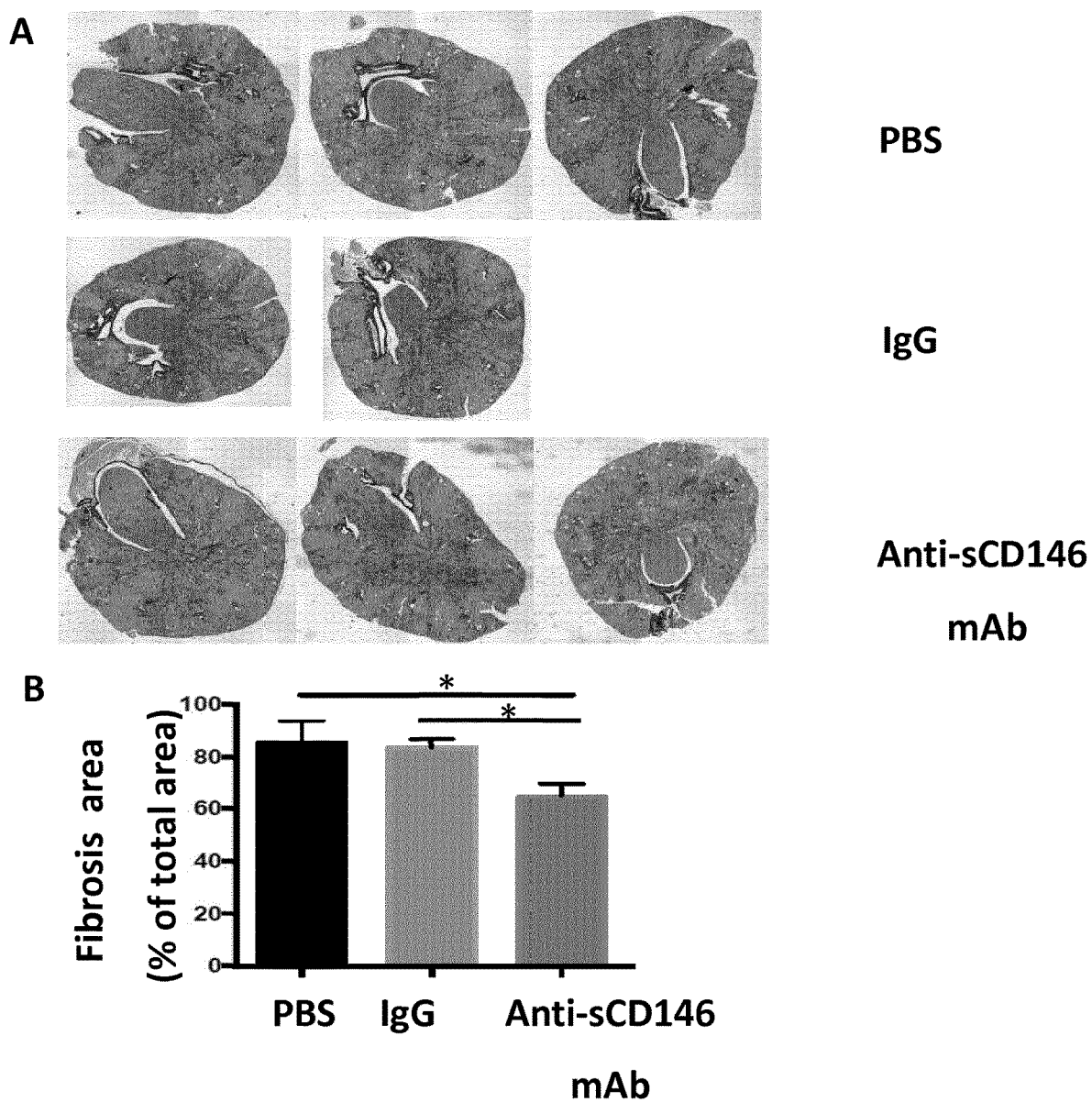

FIG. 34: Effect of anti-sCD146 antibodies on fibrosis in kidneys of mice treated with adenine A: Animals treated with adenine were injected with PBS, control IgG or the anti-sCD146 mAb. Fibrosis was detected in kidneys after coloration with Sirius red 2 weeks after the end of the diet. Representative pictures are shown.

B: Quantification of fibrosis area is expressed as a % of the fibrosis area over the total surface. Results are expressed as means +/−SE of at least 5 sections from 4 animals in each group.

EXPERIMENTAL SECTION

Herein below described experiments in particular show that:
- in two models of severe induction of renal fibrosis (model induced by glomerular basal membrane anti-serum and model of unilateral obstruction of the ureter), CD146 is sensibly increased at the level of the glomerular capillaries and the concentration of sCD146 is strongly increased in the circulating blood; the effect on fibrosis is greatly reduced when using KO mice for CD146 and the effect is prevented or reversed when the animals are injected with anti-sCD146 antibodies;
- in a model of myocardial infarction in mice, CD146 is increased around the area of fibrosis and sCD146 is increased;
- in KO animals for CD146, the amount of fibrosis is reduced after myocardial infarction compared to control animals;
- in elderly mice, the development of cardiac fibrosis is reduced in KO-CD146 mice in comparison with WT mice;
- sCD146 increases in vitro the proliferation of renal and cardiac fibroblasts and induces their transition to myofibroblasts;
- sCD146 induces in vitro an endothelial-mesenchymal transition in renal and cardiac endothelial cells; and
- sCD146 significantly induces in vitro miR21 which is frequently associated with fibrosis.

These results show that sCD146 is secreted abundantly in various pathologies associated with fibrosis, typically fibrotic human diseases, and is involved in the development of interstitial fibrosis by targeting both fibroblasts and endothelial cells. In addition, the phenomenon is prevented or reversed when the animals are treated with an anti-sCD146 antibody.

Example 1—Endothelial-Specific Deletion of CD146 Protects Against Experimental Glomerulonephritis in Mice Materials and Methods Mice Strains CD146-floxed and CD146-KO mice were generated as previously described and backcrossed for more than 10 generations into the C57BL/6J background (Bardin, N, 2009). CD146-floxed mice were first crossed with the B6.Cg-Gt(ROSA)26Sortm6 (CAG-ZsGreen1) Hze/J mice (Jackson laboratories) which express the fluorescent protein ZsGreen1 as a reporter for CRE-recombinase activity. Then, mice with endothelial cell-specific deletion of the CD146 gene were generated by further crossing CD146flox-ZsGreen animals with the Cdh5 (PAC)-CreERT2 mouse strain, a gift from Dr Ralf Adams (Wang, Y 2010). The deletion of the CD146 gene was induced by I. P. injections of tamoxifen diluted in corn oil (10 mg/ml solution, 1 mg tamoxifen/injection) and administered on 3 consecutive days. Primers for genotyping CD146 alleles were of SEQ ID NO: 22: 5'-TCACTTGACAGTGTGATGGT-3' (forward primer used to detect CD146 WT, floxed and KO alleles), of SEQ ID NO: 23: 5'-CCTTAGAAAGCAGGGATTCA-3' (reverse primer used to detect CD146 WT and floxed alleles) and of SEQ ID NO: 24:5'-CCCAAATCCTCTGGAAGACA-3' (reverse primer used to detect CD146 KO allele).

CD146 Analyses in Diverse Human Glomerulopathies

Human kidney biopsies were collected in a multicentre study (European Renal cDNA Bank-Kröner-Fresenius Biopsy Bank, ERCB) and were obtained from patients after informed consent and with approval of the local ethics committees. Pre-transplant allograft biopsies were used as control kidneys. Total RNA was isolated from microdissected glomeruli, reverse-transcribed, and linearly amplified as previously described (Djudjaj, S., 2012). Fragmentation, hybridization, staining and imaging were performed according to the Affymetrix Expression Analysis Technical Manual (Affymetrix, Santa Clara, Calif., USA). A single probe-based analysis tool, Chip-Inspector (Genomatix Software GmbH, Munich, Germany), was used for transcript annotation, total intensity normalization, significance analysis of microarrays (Cohen, C. D 2008) and transcript identification based on significantly changed probes. Pre-developed TaqMan probes (Applied Biosystems) were used for human CD146 and GAPDH detection by qPCR. mRNA expression was analyzed by standard curve quantification.

Nephrotoxic Serum-Induced Glomerulonephritis

Decomplemented nephrotoxic serum (NTS) was prepared as previously described (Mesnard L 2009; Kerroch M, 2012) and 17.5 µl of serum per gram of body weight were intravenously injected over two consecutive days (days 1 and 2). For the time course protocol, two-month old C57Bl6/J females were injected with NTS and sacrificed at day 4, 7 and 15 for tissue collection (n=6 mice for each time point). Six mice were injected with PBS and used as controls.

For the CD146-KO protocol, two-month old CD146-KO female mice and their wild type littermates were used (n=16 per group). Ten mice from each group were injected with NTS and 6 with PBS. Body weight and urine samples were taken at days 0, 4, 8 and 15. All mice were sacrificed at day 15 and blood and tissue samples were obtained.

For the CD146-floxed protocol, ten two-month old female mice were treated with tamoxifen. Six of them were injected with NTS and 4 with PBS. CD146-floxed ZsGreen mice bearing no CRE recombinase transgene were treated with tamoxifen and used as controls. (n=6 for NTS and n=4 for PBS). Body weight and urine samples were taken at days 0, 4, 8, 12 and 15. Mice were sacrificed at day 15 after obtaining blood samples.

All procedures regarding animal experimentation were in accordance with the European Union Guidelines for the Care and Use of Laboratory Animals and approved by the local ethics committee of the National Institute for Health and Medical Research (Institut National de la Santé et de la Recherche Médicale). Animals were housed at constant temperature with free access to water and food.

Histologic and Functional Parameters

Half kidneys from each animal were fixed in 4% formalin solution and embedded in paraffin. 4 µm sections were stained with Masson's trichrome for histological evaluation of renal damage. Tubular dilation was evaluated semi-quantitatively, using the following scale: 0, no tubular damage; 1, damage in 1-25% of the tubules analyzed; 2, damage in 26-50% of the tubules analyzed; 3, damage in 51-75% of the tubules analyzed; 4, damage in >76% the tubules analyzed. Glomerular crescents were measured and expressed as the % number of glomeruli presenting crescents vs total number of glomeruli. Scoring was performed in a masked manner on coded slides by two different investigators. Images were obtained with an OlympusIX83 photonic microscope at ×200 magnification. Interstitial fibrosis was assessed semiquantitatively on Sirius red stained paraffin sections at magnification of ×200. Fibrosis was then quantified using computer-based morphometric analysis software (Analysis, Olympus) that allowed the formation of a binary image in which the stained area could be automatically calculated as a percentage of the image area. BUN and proteinuria levels were measured with an enzymatic method (Konelabautomater) and expressed in millimoles per liter and grams per millimole of creatinine respectively.

Immunostainings

Immunohistochemistry was performed on 4 µm-thick paraffin-embedded tissue sections. Tissue was deparaffinized and 10 mM citric acid, pH6 at 95° C. was used for antigen retrieval. Sections were permeabilized with 0.1% triton/PBS. Antibodies against F4/80 (AbDSerotec) and CD3 (Dako), were used. The F4/80 and CD3 positive area was quantified in at least ten photographs at 200× magnification per animal, using publicly available image processing software (ImageJ; Fiji) and expressed as percentage of the total tissue area Immunofluorescence was performed on 4 µm-thick frozen sections fixed in methanol. CD146 (home-made rat anti-mouse), CD31 (Abcam), Claudin-1 (Thermo Scientific), Nestin (BD Pharmingen), Nephrin (Abcam) anti-rabbit and α-SMA (Sigma Aldrich) anti-mouse antibodies were used. Alexa fluor (Invitrogen) secondary antibodies were used for detection. Images were obtained with an OlympusIX83 photonic microscope at ×400 magnification.

Quantitative Real-Time PCR

Total RNA was extracted from half kidneys using TRI Reagent (MRC). RNA quality was verified by measuring the OD 260:280 ratio and residual genomic DNA was removed by DNase I treatment (Thermo Fisher Scientific) for 30 minutes at 37° C. A total of 1 mg RNA was transcribed to cDNA using the Maxima First Strand cDNA Synthesis Kit from Thermo Fisher Scientific per manufacturer's instructions. Real-time PCR was performed with the Roche Light Cycler 480 detection system using SYBR Green PCR Master Mix (Roche Diagnostics, Indianapolis, Ind.) under the following program: 95° C. for 5 minutes, 45 cycles at 95° C. for 15 seconds and 60° C. for 15 seconds, and 72° C. for 15 seconds. For quantitative analysis, experimental genes were normalized to HPRT expression using the DDCT method. Dissociation curves were analyzed to determine that a single product was amplified. Primer sequences are listed in table 1.

Western Blot

Proteins were extracted from renal tissue using RIPA lysis buffer (Santa Cruz Biotechnology). Western blot for CD146 (Epitomics) were performed using standard techniques as previously described (Bardin et al., 2009). GAPDH (Sigma-Aldrich) was used as loading control.

Statistical Analyses

Values are expressed as mean±SEM. Data were analyzed using one-way analysis of variance followed by protected least significant difference Fisher's test of the Statview software package. Error bars represent mean±SEM for in vivo and mean±SD for in vitro data. Results with P<0.05 were considered statistically significant.

TABLE 1

| | | |
|---|---|---|
| IL-1β | FW: | TGTAATGAAAGACGGCACACC (SEQ ID NO: 25) |
| | RV: | TCTTCTTTGGGTATTGCTTGG (SEQ ID NO: 26) |
| TNF-α | FW: | TCTTCTCATTCCTGCTTGTGG (SEQ ID NO: 27) |
| | RV: | ATGAGAGGGAGGCCATTTG (SEQ ID NO: 28) |
| ICAM-1 | FW: | CCCACGCTACCTCTGCTC (SEQ ID NO: 29) |
| | RV: | GATGGATACCTGAGCATCACC (SEQ ID NO: 30) |
| TGF-β1 | FW: | TGGAGCAACATGTGGAACTC (SEQ ID NO: 31) |
| | RV: | GTCAGCAGCCGGTTACCA (SEQ ID NO: 32) |
| Collagen-3 | FW: | TGGTTTCTTCTCACCCTTCTTC (SEQ ID NO: 33) |
| | RV: | TGCATCCCAATTCATCTACGT (SEQ ID NO: 34) |
| CD146 | FW: | TCCAGTCATCACAGATTGTCG (SEQ ID NO: 35) |
| | RV: | AAACAGGGACAGTGACCTCCT (SEQ ID NO: 36) |
| VCAM-1 | FW: | TGGTGAAATGGAATCTGAACC (SEQ ID NO: 37) |
| | RV: | CCCAGATGGTTTCCTT (SEQ ID NO: 38) |
| MCP-1 | FW: | CATCCACGTGTTGGCTCA (SEQ ID NO: 39) |
| | RV: | GATCATCTTGCTGGTGAATGAGT (SEQ ID NO: 40) |
| Collagen-1 | FW: | GCAGGTTCACCTACTCTGTCCT (SEQ ID NO: 41) |
| | RV: | CTTGCCCCATTCATTTGTCT (SEQ ID NO: 42) |
| HPRT | FW: | GGAGCGGTAGCACCTCCT (SEQ ID NO: 43) |
| | RV: | CTGGTTCATCATCGCTAATCAC (SEQ ID NO: 44) |

Results

CD146 is Induced in Damaged Glomeruli

To assess the expression of CD146 during the progression of glomerular disease, inventors induced a passive nephrotoxic serum glomerulonephritis (NTS-GN) in wild type mice Animals were sacrificed at 4, 7 and 15 days post NTS administration Immunofluorescence showed a weak expression of CD146 in glomeruli of healthy animals (FIG. 1A). CD146 expression progressively increased from day 4 to day 15 in peritubular capillaries and within damaged glomeruli. This upregulation was confirmed by western blotting of renal tissues (FIGS. 1B and 1C). CD146 knock-out mice are protected from nephrotoxic serum-induced glomerulonephritis.

To assess the role of CD146 in GN, we injected NTS in both CD146 WT and KO mice. Mice were sacrificed 15 days post NTS administration. NTS-GN resulted, as expected, in body weight increase after the induction of the disease in WT animals (FIG. 2A). In accordance, renal function was altered since both proteinuria and blood urea nitrogen (BUN) were highly increased (FIGS. 2B and 2C). In contrast, in CD146 KO mice, body weight and BUN increase were blunted. Furthermore, elevation of proteinuria was significantly lower in these mice. Quantification of histological lesions by Masson's Trichrome coloration showed that NTS injection induced less damages in CD146 KO mice (FIG. 2D). Indeed, a significant structural protection in CD146 KO animals was demonstrated by a significant decrease of both crescent formation and tubular dilation compared to WT ones (FIGS. 2E and 2F). Thus, CD146 KO animals were protected from glomerular and tubular lesions induced by NTS-GN, which preserved renal function and reduced proteinuria.

CD146 KO Mice Show Reduced Inflammation and Renal Fibrosis after NTS Injection

Evaluation of inflammatory markers in kidneys by qPCR showed that the induction of IL-1β, TNF-α and ICAM-1 mRNAs was blunted in CD146 KO mice, 15 days after NTS injection (FIGS. 3A, 3B and 3C). Accordingly, F4/80 immunostaining showed less macrophage infiltration in the renal cortex of CD146KO mice (FIGS. 3D and 3E). Furthermore, these animals displayed reduced CD3 cell infiltrates on day 15 (FIGS. 3F and 3G). Consequently, renal fibrosis was limited in mice lacking CD146. Indeed, mRNA expression of fibrotic markers such as TGF-β and collagen III was blunted in CD146 KO mice (FIGS. 3H and 3I). Quantification of Sirius Red colorations confirmed a reduction of renal interstitial fibrosis in these animals (FIG. 3J). Altogether, these data demonstrate that lack of CD146 markedly restricted renal inflammation and renal interstitial fibrosis in NTS-GN.

CD146 is Increased in the Glomerular Endothelium During the Progression of NTS-GN To identify the cell type overexpressing CD146 within damaged glomeruli after aggression, inventors performed colocalization experiments using appropriate markers of the glomerular components, at day 7 post NTS administration. CD146 was slightly expressed at basal conditions in the vascular tuft (FIG. 1A). After induction of NTS-GN, CD146 overexpression colocalized mainly with the endothelial marker CD31/PECAM (FIG. 4A). In contrast, CD146 was not detected in podocytes, as there was no colocalization with nestin (FIG. 4B). It was neither detected in parietal cells, as they did not detect any colocalization of CD146 with Claudin-1 (FIG. 4C), nor in mesangial cells (FIG. 4D). Thus, inventors' data confirmed that CD146 was highly overexpressed mainly within injured glomerular endothelial cells after the induction of the disease.

CD146 Endothelial-Specific Deletion Protects Mice Against NTS-GN

To estimate the impact of the endothelial CD146 overexpression in the progression of NTS-GN, inventors generated the CD146-EC-del mouse strain. CD146 was specifically deleted in the vascular endothelium by interbreeding mice harboring atamoxifen-inducible VE-cadherin Cre-recombinase (Wang, Y, 2010) with CD146flox-ZsGreen mice (FIG. 5A). The specificity of CD146 deletion in endothelial cells was verified by immunofluorescence, after tamoxifen injection and 15 days post NTS administration (FIG. 5B) and further confirmed by qPCR (FIG. 5C). CD146-EC-del mice showed limited increase of body weight, proteinuria and BUN (FIG. 6A-C). This functional protection was accompanied by an overall preservation of renal structure (FIG. 6D), as number of crescents (FIG. 6E) and tubular damage (FIG. 6F) were both dramatically reduced compared to respective controls 15 days after the induction of NTS-GN. Furthermore, F4/80 immunostaining showed reduced monocyte infiltration in the renal cortex of CD146-EC-del mice (FIG. 7A). In accordance, qPCR experiments showed that upregulation of both VCAM-1 and MCP1 were fully abolished (FIGS. 7B and 7C). Subsequently, TGF-β1 and Collagen I mRNAs increased expression was blunted in CD146-EC-del mice compared to control kidneys (FIGS. 7D and 7E). These data demonstrate that endothelial overexpression of CD146 promotes the progression of experimental GN in mice.

CD146 Transcript Numbers are Increased in Human Glomerulopathies

CD146 mRNA expression was analyzed in microdissected glomeruli from renal biopsies of patients suffering from diabetic nephropathy (DN, n=7), minimal change disease (MCD, n=5), IgA nephropathy (IgA, n=27), focal segmental glomerulosclerosis (FSGS, n=10), membranous glomerulonephritis (MGN, n=21), lupus nephritis (SLE, n=32) and rapidly progressive glomerulonephritis (RPGN, n=23). Compared to control biopsies (n=6), damaged glomeruli showed a pronounced transcriptional upregulation of CD146 transcripts (FIG. 8).

DISCUSSION

A variety of chronic inflammatory diseases is associated with disruptions of the inter-endothelial function and junction integrity (Wuthrich R P, 1990). Defects in the organization of endothelial junctions occur also during the progression of chronic renal diseases. Indeed, in biopsies from patients with nephropathies of several etiologies, inventors have previously reported that high expression of endothelial membranous CD146 was associated with endocapillary proliferation, proteinuria and inflammation (Daniel L, 2005). Moreover, increased levels of CD146 was consistent with changes of renal morphometry during the progression of chronic renal failure suggesting that the junctional function supported by CD146 may be altered in these pathological settings. However, the pathological significance of this overexpression remained unclear. Interestingly, in the herein described experiment, increased expression of CD146 appeared to promote renal disease since its deletion protected the kidney from immune aggression and prevent severe renal dysfunction. Inventors demonstrated that CD146 represents a novel therapeutic target against the initiation and progression of glomerulonephritis. In the present experiment CD146 was overexpressed in renal microcirculation but mainly within injured glomeruli since the early stages of the disease. CD146 was also found to be overexpressed within proximal tubules at later time points (FIG. 1A). In inventors' experimental model, the starting point of the disease is the glomerular compartment, CD146 overexpression promoted the development of glomerular and tubulo-interstitial inflammation with renal failure, proteinuria and weight gain. CD146 KO mice were protected against these alterations. CD146 was reported to be expressed in myeloid cells in mice (Despoix, N., 2008). Because colocalization experiments showed that CD146 was mainly overexpressed within injured endothelium, inventors generated a specific endothelial KO of CD146 to discern the specific role of endothelial CD146 in NTS-GN. This clearly demonstrates a major role of the endothelial cells in controlling glomerular damage but also interstitial inflammation. These results are in accordance with inventors' previous study demonstrating that endothelial CD146 is involved in the regulation of monocyte transendothelial migration in vitro (Bardin, N., 2009). Indeed, upon tumor necrosis factor-α stimulation, CD146 expression was increased at both cellular junctions and apical membrane of HUVEC and further contributed to monocyte transmigration through the endothelial monolayer. Similar results were more recently reported in a mouse model of multiple sclerosis, in which targeting endothelial CD146 decreased neuroinflammation by limiting lymphocyte extravasation on the blood brain barrier (Duan, H.; 2013).

Another interesting finding is that renal fibrosis was blunted in both CD146 KO and CD146-EC-del mice. Even if this observation is reported in a model of crescentic GN, which is a rare disease in humans, this is of particular interest as renal fibrosis is the common evolution of all kidney diseases and is highly predictive of the progression of chronic kidney disease (CKD) (Rockey, D. O 2015), Inventors believe that endothelial CD146 plays a key role in the control of the fibrotic process in response to the activation of endothelial cells. Endothelial to mesenchymal transition (Endo-MT) has been proposed to contribute to the accumulation of activated fibroblasts and myofibroblasts in fibrotic kidneys in different models of experimental nephropathy in mice (Zeisberg, E. M., 2008). In this line, the reduction of fibrosis could be partially explained by a reduction in the Endo-MT when CD146 is down-expressed. However, more recent studies demonstrated that the contribution of the Endo-MT program to the emergence of renal fibrosis was moderate (LeBleu, V. S., 2013). Another hypothesis could be the role of CD146 to induce cell activation as it has been described in the epithelial to mesenchymal transition phenomenon in other tissues, a major event in the metastatic dissemination (Zeng, Q., 2012, Liang, Y. K 2017). Inventors believe that soluble CD146 (sCD146) released by activated endothelial cells stimulates fibroblast proliferation and transition to a myofibroblast phenotype, leading to renal extracellular matrix deposition and fibrosis. GN is recognized as the second most frequent cause of end-stage renal disease (ESRD) worldwide (Chadban, S. J., 2005). Despite aggressive immunosuppressive therapies, rapidly progressive GN can lead to irreversible renal damage with CKD and frequently ESRD. Considering the need for therapeutic targets to withhold glomerular damage and tubulo-interstitial inflammation and fibrosis in GN, inventors used a powerful experimental tool haring some features with human glomerulopathies to investigate the role of CD146 in renal inflammatory injury. Indeed, injection of sheep serum rich in immunoglobulins against glomerular antigens induces an immediate inflammatory response characterized by the renal infiltration of cells of the immune system, followed by severe glomerular damage and rapid loss of renal function (LuqueY., 2017; El Machhour F., 2015; Mesnard L., 2014; Toubas J., 2011; Mesnard L., 2009). This is a robust model of rapidly progressive renal disease as mice are dying the latest 4 weeks after the induction of the disease (Kerroch M., 2012; Kavvadas 2017). Thus, the advantage of this model of GN is that it can be used to delineate the pathogenic processes leading to immune nephritis, over a quick time frame and allowed to identify several factors that potentially dictate disease severity. This has important clinical implications, both from the perspective of genetic susceptibility as well as clinical therapeutics (Fu Y, 2007). Indeed, several mediators such as cytokines, chemokines, adhesion molecules, surface receptors and extracellular matrix proteins have been shown to play a crucial role in mediating the inflammatory response in CKD (Tang WW, 1994; Le Hir M., 1998; Schwarting A., 1998; Kitching A R, 1999; Karkar A M, 2001; Kishimoto T. 2005; HeniqueC., 2016; Prakoura N., 2017). Thus, a major finding of inventors' study is that CD146 deletion is beneficial in this model of GN since in both CD146 KO and CD146-EC-del mice the progression of the disease was blunted. The therapeutic interest of specific inhibitory tools against CD146 is reinforced by the exaggerated expression of this junctional molecule within glomeruli in biopsies of patients suffering from different type of GN in comparison with healthy controls (FIG. 8). Inventors results support a major role of the endothelium in kidney to control the aggression towards all the compartments, glomeruli but also tubules. They demonstrated that endothelial CD146 plays a major role in the progression of GN and that targeting this junctional molecule represents a good therapeutic strategy to prevent the progression of acute GN towards chronic kidney disease.

Inventors also quantified in vivo the expression of CD146 in kidney sections by immunohistochemistry and the secretion of sCD146 by Elisa in the plasma of UUO (Unilateral Ureteral Obstruction)animals as compared to sham operated animals (FIG. 29). Results show that CD146 is significantly increased in kidney with UUO as compared to the contralateral kidney and that sCD146 is significantly increased in UUO animals as compared to sham-operated animals.

The effect of UUO was observed on collagen I, collagen III and fibronectin expression. Results (FIG. 30) show that UUO increased the expression of these proteins. Of interest, treatment with the anti-sCD146 antibodies before UUO or one week after UUO decreased collagen and fibronectin expression as compared to control IgG, showing that antibody treatment prevented collagen and fibronectin deposition.

The effect of UUO was observed on α-SMA expression. Results (FIGS. 31A-31B) show that UUO increased the expression of α-SMA. Of interest, treatment with the anti-sCD146 antibodies before UUO or one week after UUO decreased α-SMA expression as compared to control IgG, showing that antibody treatment prevented fibroblast activation.

The effect of anti-sCD146 treatment was observed on the mRNA expression of α-SMA and vimentin in human renal fibroblast in (in vitro) culture. Results (FIG. 32) show that treatment with the anti-sCD146 antibodies (500 ng/ml) inhibited the sCD146 induced increase in α-SMA and vimentin mRNA expression observed with sCD146.

Example 2—the Establishment of Cardiac Fibrosis is Associated with an Increase in the Expression of CD146/CD146s in a Model of Myocardial Infarction Inventors showed that, in vivo in the animal, the establishment of cardiac fibrosis is associated with an increase in the expression of CD146/CD146s in a model of myocardial infarction. They also show that, in vitro, CD146s induced differentiation of cardiac fibroblasts into myofibroblasts with effects comparable to those of TGF-β. Therefore, CD146/CD146s constitutes a novel therapeutic target aimed at limiting and/or reversing the cardiac fibrosis process.

Materials and Methods
I In Vivo Studies
The role of CD146/CD146s is examined using two murine models of cardiac fibrosis:
A first model of cardiac fibrosis induced by myocardial infarction.
A second model of constitutive cardiac fibrosis in older animals.

a) Model of Cardiac Fibrosis Induced by Myocardial Infarction

This first model was established in collaboration with the team of Doctor Francesca Rochais (CR, INSERM, UMR S 910). Mice are anaesthetized by intraperitoneal injection of a mixture of ketamine, xylazine and atropine. The animal is then intubated and placed under artificial respiration. The thorax of the animal is incised, the pericardium is opened, and permanent ligation of the left descending coronary artery is performed. Cardiac ischemia is visualized by the bleaching of the left ventricular apex under the ligation point. The thorax of the animal is then closed, and the animal is placed in a recovery cage. The survival rate of animals having undergone myocardial infarction is on average 50%. All operations are performed on 12-week-old C57BL6 males separated into 2 groups:
C57BL6-Sham mice (n=3): the animals are anaesthetized and intubated before undergoing thoracotomy without ligation of the coronary artery.
C57BL6+MI mice (n=3): the animals undergo a complete surgical procedure for inducing myocardial infarction.

All mice (SHAM and MI) are sacrificed 21 days later. The animals are anaesthetized with isoflurane, weighed, and an intracardiac blood sample is drawn before sacrifice by cervical dislocation. The hearts and the tibiae of the animals are removed.

b) Model of Constitutive Cardiac Fibrosis During Ageing
Experiments are carried out on 24-month-old female transgenic C57Bl/6 mice not expressing CD146 (CD146-KO; n=5) in comparison with C57BL/6 mice expressing CD146 (n=5). After sacrifice, the heart of each animal is removed. The hearts are prepared for histological (n=3) and immunohistochemical analysis or immediately frozen at 80° C. in order to perform RNA or protein extraction (n=1).

c) Examination of Cardiac Function
Cardiac function of the animals is evaluated using Doppler echocardiography (VisualSonicsVevo 2100, 550D probe) performed at CERIMED. Measurements were taken from images captured in M mode successively in the longitudinal (long axis) then the transverse (short axis) direction. The following parameters are measured: diastolic volume, systolic volume, for calculating the systolic ejection fraction.

d) Histology and Immunohistochemistry
Tissue preparation: The harvested hearts are rinsed with cold PBS solution, cryofixed in isopentane first cooled in liquid nitrogen, and stored at −80° C. Serial 7-μm-thick sections are cut with a cryostat through the horizontal plane of the heart so as to visualize the four cardiac chambers on the histological sections.

Sirius red staining: The sections are fixed for 3 minutes with formaldehyde (4% diluted in phosphate buffer, pH 7.4) then stained with Sirius red. The sections are immersed in Sirius red for 1 hour then staining is differentiated in acetic acid solution (0.5% in double-distilled water), dehydrated in increasing alcohol baths, cleared in xylene and mounted in resinous mounting medium (Entellan). The slides are observed under an Olympus BX-40 microscope and photographs are taken with an Olympus DP-21 camera.

Quantification is performed using the ImageJ software. After exclusion of vascular structures, the area fraction occupied by collagens (in %) is expressed by relating the area occupied by the red-stained collagens to the total tissue area.

In total, 3 sections are stained for each animal (4 animals per group) and 4 fields (×20) photographed exclusively in the left ventricle of each animal are quantified.

Determination of myocardial cell size using wheat germ agglutinin (WGA): After rehydration, the tissue sections are incubated for 45 minutes in a solution containing WGA and DAPI (1/5000) then rinsed before being mounted in aqueous medium. The slides are read on a fluorescence microscope (Nikon). The images taken are analysed using the ImageJ software. Three sections are stained for each animal (3 animals per group) and 4 fields (X20) photographed exclusively in the left ventricle of each animal are quantified. The area of the cells is determined by measuring the size of cells whose nuclei are centered.

Immunohistology

The sections are thawed and then fixed in acetone cooled for 10 minutes. For the sections for which the primary antibody is an antibody produced in a species other than the mouse, a conventional immunohistochemistry procedure was used. It consists of several steps:

A step of blocking endogenous peroxidase activity. The sections are incubated for 15 minutes in 0.6% $H_2O_2$ diluted in methanol.

A step of blocking nonspecific staining which consists in incubating the sections for 20 minutes at room temperature with normal serum from the species in which the secondary antibody was produced (5% in PBS).

The sections are then incubated in a solution containing the primary antibody, the dilution and the incubation time of which are specified in Table2.

TABLE 2

Primary antibodies and conditions for use in immunohistochemistry.

| | Item number | Dilution | Incubation time |
|---|---|---|---|
| CD146 | Abcam-75769 | 1/250 | 1 h |
| CD31 | BD Pharmingen-553370 | 1/200 | 2 h |
| α-SMA | Dako-0851. | 1/30 | 30 min |

Next, the sections are incubated in the secondary antibody solution. All operations use biotinylated antibodies (Table3).

TABLE 3

Biotinylated antibodies and conditions for use in immunohistochemistry.

| | Item number | Dilution | Incubation time |
|---|---|---|---|
| Anti-rat | BA-4000 | 1/200 | 2 h |
| Anti-rabbit | BA-1100 | 1/200 | 2 h |

The sections are placed in contact for 30 minutes with a solution containing the preformed avidin-biotin complex (Vector). Detection of peroxidase is carried out with DAB (Sigma). The sections are counterstained with hemalum (Mayer) and then dehydrated and mounted (Entellan).

Concerning the sections for which the primary antibody is an antibody produced in the mouse, a commercial kit (Vector M. O. M.) was used to neutralize the mouse IgG in order to reduce the background noise related to the use of an antibody produced in the mouse on mouse tissue.

e) Molecular Biology Analysis

The hearts are placed on ice and then opened to remove the blood clots formed in the ventricular cavities.

Tissue RNA extraction

The ground tissue obtained (100 mg) is taken up in 1 mL of QIAzol and then homogenized for 30 seconds with a Polytron on ice. A 200-μL volume of chloroform is added to the homogenate; after vigorous shaking, the samples are centrifuged at 12000 g for 15 minutes. The supernatant is collected, and the RNA is precipitated by the addition of 500 μL of isopropanol. The RNA is pelleted by centrifugation at 4° C., 12000 g, for 10 minutes. The RNA pellet obtained is washed with 75% ethanol and then taken up in 200 μL of RNase-free water. The amount of RNA is measured at 260 nm using a spectrophotometer (NanoDrop).

Reverse Transcription

Reverse transcription is performed using a High-Capacity cDNA Reverse Transcription Kit (Applied Biosystems) from 500 ng of RNA taken up in 10 μL of $H_2O$ to which is added a mixture containing dNTPs, oligo(dT)s, random primers, and MultiScribe reverse transcriptase enzyme.

The mixture is incubated in a Mastercycler Gradient device for 10 minutes at 25° C. and then 120 minutes at 37° C. Finally, the reaction is inactivated for 5 minutes at 85° C. The cDNA obtained is immediately frozen at −80° C.

Real-Time Polymerase Chain Reaction (qPCR)

PCR is performed using the Power SYBR Green PCR Master Mix Kit (Thermo Fisher Scientific). To that end, 10 ng of cDNA is added to a mixture containing 250 nM right and left primers targeting the gene of interest (Table 4) and 12.5 μL of buffer containing Taq polymerase, dNTPs and SYBR Green.

TABLE 4

PCR primers used.

| Gene of interest | Species | Right 5'-3' sequence | Left 5'-3' sequence |
|---|---|---|---|
| Collagen I | Mouse | CAATCACCTGCGTACAGAA (SEQ ID NO: 45) | TTCTGTACGCAGGTGATTG (SEQ ID NO: 46) |
| α-SMA | Human | GGCATAGAGGGAGAGCAC (SEQ ID NO: 47) | TTCGGGGAGAGGTGATGTTC (SEQ ID NO: 48) |
| Collagen I | Human | GTGCTAAAGGTGGCAARGGT (SEQ ID NO: 49) | ACCAGGTTCACCGCTAC (SEQ ID NO: 50) |
| Fibronectin | Human | ATTGCCCAATTGAGTGCTTC (SEQ ID NO: 51) | TGATGCTTGGAGAAGCTGTG (SEQ ID NO: 52) |

TABLE 4-continued

PCR primers used.

| Gene of interest | Species | Right 5'-3' sequence | Left 5'-3' sequence |
|---|---|---|---|
| HPRT | Human | GAGCTATTGTAATGACCAGTCAACAGGG (SEQ ID NO: 53) | GGATTATACTGCCTGACCAAGGAAAGC (SEQ ID NO: 54) |

Amplification is performed on the StepOnePlusthermocycler (Thermo Fisher). The samples are subjected to 40 cycles each composed of: 5 minutes at 95° C. (denaturation), 10 seconds at 95° C. (primer hybridization) and 30 seconds at 60° C. (polymerization). Fluorescence is read at the conclusion of each cycle. After determination of Ct values, the relative expression of each of the genes studied is calculated.

II. In Vitro Studies

Maintenance and Stimulation of Cardiac Fibroblasts

Human cardiac fibroblasts (HCFs) (PromoCell) are grown in Fibroblast Growth Medium 3 Supplement Pack (PromoCell) in an environment at 37° C. with controlled atmosphere. The HCFs are grown between passages 3 and 7.

To perform the stimulations, the fibroblasts are seeded at a density of 30 000 cells/cm$^2$ in complete culture medium. After 24 hours of adhesion, the cell culture medium is replaced with medium not containing growth factor (minimal medium) for 4 hours.

This medium is then replaced with minimal medium supplemented with 25, 50, 75 or 100 ng/mL of CD146s or with 2.5, 5 or 10 ng/mL of TGF-β for the proliferation study.

Cell Proliferation

Cell proliferation is determined using a proliferation kit (BrdU Assay, Roche). An anti-BrdU antibody diluted 1/100 in its diluent solution is incubated for 90 minutes at 37° C. After removal and rinsing of excess antibody, a second antibody directed specifically against anti-BrdU and coupled to peroxidase is incubated for 30 minutes at room temperature and then removed. Detection is performed by the addition of 100 μL of enzyme substrate. The reaction is stopped by addition of 50 μL of 0.1 M H$_2$SO$_4$ solution. Staining intensity, proportional to BrdU incorporation, is read on a spectrophotometer at 450 nm. The results are calculated by subtracting the background noise observed in a culture well containing no cells but having received the same amount of BrdU. Percentage of proliferation is then calculated for each condition. For each experiment, the results obtained for 6 wells per condition are averaged.

RNA Expression

Total mRNA is extracted using a purification kit (RNeasy Mini, Qiagen) then eluted in 30 μL of RNase-free water. The amount of RNA is measured at 260 nm using a spectrophotometer (NanoDrop). The RNA is then converted to cDNA using 200 ng of RNA and according to the same protocol as the tissue RNA. The gene expression study is performed by real-time PCR from 10 ng of cDNA (Table 4).

Protein Expression

The cells are lysed at 4° C. in a buffer composed of 10 mMTris-HCl (pH 8), 1 mM EDTA, 150 mMNaCl, 10% NP40, containing a protease inhibitor cocktail (Pierce, Thermo Scientific). The cell lysate obtained is centrifuged at 4° C. and 15000 g for 10 minutes. The supernatant containing solubilized proteins is collected and the amount of proteins determined using a calibration curve of bovine serum albumin (BSA) prepared from a 1 mg/mL BSA solution diluted in the lysis buffer used during sample preparation.

The samples to be assayed and the standards (25 μL) are deposited on a 96-well plate and 200 μL of BCA reagent (BCA Assay Kit, Pierce) is added. Absorbances are read at 550 nm and the protein concentration of the samples of interest is determined using the calibration standards.

The samples are then used in western blot experiments. To that end, an aliquot containing 30 μg of proteins is taken up in 4× Laemmli buffer containing a reducing agent (Invitrogen) and then heated for 10 minutes at 75° C. before being deposited on an electrophoresis gel (NuPAGE 4-12% Bis-Tris Gel, Invitrogen). After migration of the samples, the proteins are dry-transferred to a nitrocellulose membrane (iBlot 2, Invitrogen). The membrane is blocked for 45 minutes with a Tris buffer containing 0.1% Tween 20 (TBS-T) and 4% BSA. The primary antibody (Table 5) diluted in TBS-T is hybridized for 12 hours at 4° C. and then rinsed for 3×10 minutes with TBS-T. The HRP-coupled secondary antibody (TBS-T) is hybridized for 1 hour. After rinsing, HRP activity is detected using a chemiluminescent substrate (ECL, Pierce). An antibody directed against a normalizing protein (β-tubulin), the expression of which is not modified by the experimental conditions, makes it possible to normalize the quantification and then to express the results semi-quantitatively (% control). Emitted light is captured with a camera (G:BOX). The proteins of interest are visualized as black bands on a white background. The signal thus obtained is quantified by densitometry (Image Lab Software version 4.1) (Table 5).

TABLE 5

Antibodies used in western blot.

| Antibody I | Species | Dilution | Item number |
|---|---|---|---|
| GAPDH | Mouse | 1/5000 | Santa-Cruz-32233 |
| α-SMA | Mouse | 1/2000 | Dako-0851 |

Immunofluorescence

The cells are fixed for 5 minutes in 70° ethanol at 4° C. and then rinsed with PBS. After 1 hour of blocking in a PBS solution containing 5% BSA, the primary antibody (anti-α-SMA, Dako-0851) diluted 1/50 and then the secondary antibody (anti-mouse antibody) coupled to a fluorescent molecule (Alexa Fluor 488) are incubated for 1.5 hours. Rinses with PBS are performed between each step. The cells are mounted in an aqueous medium containing a nuclear stain (ProLongMountant with DAPI, Invitrogen) before being observed under a fluorescence microscope.

Results

I. Study of CD146/CD146s Expression in Two Models of Cardiac Fibrosis

The objective of the first part of this work was to study the expression of CD146/CD146s during cardiac fibrosis. To that end, inventors relied on a model of cardiac fibrosis induced by myocardial infarction and a model of constitutive cardiac fibrosis observed in older animals.

a) Cardiac Fibrosis Induced by Myocardial Infarction

Expression of Cardiac Fibrosis

Sirius red staining (FIG. 13B) reveals a fibrosis zone located at the periphery of the left ventricle of the animals. The densest zone of this collagen deposition (Fibrous or Fibrotic Zone) located at the infarcted zone no longer contains cardiomyocytes. Around this fibrosis zone, this deposition is interstitial and gradually extends into the border zone or area ("BZ" or "BA") between cardiomyocytes within the left ventricle in the MI animals.

Expression of mRNA Encoding CD146

An analysis of CD146 RNA expression (FIG. 13C) is performed by RT-PCR from microdissected tissue in the infarcted/fibrotic zone ("IZ" or "FZ"), immediately proximal to ("BZ") then distal to/remote ("DZ" or "RZ") this zone. The results obtained are compared with those obtained with RNA extracted from the left ventricle of SHAM animals. The results show that, overall, CD146 expression is increased in the left ventricle of MI animals compared with SHAM individuals. Analysis of each zone of the heart shows that CD146 expression is in particular significantly increased by a factor of 3 in the tissue zone located immediately proximal to the infarcted zone (BZ).

Immunodetection of CD146

In SHAM mice, CD146 staining is uniform and located exclusively at the periphery of myocardial cells (FIGS. 14A and 14B). In MI mice, CD146 expression is low within the fibrosis zone and remains associated with the vascular structures present in this zone (FIG. 14, "IA"). Conversely, CD146 expression is very high around the fibrotic area ("FA" or "BA"), (FIG. 14, "BA"). This perifibrotic staining, observed at the tissue scale, reveals the presence of a gradient of CD146 expression with an intensification of staining in the bordering zone and its marked decrease in the remote area ("DZ" or "RA") (FIG. 14, "IM"). Observation at high magnification shows that, in the periphery of the fibrosis zone, CD146 expression is located in the cytoplasm of myocardial cells (FIG. 14, "BA" or "BZ") and that it is substantially increased in cells located at the periphery of these cardiomyocytes.

Serum Assay of CD146

A first serum assay of CD146 (FIG. 14B) was performed from blood samples taken by intracardiac puncture in SHAM and MI animals (n=2). The preliminary results obtained show that soluble CD146 is increased in animals with MI-induced cardiac fibrosis. These first results remain to be confirmed on a new cohort of animals.

b) Model of Cardiac Fibrosis During Ageing

Expression of Fibrosis.

Sirius red staining (FIG. 15, e) shows a marked increase in staining of sections derived from hearts of older mice (24 months of age) compared with younger mice (3 months of age). The ageing of the animals is accompanied by an increase in perivascular and interstitial collagen deposits.

Immunodetection of CD146

In the model of age-related cardiac fibrosis (24 months of age), CD146 expression (FIG. 15, 1) is homogeneous and increased relative to 12-week-old SHAM animals. This increase in CD146 is located within cardiomyocytes as well as in cells located at their periphery.

II. Role of CD146 in the Development of Cardiac Fibrosis

Animals not expressing CD146 (CD146-KO) generated in the laboratory are used to show the role of CD146 in the development of cardiac fibrosis during ageing.

This study was performed on a group of WT animals (n=4) in comparison with 2-year-old female CD146-KO animals (n=4).

Cardiac Fibrosis

In WT animals, Sirius red staining reveals the presence of an accumulation of collagen between myocardial cells which isolates them from each other (FIG. 16A, a). Observation of histological sections from CD146-KO animals reveals that collagen deposition is much lower and results in the absence of individualization of myocardial cells (FIG. 16A, b). Quantification of Sirius red (FIG. 16A, c) confirms that there is a roughly 50% decrease in collagen deposition in CD146-KO animals compared with WT animals. This result is confirmed by RT-PCR analysis of type I collagen RNA expression from the heart of an animal from each experimental group.

Cardiomyocyte Size

WGA staining (FIG. 16B) makes it possible to specifically stain cell membranes and then to determine the size of cells within a tissue. Inventors' results show that myocardial cells located in the left ventricle of WT animals are larger than those of CD146-KO animals (FIG. 16B, a). This observation is also confirmed by quantification of the area of stained cells (FIG. 16B, b). Therefore, in WT mice, cardiomyocyte area is about twice that quantified in CD146-KO mice, reflecting a marked reduction of cardiomyocyte hypertrophy in these animals.

III. Role of CD146 in Acquisition of the Myofibroblast Phenotype

Observation of an increase in CD146s in MI animals and the reduction in cardiac fibrosis associated with the absence of CD146 led inventors hypothesize a role of CD146s in the recruitment/differentiation of cardiac cells resident in myofibroblasts (myoFB). Inventors thus tested the effect CD146s in differentiation of cardiac fibroblasts into myoFB.

To that end, they studied the effect of CD146 on the expression of markers associated with the myoFB phenotype (proliferation, expression of α-SMA and of fibrotic matrix proteins). All these experiments were performed using as control TGF-β, a known inducer of activation of fibroblasts into myoFB.

a) Effect of CD146s on Cell Proliferation of Cardiac Fibroblasts (HCFs)

The effect of increasing amounts of CD146s was tested on proliferation of cardiac fibroblasts (FIG. 17A). The results obtained show a significant, dose-dependent increase in cell proliferation. The maximum pro-proliferative effect of CD146s is obtained for 50 ng/mL of CD146s. This amount has been used for the subsequent experiments. This CD146s-induced increase in proliferation is comparable to that observed when the cells are stimulated by 5 ng/mL of TGF-β.

b) Effect of CD146s on α-SMA Expression

Modulation of α-SMA expression was examined in response to stimulation of HCFs by 50 ng/mL of CD146 for 48 hours.

Semiquantitative analysis of the RNA expression level shows that CD146s induces a significant (n=4), 2.5-fold overexpression of α-SMA, comparable to the induction observed when these cells are stimulated by 5 ng/mL of TGF-β (FIG. 17B). These results correlate with the analysis of α-SMA protein expression performed by western blot. Thus, 50 ng/mL of CD146 also induces a 2.5-fold increase in α-SMA protein expression level (FIG. 17C).

Indirect immunofluorescence performed using an antibody directed against α-SMA shows that this increase in α-SMA expression induced by 50 ng/mL of CD146 is associated with establishment of a smooth muscle actin network which invades the cytoplasm of the HCFs and whose organization is comparable to that of the α-SMA network observed in response to stimulation by TGF-β (FIG. 17D).

c) Effect of CD146s on Expression of Matrix Proteins

Semiquantitative RT-PCR analysis of the expression of RNAs encoding two of the matrix proteins expressed by myoFB shows that CD146s induces an increase in synthesis of fibronectin and of type I collagen (FIG. 17E) comparable to that observed in response to stimulation by TGF-β.

d) Effect of CD146s on Expression of TGF-β

The increase in expression of markers associated with the myofibroblast phenotype in response to stimulation of HCFs by CD146s (FIG. 17F) suggests that this effect could be the result of an induction of TGF-β expression. Inventors thus began a study relating to the mechanisms involved in this effect by studying the effect of TGF-β on CD146 expression. The first results (n=2) show that 50 ng/mL of CD146s induces a 2-fold increase in CD146 expression.

DISCUSSION

Cardiac fibrosis is a wound healing process which develops spontaneously in response to certain forms of heart disease such as myocardial infarction or during ageing. At present, there is a paucity of effective treatments for cardiac fibrosis, which makes this objective a major public health issue.

Inventors studied the role of CD146/CD146s in the development of cardiac fibrosis in order to consider its use as therapeutic target. They were able to show in vivo on two murine models (of myocardial infarction and of ageing) and in vitro on human cardiac fibroblasts (HCFs) that CD146/CD146s indeed has an impact on the development of cardiac fibrosis.

Inventors results show that, in MI and older animals, cardiac fibrosis is associated with overexpression of CD146. In MI animals, cardiac fibrosis, which is located at the apex and which spreads to the left ventricle, is accompanied by CD146 overexpression not in the infarcted zone but in the proximal zone with an expression gradient that decreases with distance from this zone. This overexpression of tissue CD146 is accompanied by an increase in secretion of CD146s. It is known that CD146s is generated essentially by a mechanism of cleavage of the membrane form of CD146 (Bardin et al., 2003), which could explain the concomitant increase in these two forms.

Furthermore, they were able to observe in the ageing model that the development of cardiac fibrosis is also associated with an overexpression of CD146. Indeed, the results show an increase in interstitial collagen deposition in the 24-month-old mice, which correlates with a homogeneous increase in CD146 expression throughout the left ventricle. The use of CD146-KO animals in this model confirms these results by showing a reduction in interstitial collagen deposition. Moreover, in CD146-K0 animals, the cardiomyocyte hypertrophy visible in SHAM mice is markedly decreased. In the ageing model, they confirm the action of CD146/CD146s in the appearance of constitutive cardiac fibrosis.

Cardiac fibrosis is a process that requires time to become established. Indeed, reparative fibrosis occurs in a succession of three interdependent phases: an inflammatory phase, then a proliferation phase, and finally a maturation phase. Inventors results show that CD146s induces myofibroblast differentiation with an increase in cell proliferation when the cells are stimulated withsCD146. Furthermore, this stimulation is identical to that obtained during stimulation with TGF-β, a known factor in differentiation of fibroblasts into myofibroblasts. Moreover, CD146s induces an increase in the expression of α-SMA, of fibronectin, and of type I collagen, which are markers characteristic of myoFB. These overexpressions are also comparable to those found after stimulation with TGF-β. All these results show that CD146s participates in differentiation of fibroblasts into myoFB.

Inventors preliminary results also show that CD146s is able to increase TGF-β expression, which suggests a relationship between these two molecules. The study of TGF-β expression after stimulation by CD146s will make it possible to understand one of the potential mechanisms of the molecule and to determine whether TGF-β and CD146s have additive or synergistic effects.

Other processes giving rise to myofibroblasts exist, notably differentiation of endothelial cells into mesenchymal cells by the EndoMT process. Prospective work in vitro will thus be to study the effect of CD146s on this cellular process by analysis of the expression of endothelial markers (PE-CAM-1, VE-cadherin, etc.) in comparison with mesenchymal markers (α-SMA, vimentin, fibronectin, type I collagen, etc.).

At present, there is a paucity of effective therapies for controlling cardiac fibrosis. Inventors herein show that the action of CD146/CD146s constitute a target for its treatment. Antibodies directed specifically against the soluble form of CD146 were generated by inventors. These antibodies have a blocking effect, i.e., they are able to suppress the effects of CD146s.

Example 3—Different Pro-Angiogenic Variants of Soluble CD146 are Secreted by Endothelial Cells Through Shedding and Alternative Splicing: Properties and Involvement in Fibrosis Soluble CD146 constitutes a major molecule involved in physiology and pathology, in particular to control angiogenesis. Inventors therefore investigated 1/ the mechanism of shedding of long and short CD146 isoforms that generates sCD146 in endothelial cells; 2/ the potential existence of spliced variants of sCD146; 3/ their respective functions, in particular in the regulation of angiogenesis and fibrosis; and 4/ their involvement in Systemic Sclerosis.

Methods

Cells

Endothelial Colony Forming Cells (ECFC) were cultured in endothelial EGM-2 MV medium as previously described (Delorme B et al., 2005).

HUVEC were obtained as previously described and were cultured in EGM2 medium (Kaspi et al., 2017). MEF (Mouse Embryonic Fibroblasts) were isolated from day 13. Embryos from CD146 KO or WT mice were isolated and cultured as previously described (Xu J., 2005).

Cell Proliferation Assay

Experiments were performed as previously described (Stalin et al., 2013).

Endothelial Cell Tube Formation in Spheroids

Formation of spheroid experiments was performed as previously described (Korff T. et al., 2001).

Co-Immunoprecipitation Experiments

Experiments were performed as previously described (Stalin et al., 2016).

b-Catenin/TCF Transcription Assay

Luciferase assay was performed as previously described (Kaspi et al., 2017).

Chorio-Allantoic Membrane Assay

The chorio-allantoic membrane of the chick embryo assay (CAM) was performed using a previously described protocol (Beckers et al., 1997).

Lipid Raft Preparation

Lipid rafts were isolated as previously described (Tellier et al., 2006) by sucrose density gradient centrifugation of cells treated with non-ionic detergents.

Animal Model of Systemic Sclerosis and Histological Analysis

Male CD146 KO mice (11-16 weeks) were treated with subcutaneous bleomycin and were compared with littermates WT mice as previously described (Kaspi et al., 2017).

Mice skin sections were fixed in 4% formalin and embedded into paraffin. Dermal thickness was quantified using a stereological method using a Merz grid as previously described (Kaspi et al., 2017).

siRNA Experiments

SiRNA designed to silence the different isoforms of sCD146 were generated. A control siRNA was also used in each experiment. siRNAs were introduced in endothelial cells using the Silence magmagnetofection kit as described by the manufacturer (OZ Biosciences). Silencing resulted in about 80-95% of protein expression as a function of the experiments. Sequences of the different siRNAs are given in table 6

TABLE 6

| | |
|---|---|
| siTACE | sens: 5'CAGGAUUUAAAGGUUAUGGAA<br>antisens:<br>5'UUCCAUAAACCUUUAAAUCCUG |
| siADAM10 | sens: 5'GAAUGGUAGAACAAGGUGAtt<br>antisens:<br>5'UCACCUUGUUCUACCAUUCCA |
| siMT1MMP | sens: 5'GCGAUGAAGUCUUCACUUAdTdT<br>antisens: 5'UAAGUGAAGACUUCAUCGC |
| sishCD146 | sens: 5'CAGGAGAUGGAGAGAAAUACAUCGA<br>antisens:<br>5'UCGAUGUAUUUCUCUCCAUCUCCUG |
| silgCD146 | sens: 5'CCCGUCUCGUAAGACCGAACUUGUA<br>antisens:<br>5'UACAAGUUCGGUCUUACGAGACGGG |
| siI10-sCD146 | sens: CCCUCCCUCUGGGUAGAGACCAGGU<br>antisens:<br>ACCUGGUCUCUACCCAGAGGGAGGG |
| siI5-13-sCD146 | sens: UGGACAUCUAGACGGCUGCUCGUUU<br>antisens:<br>AAACGAGCAGCCGUCUAGAUGUCCA |

RNA Isolation, Reverse Transcription and Real Time PCR

Total cellular RNA was isolated from cells, reverse transcribed into cDNA and the resulting cDNA was subjected to qPCR. Forward and reverse specific primer sequences are given in table 7.

TABLE 7

| | |
|---|---|
| GAPDH | F: GGTGGTCTCCTGACTTCAACA<br>R: GTTGCTGTAGCCAATTCGTTGT |
| CD146sh | F: CCACTGGCCTCAGCACTTCC<br>R: CTACTCACCTTTCTGGACAG |
| CD146lg | F: TGGTTTGTACACCTTGCAGAGTATTC<br>R: TGGGCAGCCGGTAGTTG |

TABLE 7-continued

| | |
|---|---|
| MT1MMP | F: TAGCGCTTCCTTCGAACATT<br>R: GCAGAAGTTTTACGGCTTGC |
| MMP2 | F: TGATCTTGACCAGAATACCATCGA<br>R: GGCTTGCGAGGAAGAAGTT |
| Tace | F: GCATTCTCAAGTCTCCACAAG<br>R: CTGGGAGAGCCAACTAAGC |
| ADAM10 | F: CAGAGTGCACACCAGGAGAA<br>R: CCCAGGTTTCAGTTTGCATT |
| I10-sCD146 | F: GGCAGAGGAAGAGACAACCA<br>R: TTGGGGTGACCTGGTCTCTA |
| I5-13-sCD146 | F: GGACATCTAGACGGTGCTC<br>R: ACAAATGCAAGCTGGAAACC |

Western-Blot Analysis

Membranes were probed with specific primary antibodies (7A4 1/3000, actin 1/5000, Tace and ADAM10 1/1000, I10-sCD146 and I5-13-sCD146 1/250) followed by secondary antibodies coupled to peroxidase. Blots were revealed with the ECL substrate (Pierce).

Quantitative Flow Cytometry

The level of membrane expression of the different isoforms of CD146 was determined by labeling cells with the antibody or the isotype matched control antibody coupled to fluorescent dye (10 µg/ml) for 1 h at 4° C. After washing, samples were analyzed by flow cytometry (Gallios™ Flow Cytometer, Beckman Coulter, Villepinte). The results were then analyzed using Kaluza software (Kaluza® Analysis Software, Beckman Coulter).

Plasmid Transfection Experiments and Clone Selection

Plasmids encoding for the different proteins were introduced in CHO cells using Fugen kit as described by the manufacturer (Promega). Stable clones were then selected with Geneticin and FACS and western blot or RT-PCR analysis was performed to identify the clone with the highest expression.

Tissue Array

TissueScan Human Normal Tissue qPCR Arrays (OriGeneTechnologies, Rockville Md.) were used to screen for I5-13-sCD146 and I10-sCD146 expression in 48 different tissues and following manufacturer's instructions.

ELISA

Shed sCD146 was assayed using the commercial ELISA assay (CY-QUANT sCD146, Biocytex, Marseille). Plates were coated with specific mouse monoclonal anti-human CD146 F(ab')2 fragments. 10 µL of sera was added to each well and incubated for 30 minutes at room temperature. After incubation, the plates were washed five times, followed by incubation with a specific HRP-coupled monoclonal antibody (7A4-HRP, 1 mg/ml, Biocytex, Marseille, France) at a 1:1 000 dilution in a specific diluent for 30 minutes at room temperature and then washed five times. 200 µL of tetramethylbenzidine (TMB) substrate was incubated for approximately 20 minutes at room temperature. The colorimetric reaction was then stopped by the addition of 100 µL of an acid solution. The intensity of the signal was directly related to the concentration of sCD146 initially contained in the sample. For detecting the two spliced isoforms of sCD146 (I5-13-sCD146 and I10-sCD146), the same immunoassay was used (Biocytex). The protocol was modified only for the second antibody (detection antibody) that was replaced by the anti-I5-13-sCD146 or anti-I10-sCD146 antibodies coupled to HRP.

Measurement of Endothelial Permeability

ECFC were seeded at 60,000 cells per well on membrane inserts (porosity 1 μm) of a 24-multiwell double chamber system (Multiwell Insert System, BD Biosciences, Le Pont de Claix, France) after siRNA transfection or not. Confluent endothelial monolayers were then incubated for 24 h in EGM-2 medium in the presence or absence of the different forms of sCD146. The FITC-dextran (sigma) was added at the apical surface of the cells and was allowed to migrate for 1.5 h at 37° C. Basolateral FITC-dextran was then measured using a Cytofluor Series 4000 Fluorescence (PerSeptiveBiosystems, Framingham, MA).

Immunofluorescence Experiments

The localization of the different isoforms of CD146 and ADAM10/Tace was examined in cells seeded on coverslip. Cells were fixed 10 minutes with paraformaldehyde at room temperature, then permeabilized with saponin (0.2%) then incubated during 30 minutes at room temperature with the anti-CD146 antibodies (1/100) and anti-Tace (1/200) or anti-ADAM10 (1/100) antibodies. Cells were then incubated with a secondary antibody associated to a fluorescent probe. In some experiments, the nucleus was stained with DAPI. Cells were then examined by confocal microscopy (Zeiss 510).

In sections of muscles from ischemic mice, vascularisation was visualized with isolectin B4 (Lifetechnologies) (1/100). Tissue sections were examined by fluorescence microscopy (Leica sp5, Leica, Nanterre, France).

Histological Analysis

The chorio-allantoic membrane of the chick embryo assay (CAM) was surgically removed and fixed in 10% buffered formaldehyde for 10 hours, dehydrated in graded alcohol, cleared in xylene and embedded in paraffin. 5 μm thick sections were cut in a plane parallel to the surface of the CAM and stained by hematoxylin-eosin which was observed under a light photomicroscope.

Induction of Hind Limb Ischemia in Mice

Female mice were subjected to unilateral hind limb ischemia by complete resection of the entire left femoral artery. After surgery, animals were split in four treatment groups: one control group injected in ischemic adductor muscles twice a week with PBS for 28 days; three experimental groups treated as the control groups with the three different recombinant human soluble CD146 (rh-sCD146, rh-I5-13-sCD146, rh-I10-sCD146) 2 μg.

Laser Doppler Blood Flow Analysis

The ratio of the ischemic versus normal hind limb blood flow was measured using a laser doppler blood flow analyzer. At different time points post-surgery (days 1, 3, 7, 14, 21 and 28), animals were subjected to 3 consecutive laser scannings over the regions of interest (leg and feet). Blood flow was expressed as the ischemic versus normal hind limb ratio.

Angiographic CT Imaging Studies

The animals were deeply anesthetised with mix of Ketamine Xylasine (100 mg/kg and 10 mg/kg respectively) and perfused intracardially with 2 ml of lipiodole. CT 3D images were obtained with a microPET/microCT rodent model scanner (nanoPET/CTO, Mediso) with features below: 70 kVp energy, exposure time of 300 ms and 720 projections and were quantified.

Subjects

Sera from 24 SSc patients admitted to internal medicine departments in Marseille (France) were analyzed. All patients fulfilled the 2013 ACR/EULAR Classification Criteria for Scleroderma and were then sub classified according to LeRoy et al criteria. As controls, inventors studied the sera of 24 age and sex matched blood donors. All samples came from a declared Biobank (DC 2012-1704) with respect of ethical directives and were stored to −80° C. prior to use.

Ethics Committee Approval

The animal experiments conformed to the directive 2010/63/EU of the European Parliament and were approved by the Institution's Animal care and Use Committee (Aix-Marseille University). The procedures described above were conducted under an institutional approved animal use protocol (Marseille Ethical Committee) and under the supervision of an authorized researcher (B. Guillet; n° 13328).

The experiments on human samples were performed retrospectively on plasmas from patients with Systemic Sclerosis. They were performed in accordance with the Helsinki declaration of 1975, revised in 1983, approved by relevant institutional review board and informed consent of the patients was obtained. B. Granel and N. Bardin analyzed the data and all authors had an access to primary clinical data.

Peptides, Plasmids, Antibodies, and Inhibitors

The recombinant human soluble form of CD146 corresponding to the shed sCD146 (rh-sCD146) was obtained from Biocytex. The rh-I5-13-sCD146 and rh-I10-sCD146 arise from the purification on the column of protein tagged with HA peptide (Trial Kit 3320A, MBL).

The plasmid encoding for Tace was from Dr F. Peiretti, UMR-S1062, Marseille, France.

The plasmid encoding for ADAM10 was a kind gift from Dr B. Charreau, UMR-S1064, Nantes, France. Polyclonal antibodies against I5-13-sCD146 and I10-sCD146 were generated by Covalab company by injecting peptides corresponding to the specific parts of the two proteins [NH2-C-YLDGPLPTPVDNPR—CONH2 (SEQ ID NO: 101) and NH2-C-RDQVTPSGVVFKLFDKKP—CONH2 (SEQ ID NO: 102), respectively]. Antibodies against ADAM-17 (ab2051), ADAM-10 (EPR5622), CD146 (clone 7A4) andactine were respectively purchase from Abcam, Millipore, Biocytex and Cell signaling.

GM6001 was from Selleck chemicals.

Statistical Analysis

Data were expressed as mean±SEM of the indicated number of experiments. Statistical analysis was performed with the Prism software (GraphPad Software Inc., San Diego, Calif.). Significant differences were determined using non parametric Mann Whitney test. A P-value <0.05 was considered as significant.

Results

Different Variants of Soluble CD146 are Generated by Shedding of the Membrane Isoforms of CD146 and Alternative Splicing in Endothelial Cells.

Secretion of soluble CD146 (sCD146) was increased in endothelial cells in response to different stimuli as TNF, VEGF, netrin, TGFb, Wnt5a (FIG. 21A). As TNF produced the higher effect, inventors analyzed sCD146 secretion in control condition and after treatment with TNF. Experiments were performed in the absence or presence of the pan-matrix metalloprotease inhibitor GM6001 in order to estimate the relative contribution of shed and spliced forms. Results showed that the GM6001-dependent part of sCD146 corresponds to around 75% of the total secretion. Therefore, 25% of the total secretion corresponds to a GM6001-resistant secretion (FIG. 21B).

Inventors performed the same type of experiments in the presence of a furin convertase inhibitor (IF). They observed that both in control and TNF conditions, IF inhibited sCD146 secretion. Of interest, in both conditions, the fraction of the secretion resistant to IF was similar (FIG. 21C).

Finally, they used different TIMP to inhibit sCD146 secretion (FIG. 21D). Results showed that TIMP-1 (1 µg/ml) was able to reduce sCD146 secretion in both conditions, TIMP-3 (1 µg/ml) was able to reduce sCD146 secretion only when the cells were treated with TNF, and no effect of TIMP-2 (1 µg/ml) was observed.

Altogether, these experiments show that 1/two different mechanisms of shedding are involved to generate sCD146 from short and long CD146, and 2/the residual fraction of sCD146 secretion resistant to GM6001 (about 25%) could depend on another mechanism, as the generation of variants of sCD146 generated by alternative splicing of the primary transcript.

Long CD146 Isoform Generates Soluble CD146 Trough an ADAM10-Dependent Shedding in Endothelial Cells Inventors analyzed the influence of long (IgCD146 siRNA) and short (shCD146 siRNA) CD146 siRNA on sCD146 secretion in endothelial cells in control condition. They observed (FIG. 22A) that, whereas IgCD146 siRNA reduced sCD146 secretion by around 75%, there was no effect of shCD146 siRNA. This indicates that in control condition, only the long CD146 isoform is involved in sCD146 secretion through a shedding process. In view of the inhibitory effects of TIMPs on sCD146 secretion in control condition (effect of TIMP-1), they tested the effect of siRNA targeting ADAM10, MT1-MMP and MMP-2. The effect of siRNA targeting Tace was also tested, as a control. Results (FIG. 22B) showed that only ADAM10 siRNA was able to inhibit sCD146 secretion and that the effect was similar to that of GM6001.

To confirm this result, inventors performed a co-immunoprecipitation experiment and showed that, in control condition, IgCD146 co-immunoprecipitated with ADAM10 whereas shCD146 and ADAM10 did not (FIG. 22C). By immunofluorescence, inventors showed that IgCD146 colocalized with ADAM10, both at the junction of endothelial cells and in the perinuclear area, in confluent ECFC. They were also colocalized in the intracellular compartment in non-confluent cells. The colocalization of IgCD146 and ADAM10 at the cellular junction in confluent cells was confirmed in another endothelial cell type, HUVEC. In contrast, shCD146 did not colocalize with ADAM10 in confluent cells.

In order to assess whether long and short forms of CD146 can complement each other, inventors silenced IgCD146 with siRNA and observed the effect on the other form. Silencing IgCD146 did not modify shCD146 mRNA expression. This is in agreement with the different localisations of the two isoforms in the endothelial cells. Inventors also analyzed the effects of ADAM10 silencing or over-expression on the mRNA expression of the two CD146 isoforms. ADAM10 silencing or over-expression did modify neither the long nor the short CD146 mRNA expression.

As IgCD146 is essentially expressed at the junction, inventors tested the effect of ADAM10 silencing and over-expression on the cellular permeability, as determined by dextran permeability (FIGS. 22E and F). Results show that treatment of ECFC with ADAM10 siRNA or transfection of the cells with the ADAM10 plasmid decreased and increased their permeability to dextran, respectively, whereas treatment with Tace siRNA or transfection with Tace plasmid did not modify it. To estimate the potential contribution of ADAM10 that is independent of CD146 cleavage, inventors performed a permeability experiment in which they compared the effect of ADAM10 over-expression in endothelial cells in the presence or absence of long CD146 siRNA. Results show that ADAM10 over-expression and long CD146 siRNA transfection significantly increased endothelial permeability. When cells were transfected with long CD146 siRNA and ADAM10 over-expressed, the effect on permeability was not significantly different from that observed in the presence of long CD146 siRNA alone. This suggested that ADAM10 essentially acted on long CD146 to control permeability in these cells.

To confirm these results, inventors expressed IgCD146 isoform in CHO cells (which do not express CD146) by transfecting the plasmid containing this isoform. A stable clone expressing a high amount of IgCD146 was selected. This clone was transitory transfected with a plasmid encoding for ADAM10 and the effect was observed on sCD146 secretion. Results show that, in the presence of ADAM10, sCD146 secretion was significantly increased. Finally, the effect of ADAM10 transfection was observed on the permeability of CHO stably transfected or not with IgCD146 (CHO-IgCD146 and CHO—C, respectively). Results showed that the permeability of CHO-IgCD146 was significantly increased in the presence of ADAM10 whereas there is no effect of ADAM10 on CHO—C.

Altogether these experiments show that, in endothelial cells, long CD146, which is expressed at the junction, is shed through ADAM10 to generate sCD146.

Short CD146 Isoform Generates Soluble CD146 Trough a Tace-Dependent Shedding in Endothelial Cells Inventors analyzed the influence of long (IgCD146 siRNA) and short (shCD146 siRNA) CD146 siRNA on sCD146 secretion after 24 h of treatment with TNF 20 ng/ml by comparison with the control condition. They confirmed (FIG. 23A) that, in control condition, only IgCD146 siRNA reduced sCD146 secretion and observed that, under TNF, both IgCD146 and shCD146 siRNA reduced sCD146 secretion by about 60% and 25%, respectively. They thus used different siRNA to identify the proteinases involved in shCD146 shedding. In view of the effects of TIMPs on sCD146 secretion under TNF (inhibition by TIMP-1 and TIMP-3), they tested the effect of siRNA targeting ADAM10, MT1-MMP and Tace. Results (FIG. 23B) showed that both ADAM10 siRNA and Tace siRNA were able to inhibit sCD146 secretion, with an additive effect when added simultaneously. Of interest, ADAM10 and Tace siRNA reduced sCD146 secretion by 60% and 25%, respectively, as observed with IgCD146 and shCD146 siRNA. This result suggested that, as IgCD146 was shed by ADAM10, shCD146 could be shed by Tace.

To confirm this hypothesis, inventors performed a co-immunoprecipitation experiment and showed that under TNF, shCD146 co-immunoprecipitated with Tace whereas IgCD146 co-immunoprecipitated with ADAM10. By immunofluorescence, they showed that shCD146 colocalized with Tace in ECFC cells under TNF. In confluent cells, shCD146 colocalized with Tace at the membrane and in the nucleus, whereas, in non-confluent cells, they essentially co-localized around the nucleus and at the membrane ruffles of migrating cells. In contrast, IgCD146 did not colocalize with Tace in confluent cells. As shown for the long CD146 isoform, silencing shCD146 did not modify IgCD146 mRNA, suggesting that both isoforms did not complement each other. Inventors also analyzed the effects of Tace silencing on the mRNA expression of the two CD146 isoforms. Tace silencing did modify neither the long nor the short CD146 mRNA expression.

As shCD146 was recently described to be present in lipid rafts of endothelial cells, and as Tace was also described in this cellular fraction, inventors analyzed the lipid raft fractions of ECFC in control condition and under TNF. In these experiments, GM6001 10 μM was added to the cells in order to avoid the shedding of the molecule. Results show that, in control condition, no shCD146 was observed in lipid rafts. In contrast, under TNF, both shCD146 and Tace were present in this cellular fraction. To confirm these results, inventors expressed shCD146 isoform in CHO cells by transfecting the plasmid containing this form. A stable clone expressing a high amount of shCD146 was selected. This clone was transitory transfected with a plasmid encoding for Tace and the effect was observed on sCD146 secretion. Results showed that in the presence of Tace, sCD146 secretion was significantly increased. Altogether, these experiments show that, in endothelial cells, short CD146 is shed through Tace to generate sCD146 in inflammatory condition (TNF).

Identification of Two New Variants of Soluble CD146 Generated by Alternative Splicing in Endothelial Cells Since inventors observed that a fraction of the sCD146 secretion was GM6001-insensitive and was thus independent of the shedding of the membranes forms of CD146 (See FIG. 21), they hypothesized that this fraction could be due to the generation of additional forms of sCD146 generated by alternative splicing of the primary transcript. To test this hypothesis, they performed RNA seq on ECFC cells. Results showed the existence of at least two additional isoforms of sCD146. One of these isoforms contained the intron 10 of the molecule (I10-sCD146 isoform). Another one contained both the introns 5 and 13 of the molecule (I5-13-sCD146 isoform). FIG. 24A gives a schematic representation of these two isoforms in comparison with the shed form and SEQ ID NO:8/19 and SEQ ID NO: 9/20 give the sequences of these isoforms (I5-13 and I10 respectively)

Inventors verified the expression of I10-sCD146 and I5-13-sCD146 transcripts in ECFC and in other endothelial cells, HUVEC. Results show that both transcripts are present in ECFC and HUVEC (FIG. 24B) and that they are expressed as protein as demonstrated by immunofluorescence on ECFC and by western-blot in ECFC supernatants. Inventors tested the effect of the different stimuli that did affect membrane CD146 shedding (see FIG. 21A) on the mRNA expression of the two spliced variants. Of interest, they are differentially modulated. Indeed, I5-13-sCD146 was up-regulated at the mRNA level by TNF and Wnt5a and was not modified by the shed form of CD146, VEGF, TGFb, netrin and Wnt3a. In contrast, I10-sCD146 was not up-regulated at the mRNA level by these different factors. The mRNA level of I10-sCD146 variant was even down-regulated by VEGF, netrin and Wnt3a (FIG. 24C).

In order to evaluate the interaction between these new splice variants and the expression of the other CD146 isoforms, inventors performed siRNA experiments. Results show that neither long CD146 siRNA nor short CD146 siRNA influenced the expression of I10-sCD146 or I5-13-sCD146 at the mRNA level. Likewise, siRNA against I10-sCD146 or I5-13-sCD146 did not modify short or long CD146 mRNA expression. Finally, treatment of endothelial cells with recombinant I10-sCD146 or I5-13-sCD146 proteins did not modify the expression of short CD146, long CD146, I5-13-sCD146 and I10-sCD146 at the mRNA level. These data are in favour of the fact that the different isoforms do not complement each other.

Altogether, these experiments show that, in addition to the shedding of the membrane CD146 isoforms, sCD146 is also generated as two novel spliced variants of the primary transcript.

I5-13-sCD146 and I10-sCD146 Isoforms of Soluble CD146 Display Pro-Angiogenic Effects In Vitro and In Vivo Since ECFC constitute a useful model for ex vivo angiogenesis studies, inventors evaluated the effect of the two spliced sCD146 isoforms (II 0-sCD146 and I5-13-sCD146) on ECFC proliferation. Experiments were performed in the presence of GM6001 in order to prevent membrane CD146 shedding and thus to observe only the effects of these novel isoforms. Results showed that both siRNA targeting I10-sCD146 and I5-13-sCD146 inhibited the proliferation of ECFC (FIG. 25A). The efficiency of both siRNA was verified. Plasmids encoding for both isoforms were also transfected into ECFC to examine their effect on proliferation. Results (FIG. 25B) show that both plasmids significantly increased the proliferation. The angiogenic potential of these two sCD146 isoforms was also estimated after generation of the recombinant proteins. Recombinant I10-sCD146 and I5-13-sCD146 proteins (rh-I10-sCD146 and rh-I5-13-sCD146, respectively) were produced and characterized. Their effect was tested on the proliferation of ECFC and compared to that of the recombinant shed sCD146 form (rh-sCD146) (FIG. 25C).

Results show that rh-I10-sCD146, rh-I5-13-sCD146 and rh-sCD146 increased endothelial cells proliferation, even if the effect of rh-I5-13-sCD146 appeared to be of lower magnitude. They also increased vascularisation in a chorio-allantoic membrane assay (FIG. 25D). Inventors performed experiments of capillary-like formation in 3D (spheroid experiments) with the three recombinant proteins. Results show that the three recombinant proteins increased the ability to generate pseudo-capillaries, as measured by the number of sprouts and cumulative sprout length (FIG. 25E). Here again, the effect of I5-13-sCD146 appears to be of lower magnitude, as compared to shed sCD146 or I10-sCD146. Pro-angiogenic properties of the different forms of sCD146 led inventors to investigate their angiogenic effect in a mouse model of hind limb ischemia. Ischemic mice were locally treated twice a week with 2 μg of rhsCD146, rh-I10-sCD146, rh-I5-13-sCD146 and VEGF for 28 days and blood flow was estimated by laser-Doppler. Results show that the three forms were able to increase blood flow as compared to animals treated with PBS and that the effect observed with the different forms of sCD146 was even greater than that observed with VEGF (FIG. 26A). Of interest, the effect of I10-sCD146 appeared faster than with the other molecules since a significant effect was observed as soon as 3 days after the first injection. Labelling of muscle with isolectin B4 showed that vascularisation was increased in animals treated with rh-I10-sCD146, rh-I5-13-sCD146, rh-sCD146 and VEGF, as compared to control animals treated with PBS (FIG. 26B). Finally, angiography pictures showed also an increase in the number of vessels in the legs treated with rh-I10-sCD146, rh-I5-13-sCD146 and rhsCD146, as compared to legs treated with PBS (FIG. 26C). Quantification shows that the vessel density was significantly increased in calf, thigh and whole leg when treated with rh-sCD146, rh-I10-sCD146, rh-I5-13-sCD146 and VEGF. In all experiments, I10-sCD146 and shed sCD146 presented the higher effect, as compared to I5-13-sCD146. Finally, as they have shown that the shedding of long CD146 isoform by ADAM10 is associated with an increased transendothelial permeability (see FIG. 22), inventors analyzed whether the novel spliced variants I10-sCD146 and I5-13-sCD146 could modify this permeability. Results show that neither siRNA transfection nor treatment with recombinant proteins corresponding to these variants modified transendothelial permeability.

Altogether, these results show that both the shed forms of sCD146 and the spliced variants display proangiogenic effects, as VEGF. I10-sCD146 and shed sCD146 appear to display the higher pro-angiogenic effects, as compared to I5-13-sCD146.

I5-13-sCD146 and I10-sCD146 Display Differential Effects on Fibrosis and are Differentially Modulated in Systemic Sclerosis Inventors analyzed the mRNA levels of the newly identified sCD146 variants using tissue array. Results are given in FIG. 28. Whereas many organs did not express I5-13-sCD146 or I10sCD146, lung, lymph node, or rectum, highly expressed the two isoforms of sCD146. Of interest, peripheral blood lymphocytes expressed high levels of I5-13-sCD146 but did not express I10-sCD146. Since I5-13-sCD146 and I10-sCD146 are highly expressed in lung and differentially modulated by TNF and Wnt5a/3a, inventors decided to focus on the expression of these isoforms in Systemic Sclerosis (SSc). Inventors thus determined the concentration of shed sCD146, I5-13-sCD146 and I10-sCD146 in the sera of SSc patients, as compared to control patients (FIG. 27A). Results show that shed sCD146 and I5-13-sCD146 were significantly increased in patients with SSc whereas I10-sCD146 was decreased. Of interest, inventors observed that I5-13-sCD146 concentration was significantly higher in the sera of patients with pulmonary fibrosis, as compared to patients without pulmonary disease (inset).

As it was recently reported by inventors that the canonical Wnt pathway, which is involved in SSc fibrogenesis, is modulated by sCD146 (Kaspi et al., 2017), inventors analyzed the effect of the different soluble forms on a model of b-catenin/TCF transcription activity in Mouse Embryonic Fibroblasts (MEF). Inventors first showed (FIG. 27B, left part) that MEF from CD146 KO mice were more sensitive to bleomycin than MEF from WT mice. They thus used MEF from CD146 KO mice to analyze the effect of shed sCD146, I10-sCD146 and I5-13-sCD146. Results (FIG. 27B, right part) show that sCD146 and I10-sCD146 decreased b-catenin/TCF transcription activity whereas I5-13-sCD146 increased it.

To go further in the mechanism, inventors used an animal model of Systemic Sclerosis induced by bleomycin (Kaspi et al., 2017) Animals treated with bleomycin were subcutaneously injected with shed sCD146, I5-13-sCD146 or I10-sCD146. Then the dermal thickness, the aspect of the skin and the vessel density were analyzed. Results show that bleomycin treatment led to an increase in dermal thickness. Treatment with sCD146 or I10-sCD146 reduced this dermal thickness to the value observed in control animals. In contrast, there was no significant effect of I5-13-sCD146 (FIG. 27 C). Of interest, a reduced vascularization of the skin was observed at a macroscopic level in the animals treated with bleomycin (FIG. 27D). Treatment with shed sCD146 and I10-sCD146 led to an increased vascularisation also observed at macroscopic level, whereas treatment with I5-13-sCD146 did not. These results were confirmed after labelling with isolectin-b4. Vessel density was decreased in bleomycin-treated animals and this effect was significantly reversed by sCD146 and I10-sCD146. In contrast, there was no effect of I5-13-sCD146 (FIG. 27E).

Altogether, these results show that I5-13-sCD146 is pro-fibrotic and is highly increased in the sera of SSc patients with pulmonary fibrosis. In contrast, I10-sCD146 and shed sCD146 are anti-fibrotic and are able to reduce fibrosis in an animal model of SSc.

DISCUSSION

In this study, inventors demonstrated that multiple isoforms of sCD146 are secreted by endothelial cells and determined their mechanisms of generation. They identified for the first time the proteases involved in the shedding of both membrane CD146 isoforms and reported the existence of two supplementary isoforms generated by alternative splicing of the primary transcript and encoding for additional sCD146 proteins. These isoforms display different properties related to the regulation of angiogenesis and fibrosis. The fact that one molecule could exist as different forms highlights its importance in physiology and/or pathology. Of interest, different spliced variants have been identified for many proteins, and in particular for another highly proangiogenic molecule, VEGF. Thus, soluble CD146 could also constitute a large family of proteins with numerous spliced variants.

Concerning the shed form of CD146, inventors have demonstrated that it is generated by two different ADAMs as a function of the membrane CD146 isoform. Indeed, the long form is shed by ADAM10 whereas the short form is shed by Tace. Of interest, inventors have recently shown that the short isoform of CD146 displayed a complete proteolytic processing with the shedding of the extracellular part followed by the shedding of the intracellular part through presenilin-1, generating an intracellular domain (shCD146-ICD). In contrast, the long isoform displayed only an extracellular shedding (Stalin et al., 2016). Inventors showed that the short CD146 isoform could thus display direct transcriptional effects through shCD146-ICD translocation into the nucleus. In the present study, they show that the ADAM involved in shCD146 shedding is Tace. Of interest, Tace and presenilin-1 are often associated to generate sequential shedding of proteins. Thus, notch is also processed through these two molecules, also leading to the generation of a NICD with transcriptional effects (Gudey et al., 2014).

In addition to the shed form of CD146, inventor's study shows that endothelial cells are able to secrete at least two other forms of sCD146. These two isoforms are generated by alternative splicing. The first property that they evidenced for these two novel isoforms is their pro-angiogenic capacity, as already described for the shed form (Harhouri K. et al., 2010). Of interest, I10-sCD146 and shed sCD146 displayed higher angiogenic capacities than I5-13-sCD146 and I10-sCD146 displayed faster effects since its angiogenic effects could be observed as soon as 3 days after the injection of the molecule in ischemic animals. Different angiogenic factors have been shown to exist as different isoforms with various angiogenic capacities. Thus, the major angiogenic molecule VEGF displays many different isoforms (Guyot M. et al., 2015). These isoforms display different receptors that can be expressed in distinct cells and affect angiogenesis/lymphangiogenesis (Jussila L. et al., 2002). Of interest, different isoforms can also bind the same receptor and induce different signal transduction and trafficking that will elicit diverse cellular outcome (Fearnley G W et al., 2016). For VEGFs, at least four different receptors have been identified, VEGFR1/2/3 and neuropilin-1. These receptors are involved in angiogenesis but also in lymphangiogenesis. Further studies will be necessary to determine if the different sCD146 variants bind different receptors and whether they are also involved in lymphangiogenesis. Recently, both pro-angiogenic and anti-angiogenic isoforms of VEGF have been described. This is of major interest since, in tumors, both types of molecules are expressed. However, they are both inhibited by anti-VEGF molecules as bevacizumab, reducing the effect of the therapy (Biselli-Chicote P M et al., 2012). Inventors have recently shown that in clear cell renal cell carcinoma, soluble CD146 constituted a predictive marker of sunitinib efficacy and that one of the mechanisms of resistance to sunitinib may depend on a huge increase of the molecule (Dufies M. et al., 2018). As the additional spliced variants described in this study are also pro-angiogenic, it will be of interest to analyze their implication in this phenomenon. Of interest, inventors have shown that the two additional isoforms of sCD146 are also involved in the control of fibrosis, in particular in Systemic Sclerosis (SSc). SSc is characterized by a huge fibrosis and a dysregulated angiogenesis. Abnormalities in many factors have been reported (Hummers L K et al., 2009). In the present study, inventors showed that I5-13-sCD146 splice variant is increased by Wnt5a and TNF, and that the protein is significantly enhanced in the sera of SSc patients whereas I10-sCD146 is decreased by Wnt3A and VEGF, and is decreased in SSc. The observed regulation of the two isoforms in the sera of patients is in agreement with the described increase of TNF, Wnt3a and VEGF in SSc patients. This result is important since it confirms the involvement of CD146/sCD146 in SSc and shows that the different pro-angiogenic forms of sCD146 are modulated in the pathology. Using an in vivo model of SSc induced by bleomycin in the mouse, inventors have shown that shed sCD146 and I10-sCD146 were able to reduce SSc as determined by dermal thickness whereas I5-13-sCD146 did not. Of interest, shed sCD146 and I10-sCD146 were able to increase the vessel density in the dermis of these animals whereas I5-13-sCD146 did not. Thus, whereas all forms are proangiogenic, only sCD146 and I10-sCD146 were able to stimulate the generation of new vessels in this model. This suggests that the different forms of sCD146 could be involved in different pathways and that their effects could be balanced as a function of the pathological conditions. In this way, shed sCD146 and I10-sCD146 were also able to reduce b-catenin/TCF transcription activity in the in vitro model of MEF, suggesting a potential decrease in skin fibrosis through a down-regulation of the Wntcanonical pathway. In contrast, I5-13-sCD146 increased it. These results are clearly in favour of the fact that I5-13-sCD146 could act through a different receptor and trigger different signalling pathways, as compared to sCD146 and I10-sCD146.

Altogether, these data show that I10-sCD146 and I5-13-sCD146 constitute novel biomarkers in SSc. In particular, the fact that I5-13-sCD146 was significantly increased in SSc patients with pulmonary fibrosis as compared to patients without pulmonary fibrosis, indicates that it could constitute a marker of severity of the pathology. Moreover, shed sCD146 and I10-sCD146, in contrast to I5-13-sCD146, display therapeutic effects in SSc by increasing vascularisation and by reducing fibrosis. In conclusion, this study identifies the two proteinases involved in the shedding of the two membrane isoforms of CD146 and identifies two additional isoforms of sCD146 generated by alternative splicing. All these variants display pro-angiogenic properties and appear to constitute a novel family of pro-angiogenic molecules, as described for VEGF. In contrast, they are differentially regulated in the serum of patients with Systemic Sclerosis and display differential fibrotic properties.

Example 4—Effect of sCD146 Blocking with Specific Antibodies on the Development of Fibrosis in a Model of Renal Interstitial Fibrosis Induced by Adenine Diet in the Mouse Inventors induced chronic kidney disease associated with interstitial fibrosis by using an adenine diet. This induces a crystalline nephropathy that progresses to tubulointerstitial fibrosis. The C57BL/6 mice were 8 weeks old and were fed for 12 days with a diet incorporating 0.25% adenine (A04 Ade 0.25%, Safe). Control mice were fed with a normal diet (A04, Safe). After 12 days, the diet was stopped and animals were used immediately or 1, 2 or 3 weeks after the end of the diet.

Results show that 2 weeks after the end of the adenine diet, animals displayed interstitial kidney fibrosis, whereas there was no fibrosis in control animals (FIG. 33A). This fibrosis was accompanied by an increase in TGFb, Collagene Ia and aSMA as observed at the mRNA level (FIG. 33B). The aSMA protein was also significantly increased (FIG. 33C). Finally, they observed a progressive increase in the mRNA expression of CD146 which was significant 2 and 3 weeks after the end of the adenine diet (FIG. 33D). In order to prevent the development of fibrosis, inventors treated animals IV with 10 µg of the anti-sCD146 antibody twice a week from the beginning of the adenine diet until the sacrifice which occurred 2 weeks after the end of the diet. Results show that at the sacrifice, both control animals and animals treated with control IgG developed high fibrosis. Of interest, animals treated with anti-sCD146 antibodies showed a significantly decreased interstitial fibrosis (FIGS. 34A and 34B).

REFERENCES

Alais, S., Allioli, N., Pujades, C., Duband, J. L., Vainio, O., Imhof, B. A., Dunon, D. HEMCAM/CD146 downregulates cell surface expression of beta1 integrins. Journal of cell science 114:1847-1859 (2001)

Anfosso, F., Bardin, N., Vivier, E., Sabatier, F., Sampol, J., Dignat-George, F. Outside-in signaling pathway linked to CD146 engagement in human endothelial cells. J Biol Chem 276:1564-1569 (2001) Solovey, A. N., Gui, L., Chang, L., Enenstein, J., Browne, P. V, Hebbel, R. P. Identification and functional assessment of endothelial P1H12. J Lab Clin Med. 138:322-31 (2001)

Arima et al., "Specific inhibition of Interleukin-10 Production in Murine Macrophage-Like Cells by Phosphorothioate Antisense Oligonucleotides," Antisense Nucl. Acid Drug Dev. 8:319-327 (1998);

Bardin, N., Anfosso, F., Masse, J. M., Cramer, E., Sabatier, F., Le Bivic, A., Sampol, J., Dignat-George, F. Identification of CD146 as a component of the endothelial junction involved in the control of cell-cell cohesion. Blood 98:3677-3684 (2001)

Bardin, N., Blot-Chabaud, M., Despoix, N., Kebir, A., Harhouri, K., Arsanto, J. P., Espinosa, L., Perrin, P., Robert, S., Vely, F., Sabatier, F., Le Bivic, A., Kaplanski, G., Sampol, J., Dignat-George, F. CD146 and its soluble form regulate monocyte transendothelial migration. Arteriosclerosis, thrombosis, and vascular biology 29:746-753 (2009)

Bardin, N., Moal, V., Anfosso, F., Daniel, L., Brunet, P., Sampol, J., Dignat-George, F. Soluble CD146, a novel endothelial marker, is increased in physiopathological settings linked to endothelial junctional alteration. ThrombHaemost. 90:915-920 (2003)

Bardin, N., Reumaux, D., Geboes, K., Colombel, J. F., Blot-Chabaud, M., Sampol, J., Duthilleul, P., Dignat-George, F. Increased expression of CD146, a new marker of the endothelial junction in active inflammatory bowel disease. Inflammatory bowel diseases 12:16-21 (2006)

Beckers M, Gladis-Villanueva M, Hamann W, Schmutzler W, Zwadlo-Klarwasser G. The use of the chorio-allantoic membrane of the chick embryo as test for anti-inflammatory activity. Inflamm Res Off J Eur Histamine Res Soc Al. 1997; 46:29-30.

Biernacka, A., and Frangogiannis, N. G. (2011). Aging and Cardiac Fibrosis. Aging Dis. 2, 158-173.

Boneberg, E. M., Illges, H., Legler, D. F., Furstenberger, G. Soluble CD146 is generated by ectodomain shedding of membrane CD146 in a calcium-induced, matrix metalloprotease-dependent process. Microvascular research 78:325-331 (2009)

Chadban, S. J., Atkins, R. C. Glomerulonephritis. Lancet. 365:1797-1806 (2005)

Chan, B., Sinha, S., Cho, D., Ramchandran, R., Sukhatme, V. P. Critical roles of CD146 in zebrafish vascular development. Dev Dyn232:232-244 (2005)

Chaturvedi, R. R., Herron, T., Simmons, R., Shore, D., Kumar, P., Sethia, B., Chua, F., Vassiliadis, E., and Kentish, J. C. (2010). Passive Stiffness of Myocardium From Congenital Heart Disease and Implications for Diastole. Circulation 121, 979-988.

Chen, W., and Frangogiannis, N. G. (2010). The role of inflammatory and fibrogenic pathways in heart failure associated with aging. Heart Fail. Rev. 15, 415-422.

Cohen, C. D., Lindenmeyer, M. T., Eichinger, F., et al. Improved elucidationof biological processes linked to diabetic nephropathy bysingle probe-based microarray data analysis. PLoS One3:e2937 (2008)

Daniel, L., Bardin, N., Moal, V., Dignat-George, F., Berland, Y., Figarella-Branger, D. Tubular CD146 expression in nephropathies is related to chronic renal failure. Nephron Exp Nephro 199:e105-111 (2005)

Delorme B, Basire A, Gentile C, Sabatier F, Monsonis F, Desouches C, Blot-Chabaud M, Uzan G, Sampol J, Dignat-George F. Presence of endothelial progenitor cells, distinct from mature endothelial cells, within human CD146+ blood cells. ThrombHaemost. 2005; 94:1270-1279.

Despoix N, Walzer T, Jouve N, Blot-Chabaud M, Bardin N, Paul P, Lyonnet L, Vivier E, Dignat-George F, Vely F. Mouse CD146/MCAM is a marker of natural killer cell maturation. Eur J Immunol. 2008; 38: 2855-64

Djudjaj, S., Chatziantoniou, C., Raffetseder, U., Guerrot, D., Dussaule, J. C., Boor, P., Kerroch, M., Hanssen, L., Brandt, S., Dittrich, A., Ostendorf, T., Floege, J., Zhu, C., Lindenmeyer, M., Cohen, C. D., Mertens, P. R. Notch-3 receptor activation drives inflammation and fibrosis following tubulointerstitial kidney injury. J Pathol. 228:286-299 (2012)

Duan, H., Xing, S., Luo, Y., Feng, L., Gramaglia, I., Zhang, Y., Lu, D., Zeng, Q., Fan, K., Feng, J., Yang, D., Qin, Z., Couraud, P. O., Romero, I. A., Weksler, B., Yan, X. Targeting endothelial CD146 attenuates neuroinflammation by limiting lymphocyte extravasation to the CNS. Sci Rep. 3:1687 (2013)

El Machhour F, Keuylian Z, Kavvadas P, Dussaule J C, Chatziantoniou C. Activation of Notch3 in Glomeruli Promotes the Development of Rapidly Progressive Renal Disease. J Am SocNephrol. 2015 July; 26(7):1561-75. doi: 10.1681/ASN.2013090968. Epub 2014 November 24.

Fire, A. et al., "Potent and Specific Genetic Interference by Double-Stranded RNA in *Caenorhabditis elegans*" Nature 391:806-811 (1998)

Fu Y, Du Y, Mohan C. Experimental anti-GBM disease as a tool for studying spontaneous lupus nephritis. Clin Immunol. 2007; 124:109-118.

George, F., Poncelet, P., Laurent, J. C., Massot, O., Amoux, D., Lequeux, N., Ambrosi, P., Chicheportiche, C., Sampol, J. Cytofluorometric detection of human endothelial cells in whole blood using S-Endo 1 monoclonal antibody. J. Immunol Methods. 139:65-75. (1991)

Gesteland et al., eds, "The RNA World" (3rd, Cold Spring Harbor Laboratory Press, Cold Spring Harbor, N.Y., 2006), pp. 535-565

Gudey S K, Sundar R, Mu Y, Wallenius A, Zang G, Bergh A, Heldin C-H, Landström M. TRAF6 stimulates the tumor-promoting effects of TGFβ type I receptor through polyubiquitination and activation of presenilin 1. Sci Signal. 2014; 7:ra2.

Guezguez, B., Vigneron, P., Lamerant, N., Kieda, C., Jaffredo, T., Dunon, D. Dual role of melanoma cell adhesion molecule (MCAM)/CD146 in lymphocyte endothelium interaction: MCAM/CD146 promotes rolling via microvilli induction in lymphocyte and is an endothelial adhesion receptor. J Immuno 1179:6673-6685 (2007)

Guyot M, Pagès G. VEGF Splicing and the Role of VEGF Splice Variants: From Physiological-Pathological Conditions to Specific Pre-mRNA Splicing. Methods Mol Biol Clifton NJ. 2015; 1332:3-23.

Halt K J, Pärssinen H E, Junttila S M, Saarela U, Sims-Lucas S, Koivunen P, Myllyharju J, Quaggin S, Skovorodkin I N, Vainio S J. CD146(+) cells are essential for kidney vasculature development. Kidney Int. 2016 August; 90(2):311-324.

J. E. Hambor et al., "Use of an Epstein-Ban Virus Episomal Replicon for Anti-Sense RNA-Mediated Gene Inhibition in a Human Cytotoxic T-Cell Clone," Proc. Natl. Acad. Sci. U.S.A. 85:4010-4014 (1988);

Harhouri, K., Kebir, A., Guillet, B., Foucault-Bertaud, A., Voytenko, S., Piercecchi-Marti, M. D., Berenguer, C., Lamy, E., Vely, F., Pisano, P., Ouafik, L., Sabatier, F., Sampol, J., Bardin, N., Dignat-George, F., Blot-Chabaud, M. Soluble CD146 displays angiogenic properties and promotes neovascularization in experimental hind-limb ischemia. Blood. 115:3843-3851 (2010)

Harlow & Lane, Using Antibodies, A Laboratory Manual, Cold Spring Harbor Laboratory Press, Cold Spring Harbor, N.Y., 1998; Kohler & Milstein, Nature 256: 495-497 (1975)

Henique C, Bollee G, Lenoir O, Dhaun N, Camus M, Chipont A, Flosseau K, Mandet C, Yamamoto M, Karras A, Thervet E, Bruneval P, Nochy D, Mesnard L, Tharaux P L. Nuclear Factor Erythroid 2-Related Factor 2 Drives Podocyte-Specific Expression of Peroxisome Proliferator-Activated Receptor γ Essential for Resistance to Crescentic G N. J Am SocNephrol. 2016 January; 27(1):172-88. doi: 10.1681/ASN.2014111080. Epub 2015 May 21.

Hou et al., "Effect of Antisense Oligodeoxynucleotides Directed to Individual Calmodulin Gene Transcripts on the Proliferation and Differentiation of PC12 Cells," Antisense Nucl. Acid Drug Dev. 8:295-308 (1998)

Jouve, N., Bachelier, R., Despoix, N., Blin, M. G., Matinzadeh, M. K., Poitevin, S., Aurrand-Lions, M., Fallague, K., Bardin, N., Blot-Chabaud, M., Vely, F., Dignat-George, F., Leroyer, A. S. CD146 mediates VEGF-induced melanoma cell extravasation through FAK activation. Int J Cancer. 137:50-60 (2015)

Jussila L, Alitalo K. Vascular growth factors and lymphangiogenesis. Physiol Rev. 2002; 82:673-700.

Kebir, A., Harhouri, K., Guillet, B., Liu, J. W., Foucault-Bertaud, A., Lamy, E., Kaspi, E., Elganfoud, N., Vely, F., Sabatier, F., Sampol, J., Pisano, P., Kruithof, E. K., Bardin, N., Dignat-George, F., Blot-Chabaud, M. CD146 short isoform increases the proangiogenic potential of endothelial progenitor cells in vitro and in vivo. Circ Res. 107:66-75 (2010)

Karkar A M, Smith J, Pusey C D. Prevention and treatment of experimental crescentic glomerulonephritis by blocking tumour necrosis factor-alpha. Nephrol Dial Transplant. 2001; 16:518-524.

Kaspi E, Heim X, Granel B, Guillet B, Stalin J, Nollet M, Bertaud-Foucault A, Robaglia-Schlupp A, Roll P, Cau P, Leroyer A, Bachelier R, Benyamine A, Dignat-George F, Blot-Chabaud M, Bardin N. Identification of CD146 as a novel molecular actor involved in systemic sclerosis. J Allergy Clin Immunol. 2017;

Kavvadas P, Abed A, Poulain C, Authier F, Labéjof L P, Calmont A, Afieri C, Prakoura N, Dussaule J C, Chatziantoniou C, Chadjichristos C E. Decreased Expression of Connexin 43 Blunts the Progression of Experimental G N. J Am Soc Nephrol. 2017 Jun. 30. pii: ASN.2016111211. doi: 10.1681/ASN.2016111211. [Epub ahead of print]

Kerroch M, Guerrot D, Vandermeersch S, Placier S, Mesnard L, Jouanneau C, Rondeau E, Ronco P, Boffa J J, Chatziantoniou C, Dussaule J C. Genetic inhibition of discoidin domain receptor 1 protects mice against crescentic glomerulonephritis. FASEB J. 2012 October; 26(10):4079-91. doi: 10.1096/fj.11-194902. Epub 2012 Jul. 2.

Kennerdell & R. W. Carthew, "Use of dsDNA-Mediated Genetic Interference to Demonstrate that frizzled and frizzled 2 Act in the Wingless Pathway," CeJ 95:1017-1026 (1998);

Kitching A R, Holdsworth S R, Tipping P G. IFN-gamma mediates crescent formation and cell-mediated immune injury in murine glomerulonephritis. J Am SocNephrol. 1999; 10:752-759.

Kishimoto T. Interleukin-6: from basic science to medicine—40 years in immunology. Annu Rev Immunol. 2005; 23:1-21

Korff T, Kimmina S, Martiny-Baron G, Augustin H G. Blood vessel maturation in a 3-dimensional spheroidal coculture model: direct contact with smooth muscle cells regulates endothelial cell quiescence and abrogates VEGF responsiveness. FASEB J Off Publ Fed Am Soc Exp Biol. 2001; 15:447-457.

Kozbor et al., Immunology Today 4:72 (1983); and Cole et al., pp. 77-96 in Monoclonal Antibodies and Cancer Therapy, 1985

LeBleu, V. S., Taduri, G., O'Connell, J., Teng, Y., Cooke, V. G., Woda, C., Sugimoto, H., Kalluri, R. Origin and function of myofibroblasts in kidney fibrosis. Nat Med. 19:1047-1053 (2013)

Le Hir M, Haas C, Marino M, Ryffel B. Prevention of crescentic glomerulonephritis induced by anti-glomerular membrane antibody in tumor necrosis factor-deficient mice. Lab Invest. 1998; 78:1625-1631

Liang, Y. K., Zeng, Xiao, Y. S., Wu Y., Ouyang, Y. X., Chen, M., Li, Y. C., Lin, H. Y., Wei, X. L., Zhang, Y. Q., Kruyt, F. A., Zhang, G. J. MCAM/CD146 promotes tamoxifen resistance in breast cancer cells through induction of epithelial-mesenchymal transition, decreased ERα expression and AKT activation. Cancer Lett. 386:65-76 (2017)

Lichtenstein & W. Nellen, eds., "Antisense Technology: A Practical Approach" (IRL Press, Oxford, 1997)

Luque Y, Cathelin D, Vandermeersch S, Xu X, Sohier J, Placier S, Xu-Dubois Y C, Louis K, Hertig A, Bories J C, Vasseur F, Campagne F, Di Santo J P, Vosshenrich C, Rondeau E, Mesnard L. Glomerular common gamma chain confers B- and T-cell-independent protection against glomerulonephritis. Kidney Int. 2017 May; 91(5):1146-1158. doi: 10.1016/j. kint. 2016.10.037. Epub 2017 Jan. 19.

Marcus-Sekura, "Techniques for Using Antisense Oligodeoxy ribonucleotides to Study Gene Expression," Anal. Biochem. 172:289-295 (1988);

Mathieson, P. W. Glomerulonephritis. SeminImmunopathol. 29:315-316 (2007)

Mays, P. K., McAnulty, R. J., Campa, J. S., and Laurent, G. J. (1991). Age-related changes in collagen synthesis and degradation in rat tissues. Importance of degradation of newly synthesized collagen in regulating collagen production. Biochem. J. 276, 307-313.

Mesnard L, Cathelin D, Vandermeersch S, Rafat C, Luque Y, Sohier J, Nochy D, Garcon L, Callard P, Jouanneau C, Verpont M C, Tharaux P L, Hertig A, Rondeau E. Genetic background-dependent thrombotic microangiopathy is related to vascular endothelial growth factor receptor 2 signaling during anti-glomerular basement membrane glomerulonephritis in mice. Am J Pathol. 2014 September; 184(9):2438-49. doi: 10.1016/j.ajpath.2014.05.020. Epub 2014 Jul. 6.

Mesnard L, Keller A C, Michel M L, Vandermeersch S, Rafat C, Letavernier E, Tillet Y, Rondeau E, Leite-de-Moraes M C. Invariant natural killer T cells and TGF-beta attenuate anti-GBM glomerulonephritis. J Am SocNephrol. 2009 June; 20(6):1282-92. doi: 10.1681/ASN.2008040433. Epub 2009 May 21.

Moeller, M. J., Smeets, B. Novel target in the treatment of RPGN: the activated parietal cell. Nephrol Dial Transplant. 28:489-492(2013)

Pasquier, E., Bardin, N., De Saint Martin, L., Le Martelot, M. T., Bohec, C., Roche, S., Mottier, D., Dignat-George, F. The first assessment of soluble CD146 in women with unexplained pregnancy loss. A new insight? Thromb Haemost 94:1280-1284 (2005)

Prakoura N, Kavvadas P, Konnann R, Dussaule J C, Chadjichristos C E, Chatziantoniou CNFκB-Induced Periostin Activates Integrin-β3 Signaling to Promote Renal Injury in GN. J Am SocNephrol. 2017 May; 28(5):1475-1490. doi: 10.1681/ASN.2016070709. Epub 2016 Dec. 5.

Rockey, D. C., Bell, P. D., Hill, J. A. Fibrosis—a common pathway to organ injury and failure. NEngl J Med.372: 1138-1149 (2015)

Schwarting A, Wada T, Kinoshita K, Tesch G, Kelley V R. IFN-gamma receptor signaling is essential for the initiation, acceleration, and destruction of autoimmune kidney disease in MRL-Fas (lpr) mice. J. Immunol. 1998; 161:494-503.

Stalin J, Harhouri K, Hubert L, Subrini C, Lafitte D, Lissitzky J-C, Elganfoud N, Robert S, Foucault-Bertaud A, Kaspi E, Sabatier F, Aurrand-Lions M, Bardin N, Holmgren L, Dignat-George F, Blot-Chabaud M. Soluble melanoma cell adhesion molecule (sMCAM/ sCD146) promotes angiogenic effects on endothelial progenitor cells through angiomotin. J Biol Chem. 2013; 288:8991-9000.

Stalin J, Nollet M, Garigue P, Fernandez S, Vivancos L, Essaadi A, Muller A, Bachelier R, Foucault-Bertaud A, Fugazza L, Leroyer A S, Bardin N, Guillet B, Dignat-George F, Blot-Chabaud M. Targetingsoluble CD146 with a neutralizing antibody inhibits vascularization, growth and survival of CD146-positive tumors. Oncogene. 2016; 35:5489-5500.

Taira, E., Nagino, T., Taniura, H., Takaha, N., Kim, C. H., Kuo, C. H., Li, B. S., Higuchi, H., Miki, N. Expression and functional analysis of a novel isoform of gicerin, an immunoglobulin superfamily cell adhesion molecule. The Journal of biological chemistry 270:28681-28687 (1995)

Tang WW, Feng L, Vannice J L, Wilson C R Interleukin-1 receptor antagonist ameliorates experimental anti-glomerular basement membrane antibody-associated glomerulonephritis. J Clin Invest. 1994; 93:273-279.

Toubas J, Beck S, Pageaud A L, Huby A C, Mael-Ainin M, Dussaule J C, Chatziantoniou C, Chadjichristos C E. Alteration of connexin expression is an early signal for chronic kidney disease. Am J Physiol Renal Physiol. 2011 July; 301(1):F24-32. doi: 10.1152/ajprenal.00255.2010. Epub 2011 Mar. 23

J. Sambrook & D. R. Russell, "Molecular Cloning: A Laboratory Manual" (3rd, Cold Spring Harbor Laboratory Press, Cold Spring Harbor, 2001

Talman, V., and Ruskoaho, H. (2016). Cardiac fibrosis in myocardial infarction from repair and remodeling to regeneration. Cell Tissue Res. 365, 563-581.

Tellier E, Canault M, Poggi M, Bonardo B, Nicolay A, Alessi M-C, Nalbone G, Peiretti F. HDLs activate ADAM17-dependent shedding. J Cell Physiol. 2008; 214:687-693.

Vainio, O., Dunon, D., Aissi, F., Dangy, J. P., McNagny, K. M., Imhof, B. A. HEMCAM, an adhesion molecule expressed by c-kit+ hemopoietic progenitors. The Journal of cell biology 135:1655-1668 (1996)

Wang N, Fan Y, Ni P, Wang F, Gao X, Xue Q, Tang L. High glucose effect on the role of CD146 in human proximal tubular epithelial cells in vitro. J Nephrol. 2008 November-December; 21(6):931-40.

Wang, Y., Nakayama, M., Pitulescu, M. E., Schmidt, T. S., Bochenek, M. L., Sakakibara, A., Adams, S., Davy, A., Deutsch, U., Läthi, U., Barberis, A., Benjamin, L. E., Mäkinen, T., Nobes, C. D., Adams, R. H. Ephrin-B2 controls VEGF-inducedangiogenesis and lymphangiogenesis. Nature 465:483-866 (2010)

Wianni& M. Zernicka-Goetz, "Specific Interference with Gene Function by Double-Stranded RNA in Early Mouse Development," Nat. Cell Biol. 2:70-75 (2000)

Weber, K. T. (1989). Cardiac interstitium in health and disease: The fibrillar collagen network. J. Am. Coll. Cardiol. 13, 1637-1652.

Wuthrich R P, Jevnikar A M, Takei F, Glimcher L H, Kelley V E. Intercellular adhesion molecule-1 (ICAM-1) expression is upregulated in autoimmune murine lupus nephritis. Am J Pathol. 1990; 136:441-450.

Xu J. Preparation, culture, and immortalization of mouse embryonic fibroblasts. CurrProtoc Mol Biol. 2005; Chapter 28: Unit 28.1.

Yan, X., Lin, Y., Yang, D., Shen, Y., Yuan, M., Zhang, Z., Li, P., Xia, H., Li, L., Luo, D., Liu, Q., Mann, K., Bader, B. L. A novel anti-CD146 monoclonal antibody, AA98, inhibits angiogenesis and tumor growth. Blood 102: 184-191 (2003)

Zeisberg, E. M., Potenta, S. E., Sugimoto, H., Zeisberg, M., Kalluri, R. Fibroblasts in kidney fibrosis emerge via endothelial-to-mesenchymal transition. J Am SocNephrol. 19:2282-2287 (2008)

Zeng, Q., Li, W., Lu, D., Wu, Z., Duan, H., Luo, Y., Feng, J., Yang, D., Fu, L., Yan, X. CD146, an epithelial-mesenchymal transition inducer, is associated with triple-negative breast cancer. Proc Natl Acad Sci USA. 109:1127-1132 (2012)

The invention claimed is:
1. An in vitro or ex vivo method of detecting predisposition to or of diagnosing and/or prognosing cardiac or renal fibrosis in a subject, the method comprises the steps of i) determining the soluble CD146 protein expression level in a biological sample of the subject, said soluble CD146 protein being selected from SEQ ID NO:1, SEQ ID NO:2, SEQ ID NO:3, SEQ ID NO:4, SEQ ID NO:5, SEQ ID NO:6 and SEQ ID NO:7, ii) comparing the expression level determined at step i) with a reference value and iii) concluding that the subject has predisposition to cardiac or renal fibrosis, is affected by cardiac or renal fibrosis or has a poor prognosis of cardiac or renal fibrosis, when the level determined at step i) is higher than the reference value or concluding that the patient has no predisposition to cardiac or renal fibrosis, is not affected by cardiac or renal fibrosis or has a good prognosis of cardiac or renal fibrosis when the level determined at step i) is lower than the reference value, said method further comprising the administration of an inhibitor of a soluble CD146 protein selected from SEQ ID NO: 1, SEQ ID NO: 2, SEQ ID NO: 3, SEQ ID NO: 4, SEQ ID NO: 5, SEQ ID NO: 6 and SEQ ID NO: 7 to a subject identified in step iii) as having predisposition to cardiac or renal fibrosis, as being affected by cardiac or renal fibrosis or as having a poor prognosis of cardiac or renal fibrosis, wherein the inhibitor is an antibody comprising:
a) heavy chain variable region (VH) CDR polypeptide sequences of SEQ ID NO: 87, SEQ ID NO: 88, and SEQ ID NO: 89, and the light chain variable region (VL) CDR polypeptide sequences of SEQ ID NO: 90, sequence QVS and SEQ ID NO: 91;
b) a light chain variable region (VL) comprising SEQ ID NO: 93 and a heavy chain variable region (VH) comprising SEQ ID NO: 92;
c) heavy chain variable region (VH) CDR polypeptide sequences of SEQ ID NO: 94, SEQ ID NO: 95, and SEQ ID NO: 96, and the light chain variable region (VL) CDR polypeptide sequence of SEQ ID NO: 97, sequence FAS and SEQ ID NO: 98; or
d) a light chain variable region (VL) comprising SEQ ID NO: 100 and a heavy chain variable region (VH) comprising SEQ ID NO: 99.

2. An in vitro or ex vivo method of detecting predisposition to or of diagnosing and/or prognosing fibrosis in a subject comprises the steps of i) determining the I5-13 soluble CD146 protein expression level in a biological sample of the subject, ii) comparing the expression level determined at step i) with a reference value and iii) concluding that the subject has predisposition to fibrosis, is affected by fibrosis or has a poor prognosis of fibrosis, when the level determined at step i) is higher than the reference value or concluding that the patient has no predisposition to fibrosis, is not affected by fibrosis or has a good prognosis of fibrosis when the level determined at step i) is lower than the reference value, said method further comprising the administration of an inhibitor of the I5-13 soluble CD146 protein of SEQ ID NO: 8 to a subject who has been identified in step iii) as having predisposition to fibrosis, as being affected by fibrosis or as having a poor prognosis of fibrosis, wherein the inhibitor is an antibody comprising:
a) heavy chain variable region (VH) CDR polypeptide sequences of SEQ ID NO: 87, SEQ ID NO: 88, and SEQ ID NO: 89, and the light chain variable region (VL) CDR polypeptide sequences of SEQ ID NO: 90, sequence QVS and SEQ ID NO: 91;
b) a light chain variable region (VL) comprising SEQ ID NO: 93 and a heavy chain variable region (VH) comprising SEQ ID NO: 92;
c) heavy chain variable region (VH) CDR polypeptide sequences of SEQ ID NO: 94, SEQ ID NO: 95, and SEQ ID NO: 96, and the light chain variable region (VL) CDR polypeptide sequence of SEQ ID NO: 97, sequence FAS and SEQ ID NO: 98; or
d) a light chain variable region (VL) comprising SEQ ID NO: 100 and a heavy chain variable region (VH) comprising SEQ ID NO: 99.

3. An in vitro or ex vivo method of:
a) monitoring cardiac or renal fibrosis in a subject comprising determining the soluble CD146 protein level of expression in a biological sample of the subject at two or more time points, said soluble CD146 protein being selected from SEQ ID NO:1, SEQ ID NO:2, SEQ ID NO:3, SEQ ID NO:4, SEQ ID NO:5, SEQ ID NO:6 and SEQ ID NO:7, wherein a higher soluble CD146 protein level of expression in a biological sample of the subject at a later time point, compared to a reference value obtained in a biological sample of the subject at an earlier time point, is indicative of fibrosis increase in the subject whereas a lower soluble CD146 protein level is indicative of a fibrosis decrease and an equal soluble CD146 protein level indicates that fibrosis does not progress in the subject; or
b) monitoring fibrosis in a subject comprising determining the I5-13 soluble CD146 protein of SEQ ID NO:8 level of expression in a biological sample of the subject at two or more time points, wherein a higher soluble CD146 protein level of expression in a biological sample of the subject at a later time point, compared to a reference value obtained in a biological sample of the subject at an earlier time point, is indicative of fibrosis increase in the subject whereas a lower human soluble CD146 protein level is indicative of a fibrosis decrease and an equal human soluble CD146 protein level indicates that fibrosis does not progress in the subject,
wherein when an increase of fibrosis is monitored in the subject, said method further comprises the administration of an inhibitor of the I5-13 soluble CD146 protein of SEQ ID NO: 8 or of a soluble CD146 protein selected from SEQ ID NO: 1, SEQ ID NO: 2, SEQ ID NO: 3, SEQ ID NO: 4, SEQ ID NO: 5, SEQ ID NO: 6 and SEQ ID NO: 7 to the subject,
wherein the inhibitor is an antibody comprising:
a) heavy chain variable region (VH) CDR polypeptide sequences of SEQ ID NO: 87, SEQ ID NO: 88, and SEQ ID NO: 89, and the light chain variable region (VL) CDR polypeptide sequences of SEQ ID NO: 90, sequence QVS and SEQ ID NO: 91;
b) a light chain variable region (VL) comprising SEQ ID NO: 93 and a heavy chain variable region (VH) comprising SEQ ID NO: 92;
c) heavy chain variable region (VH) CDR polypeptide sequences of SEQ ID NO: 94, SEQ ID NO: 95, and SEQ ID NO: 96, and the light chain variable region (VL) CDR polypeptide sequence of SEQ ID NO: 97, sequence FAS and SEQ ID NO: 98; or
d) a light chain variable region (VL) comprising SEQ ID NO: 100 and a heavy chain variable region (VH) comprising SEQ ID NO: 99.

4. A method of treating cardiac and/or renal fibrosis in a subject comprising the administration of a composition comprising an inhibitor of a soluble CD146 protein selected from SEQ ID NO: 1, SEQ ID NO: 2, SEQ ID NO: 3, SEQ ID NO: 4, SEQ ID NO: 5, SEQ ID NO: 6 and SEQ ID NO: 7 and a pharmaceutically acceptable carrier to said subject, wherein the inhibitor is an antibody comprising:
- a) heavy chain variable region (VH) CDR polypeptide sequences of SEQ ID NO: 87, SEQ ID NO: 88, and SEQ ID NO: 89, and the light chain variable region (VL) CDR polypeptide sequences of SEQ ID NO: 90, sequence QVS and SEQ ID NO: 91;
- b) a light chain variable region (VL) comprising SEQ ID NO: 93 and a heavy chain variable region (VH) comprising SEQ ID NO: 92;
- c) heavy chain variable region (VH) CDR polypeptide sequences of SEQ ID NO: 94, SEQ ID NO: 95, and SEQ ID NO: 96, and the light chain variable region (VL) CDR polypeptide sequence of SEQ ID NO: 97, sequence FAS and SEQ ID NO 98; or
- d) a light chain variable region (VL) comprising SEQ ID NO: 100 and a heavy chain variable region (VH) comprising SEQ ID NO: 99.

5. A method of treating fibrosis in a subject comprising the administration of a composition comprising an inhibitor of the I5-13 soluble CD146 protein of SEQ ID NO:8 and a pharmaceutically acceptable carrier to said subject, wherein the inhibitor is an antibody comprising:
- a) heavy chain variable region (VH) CDR polypeptide sequences of SEQ ID NO: 87, SEQ ID NO: 88, and SEQ ID NO: 89, and the light chain variable region (VL) CDR polypeptide sequences of SEQ ID NO: 90, sequence QVS and SEQ ID NO: 91;
- b) a light chain variable region (VL) comprising SEQ ID NO: 93 and a heavy chain variable region (VH) comprising SEQ ID NO: 92;
- c) heavy chain variable region (VH) CDR polypeptide sequences of SEQ ID NO: 94, SEQ ID NO: 95, and SEQ ID NO: 96, and the light chain variable region (VL) CDR polypeptide sequence of SEQ ID NO: 97, sequence FAS and SEQ ID NO: 98; or
- d) a light chain variable region (VL) comprising SEQ ID NO: 100 and a heavy chain variable region (VH) comprising SEQ ID NO: 99.

6. The method according to claim 5, wherein the fibrosis is pulmonary fibrosis.

* * * * *

SEQUENCE LISTING

<160> NUMBER OF SEQ ID NOS: 102

<210> SEQ ID NO 1
<211> LENGTH: 552
<212> TYPE: PRT
<213> ORGANISM: Homo sapiens

<400> SEQUENCE: 1

Met Gly Leu Pro Arg Leu Val Cys Ala Phe Leu Leu Ala Ala Cys Cys
1               5                   10                  15

Cys Cys Pro Arg Val Ala Gly Val Pro Gly Glu Ala Glu Gln Pro Ala
                20                  25                  30

Pro Glu Leu Val Glu Val Glu Val Gly Ser Thr Ala Leu Leu Lys Cys
            35                  40                  45

Gly Leu Ser Gln Ser Gln Gly Asn Leu Ser His Val Asp Trp Phe Ser
        50                  55                  60

Val His Lys Glu Lys Arg Thr Leu Ile Phe Arg Val Arg Gln Gly Gln
65                  70                  75                  80

Gly Gln Ser Glu Pro Gly Glu Tyr Glu Gln Arg Leu Ser Leu Gln Asp
                85                  90                  95

Arg Gly Ala Thr Leu Ala Leu Thr Gln Val Thr Pro Gln Asp Glu Arg
            100                 105                 110

```
Ile Phe Leu Cys Gln Gly Lys Arg Pro Arg Ser Gln Glu Tyr Arg Ile
            115                 120                 125

Gln Leu Arg Val Tyr Lys Ala Pro Glu Pro Asn Ile Gln Val Asn
    130                 135                 140

Pro Leu Gly Ile Pro Val Asn Ser Lys Glu Pro Glu Glu Val Ala Thr
145                 150                 155                 160

Cys Val Gly Arg Asn Gly Tyr Pro Ile Pro Gln Val Ile Trp Tyr Lys
                165                 170                 175

Asn Gly Arg Pro Leu Lys Glu Glu Lys Asn Arg Val His Ile Gln Ser
                180                 185                 190

Ser Gln Thr Val Glu Ser Ser Gly Leu Tyr Thr Leu Gln Ser Ile Leu
            195                 200                 205

Lys Ala Gln Leu Val Lys Glu Asp Lys Asp Ala Gln Phe Tyr Cys Glu
    210                 215                 220

Leu Asn Tyr Arg Leu Pro Ser Gly Asn His Met Lys Glu Ser Arg Glu
225                 230                 235                 240

Val Thr Val Pro Val Phe Tyr Pro Thr Glu Lys Val Trp Leu Glu Val
                245                 250                 255

Glu Pro Val Gly Met Leu Lys Glu Gly Asp Arg Val Glu Ile Arg Cys
            260                 265                 270

Leu Ala Asp Gly Asn Pro Pro Pro His Phe Ser Ile Ser Lys Gln Asn
    275                 280                 285

Pro Ser Thr Arg Glu Ala Glu Glu Thr Thr Asn Asp Asn Gly Val
290                 295                 300

Leu Val Leu Glu Pro Ala Arg Lys Glu His Ser Gly Arg Tyr Glu Cys
305                 310                 315                 320

Gln Ala Trp Asn Leu Asp Thr Met Ile Ser Leu Leu Ser Glu Pro Gln
                325                 330                 335

Glu Leu Leu Val Asn Tyr Val Ser Asp Val Arg Val Ser Pro Ala Ala
            340                 345                 350

Pro Glu Arg Gln Glu Gly Ser Ser Leu Thr Leu Thr Cys Glu Ala Glu
    355                 360                 365

Ser Ser Gln Asp Leu Glu Phe Gln Trp Leu Arg Glu Glu Thr Asp Gln
370                 375                 380

Val Leu Glu Arg Gly Pro Val Leu Gln Leu His Asp Leu Lys Arg Glu
385                 390                 395                 400

Ala Gly Gly Gly Tyr Arg Cys Val Ala Ser Val Pro Ser Ile Pro Gly
                405                 410                 415

Leu Asn Arg Thr Gln Leu Val Lys Leu Ala Ile Phe Gly Pro Pro Trp
            420                 425                 430

Met Ala Phe Lys Glu Arg Lys Val Trp Val Lys Glu Asn Met Val Leu
    435                 440                 445

Asn Leu Ser Cys Glu Ala Ser Gly His Pro Arg Pro Thr Ile Ser Trp
450                 455                 460

Asn Val Asn Gly Thr Ala Ser Glu Gln Asp Gln Asp Pro Gln Arg Val
465                 470                 475                 480

Leu Ser Thr Leu Asn Val Leu Val Thr Pro Glu Leu Leu Glu Thr Gly
                485                 490                 495

Val Glu Cys Thr Ala Ser Asn Asp Leu Gly Lys Asn Thr Ser Ile Leu
            500                 505                 510

Phe Leu Glu Leu Val Asn Leu Thr Thr Leu Thr Pro Asp Ser Asn Thr
    515                 520                 525
```

```
Thr Thr Gly Leu Ser Thr Ser Thr Ala Ser Pro His Thr Arg Ala Asn
    530                 535                 540

Ser Thr Ser Thr Glu Arg Lys Leu
545                 550

<210> SEQ ID NO 2
<211> LENGTH: 553
<212> TYPE: PRT
<213> ORGANISM: Homo sapiens

<400> SEQUENCE: 2

Met Gly Leu Pro Arg Leu Val Cys Ala Phe Leu Leu Ala Ala Cys Cys
1               5                   10                  15

Cys Cys Pro Arg Val Ala Gly Val Pro Gly Glu Ala Glu Gln Pro Ala
            20                  25                  30

Pro Glu Leu Val Glu Val Glu Val Gly Ser Thr Ala Leu Leu Lys Cys
        35                  40                  45

Gly Leu Ser Gln Ser Gln Gly Asn Leu Ser His Val Asp Trp Phe Ser
    50                  55                  60

Val His Lys Glu Lys Arg Thr Leu Ile Phe Arg Val Arg Gln Gly Gln
65                  70                  75                  80

Gly Gln Ser Glu Pro Gly Glu Tyr Glu Gln Arg Leu Ser Leu Gln Asp
                85                  90                  95

Arg Gly Ala Thr Leu Ala Leu Thr Gln Val Thr Pro Gln Asp Glu Arg
            100                 105                 110

Ile Phe Leu Cys Gln Gly Lys Arg Pro Arg Ser Gln Glu Tyr Arg Ile
        115                 120                 125

Gln Leu Arg Val Tyr Lys Ala Pro Glu Glu Pro Asn Ile Gln Val Asn
    130                 135                 140

Pro Leu Gly Ile Pro Val Asn Ser Lys Glu Pro Glu Glu Val Ala Thr
145                 150                 155                 160

Cys Val Gly Arg Asn Gly Tyr Pro Ile Pro Gln Val Ile Trp Tyr Lys
                165                 170                 175

Asn Gly Arg Pro Leu Lys Glu Glu Lys Asn Arg Val His Ile Gln Ser
            180                 185                 190

Ser Gln Thr Val Glu Ser Ser Gly Leu Tyr Thr Leu Gln Ser Ile Leu
        195                 200                 205

Lys Ala Gln Leu Val Lys Glu Asp Lys Asp Ala Gln Phe Tyr Cys Glu
    210                 215                 220

Leu Asn Tyr Arg Leu Pro Ser Gly Asn His Met Lys Glu Ser Arg Glu
225                 230                 235                 240

Val Thr Val Pro Val Phe Tyr Pro Thr Glu Lys Val Trp Leu Glu Val
                245                 250                 255

Glu Pro Val Gly Met Leu Lys Glu Gly Asp Arg Val Glu Ile Arg Cys
            260                 265                 270

Leu Ala Asp Gly Asn Pro Pro Pro His Phe Ser Ile Ser Lys Gln Asn
        275                 280                 285

Pro Ser Thr Arg Glu Ala Glu Glu Thr Thr Asn Asp Asn Gly Val
    290                 295                 300

Leu Val Leu Glu Pro Ala Arg Lys Glu His Ser Gly Arg Tyr Glu Cys
305                 310                 315                 320

Gln Ala Trp Asn Leu Asp Thr Met Ile Ser Leu Leu Ser Glu Pro Gln
                325                 330                 335

Glu Leu Leu Val Asn Tyr Val Ser Asp Val Arg Val Ser Pro Ala Ala
            340                 345                 350
```

```
Pro Glu Arg Gln Glu Gly Ser Ser Leu Thr Leu Thr Cys Glu Ala Glu
            355                 360                 365

Ser Ser Gln Asp Leu Glu Phe Gln Trp Leu Arg Glu Glu Thr Asp Gln
        370                 375                 380

Val Leu Glu Arg Gly Pro Val Leu Gln Leu His Asp Leu Lys Arg Glu
385                 390                 395                 400

Ala Gly Gly Gly Tyr Arg Cys Val Ala Ser Val Pro Ser Ile Pro Gly
                405                 410                 415

Leu Asn Arg Thr Gln Leu Val Lys Leu Ala Ile Phe Gly Pro Pro Trp
            420                 425                 430

Met Ala Phe Lys Glu Arg Lys Val Trp Val Lys Glu Asn Met Val Leu
        435                 440                 445

Asn Leu Ser Cys Glu Ala Ser Gly His Pro Arg Pro Thr Ile Ser Trp
    450                 455                 460

Asn Val Asn Gly Thr Ala Ser Glu Gln Asp Gln Asp Pro Gln Arg Val
465                 470                 475                 480

Leu Ser Thr Leu Asn Val Leu Val Thr Pro Glu Leu Leu Glu Thr Gly
                485                 490                 495

Val Glu Cys Thr Ala Ser Asn Asp Leu Gly Lys Asn Thr Ser Ile Leu
            500                 505                 510

Phe Leu Glu Leu Val Asn Leu Thr Thr Leu Thr Pro Asp Ser Asn Thr
        515                 520                 525

Thr Thr Gly Leu Ser Thr Ser Thr Ala Ser Pro His Thr Arg Ala Asn
    530                 535                 540

Ser Thr Ser Thr Glu Arg Lys Leu Pro
545                 550

<210> SEQ ID NO 3
<211> LENGTH: 554
<212> TYPE: PRT
<213> ORGANISM: Homo sapiens

<400> SEQUENCE: 3

Met Gly Leu Pro Arg Leu Val Cys Ala Phe Leu Leu Ala Ala Cys Cys
1               5                   10                  15

Cys Cys Pro Arg Val Ala Gly Val Pro Gly Glu Ala Glu Gln Pro Ala
            20                  25                  30

Pro Glu Leu Val Glu Val Glu Val Gly Ser Thr Ala Leu Leu Lys Cys
        35                  40                  45

Gly Leu Ser Gln Ser Gln Gly Asn Leu Ser His Val Asp Trp Phe Ser
    50                  55                  60

Val His Lys Glu Lys Arg Thr Leu Ile Phe Arg Val Arg Gln Gly Gln
65                  70                  75                  80

Gly Gln Ser Glu Pro Gly Glu Tyr Glu Gln Arg Leu Ser Leu Gln Asp
                85                  90                  95

Arg Gly Ala Thr Leu Ala Leu Thr Gln Val Thr Pro Gln Asp Glu Arg
            100                 105                 110

Ile Phe Leu Cys Gln Gly Lys Arg Pro Arg Ser Gln Glu Tyr Arg Ile
        115                 120                 125

Gln Leu Arg Val Tyr Lys Ala Pro Glu Glu Pro Asn Ile Gln Val Asn
    130                 135                 140

Pro Leu Gly Ile Pro Val Asn Ser Lys Glu Pro Glu Glu Val Ala Thr
145                 150                 155                 160

Cys Val Gly Arg Asn Gly Tyr Pro Ile Pro Gln Val Ile Trp Tyr Lys
```

```
            165                 170                 175
Asn Gly Arg Pro Leu Lys Glu Lys Asn Arg Val His Ile Gln Ser
            180                 185                 190

Ser Gln Thr Val Glu Ser Ser Gly Leu Tyr Thr Leu Gln Ser Ile Leu
            195                 200                 205

Lys Ala Gln Leu Val Lys Glu Asp Lys Asp Ala Gln Phe Tyr Cys Glu
            210                 215                 220

Leu Asn Tyr Arg Leu Pro Ser Gly Asn His Met Lys Glu Ser Arg Glu
225                 230                 235                 240

Val Thr Val Pro Val Phe Tyr Pro Thr Glu Lys Val Trp Leu Glu Val
                245                 250                 255

Glu Pro Val Gly Met Leu Lys Glu Gly Asp Arg Val Glu Ile Arg Cys
            260                 265                 270

Leu Ala Asp Gly Asn Pro Pro His Phe Ser Ile Ser Lys Gln Asn
            275                 280                 285

Pro Ser Thr Arg Glu Ala Glu Glu Thr Thr Asn Asp Asn Gly Val
            290                 295                 300

Leu Val Leu Glu Pro Ala Arg Lys Glu His Ser Gly Arg Tyr Glu Cys
305                 310                 315                 320

Gln Ala Trp Asn Leu Asp Thr Met Ile Ser Leu Leu Ser Glu Pro Gln
                325                 330                 335

Glu Leu Leu Val Asn Tyr Val Ser Asp Val Arg Val Ser Pro Ala Ala
            340                 345                 350

Pro Glu Arg Gln Glu Gly Ser Ser Leu Thr Leu Thr Cys Glu Ala Glu
            355                 360                 365

Ser Ser Gln Asp Leu Glu Phe Gln Trp Leu Arg Glu Glu Thr Asp Gln
            370                 375                 380

Val Leu Glu Arg Gly Pro Val Leu Gln Leu His Asp Leu Lys Arg Glu
385                 390                 395                 400

Ala Gly Gly Gly Tyr Arg Cys Val Ala Ser Val Pro Ser Ile Pro Gly
                405                 410                 415

Leu Asn Arg Thr Gln Leu Val Lys Leu Ala Ile Phe Gly Pro Pro Trp
            420                 425                 430

Met Ala Phe Lys Glu Arg Lys Val Trp Val Lys Glu Asn Met Val Leu
            435                 440                 445

Asn Leu Ser Cys Glu Ala Ser Gly His Pro Arg Pro Thr Ile Ser Trp
            450                 455                 460

Asn Val Asn Gly Thr Ala Ser Glu Gln Asp Gln Asp Pro Gln Arg Val
465                 470                 475                 480

Leu Ser Thr Leu Asn Val Leu Val Thr Pro Glu Leu Leu Glu Thr Gly
                485                 490                 495

Val Glu Cys Thr Ala Ser Asn Asp Leu Gly Lys Asn Thr Ser Ile Leu
            500                 505                 510

Phe Leu Glu Leu Val Asn Leu Thr Thr Leu Thr Pro Asp Ser Asn Thr
            515                 520                 525

Thr Thr Gly Leu Ser Thr Ser Thr Ala Ser Pro His Thr Arg Ala Asn
            530                 535                 540

Ser Thr Ser Thr Glu Arg Lys Leu Pro Glu
545                 550

<210> SEQ ID NO 4
<211> LENGTH: 555
<212> TYPE: PRT
<213> ORGANISM: Homo sapiens
```

<400> SEQUENCE: 4

```
Met Gly Leu Pro Arg Leu Val Cys Ala Phe Leu Leu Ala Ala Cys Cys
1               5                   10                  15

Cys Cys Pro Arg Val Ala Gly Val Pro Gly Glu Ala Glu Gln Pro Ala
            20                  25                  30

Pro Glu Leu Val Glu Val Glu Val Gly Ser Thr Ala Leu Leu Lys Cys
            35                  40                  45

Gly Leu Ser Gln Ser Gln Gly Asn Leu Ser His Val Asp Trp Phe Ser
    50                  55                  60

Val His Lys Glu Lys Arg Thr Leu Ile Phe Arg Val Arg Gln Gly Gln
65                  70                  75                  80

Gly Gln Ser Glu Pro Gly Glu Tyr Glu Gln Arg Leu Ser Leu Gln Asp
            85                  90                  95

Arg Gly Ala Thr Leu Ala Leu Thr Gln Val Thr Pro Gln Asp Glu Arg
            100                 105                 110

Ile Phe Leu Cys Gln Gly Lys Arg Pro Arg Ser Gln Glu Tyr Arg Ile
            115                 120                 125

Gln Leu Arg Val Tyr Lys Ala Pro Glu Glu Pro Asn Ile Gln Val Asn
    130                 135                 140

Pro Leu Gly Ile Pro Val Asn Ser Lys Glu Pro Glu Glu Val Ala Thr
145                 150                 155                 160

Cys Val Gly Arg Asn Gly Tyr Pro Ile Pro Gln Val Ile Trp Tyr Lys
            165                 170                 175

Asn Gly Arg Pro Leu Lys Glu Glu Lys Asn Arg Val His Ile Gln Ser
            180                 185                 190

Ser Gln Thr Val Glu Ser Ser Gly Leu Tyr Thr Leu Gln Ser Ile Leu
    195                 200                 205

Lys Ala Gln Leu Val Lys Glu Asp Lys Asp Ala Gln Phe Tyr Cys Glu
210                 215                 220

Leu Asn Tyr Arg Leu Pro Ser Gly Asn His Met Lys Glu Ser Arg Glu
225                 230                 235                 240

Val Thr Val Pro Val Phe Tyr Pro Thr Glu Lys Val Trp Leu Glu Val
            245                 250                 255

Glu Pro Val Gly Met Leu Lys Glu Gly Asp Arg Val Glu Ile Arg Cys
            260                 265                 270

Leu Ala Asp Gly Asn Pro Pro His Phe Ser Ile Ser Lys Gln Asn
    275                 280                 285

Pro Ser Thr Arg Glu Ala Glu Glu Thr Thr Asn Asp Asn Gly Val
290                 295                 300

Leu Val Leu Glu Pro Ala Arg Lys Glu His Ser Gly Arg Tyr Glu Cys
305                 310                 315                 320

Gln Ala Trp Asn Leu Asp Thr Met Ile Ser Leu Leu Ser Glu Pro Gln
            325                 330                 335

Glu Leu Leu Val Asn Tyr Val Ser Asp Val Arg Val Ser Pro Ala Ala
            340                 345                 350

Pro Glu Arg Gln Glu Gly Ser Ser Leu Thr Leu Thr Cys Glu Ala Glu
            355                 360                 365

Ser Ser Gln Asp Leu Glu Phe Gln Trp Leu Arg Glu Glu Thr Asp Gln
    370                 375                 380

Val Leu Glu Arg Gly Pro Val Leu Gln Leu His Asp Leu Lys Arg Glu
385                 390                 395                 400

Ala Gly Gly Gly Tyr Arg Cys Val Ala Ser Val Pro Ser Ile Pro Gly
```

```
                        405                 410                 415
Leu Asn Arg Thr Gln Leu Val Lys Leu Ala Ile Phe Gly Pro Pro Trp
            420                 425                 430

Met Ala Phe Lys Glu Arg Lys Val Trp Val Lys Glu Asn Met Val Leu
            435                 440                 445

Asn Leu Ser Cys Glu Ala Ser Gly His Pro Arg Pro Thr Ile Ser Trp
            450                 455                 460

Asn Val Asn Gly Thr Ala Ser Glu Gln Asp Gln Asp Pro Gln Arg Val
465                 470                 475                 480

Leu Ser Thr Leu Asn Val Leu Val Thr Pro Glu Leu Leu Glu Thr Gly
                485                 490                 495

Val Glu Cys Thr Ala Ser Asn Asp Leu Gly Lys Asn Thr Ser Ile Leu
            500                 505                 510

Phe Leu Glu Leu Val Asn Leu Thr Thr Leu Thr Pro Asp Ser Asn Thr
            515                 520                 525

Thr Thr Gly Leu Ser Thr Ser Thr Ala Ser Pro His Thr Arg Ala Asn
            530                 535                 540

Ser Thr Ser Thr Glu Arg Lys Leu Pro Glu Pro
545                 550                 555

<210> SEQ ID NO 5
<211> LENGTH: 556
<212> TYPE: PRT
<213> ORGANISM: Homo sapiens

<400> SEQUENCE: 5

Met Gly Leu Pro Arg Leu Val Cys Ala Phe Leu Leu Ala Ala Cys Cys
1               5                   10                  15

Cys Cys Pro Arg Val Ala Gly Val Pro Gly Glu Ala Glu Gln Pro Ala
            20                  25                  30

Pro Glu Leu Val Glu Val Glu Val Gly Ser Thr Ala Leu Leu Lys Cys
            35                  40                  45

Gly Leu Ser Gln Ser Gln Gly Asn Leu Ser His Val Asp Trp Phe Ser
        50                  55                  60

Val His Lys Glu Lys Arg Thr Leu Ile Phe Arg Val Arg Gln Gly Gln
65              70                  75                  80

Gly Gln Ser Glu Pro Gly Glu Tyr Glu Gln Arg Leu Ser Leu Gln Asp
                85                  90                  95

Arg Gly Ala Thr Leu Ala Leu Thr Gln Val Thr Pro Gln Asp Glu Arg
            100                 105                 110

Ile Phe Leu Cys Gln Gly Lys Arg Pro Arg Ser Gln Glu Tyr Arg Ile
            115                 120                 125

Gln Leu Arg Val Tyr Lys Ala Pro Glu Glu Pro Asn Ile Gln Val Asn
        130                 135                 140

Pro Leu Gly Ile Pro Val Asn Ser Lys Glu Pro Glu Glu Val Ala Thr
145                 150                 155                 160

Cys Val Gly Arg Asn Gly Tyr Pro Ile Pro Gln Val Ile Trp Tyr Lys
                165                 170                 175

Asn Gly Arg Pro Leu Lys Glu Glu Lys Asn Arg Val His Ile Gln Ser
            180                 185                 190

Ser Gln Thr Val Glu Ser Ser Gly Leu Tyr Thr Leu Gln Ser Ile Leu
            195                 200                 205

Lys Ala Gln Leu Val Lys Glu Asp Lys Asp Ala Gln Phe Tyr Cys Glu
        210                 215                 220
```

```
Leu Asn Tyr Arg Leu Pro Ser Gly Asn His Met Lys Glu Ser Arg Glu
225                 230                 235                 240

Val Thr Val Pro Val Phe Tyr Pro Thr Glu Lys Val Trp Leu Glu Val
            245                 250                 255

Glu Pro Val Gly Met Leu Lys Glu Gly Asp Arg Val Glu Ile Arg Cys
        260                 265                 270

Leu Ala Asp Gly Asn Pro Pro His Phe Ser Ile Ser Lys Gln Asn
    275                 280                 285

Pro Ser Thr Arg Glu Ala Glu Glu Thr Thr Asn Asp Asn Gly Val
290                 295                 300

Leu Val Leu Glu Pro Ala Arg Lys Glu His Ser Gly Arg Tyr Glu Cys
305                 310                 315                 320

Gln Ala Trp Asn Leu Asp Thr Met Ile Ser Leu Leu Ser Glu Pro Gln
            325                 330                 335

Glu Leu Leu Val Asn Tyr Val Ser Asp Val Arg Val Ser Pro Ala Ala
            340                 345                 350

Pro Glu Arg Gln Glu Gly Ser Ser Leu Thr Leu Thr Cys Glu Ala Glu
        355                 360                 365

Ser Ser Gln Asp Leu Glu Phe Gln Trp Leu Arg Glu Glu Thr Asp Gln
370                 375                 380

Val Leu Glu Arg Gly Pro Val Leu Gln Leu His Asp Leu Lys Arg Glu
385                 390                 395                 400

Ala Gly Gly Gly Tyr Arg Cys Val Ala Ser Val Pro Ser Ile Pro Gly
                405                 410                 415

Leu Asn Arg Thr Gln Leu Val Lys Leu Ala Ile Phe Gly Pro Pro Trp
            420                 425                 430

Met Ala Phe Lys Glu Arg Lys Val Trp Val Lys Glu Asn Met Val Leu
            435                 440                 445

Asn Leu Ser Cys Glu Ala Ser Gly His Pro Arg Pro Thr Ile Ser Trp
    450                 455                 460

Asn Val Asn Gly Thr Ala Ser Glu Gln Asp Gln Asp Pro Gln Arg Val
465                 470                 475                 480

Leu Ser Thr Leu Asn Val Leu Val Thr Pro Glu Leu Leu Glu Thr Gly
            485                 490                 495

Val Glu Cys Thr Ala Ser Asn Asp Leu Gly Lys Asn Thr Ser Ile Leu
        500                 505                 510

Phe Leu Glu Leu Val Asn Leu Thr Thr Leu Thr Pro Asp Ser Asn Thr
            515                 520                 525

Thr Thr Gly Leu Ser Ser Thr Ala Ser Pro His Thr Arg Ala Asn
    530                 535                 540

Ser Thr Ser Thr Glu Arg Lys Leu Pro Glu Pro Glu
545                 550                 555

<210> SEQ ID NO 6
<211> LENGTH: 557
<212> TYPE: PRT
<213> ORGANISM: Homo sapiens

<400> SEQUENCE: 6

Met Gly Leu Pro Arg Leu Val Cys Ala Phe Leu Leu Ala Ala Cys Cys
1               5                   10                  15

Cys Cys Pro Arg Val Ala Gly Val Pro Gly Glu Ala Glu Gln Pro Ala
            20                  25                  30

Pro Glu Leu Val Glu Val Glu Val Gly Ser Thr Ala Leu Leu Lys Cys
        35                  40                  45
```

-continued

```
Gly Leu Ser Gln Ser Gln Gly Asn Leu Ser His Val Asp Trp Phe Ser
    50                  55                  60
Val His Lys Glu Lys Arg Thr Leu Ile Phe Arg Val Arg Gln Gly Gln
65                  70                  75                  80
Gly Gln Ser Glu Pro Gly Glu Tyr Glu Gln Arg Leu Ser Leu Gln Asp
                85                  90                  95
Arg Gly Ala Thr Leu Ala Leu Thr Gln Val Thr Pro Gln Asp Glu Arg
            100                 105                 110
Ile Phe Leu Cys Gln Gly Lys Arg Pro Arg Ser Gln Glu Tyr Arg Ile
        115                 120                 125
Gln Leu Arg Val Tyr Lys Ala Pro Glu Glu Pro Asn Ile Gln Val Asn
    130                 135                 140
Pro Leu Gly Ile Pro Val Asn Ser Lys Glu Pro Glu Glu Val Ala Thr
145                 150                 155                 160
Cys Val Gly Arg Asn Gly Tyr Pro Ile Pro Gln Val Ile Trp Tyr Lys
                165                 170                 175
Asn Gly Arg Pro Leu Lys Glu Glu Lys Asn Arg Val His Ile Gln Ser
            180                 185                 190
Ser Gln Thr Val Glu Ser Ser Gly Leu Tyr Thr Leu Gln Ser Ile Leu
        195                 200                 205
Lys Ala Gln Leu Val Lys Glu Asp Lys Asp Ala Gln Phe Tyr Cys Glu
    210                 215                 220
Leu Asn Tyr Arg Leu Pro Ser Gly Asn His Met Lys Glu Ser Arg Glu
225                 230                 235                 240
Val Thr Val Pro Val Phe Tyr Pro Thr Glu Lys Val Trp Leu Glu Val
                245                 250                 255
Glu Pro Val Gly Met Leu Lys Glu Gly Asp Arg Val Glu Ile Arg Cys
            260                 265                 270
Leu Ala Asp Gly Asn Pro Pro His Phe Ser Ile Ser Lys Gln Asn
        275                 280                 285
Pro Ser Thr Arg Glu Ala Glu Glu Thr Thr Asn Asp Asn Gly Val
    290                 295                 300
Leu Val Leu Glu Pro Ala Arg Lys Glu His Ser Gly Arg Tyr Glu Cys
305                 310                 315                 320
Gln Ala Trp Asn Leu Asp Thr Met Ile Ser Leu Leu Ser Glu Pro Gln
                325                 330                 335
Glu Leu Leu Val Asn Tyr Val Ser Asp Val Arg Val Ser Pro Ala Ala
            340                 345                 350
Pro Glu Arg Gln Glu Gly Ser Ser Leu Thr Leu Thr Cys Glu Ala Glu
        355                 360                 365
Ser Ser Gln Asp Leu Glu Phe Gln Trp Leu Arg Glu Glu Thr Asp Gln
    370                 375                 380
Val Leu Glu Arg Gly Pro Val Leu Gln Leu His Asp Leu Lys Arg Glu
385                 390                 395                 400
Ala Gly Gly Gly Tyr Arg Cys Val Ala Ser Val Pro Ser Ile Pro Gly
                405                 410                 415
Leu Asn Arg Thr Gln Leu Val Lys Leu Ala Ile Phe Gly Pro Pro Trp
            420                 425                 430
Met Ala Phe Lys Glu Arg Lys Val Trp Val Lys Glu Asn Met Val Leu
        435                 440                 445
Asn Leu Ser Cys Glu Ala Ser Gly His Pro Arg Pro Thr Ile Ser Trp
    450                 455                 460
```

```
Asn Val Asn Gly Thr Ala Ser Glu Gln Asp Gln Asp Pro Gln Arg Val
465                 470                 475                 480

Leu Ser Thr Leu Asn Val Leu Val Thr Pro Glu Leu Leu Glu Thr Gly
            485                 490                 495

Val Glu Cys Thr Ala Ser Asn Asp Leu Gly Lys Asn Thr Ser Ile Leu
        500                 505                 510

Phe Leu Glu Leu Val Asn Leu Thr Thr Leu Thr Pro Asp Ser Asn Thr
    515                 520                 525

Thr Thr Gly Leu Ser Thr Ser Thr Ala Ser Pro His Thr Arg Ala Asn
530                 535                 540

Ser Thr Ser Thr Glu Arg Lys Leu Pro Glu Pro Glu Ser
545                 550                 555

<210> SEQ ID NO 7
<211> LENGTH: 558
<212> TYPE: PRT
<213> ORGANISM: Homo sapiens

<400> SEQUENCE: 7

Met Gly Leu Pro Arg Leu Val Cys Ala Phe Leu Leu Ala Ala Cys Cys
1               5                   10                  15

Cys Cys Pro Arg Val Ala Gly Val Pro Gly Glu Ala Glu Gln Pro Ala
            20                  25                  30

Pro Glu Leu Val Glu Val Glu Val Gly Ser Thr Ala Leu Leu Lys Cys
        35                  40                  45

Gly Leu Ser Gln Ser Gln Gly Asn Leu Ser His Val Asp Trp Phe Ser
    50                  55                  60

Val His Lys Glu Lys Arg Thr Leu Ile Phe Arg Val Arg Gln Gly Gln
65                  70                  75                  80

Gly Gln Ser Glu Pro Gly Glu Tyr Glu Gln Arg Leu Ser Leu Gln Asp
                85                  90                  95

Arg Gly Ala Thr Leu Ala Leu Thr Gln Val Thr Pro Gln Asp Glu Arg
            100                 105                 110

Ile Phe Leu Cys Gln Gly Lys Arg Pro Arg Ser Gln Glu Tyr Arg Ile
        115                 120                 125

Gln Leu Arg Val Tyr Lys Ala Pro Glu Glu Pro Asn Ile Gln Val Asn
    130                 135                 140

Pro Leu Gly Ile Pro Val Asn Ser Lys Glu Pro Glu Glu Val Ala Thr
145                 150                 155                 160

Cys Val Gly Arg Asn Gly Tyr Pro Ile Pro Gln Val Ile Trp Tyr Lys
                165                 170                 175

Asn Gly Arg Pro Leu Lys Glu Glu Lys Asn Arg Val His Ile Gln Ser
            180                 185                 190

Ser Gln Thr Val Glu Ser Ser Gly Leu Tyr Thr Leu Gln Ser Ile Leu
        195                 200                 205

Lys Ala Gln Leu Val Lys Glu Asp Lys Asp Ala Gln Phe Tyr Cys Glu
    210                 215                 220

Leu Asn Tyr Arg Leu Pro Ser Gly Asn His Met Lys Glu Ser Arg Glu
225                 230                 235                 240

Val Thr Val Pro Val Phe Tyr Pro Thr Glu Lys Val Trp Leu Glu Val
                245                 250                 255

Glu Pro Val Gly Met Leu Lys Glu Gly Asp Arg Val Glu Ile Arg Cys
            260                 265                 270

Leu Ala Asp Gly Asn Pro Pro Pro His Phe Ser Ile Ser Lys Gln Asn
        275                 280                 285
```

```
Pro Ser Thr Arg Glu Ala Glu Glu Thr Thr Asn Asp Asn Gly Val
    290                 295                 300

Leu Val Leu Glu Pro Ala Arg Lys Glu His Ser Gly Arg Tyr Glu Cys
305                 310                 315                 320

Gln Ala Trp Asn Leu Asp Thr Met Ile Ser Leu Ser Glu Pro Gln
                325                 330                 335

Glu Leu Leu Val Asn Tyr Val Ser Asp Val Arg Val Ser Pro Ala Ala
                340                 345                 350

Pro Glu Arg Gln Glu Gly Ser Ser Leu Thr Leu Thr Cys Glu Ala Glu
                355                 360                 365

Ser Ser Gln Asp Leu Glu Phe Gln Trp Leu Arg Glu Glu Thr Asp Gln
    370                 375                 380

Val Leu Glu Arg Gly Pro Val Leu Gln Leu His Asp Leu Lys Arg Glu
385                 390                 395                 400

Ala Gly Gly Gly Tyr Arg Cys Val Ala Ser Val Pro Ser Ile Pro Gly
                405                 410                 415

Leu Asn Arg Thr Gln Leu Val Lys Leu Ala Ile Phe Gly Pro Pro Trp
                420                 425                 430

Met Ala Phe Lys Glu Arg Lys Val Trp Val Lys Glu Asn Met Val Leu
        435                 440                 445

Asn Leu Ser Cys Glu Ala Ser Gly His Pro Arg Pro Thr Ile Ser Trp
    450                 455                 460

Asn Val Asn Gly Thr Ala Ser Glu Gln Asp Gln Asp Pro Gln Arg Val
465                 470                 475                 480

Leu Ser Thr Leu Asn Val Leu Val Thr Pro Glu Leu Leu Glu Thr Gly
                485                 490                 495

Val Glu Cys Thr Ala Ser Asn Asp Leu Gly Lys Asn Thr Ser Ile Leu
            500                 505                 510

Phe Leu Glu Leu Val Asn Leu Thr Thr Leu Thr Pro Asp Ser Asn Thr
        515                 520                 525

Thr Thr Gly Leu Ser Thr Ser Thr Ala Ser Pro His Thr Arg Ala Asn
    530                 535                 540

Ser Thr Ser Thr Glu Arg Lys Leu Pro Glu Pro Glu Ser Arg
545                 550                 555

<210> SEQ ID NO 8
<211> LENGTH: 527
<212> TYPE: PRT
<213> ORGANISM: Homo sapiens

<400> SEQUENCE: 8

Met Val Tyr Ile Val Arg Gln Phe Leu Leu Tyr Asn Val Ser Gly Ser
1               5                   10                  15

Val Tyr Leu Asp Gln Leu Ile Val Leu Leu Thr Ala Lys Phe Ser Ile
                20                  25                  30

Leu Arg Ile Ala Gly Ser Arg Val His His Ser Pro Phe Ser Gly His
            35                  40                  45

Leu Asp Gly Cys Ser Phe Leu Ser Leu Gln His Ser Leu His Thr Ser
        50                  55                  60

Leu Asp Met Ser Arg His Glu Asn Val Phe Leu Gly Leu Thr Leu Ser
65                  70                  75                  80

Ser Lys Ser Ala Gly Leu Lys Gly Phe Gln Leu Ala Phe Val Pro Gly
                85                  90                  95

Leu Leu Gln Gly Thr Gly Gly Tyr Leu Asp Gly Pro Leu Pro Thr Pro
```

```
            100                 105                 110
Val Asp Asn Pro Arg Val Gly Leu Glu Val Gly Leu Arg Leu Ser Leu
            115                 120                 125

Pro Pro Leu Pro Pro Cys Pro Gly Val His Ile Gln Ser Ser Gln Thr
            130                 135             140

Val Glu Ser Ser Gly Leu Tyr Thr Leu Gln Ser Ile Leu Lys Ala Gln
145                 150                 155                 160

Leu Val Lys Glu Asp Lys Asp Ala Gln Phe Tyr Cys Glu Leu Asn Tyr
                165                 170                 175

Arg Leu Pro Ser Gly Asn His Met Lys Glu Ser Arg Glu Val Thr Val
            180                 185                 190

Pro Val Phe Tyr Pro Thr Glu Lys Val Trp Leu Glu Val Glu Pro Val
            195                 200                 205

Gly Met Leu Lys Glu Gly Asp Arg Val Glu Ile Arg Cys Leu Ala Asp
            210                 215                 220

Gly Asn Pro Pro Pro His Phe Ser Ile Ser Lys Gln Asn Pro Ser Thr
225                 230                 235                 240

Arg Glu Ala Glu Glu Thr Thr Asn Asp Asn Gly Val Leu Val Leu
            245                 250                 255

Glu Pro Ala Arg Lys Glu His Ser Gly Arg Tyr Glu Cys Gln Gly Leu
            260                 265                 270

Asp Leu Asp Thr Met Ile Ser Leu Leu Ser Glu Pro Gln Glu Leu Leu
            275                 280                 285

Val Asn Tyr Val Ser Asp Val Arg Val Ser Pro Ala Ala Pro Glu Arg
            290                 295                 300

Gln Glu Gly Ser Ser Leu Thr Leu Thr Cys Glu Ala Glu Ser Ser Gln
305                 310                 315                 320

Asp Leu Glu Phe Gln Trp Leu Arg Glu Glu Thr Gly Gln Val Leu Glu
            325                 330                 335

Arg Gly Pro Val Leu Gln Leu His Asp Leu Lys Arg Glu Ala Gly Gly
            340                 345                 350

Gly Tyr Arg Cys Val Ala Ser Val Pro Ser Ile Pro Gly Leu Asn Arg
            355                 360                 365

Thr Gln Leu Val Asn Val Ala Ile Phe Gly Pro Pro Trp Met Ala Phe
            370                 375                 380

Lys Glu Arg Lys Val Trp Val Lys Glu Asn Met Val Leu Asn Leu Ser
385                 390                 395                 400

Cys Glu Ala Ser Gly His Pro Arg Pro Thr Ile Ser Trp Asn Val Asn
                405                 410                 415

Gly Thr Ala Ser Glu Gln Asp Gln Asp Pro Gln Arg Val Leu Ser Thr
            420                 425                 430

Leu Asn Val Leu Val Thr Pro Glu Leu Leu Glu Thr Gly Val Glu Cys
            435                 440                 445

Thr Ala Ser Asn Asp Leu Gly Lys Asn Thr Ser Ile Leu Phe Leu Glu
            450                 455                 460

Leu Val Asn Leu Thr Thr Leu Thr Pro Asp Ser Asn Thr Thr Thr Gly
465                 470                 475                 480

Leu Ser Thr Ser Thr Ala Ser Pro His Thr Arg Ala Asn Ser Thr Ser
            485                 490                 495

Thr Gly Lys Pro Gly Leu Ala Arg Glu Gln Gly Cys Ala Arg Ala Ser
            500                 505                 510

Phe Leu Pro Cys Pro Ser Pro Glu Ser Pro Val Gln Lys Gly Glu
            515                 520                 525
```

<210> SEQ ID NO 9
<211> LENGTH: 467
<212> TYPE: PRT
<213> ORGANISM: Homo sapiens

<400> SEQUENCE: 9

```
Met Gly Leu Pro Arg Leu Val Cys Ala Phe Leu Leu Ala Ala Cys Cys
1               5                   10                  15

Cys Cys Pro Arg Val Ala Gly Val Pro Gly Glu Ala Glu Gln Pro Ala
            20                  25                  30

Pro Glu Leu Val Glu Val Glu Val Gly Ser Thr Ala Leu Leu Lys Cys
        35                  40                  45

Gly Leu Ser Gln Ser Gln Gly Asn Leu Ser His Val Asp Trp Phe Ser
    50                  55                  60

Val His Lys Glu Lys Arg Thr Leu Ile Phe Arg Val Arg Gln Gly Gln
65                  70                  75                  80

Gly Gln Ser Glu Pro Gly Glu Tyr Glu Gln Arg Leu Ser Leu Gln Asp
                85                  90                  95

Arg Gly Ala Thr Leu Ala Leu Thr Gln Val Thr Pro Gln Asp Glu Arg
            100                 105                 110

Ile Phe Leu Cys Gln Gly Lys Arg Pro Arg Ser Gln Glu Tyr Arg Ile
        115                 120                 125

Gln Leu Arg Val Tyr Lys Ala Pro Glu Glu Pro Asn Ile Gln Val Asn
    130                 135                 140

Pro Leu Gly Ile Pro Val Asn Ser Lys Glu Pro Glu Glu Val Ala Thr
145                 150                 155                 160

Cys Val Gly Arg Asn Gly Tyr Pro Ile Pro Gln Val Ile Trp Tyr Lys
                165                 170                 175

Asn Gly Arg Pro Leu Lys Glu Glu Lys Asn Arg Val His Ile Gln Ser
            180                 185                 190

Ser Gln Thr Val Glu Ser Ser Gly Leu Tyr Thr Leu Gln Ser Ile Leu
        195                 200                 205

Lys Ala Gln Leu Val Lys Glu Asp Lys Asp Ala Gln Phe Tyr Cys Glu
    210                 215                 220

Leu Asn Tyr Arg Leu Pro Ser Gly Asn His Met Lys Glu Ser Arg Glu
225                 230                 235                 240

Val Thr Val Pro Val Phe Tyr Pro Thr Glu Lys Val Trp Leu Glu Val
                245                 250                 255

Glu Pro Val Gly Met Leu Lys Glu Gly Asp Arg Val Glu Ile Arg Cys
            260                 265                 270

Leu Ala Asp Gly Asn Pro Pro Pro His Phe Ser Ile Ser Lys Gln Asn
        275                 280                 285

Pro Ser Thr Arg Glu Ala Glu Glu Thr Thr Asn Asp Asn Gly Val
    290                 295                 300

Leu Val Leu Glu Pro Ala Arg Lys Glu His Ser Gly Arg Tyr Glu Cys
305                 310                 315                 320

Gln Gly Leu Asp Leu Asp Thr Met Ile Ser Leu Leu Ser Glu Pro Gln
                325                 330                 335

Glu Leu Leu Val Asn Tyr Val Ser Asp Val Arg Val Ser Pro Ala Ala
            340                 345                 350

Pro Glu Arg Gln Glu Gly Ser Ser Leu Thr Leu Thr Cys Glu Ala Glu
        355                 360                 365

Ser Ser Gln Asp Leu Glu Phe Gln Trp Leu Arg Glu Glu Thr Gly Gln
```

```
                370                 375                 380
Val Leu Glu Arg Gly Pro Val Leu Gln Leu His Asp Leu Lys Arg Glu
385                 390                 395                 400

Ala Gly Gly Gly Tyr Arg Cys Val Ala Ser Val Pro Ser Ile Pro Gly
                405                 410                 415

Leu Asn Arg Thr Gln Leu Val Asn Val Ala Ile Phe Gly Glu Ala Leu
                420                 425                 430

Pro Leu Gly Arg Asp Gln Val Thr Pro Ser Gly Val Val Phe Lys Leu
                435                 440                 445

Phe Asp Lys Lys Pro Ala Ala Leu Gly Ser Ser Gly Ala Glu Gly
                450                 455                 460

Glu Ala Gly
465

<210> SEQ ID NO 10
<211> LENGTH: 646
<212> TYPE: PRT
<213> ORGANISM: Homo sapiens

<400> SEQUENCE: 10

Met Gly Leu Pro Arg Leu Val Cys Ala Phe Leu Leu Ala Ala Cys Cys
1               5                   10                  15

Cys Cys Pro Arg Val Ala Gly Val Pro Gly Glu Ala Glu Gln Pro Ala
                20                  25                  30

Pro Glu Leu Val Glu Val Glu Val Gly Ser Thr Ala Leu Leu Lys Cys
                35                  40                  45

Gly Leu Ser Gln Ser Gln Gly Asn Leu Ser His Val Asp Trp Phe Ser
            50                  55                  60

Val His Lys Glu Lys Arg Thr Leu Ile Phe Arg Val Arg Gln Gly Gln
65                  70                  75                  80

Gly Gln Ser Glu Pro Gly Glu Tyr Glu Gln Arg Leu Ser Leu Gln Asp
                85                  90                  95

Arg Gly Ala Thr Leu Ala Leu Thr Gln Val Thr Pro Gln Asp Glu Arg
                100                 105                 110

Ile Phe Leu Cys Gln Gly Lys Arg Pro Arg Ser Gln Glu Tyr Arg Ile
                115                 120                 125

Gln Leu Arg Val Tyr Lys Ala Pro Glu Glu Pro Asn Ile Gln Val Asn
                130                 135                 140

Pro Leu Gly Ile Pro Val Asn Ser Lys Glu Pro Glu Glu Val Ala Thr
145                 150                 155                 160

Cys Val Gly Arg Asn Gly Tyr Pro Ile Pro Gln Val Ile Trp Tyr Lys
                165                 170                 175

Asn Gly Arg Pro Leu Lys Glu Glu Lys Asn Arg Val His Ile Gln Ser
                180                 185                 190

Ser Gln Thr Val Glu Ser Ser Gly Leu Tyr Thr Leu Gln Ser Ile Leu
                195                 200                 205

Lys Ala Gln Leu Val Lys Glu Asp Lys Asp Ala Gln Phe Tyr Cys Glu
                210                 215                 220

Leu Asn Tyr Arg Leu Pro Ser Gly Asn His Met Lys Glu Ser Arg Glu
225                 230                 235                 240

Val Thr Val Pro Val Phe Tyr Pro Thr Glu Lys Val Trp Leu Glu Val
                245                 250                 255

Glu Pro Val Gly Met Leu Lys Glu Gly Asp Arg Val Glu Ile Arg Cys
                260                 265                 270
```

```
Leu Ala Asp Gly Asn Pro Pro His Phe Ser Ile Ser Lys Gln Asn
            275                 280                 285

Pro Ser Thr Arg Glu Ala Glu Glu Thr Thr Asn Asp Asn Gly Val
290                 295                 300

Leu Val Leu Glu Pro Ala Arg Lys Glu His Ser Gly Arg Tyr Glu Cys
305                 310                 315                 320

Gln Ala Trp Asn Leu Asp Thr Met Ile Ser Leu Ser Glu Pro Gln
            325                 330                 335

Glu Leu Leu Val Asn Tyr Val Ser Asp Val Arg Val Ser Pro Ala Ala
                340                 345                 350

Pro Glu Arg Gln Glu Gly Ser Ser Leu Thr Leu Thr Cys Glu Ala Glu
            355                 360                 365

Ser Ser Gln Asp Leu Glu Phe Gln Trp Leu Arg Glu Glu Thr Asp Gln
370                 375                 380

Val Leu Glu Arg Gly Pro Val Leu Gln Leu His Asp Leu Lys Arg Glu
385                 390                 395                 400

Ala Gly Gly Gly Tyr Arg Cys Val Ala Ser Val Pro Ser Ile Pro Gly
                405                 410                 415

Leu Asn Arg Thr Gln Leu Val Lys Leu Ala Ile Phe Gly Pro Pro Trp
            420                 425                 430

Met Ala Phe Lys Glu Arg Lys Val Trp Val Lys Glu Asn Met Val Leu
            435                 440                 445

Asn Leu Ser Cys Glu Ala Ser Gly His Pro Arg Pro Thr Ile Ser Trp
450                 455                 460

Asn Val Asn Gly Thr Ala Ser Glu Gln Asp Gln Asp Pro Gln Arg Val
465                 470                 475                 480

Leu Ser Thr Leu Asn Val Leu Val Thr Pro Glu Leu Leu Glu Thr Gly
                485                 490                 495

Val Glu Cys Thr Ala Ser Asn Asp Leu Gly Lys Asn Thr Ser Ile Leu
            500                 505                 510

Phe Leu Glu Leu Val Asn Leu Thr Thr Leu Thr Pro Asp Ser Asn Thr
            515                 520                 525

Thr Thr Gly Leu Ser Thr Ser Thr Ala Ser Pro His Thr Arg Ala Asn
530                 535                 540

Ser Thr Ser Thr Glu Arg Lys Leu Pro Glu Pro Glu Ser Arg Gly Val
545                 550                 555                 560

Val Ile Val Ala Val Ile Val Cys Ile Leu Val Leu Ala Val Leu Gly
                565                 570                 575

Ala Val Leu Tyr Phe Leu Tyr Lys Lys Gly Lys Leu Pro Cys Arg Arg
            580                 585                 590

Ser Gly Lys Gln Glu Ile Thr Leu Pro Pro Ser Arg Lys Thr Glu Leu
            595                 600                 605

Val Val Glu Val Lys Ser Asp Lys Leu Pro Glu Glu Met Gly Leu Leu
610                 615                 620

Gln Gly Ser Ser Gly Asp Lys Arg Ala Pro Gly Asp Gln Gly Glu Lys
625                 630                 635                 640

Tyr Ile Asp Leu Arg His
                645

<210> SEQ ID NO 11
<211> LENGTH: 604
<212> TYPE: PRT
<213> ORGANISM: Homo sapiens

<400> SEQUENCE: 11
```

```
Met Gly Leu Pro Arg Leu Val Cys Ala Phe Leu Leu Ala Ala Cys Cys
1               5                   10                  15
Cys Cys Pro Arg Val Ala Gly Val Pro Gly Glu Ala Glu Gln Pro Ala
                20                  25                  30
Pro Glu Leu Val Glu Val Glu Val Gly Ser Thr Ala Leu Leu Lys Cys
        35                  40                  45
Gly Leu Ser Gln Ser Gln Gly Asn Leu Ser His Val Asp Trp Phe Ser
    50                  55                  60
Val His Lys Glu Lys Arg Thr Leu Ile Phe Arg Val Arg Gln Gly Gln
65                  70                  75                  80
Gly Gln Ser Glu Pro Gly Glu Tyr Glu Gln Arg Leu Ser Leu Gln Asp
                85                  90                  95
Arg Gly Ala Thr Leu Ala Leu Thr Gln Val Thr Pro Gln Asp Glu Arg
                100                 105                 110
Ile Phe Leu Cys Gln Gly Lys Arg Pro Arg Ser Gln Glu Tyr Arg Ile
            115                 120                 125
Gln Leu Arg Val Tyr Lys Ala Pro Glu Glu Pro Asn Ile Gln Val Asn
    130                 135                 140
Pro Leu Gly Ile Pro Val Asn Ser Lys Glu Pro Glu Glu Val Ala Thr
145                 150                 155                 160
Cys Val Gly Arg Asn Gly Tyr Pro Ile Pro Gln Val Ile Trp Tyr Lys
                165                 170                 175
Asn Gly Arg Pro Leu Lys Glu Glu Lys Asn Arg Val His Ile Gln Ser
                180                 185                 190
Ser Gln Thr Val Glu Ser Ser Gly Leu Tyr Thr Leu Gln Ser Ile Leu
            195                 200                 205
Lys Ala Gln Leu Val Lys Glu Asp Lys Asp Ala Gln Phe Tyr Cys Glu
    210                 215                 220
Leu Asn Tyr Arg Leu Pro Ser Gly Asn His Met Lys Glu Ser Arg Glu
225                 230                 235                 240
Val Thr Val Pro Val Phe Tyr Pro Thr Glu Lys Val Trp Leu Glu Val
                245                 250                 255
Glu Pro Val Gly Met Leu Lys Glu Gly Asp Arg Val Glu Ile Arg Cys
                260                 265                 270
Leu Ala Asp Gly Asn Pro Pro His Phe Ser Ile Ser Lys Gln Asn
    275                 280                 285
Pro Ser Thr Arg Glu Ala Glu Glu Thr Thr Asn Asp Asn Gly Val
    290                 295                 300
Leu Val Leu Glu Pro Ala Arg Lys Glu His Ser Gly Arg Tyr Glu Cys
305                 310                 315                 320
Gln Ala Trp Asn Leu Asp Thr Met Ile Ser Leu Leu Ser Glu Pro Gln
                325                 330                 335
Glu Leu Leu Val Asn Tyr Val Ser Asp Val Arg Val Ser Pro Ala Ala
                340                 345                 350
Pro Glu Arg Gln Glu Gly Ser Ser Leu Thr Leu Thr Cys Glu Ala Glu
                355                 360                 365
Ser Ser Gln Asp Leu Glu Phe Gln Trp Leu Arg Glu Glu Thr Asp Gln
    370                 375                 380
Val Leu Glu Arg Gly Pro Val Leu Gln Leu His Asp Leu Lys Arg Glu
385                 390                 395                 400
Ala Gly Gly Gly Tyr Arg Cys Val Ala Ser Val Pro Ser Ile Pro Gly
                405                 410                 415
```

Leu Asn Arg Thr Gln Leu Val Lys Leu Ala Ile Phe Gly Pro Pro Trp
                420                 425                 430

Met Ala Phe Lys Glu Arg Lys Val Trp Val Lys Glu Asn Met Val Leu
            435                 440                 445

Asn Leu Ser Cys Glu Ala Ser Gly His Pro Arg Pro Thr Ile Ser Trp
        450                 455                 460

Asn Val Asn Gly Thr Ala Ser Glu Gln Asp Gln Asp Pro Gln Arg Val
465                 470                 475                 480

Leu Ser Thr Leu Asn Val Leu Val Thr Pro Glu Leu Leu Glu Thr Gly
                485                 490                 495

Val Glu Cys Thr Ala Ser Asn Asp Leu Gly Lys Asn Thr Ser Ile Leu
            500                 505                 510

Phe Leu Glu Leu Val Asn Leu Thr Thr Leu Thr Pro Asp Ser Asn Thr
        515                 520                 525

Thr Thr Gly Leu Ser Thr Ser Thr Ala Ser Pro His Thr Arg Ala Asn
530                 535                 540

Ser Thr Ser Thr Glu Arg Lys Leu Pro Glu Pro Glu Ser Arg Gly Val
545                 550                 555                 560

Val Ile Val Ala Val Ile Val Cys Ile Leu Val Leu Ala Val Leu Gly
                565                 570                 575

Ala Val Leu Tyr Phe Leu Tyr Lys Lys Gly Lys Leu Pro Cys Arg Arg
            580                 585                 590

Ser Gly Lys Gln Glu Met Glu Arg Asn Thr Ser Ile
            595                 600

<210> SEQ ID NO 12
<211> LENGTH: 1656
<212> TYPE: DNA
<213> ORGANISM: Homo sapiens

<400> SEQUENCE: 12

```
atgggcttc ccaggctggt ctgcgccttc ttgctcgccg cctgctgctg ctgtcctcgc     60
gtcgcgggtg tgcccggaga ggctgagcag cctgcgcctg agctggtgga ggtggaagtg    120
ggcagcacag cccttctgaa gtgcggcctc tcccagtccc aaggcaacct cagccatgtc    180
gactggtttt ctgtccacaa ggagaagcgg acgctcatct tccgtgtgcg ccagggccag    240
ggccagagcg aacctgggga gtacgagcag cggctcagcc tccaggacag aggggctact    300
ctggccctga ctcaagtcac cccccaagac gagcgcatct tcttgtgcca gggcaagcgc    360
cctcggtccc aggagtaccg catccagctc cgcgtctaca agctccggag ggagccaaac    420
atccaggtca ccccctggg catccctgtg aacagtaagg agcctgagga ggtcgctacc    480
tgtgtaggga ggaacgggta ccccattcct caagtcatct ggtacaagaa tggccggcct    540
ctgaaggagg agaagaaccg ggtccacatt cagtcgtccc agactgtgga gtcgagtggt    600
ttgtacacct tgcagagtat tctgaaggca cagctggtta agaagacaa agatgcccag    660
tttttactgtg agctcaacta ccggctgccc agtgggaacc acatgaagga gtccagggaa    720
gtcaccgtcc ctgttttcta cccgacagaa aaagtgtggc tggaagtgga gcccgtggga    780
atgctgaagg aaggggaccg cgtggaaatc aggtgtttgg ctgatggcaa ccctccacca    840
cacttcagca tcagcaagca gaaccccagc accagggagg cagaggaaga gacaaccaac    900
gacaacgggg tcctggtgct ggagcctgcc cggaaggaac acagtgggcg ctatgaatgt    960
cagggcctgg acttgacac catgatatcg ctgctgagtg aaccacagga actactggtg   1020
aactatgtgt ctgacgtccg agtgagtccc gcagcccctg agagacagga aggcagcagc   1080
```

```
ctcaccctga cctgtgaggc agagagtagc caggacctcg agttccagtg gctgagagaa      1140
gagacaggcc aggtgctgga aaggggggcct gtgcttcagt tgcatgacct gaaacgggag     1200
gcaggaggcg gctatcgctg cgtggcgtct gtgcccagca tacccggcct gaaccgcaca      1260
cagctggtca acgtggccat ttttggcccc ccttggatgg cattcaagga gaggaaggtg     1320
tgggtgaaag agaatatggt gttgaatctg tcttgtgaag cgtcagggca ccccggccc      1380 accatctcct ggaacgtcaa cggcacggca agtgaacaag accaagatcc acagcgagtc    1440
ctgagcaccc tgaatgtcct cgtgaccccg gagctgttgg agacaggtgt tgaatgcacg     1500
gcctccaacg acctgggcaa aaacaccagc atcctcttcc tggagctggt caatttaacc    1560
accctcacac cagactccaa cacaaccact ggcctcagca cttccactgc cagtcctcat    1620
accagagcca acagcacctc cacagagaga aagctg      1656
```

<210> SEQ ID NO 13
<211> LENGTH: 1659
<212> TYPE: DNA
<213> ORGANISM: Homo sapiens

<400> SEQUENCE: 13

```
atggggcttc ccaggctggt ctgcgccttc ttgctcgccg cctgctgctg ctgtcctcgc       60
gtcgcgggtg tgcccggaga ggctgagcag cctgcgcctg agctggtgga ggtggaagtg      120
ggcagcacag cccttctgaa gtgcggcctc tcccagtccc aaggcaacct cagccatgtc      180
gactggtttt ctgtccacaa ggagaagcgg acgctcatct ccgtgtgcg ccagggccag       240 ggccagagcg aacctgggga gtacgagcag cggctcagcc tccaggacag aggggctact      300
ctggccctga ctcaagtcac cccccaagac gagcgcatct tcttgtgcca gggcaagcgc      360
cctcggtccc aggagtaccg catccagctc cgcgtctaca aagctccgga ggagccaaac      420
atccaggtca ccccctgggg catccctgtg aacagtaagg agcctgagga ggtcgctacc     480
tgtgtaggga ggaacgggta ccccattcct caagtcatct ggtacaagaa tggccggcct     540
ctgaaggagg agaagaaccg ggtccacatt cagtcgtccc agactgtgga gtcgagtggt     600
ttgtacacct tgcagagtat tctgaaggca cagctggtta agaagacaa agatgcccag      660 tttttactgtg agctcaacta ccggctgccc agtgggaacc acatgaagga gtccagggaa    720
gtcaccgtcc ctgtttttcta cccgacagaa aaagtgtggc tggaagtgga gcccgtggga    780
atgctgaagg aaggggaccg cgtggaaatc aggtgtttgg ctgatggcaa ccctccacca    840
cacttcagca tcagcaagca gaaccccagc accaggagg cagaggaaga acaaccaac     900 gacaacgggg tcctggtgct ggagcctgcc cggaaggaac acagtgggcg ctatgaatgt   960
cagggcctgg acttggacac catgatatcg ctgctgagtg aaccacagga actactggtg   1020
aactatgtgt ctgacgtccg agtgagtccc gcagccctg agagacagga aggcagcagc    1080
ctcaccctga cctgtgaggc agagagtagc caggacctcg agttccagtg gctgagagaa    1140
gagacaggcc aggtgctgga aaggggggcct gtgcttcagt tgcatgacct gaaacgggag  1200
gcaggaggcg gctatcgctg cgtggcgtct gtgcccagca tacccggcct gaaccgcaca    1260
cagctggtca acgtggccat ttttggcccc ccttggatgg cattcaagga gaggaaggtg   1320
tgggtgaaag agaatatggt gttgaatctg tcttgtgaag cgtcagggca ccccggccc    1380 accatctcct ggaacgtcaa cggcacggca agtgaacaag accaagatcc acagcgagtc  1440
ctgagcaccc tgaatgtcct cgtgaccccg gagctgttgg agacaggtgt tgaatgcacg   1500
```

```
gcctccaacg acctgggcaa aaacaccagc atcctcttcc tggagctggt caatttaacc    1560
accctcacac cagactccaa cacaaccact ggcctcagca cttccactgc cagtcctcat    1620
accagagcca acagcacctc cacagagaga aagctgccg                           1659

<210> SEQ ID NO 14
<211> LENGTH: 1662
<212> TYPE: DNA
<213> ORGANISM: Homo sapiens

<400> SEQUENCE: 14
atggggcttc ccaggctggt ctgcgccttc ttgctcgccg cctgctgctg ctgtcctcgc      60
gtcgcgggtg tgcccggaga ggctgagcag cctgcgcctg agctggtgga ggtggaagtg    120
ggcagcacag cccttctgaa gtgcggcctc tcccagtccc aaggcaacct cagccatgtc    180
gactggtttt ctgtccacaa ggagaagcgg acgctcatct ccgtgtgcg ccagggccag    240 ggccagagcg aacctgggga gtacgagcag cggctcagcc tccaggacag aggggctact    300
ctggccctga ctcaagtcac cccccaagac gagcgcatct tcttgtgcca gggcaagcgc    360
cctcggtccc aggagtaccg catccagctc cgcgtctaca agctccgga ggagccaaac    420 atccaggtca ccccctggg catccctgtg aacagtaagg agcctgagga ggtcgctacc    480
tgtgtaggga ggaacgggta ccccattcct caagtcatct ggtacaagaa tggccggcct    540
ctgaaggagg agaagaaccg ggtccacatt cagtcgtccc agactgtgga gtcgagtggt    600
ttgtacacct tgcagagtat tctgaaggca cagctggtta agaagacaa agatgcccag    660 ttttactgtg agctcaacta ccggctgccc agtgggaacc acatgaagga gtccagggaa    720
gtcaccgtcc ctgttttcta cccgacagaa aaagtgtggc tggaagtgga gcccgtggga    780
atgctgaagg aaggggaccg cgtggaaatc aggtgtttgg ctgatggcaa ccctccacca    840
cacttcagca tcagcaagca gaaccccagc accagggagg cagaggaaga gacaaccaac    900
gacaacgggg tcctggtgct ggagcctgcc cggaaggaac acagtgggcg ctatgaatgt    960
cagggcctgg acttggacac catgatatcg ctgctgagtg aaccacagga actactggtg   1020
aactatgtgt ctgacgtccg agtgagtccc gcagcccctg agacaggaag gcagcagc   1080 ctcaccctga cctgtgaggc agagagtagc caggacctcg agttccagtg gctgagagaa   1140
gagacaggcc aggtgctgga aggggggcct gtgcttcagt tgcatgacct gaaacgggag   1200
gcaggaggcg gctatcgctg cgtggcgtct gtgcccagca tacccggcct gaaccgcaca   1260
cagctggtca acgtggccat ttttggcccc ccttggatgg cattcaagga gaggaaggtg   1320
tgggtgaaag agaatatggt gttgaatctg tcttgtgaag cgtcagggca ccccggccc   1380 accatctcct ggaacgtcaa cggcacggca agtgaacaag accaagatcc acagcgagtc   1440
ctgagcaccc tgaatgtcct cgtgaccccg gagctgttgg agacaggtgt tgaatgcacg   1500
gcctccaacg acctgggcaa aaacaccagc atcctcttcc tggagctggt caatttaacc   1560
accctcacac cagactccaa cacaaccact ggcctcagca cttccactgc cagtcctcat   1620
accagagcca acagcacctc cacagagaga aagctgccgg ag                     1662

<210> SEQ ID NO 15
<211> LENGTH: 1665
<212> TYPE: DNA
<213> ORGANISM: Homo sapiens

<400> SEQUENCE: 15
atggggcttc ccaggctggt ctgcgccttc ttgctcgccg cctgctgctg ctgtcctcgc      60
```

```
gtcgcgggtg tgcccggaga ggctgagcag cctgcgcctg agctggtgga ggtggaagtg    120
ggcagcacag cccttctgaa gtgcggcctc tcccagtccc aaggcaacct cagccatgtc    180
gactggtttt ctgtccacaa ggagaagcgg acgctcatct ccgtgtgcg ccagggccag     240 ggccagagcg aacctgggga gtacgagcag cggctcagcc tccaggacag aggggctact    300
ctggccctga ctcaagtcac cccccaagac gagcgcatct tcttgtgcca gggcaagcgc    360
cctcggtccc aggagtaccg catccagctc cgcgtctaca agctccgga ggagccaaac    420 atccaggtca accccctggg catccctgtg aacagtaagg agcctgagga ggtcgctacc    480
tgtgtaggga ggaacgggta ccccattcct caagtcatct ggtacaagaa tggccggcct    540
ctgaaggagg agaagaaccg ggtccacatt cagtcgtccc agactgtgga gtcgagtggt    600
ttgtacacct tgcagagtat tctgaaggca cagctggtta agaagacaa agatgcccag    660 ttttactgtg agctcaacta ccggctgccc agtgggaacc acatgaagga gtccagggaa    720
gtcaccgtcc ctgttttcta cccgacagaa aaagtgtggc tggaagtgga gcccgtggga    780
atgctgaagg aaggggaccg cgtggaaatc aggtgtttgg ctgatggcaa ccctccacca    840
cacttcagca tcagcaagca gaaccccagc accaggagg cagaggaaga acaaccaac     900 gacaacgggg tcctggtgct ggagcctgcc cggaaggaac acagtgggcg ctatgaatgt    960
cagggcctgg acttgacac catgatatcg ctgctgagtg aaccacagga actactggtg    1020
aactatgtgt ctgacgtccg agtgagtccc gcagccctg agacagga aggcagcagc     1080 ctcaccctga cctgtgaggc agagagtagc caggacctcg agttccagtg gctgagagaa    1140
gagacaggcc aggtgctgga aggggggcct gtgcttcagt tgcatgacct gaaacgggag    1200
gcaggaggcg gctatcgctg cgtggcgtct gtgcccagca tacccggcct gaaccgcaca    1260
cagctggtca acgtggccat ttttggcccc ccttggatgg cattcaagga gaggaaggtg    1320
tgggtgaaag agaatatggt gttgaatctg tcttgtgaag cgtcagggca ccccggccc    1380 accatctcct ggaacgtcaa cggcacggca agtgaacaag accaagatcc acagcgagtc    1440
ctgagcaccc tgaatgtcct cgtgaccccg gagctgttgg agacaggtgt tgaatgcacg    1500
gcctccaacg acctgggcaa aaacaccagc atcctcttcc tggagctggt caatttaacc    1560
accctcacac cagactccaa cacaaccact ggcctcagca cttccactgc cagtcctcat    1620
accagagcca acagcacctc cacagagaga aagctgccgg agccg                   1665

<210> SEQ ID NO 16
<211> LENGTH: 1668
<212> TYPE: DNA
<213> ORGANISM: Homo sapiens

<400> SEQUENCE: 16
atggggcttc ccaggctggt ctgcgccttc ttgctcgccg cctgctgctg ctgtcctcgc     60
gtcgcgggtg tgcccggaga ggctgagcag cctgcgcctg agctggtgga ggtggaagtg    120
ggcagcacag cccttctgaa gtgcggcctc tcccagtccc aaggcaacct cagccatgtc    180
gactggtttt ctgtccacaa ggagaagcgg acgctcatct ccgtgtgcg ccagggccag     240 ggccagagcg aacctgggga gtacgagcag cggctcagcc tccaggacag aggggctact    300
ctggccctga ctcaagtcac cccccaagac gagcgcatct tcttgtgcca gggcaagcgc    360
cctcggtccc aggagtaccg catccagctc cgcgtctaca agctccgga ggagccaaac    420 atccaggtca accccctggg catccctgtg aacagtaagg agcctgagga ggtcgctacc    480
```

```
tgtgtaggga ggaacgggta ccccattcct caagtcatct ggtacaagaa tggccggcct    540
ctgaaggagg agaagaaccg ggtccacatt cagtcgtccc agactgtgga gtcgagtggt    600
ttgtacacct tgcagagtat tctgaaggca cagctggtta agaagacaa  agatgcccag    660 ttttactgtg agctcaacta ccggctgccc agtgggaacc acatgaagga gtccagggaa    720
gtcaccgtcc ctgttttcta cccgacagaa aaagtgtggc tggaagtgga gcccgtggga    780
atgctgaagg aaggggaccg cgtggaaatc aggtgtttgg ctgatggcaa ccctccacca    840
cacttcagca tcagcaagca gaaccccagc accagggagg cagaggaaga gacaaccaac    900
gacaacgggg tcctggtgct ggagcctgcc cggaaggaac acagtgggcg ctatgaatgt    960
cagggcctgg acttggacac catgatatcg ctgctgagtg aaccacagga actactggtg    1020
aactatgtgt ctgacgtccg agtgagtccc gcagcccctg agagacagga aggcagcagc    1080
ctcaccctga cctgtgaggc agagagtagc caggacctcg agttccagtg gctgagagaa    1140
gagacaggcc aggtgctgga aggggggcct gtgcttcagt tgcatgacct gaaacgggag    1200
gcaggaggcg gctatcgctg cgtggcgtct gtgcccagca tacccggcct gaaccgcaca    1260
cagctggtca acgtgccat  ttttggcccc ccttggatgg cattcaagga gaggaaggtg    1320
tgggtgaaag agaatatggt gttgaatctg tcttgtgaag cgtcagggca ccccaggccc    1380
accatctcct ggaacgtcaa cggcacggca agtgaacaag accaagatcc acagcgagtc    1440
ctgagcaccc tgaatgtcct cgtgaccccg gagctgttgg agacaggtgt tgaatgcacg    1500
gcctccaacg acctgggcaa aaacaccagc atcctcttcc tggagctggt caatttaacc    1560
accctcacac cagactccaa cacaaccact ggcctcagca cttccactgc cagtcctcat    1620
accagagcca acagcaccctc cacagagaga aagctgccgg agccggag              1668
```

<210> SEQ ID NO 17  
<211> LENGTH: 1671  
<212> TYPE: DNA  
<213> ORGANISM: Homo sapiens

<400> SEQUENCE: 17

```
atggggcttc ccaggctggt ctgcgccttc ttgctcgccg cctgctgctg ctgtcctcgc     60
gtcgcgggtg tgcccggaga ggctgagcag cctgcgcctg agctggtgga ggtggaagtg    120
ggcagcacag cccttctgaa gtgcggcctc tcccagtccc aaggcaacct cagccatgtc    180
gactggtttt ctgtccacaa ggagaagcgg acgctcatct tccgtgtgcg ccagggccag    240
ggccagagcg aacctgggga gtacgagcag cggctcagcc tccaggacag aggggctact    300
ctggccctga ctcaagtcac cccccaagac gagcgcatct tcttgtgcca gggcaagcgc    360
cctcggtccc aggagtaccg catccagctc cgcgtctaca agctccggaa ggagccaaac    420
atccaggtca ccccctggg  catccctgtg aacagtaagg agcctgagga ggtcgctacc    480
tgtgtaggga ggaacgggta ccccattcct caagtcatct ggtacaagaa tggccggcct    540
ctgaaggagg agaagaaccg ggtccacatt cagtcgtccc agactgtgga gtcgagtggt    600
ttgtacacct tgcagagtat tctgaaggca cagctggtta agaagacaa  agatgcccag    660 ttttactgtg agctcaacta ccggctgccc agtgggaacc acatgaagga gtccagggaa    720
gtcaccgtcc ctgttttcta cccgacagaa aaagtgtggc tggaagtgga gcccgtggga    780
atgctgaagg aaggggaccg cgtggaaatc aggtgtttgg ctgatggcaa ccctccacca    840
cacttcagca tcagcaagca gaaccccagc accagggagg cagaggaaga gacaaccaac    900
gacaacgggg tcctggtgct ggagcctgcc cggaaggaac acagtgggcg ctatgaatgt    960
```

```
cagggcctgg acttggacac catgatatcg ctgctgagtg aaccacagga actactggtg    1020
aactatgtgt ctgacgtccg agtgagtccc gcagcccctg agagacagga aggcagcagc    1080
ctcaccctga cctgtgaggc agagagtagc caggacctcg agttccagtg gctgagagaa    1140
gagacaggcc aggtgctgga aagggggcct gtgcttcagt tgcatgacct gaaacgggag    1200
gcaggaggcg gctatcgctg cgtggcgtct gtgcccagca tacccggcct gaaccgcaca    1260
cagctggtca acgtggccat ttttggcccc ccttggatgg cattcaagga gaggaaggtg    1320
tgggtgaaag agaatatggt gttgaatctg tcttgtgaag cgtcagggca ccccggccc     1380 accatctcct ggaacgtcaa cggcacggca agtgaacaag accaagatcc acagcgagtc    1440
ctgagcaccc tgaatgtcct cgtgaccccg agctgttgg agacaggtgt tgaatgcacg     1500
gcctccaacg acctgggcaa aaacaccagc atcctcttcc tggagctggt caatttaacc    1560
accctcacac cagactccaa cacaaccact ggcctcagca cttccactgc cagtcctcat    1620
accagagcca acagcacctc cacagagaga aagctgccgg agccggagag c             1671

<210> SEQ ID NO 18
<211> LENGTH: 1674
<212> TYPE: DNA
<213> ORGANISM: Homo sapiens

<400> SEQUENCE: 18
atggggcttc ccaggctggt ctgcgccttc ttgctcgccg cctgctgctg ctgtcctcgc      60
gtcgcgggtg tgcccggaga ggctgagcag cctgcgcctg agctggtgga ggtggaagtg    120
ggcagcacag cccttctgaa gtgcggcctc tcccagtccc aaggcaacct cagccatgtc    180
gactggtttt ctgtccacaa ggagaagcgg acgctcatct tccgtgtgcg ccagggccag    240
ggccagagcg aacctgggga gtacgagcag cggctcagcc tccaggacag aggggctact    300
ctggccctga ctcaagtcac cccccaagac gagcgcatct tcttgtgcca gggcaagcgc    360
cctcggtccc aggagtaccg catccagctc cgcgtctaca aagctccgga ggagccaaac    420
atccaggtca ccccctgggg catccctgtg aacagtaagg agcctgagga ggtcgctacc    480
tgtgtaggga ggaacgggta ccccattcct caagtcatct ggtacaagaa tggccggcct    540
ctgaaggagg agaagaaccg ggtccacatt cagtcgtccc agactgtgga gtcgagtggt    600
ttgtacacct tgcagagtat tctgaaggca cagctggtta agaagacaaa gatgcccag     660 ttttactgtg agctcaacta ccggctgccc agtgggaacc acatgaagga gtccagggaa    720
gtcaccgtcc ctgttttcta cccgacagaa aaagtgtggc tggaagtgga gcccgtggga    780
atgctgaagg aaggggaccg cgtggaaatc aggtgtttgg ctgatggcaa ccctccacca    840
cacttcagca tcagcaagca gaaccccagc accaggaggg cagaggaaga cacaaccaac    900
gacaacgggg tcctggtgct ggagcctgcc cggaaggaac acagtgggcg ctatgaatgt    960
cagggcctgg acttggacac catgatatcg ctgctgagtg aaccacagga actactggtg    1020
aactatgtgt ctgacgtccg agtgagtccc gcagcccctg agagacagga aggcagcagc    1080
ctcaccctga cctgtgaggc agagagtagc caggacctcg agttccagtg gctgagagaa    1140
gagacaggcc aggtgctgga aagggggcct gtgcttcagt tgcatgacct gaaacgggag    1200
gcaggaggcg gctatcgctg cgtggcgtct gtgcccagca tacccggcct gaaccgcaca    1260
cagctggtca acgtggccat ttttggcccc ccttggatgg cattcaagga gaggaaggtg    1320
tgggtgaaag agaatatggt gttgaatctg tcttgtgaag cgtcagggca ccccggccc     1380
```

| | |
|---|---:|
| accatctcct ggaacgtcaa cggcacggca agtgaacaag accaagatcc acagcgagtc | 1440 |
| ctgagcaccc tgaatgtcct cgtgaccccg gagctgttgg agacaggtgt tgaatgcacg | 1500 |
| gcctccaacg acctgggcaa aaacaccagc atcctcttcc tggagctggt caatttaacc | 1560 |
| accctcacac cagactccaa cacaaccact ggcctcagca cttccactgc cagtcctcat | 1620 |
| accagagcca acagcacctc cacagagaga aagctgccgg agccggagag ccgg | 1674 |

<210> SEQ ID NO 19
<211> LENGTH: 1584
<212> TYPE: DNA
<213> ORGANISM: Homo sapiens

<400> SEQUENCE: 19

| | |
|---|---:|
| atggtataca ttgttagaca atttcttta tacaatgttt ctgggtcagt ctatttagat | 60 |
| caactgatcg ttttgcttac tgccaagttt tccatactac gcatagcagg tagtcgagtt | 120 |
| caccattccc catttagtgg acatctagac ggctgctcgt ttttatcatt gcagcattct | 180 |
| ttgcacacat ccttggatat gagcagacat gaaaatgttt ttctagggtt gacactgagc | 240 |
| agtaaaagtg ctgggttgaa gggtttccag cttgcatttg tacctggcct tctacagggg | 300 |
| acaggggct atttagatgg tcccctgcca accccagtgg acaaccctag ggtgggctg | 360 |
| gaggtggggc tgaggctgag tcttcctccc cttcctccct gcccagggt ccacattcag | 420 |
| tcgtcccaga ctgtggagtc gagtggtttg tacaccttgc agagtattct gaaggcacag | 480 |
| ctggttaaag aagacaaaga tgcccagttt tactgtgagc tcaactaccg gctgcccagt | 540 |
| gggaaccaca tgaaggagtc cagggaagtc accgtccctg ttttctaccc gacagaaaaa | 600 |
| gtgtggctgg aagtggagcc cgtgggaatg ctgaaggaag gggaccgcgt ggaaatcagg | 660 |
| tgtttggctg atgcaacccc tccaccacac ttcagcatca gcaagcagaa ccccagcacc | 720 |
| agggaggcag aggaagagac aaccaacgac aacggggtcc tggtgctgga gcctgcccgg | 780 |
| aaggaacaca gtgggcgcta tgaatgtcag ggcctggact tggacaccat gatatcgctg | 840 |
| ctgagtgaac cacaggaact actggtgaac tatgtgtctg acgtccgagt gagtccgca | 900 |
| gcccctgaga cacaggaagg cagcagcctc accctgacct gtgaggcaga gagtagccag | 960 |
| gacctcgagt tccagtggct gagagaagag acaggccagg tgctggaaag ggggcctgtg | 1020 |
| cttcagttgc atgacctgaa cgggaggca ggaggcggct atcgctgcgt ggcgtctgtg | 1080 |
| cccagcatac ccggcctgaa ccgcacacag ctggtcaacg tggccatttt tggcccccct | 1140 |
| tgatggcat tcaaggagag gaaggtgtgg gtgaaagaga atatggtgtt gaatctgtct | 1200 |
| tgtgaagcgt cagggcaccc ccggcccacc atctcctgga acgtcaacgg cacggcaagt | 1260 |
| gaacaagacc aagatccaca gcgagtcctg agcaccctga atgtcctcgt gaccccggag | 1320 |
| ctgttggaga caggtgttga atgcacggcc tccaacgacc tgggcaaaaa caccagcatc | 1380 |
| ctcttcctgg agctggtcaa tttaaccacc ctcacaccag actccaacac aaccactggc | 1440 |
| ctcagcactt ccactgccag tcctcatacc agagccaaca gcacctccac aggtaagcca | 1500 |
| ggcctggcaa gagaacaggg ctgtgccagg gcatcctttc tgccctgtcc ctccccagag | 1560 |
| agccctgtcc agaaaggtga gtag | 1584 |

<210> SEQ ID NO 20
<211> LENGTH: 1403
<212> TYPE: DNA
<213> ORGANISM: Homo sapiens

<400> SEQUENCE: 20

```
atgggg cttc ccaggctggt ctgcgccttc ttgctcgccg cctgctgctg ctgtcctcgc    60
gtcgcgggtg tgcccggaga ggctgagcag cctgcgcctg agctggtgga ggtggaagtg    120
ggcagcacag cccttctgaa gtgcggcctc tcccagtccc aaggcaacct cagccatgtc    180
gactggtttt ctgtccacaa ggagaagcgg acgctcatct ccgtgtgcg ccagggccag    240
ggccagagcg aacctgggga gtacgagcag cggctcagcc tccaggacag aggggctact    300
ctggccctga ctcaagtcac cccccaagac gagcgcatct tcttgtgcca gggcaagcgc    360
cctcggtccc aggagtaccg catccagctc cgcgtctaca agctccgga ggagccaaac    420
atccaggtca accccctggg catccctgtg aacagtaagg agcctgagga ggtcgctacc    480
tgtgtaggga ggaacgggta ccccattcct caagtcatct ggtacaagaa tggccggcct    540
ctgaaggagg agaagaaccg ggtccacatt cagtcgtccc agactgtgga gtcgagtggt    600
ttgtacacct tgcagagtat tctgaaggca cagctggtta agaagacaa agatgcccag    660
tttttactgtg agctcaacta ccggctgccc agtgggaacc acatgaagga gtccaggaa    720
gtcaccgtcc ctgttttcta cccgacagaa aaagtgtggc tggaagtgga gcccgtggga    780
atgctgaagg aagggaccg cgtggaaatc aggtgtttgg ctgatggcaa ccctccacca    840
cacttcagca tcagcaagca gaaccccag caccagggag gcagaggaaga gacaaccaac    900
gacaacgggg tcctggtgct ggagcctgcc cggaaggaac acagtgggcg ctatgaatgt    960
cagggcctgg acttggacac catgatatcg ctgctgagtg aaccacagga actactggtg   1020
aactatgtgt ctgacgtccg agtgagtccc gcagcccctg agagacagga aggcagcagc   1080
ctcaccctga cctgtgaggc agagagtagc caggacctcg agttccagtg gctgagagaa   1140
gagacaggcc aggtgctgga aggggggcct gtgcttcagt tgcatgacct gaaacgggag   1200
gcaggaggcg gctatcgctg cgtggcgtct gtgcccagca tacccggcct gaaccgcaca   1260
cagctggtca acgtggccat ttttggtgag gccctccctc tgggtagaga ccaggtcacc   1320
ccaagtgggt ggttttaag ctctttgaca aaaagccacc tgctgccctg gggagctctg   1380
gtgcggaggg ggaggcaggc tag                                            1403
```

<210> SEQ ID NO 21
<211> LENGTH: 1815
<212> TYPE: DNA
<213> ORGANISM: Homo sapiens

<400> SEQUENCE: 21

```
atgggg cttc ccaggctggt ctgcgccttc ttgctcgccg cctgctgctg ctgtcctcgc    60
gtcgcgggtg tgcccggaga ggctgagcag cctgcgcctg agctggtgga ggtggaagtg    120
ggcagcacag cccttctgaa gtgcggcctc tcccagtccc aaggcaacct cagccatgtc    180
gactggtttt ctgtccacaa ggagaagcgg acgctcatct ccgtgtgcg ccagggccag    240
ggccagagcg aacctgggga gtacgagcag cggctcagcc tccaggacag aggggctact    300
ctggccctga ctcaagtcac cccccaagac gagcgcatct tcttgtgcca gggcaagcgc    360
cctcggtccc aggagtaccg catccagctc cgcgtctaca agctccgga ggagccaaac    420
atccaggtca accccctggg catccctgtg aacagtaagg agcctgagga ggtcgctacc    480
tgtgtaggga ggaacgggta ccccattcct caagtcatct ggtacaagaa tggccggcct    540
ctgaaggagg agaagaaccg ggtccacatt cagtcgtccc agactgtgga gtcgagtggt    600
ttgtacacct tgcagagtat tctgaaggca cagctggtta agaagacaa agatgcccag    660
```

```
ttttactgtg agctcaacta ccggctgccc agtgggaacc acatgaagga gtccagggaa    720
gtcaccgtcc ctgttttcta cccgacagaa aaagtgtggc tggaagtgga gcccgtggga    780
atgctgaagg aagggaccg cgtggaaatc aggtgtttgg ctgatggcaa ccctccacca    840
cacttcagca tcagcaagca gaaccccagc accaggagg cagaggaaga gacaaccaac    900
gacaacgggg tcctggtgct ggagcctgcc cggaaggaac acagtgggcg ctatgaatgt    960
cagggcctgg acttggacac catgatatcg ctgctgagtg aaccacagga actactggtg   1020
aactatgtgt ctgacgtccg agtgagtccc gcagcccctg agagacagga aggcagcagc   1080
ctcaccctga cctgtgaggc agagagtagc caggacctcg agttccagtg gctgagagaa   1140
gagacaggcc aggtgctgga aggggggcct gtgcttcagt tgcatgacct gaaacgggag   1200
gcaggaggcg gctatcgctg cgtggcgtct gtgcccagca tacccggcct gaaccgcaca   1260
cagctggtca acgtggccat ttttggcccc ccttggatgg cattcaagga gaggaaggtg   1320
tgggtgaaag agaatatggt gttgaatctg tcttgtgaag cgtcagggca ccccggccc   1380 accatctcct ggaacgtcaa cggcacggca agtgaacaag accaagatcc acagcgagtc   1440
ctgagcaccc tgaatgtcct cgtgaccccg gagctgttgg agacaggtgt tgaatgcacg   1500
gcctccaacg acctgggcaa aaacaccagc atcctcttcc tggagctggt caatttaacc   1560
accctcacac cagactccaa cacaaccact ggcctcagca cttccactgc cagtcctcat   1620
accagagcca acagcacctc cacagagaga aagctgccgg agccggagag ccggggcgtg   1680
gtcatcgtgg ctgtgattgt gtgcatcctg gtcctggcgg tgctgggcgc tgtcctctat   1740
ttcctctata agaagggcaa gctgccgtgc aggagctcag ggaagcagga gatggagaga   1800
aatacatcga tctga                                                    1815
```

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
tcacttgaca gtgtgatggt                                                20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
ccttagaaag cagggattca                                                20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
cccaaatcct ctggaagaca                                                20

<210> SEQ ID NO 25
<211> LENGTH: 21

```
<212> TYPE: DNA
<213> ORGANISM: Artificial Sequence
<220> FEATURE:
<223> OTHER INFORMATION: Primer

<400> SEQUENCE: 25
tgtaatgaaa gacggcacac c                                              21

<210> SEQ ID NO 26
<211> LENGTH: 21
<212> TYPE: DNA
<213> ORGANISM: Artificial Sequence
<220> FEATURE:
<223> OTHER INFORMATION: Primer

<400> SEQUENCE: 26
tcttctttgg gtattgcttg g                                              21

<210> SEQ ID NO 27
<211> LENGTH: 21
<212> TYPE: DNA
<213> ORGANISM: Artificial Sequence
<220> FEATURE:
<223> OTHER INFORMATION: Primer

<400> SEQUENCE: 27
tcttctcatt cctgcttgtg g                                              21

<210> SEQ ID NO 28
<211> LENGTH: 19
<212> TYPE: DNA
<213> ORGANISM: Artificial Sequence
<220> FEATURE:
<223> OTHER INFORMATION: Primer

<400> SEQUENCE: 28
atgagaggga ggccatttg                                                 19

<210> SEQ ID NO 29
<211> LENGTH: 18
<212> TYPE: DNA
<213> ORGANISM: Artificial Sequence
<220> FEATURE:
<223> OTHER INFORMATION: Primer

<400> SEQUENCE: 29
cccacgctac ctctgctc                                                  18

<210> SEQ ID NO 30
<211> LENGTH: 21
<212> TYPE: DNA
<213> ORGANISM: Artificial Sequence
<220> FEATURE:
<223> OTHER INFORMATION: Primer

<400> SEQUENCE: 30
gatggatacc tgagcatcac c                                              21

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
```

```
tggagcaaca tgtggaactc                                              20

<210> SEQ ID NO 32
<211> LENGTH: 18
<212> TYPE: DNA
<213> ORGANISM: Artificial Sequence
<220> FEATURE:
<223> OTHER INFORMATION: Primer

<400> SEQUENCE: 32
gtcagcagcc ggttacca                                                18

<210> SEQ ID NO 33
<211> LENGTH: 22
<212> TYPE: DNA
<213> ORGANISM: Artificial Sequence
<220> FEATURE:
<223> OTHER INFORMATION: Primer

<400> SEQUENCE: 33
tggtttcttc tcacccttct tc                                           22

<210> SEQ ID NO 34
<211> LENGTH: 21
<212> TYPE: DNA
<213> ORGANISM: Artificial Sequence
<220> FEATURE:
<223> OTHER INFORMATION: Primer

<400> SEQUENCE: 34
tgcatcccaa ttcatctacg t                                            21

<210> SEQ ID NO 35
<211> LENGTH: 21
<212> TYPE: DNA
<213> ORGANISM: Artificial Sequence
<220> FEATURE:
<223> OTHER INFORMATION: Primer

<400> SEQUENCE: 35
tccagtcatc acagattgtc g                                            21

<210> SEQ ID NO 36
<211> LENGTH: 21
<212> TYPE: DNA
<213> ORGANISM: Artificial Sequence
<220> FEATURE:
<223> OTHER INFORMATION: Primer

<400> SEQUENCE: 36
aaacagggac agtgacctcc t                                            21

<210> SEQ ID NO 37
<211> LENGTH: 21
<212> TYPE: DNA
<213> ORGANISM: Artificial Sequence
<220> FEATURE:
<223> OTHER INFORMATION: Primer

<400> SEQUENCE: 37
tggtgaaatg gaatctgaac c                                            21

<210> SEQ ID NO 38
<211> LENGTH: 16
<212> TYPE: DNA
<213> ORGANISM: Artificial Sequence
```

```
<220> FEATURE:
<223> OTHER INFORMATION: Primer

<400> SEQUENCE: 38
cccagatggt ttcctt                                                    16

<210> SEQ ID NO 39
<211> LENGTH: 18
<212> TYPE: DNA
<213> ORGANISM: Artificial Sequence
<220> FEATURE:
<223> OTHER INFORMATION: Primer

<400> SEQUENCE: 39
catccacgtg ttggctca                                                  18

<210> SEQ ID NO 40
<211> LENGTH: 23
<212> TYPE: DNA
<213> ORGANISM: Artificial Sequence
<220> FEATURE:
<223> OTHER INFORMATION: Primer

<400> SEQUENCE: 40
gatcatcttg ctggtgaatg agt                                            23

<210> SEQ ID NO 41
<211> LENGTH: 22
<212> TYPE: DNA
<213> ORGANISM: Artificial Sequence
<220> FEATURE:
<223> OTHER INFORMATION: Primer

<400> SEQUENCE: 41
gcaggttcac ctactctgtc ct                                             22

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
cttgccccat tcatttgtct                                                20

<210> SEQ ID NO 43
<211> LENGTH: 18
<212> TYPE: DNA
<213> ORGANISM: Artificial Sequence
<220> FEATURE:
<223> OTHER INFORMATION: Primer

<400> SEQUENCE: 43
ggagcggtag cacctcct                                                  18

<210> SEQ ID NO 44
<211> LENGTH: 22
<212> TYPE: DNA
<213> ORGANISM: Artificial Sequence
<220> FEATURE:
<223> OTHER INFORMATION: Primer

<400> SEQUENCE: 44
ctggttcatc atcgctaatc ac                                             22
```

```
<210> SEQ ID NO 45
<211> LENGTH: 19
<212> TYPE: DNA
<213> ORGANISM: Artificial Sequence
<220> FEATURE:
<223> OTHER INFORMATION: Primer

<400> SEQUENCE: 45
caatcacctg cgtacagaa                                                    19

<210> SEQ ID NO 46
<211> LENGTH: 19
<212> TYPE: DNA
<213> ORGANISM: Artificial Sequence
<220> FEATURE:
<223> OTHER INFORMATION: Primer

<400> SEQUENCE: 46
ttctgtacgc aggtgattg                                                    19

<210> SEQ ID NO 47
<211> LENGTH: 18
<212> TYPE: DNA
<213> ORGANISM: Artificial Sequence
<220> FEATURE:
<223> OTHER INFORMATION: Primer

<400> SEQUENCE: 47
ggcatagagg gagagcac                                                     18

<210> SEQ ID NO 48
<211> LENGTH: 20
<212> TYPE: DNA
<213> ORGANISM: Artificial Sequence
<220> FEATURE:
<223> OTHER INFORMATION: Primer

<400> SEQUENCE: 48
ttcggggaga ggtgatgttc                                                   20

<210> SEQ ID NO 49
<211> LENGTH: 20
<212> TYPE: DNA
<213> ORGANISM: Artificial Sequence
<220> FEATURE:
<223> OTHER INFORMATION: Primer

<400> SEQUENCE: 49
gtgctaaagg tggcaarggt                                                   20

<210> SEQ ID NO 50
<211> LENGTH: 17
<212> TYPE: DNA
<213> ORGANISM: Artificial Sequence
<220> FEATURE:
<223> OTHER INFORMATION: Primer

<400> SEQUENCE: 50
accaggttca ccgctac                                                      17

<210> SEQ ID NO 51
<211> LENGTH: 20
<212> TYPE: DNA
<213> ORGANISM: Artificial Sequence
<220> FEATURE:
<223> OTHER INFORMATION: Primer
```

```
<400> SEQUENCE: 51
attgcccaat tgagtgcttc                                                   20

<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
tgatgcttgg agaagctgtg                                                   20

<210> SEQ ID NO 53
<211> LENGTH: 28
<212> TYPE: DNA
<213> ORGANISM: Artificial Sequence
<220> FEATURE:
<223> OTHER INFORMATION: Primer

<400> SEQUENCE: 53
gagctattgt aatgaccagt caacaggg                                          28

<210> SEQ ID NO 54
<211> LENGTH: 27
<212> TYPE: DNA
<213> ORGANISM: Artificial Sequence
<220> FEATURE:
<223> OTHER INFORMATION: Primer

<400> SEQUENCE: 54
ggattatact gcctgaccaa ggaaagc                                           27

<210> SEQ ID NO 55
<211> LENGTH: 21
<212> TYPE: DNA
<213> ORGANISM: Artificial Sequence
<220> FEATURE:
<223> OTHER INFORMATION: GAPDH forward primer

<400> SEQUENCE: 55
ggtggtctcc tgacttcaac a                                                 21

<210> SEQ ID NO 56
<211> LENGTH: 22
<212> TYPE: DNA
<213> ORGANISM: Artificial Sequence
<220> FEATURE:
<223> OTHER INFORMATION: GAPDH reverse primer

<400> SEQUENCE: 56
gttgctgtag ccaattcgtt gt                                                22

<210> SEQ ID NO 57
<211> LENGTH: 20
<212> TYPE: DNA
<213> ORGANISM: Artificial Sequence
<220> FEATURE:
<223> OTHER INFORMATION: CD146sh forward primer

<400> SEQUENCE: 57
ccactggcct cagcacttcc                                                   20

<210> SEQ ID NO 58
```

```
<211> LENGTH: 20
<212> TYPE: DNA
<213> ORGANISM: Artificial Sequence
<220> FEATURE:
<223> OTHER INFORMATION: CD146sh reverse primer

<400> SEQUENCE: 58
ctactcacct ttctggacag                                                    20

<210> SEQ ID NO 59
<211> LENGTH: 26
<212> TYPE: DNA
<213> ORGANISM: Artificial Sequence
<220> FEATURE:
<223> OTHER INFORMATION: CD146lg forward primer

<400> SEQUENCE: 59
tggtttgtac accttgcaga gtattc                                             26

<210> SEQ ID NO 60
<211> LENGTH: 17
<212> TYPE: DNA
<213> ORGANISM: Artificial Sequence
<220> FEATURE:
<223> OTHER INFORMATION: CD146lg reverse primer

<400> SEQUENCE: 60
tgggcagccg gtagttg                                                       17

<210> SEQ ID NO 61
<211> LENGTH: 20
<212> TYPE: DNA
<213> ORGANISM: Artificial Sequence
<220> FEATURE:
<223> OTHER INFORMATION: MT1MMP forward sequence

<400> SEQUENCE: 61
tagcgcttcc ttcgaacatt                                                    20

<210> SEQ ID NO 62
<211> LENGTH: 20
<212> TYPE: DNA
<213> ORGANISM: Artificial Sequence
<220> FEATURE:
<223> OTHER INFORMATION: MT1MMP reverse primer

<400> SEQUENCE: 62
gcagaagttt tacggcttgc                                                    20

<210> SEQ ID NO 63
<211> LENGTH: 24
<212> TYPE: DNA
<213> ORGANISM: Artificial Sequence
<220> FEATURE:
<223> OTHER INFORMATION: MMP2 forward sequence

<400> SEQUENCE: 63
tgatcttgac cagaatacca tcga                                               24

<210> SEQ ID NO 64
<211> LENGTH: 19
<212> TYPE: DNA
<213> ORGANISM: Artificial Sequence
<220> FEATURE:
<223> OTHER INFORMATION: MMP2 reverse sequence

<400> SEQUENCE: 64
```
ggcttgcgag gaagaagtt                                                19

<210> SEQ ID NO 65
<211> LENGTH: 21
<212> TYPE: DNA
<213> ORGANISM: Artificial Sequence
<220> FEATURE:
<223> OTHER INFORMATION: Tace forward sequence

<400> SEQUENCE: 65
gcattctcaa gtctccacaa g                                             21

<210> SEQ ID NO 66
<211> LENGTH: 19
<212> TYPE: DNA
<213> ORGANISM: Artificial Sequence
<220> FEATURE:
<223> OTHER INFORMATION: Tace reverse sequence

<400> SEQUENCE: 66
ctgggagagc caactaagc                                                19

<210> SEQ ID NO 67
<211> LENGTH: 20
<212> TYPE: DNA
<213> ORGANISM: Artificial Sequence
<220> FEATURE:
<223> OTHER INFORMATION: ADAM10 forward sequence

<400> SEQUENCE: 67
cagagtgcac accaggagaa                                               20

<210> SEQ ID NO 68
<211> LENGTH: 20
<212> TYPE: DNA
<213> ORGANISM: Artificial Sequence
<220> FEATURE:
<223> OTHER INFORMATION: ADAM10 reverse sequence

<400> SEQUENCE: 68
cccaggtttc agtttgcatt                                               20

<210> SEQ ID NO 69
<211> LENGTH: 20
<212> TYPE: DNA
<213> ORGANISM: Artificial Sequence
<220> FEATURE:
<223> OTHER INFORMATION: I10-sCD146 forward primer

<400> SEQUENCE: 69
ggcagaggaa gagacaacca                                               20

<210> SEQ ID NO 70
<211> LENGTH: 20
<212> TYPE: DNA
<213> ORGANISM: Artificial Sequence
<220> FEATURE:
<223> OTHER INFORMATION: I10-sCD146 reverse primer

<400> SEQUENCE: 70
ttggggtgac ctggtctcta                                               20

<210> SEQ ID NO 71
<211> LENGTH: 19
<212> TYPE: DNA

```
<213> ORGANISM: Artificial Sequence
<220> FEATURE:
<223> OTHER INFORMATION: I5-13-sCD146 forward primer

<400> SEQUENCE: 71
ggacatctag acggtgctc                                                    19

<210> SEQ ID NO 72
<211> LENGTH: 20
<212> TYPE: DNA
<213> ORGANISM: Artificial Sequence
<220> FEATURE:
<223> OTHER INFORMATION: I5-13-sCD146 reverse primer

<400> SEQUENCE: 72
acaaatgcaa gctggaaacc                                                   20

<210> SEQ ID NO 73
<211> LENGTH: 21
<212> TYPE: RNA
<213> ORGANISM: Artificial Sequence
<220> FEATURE:
<223> OTHER INFORMATION: siTACE sens siRNA

<400> SEQUENCE: 73
caggauuuaa agguuaugga a                                                 21

<210> SEQ ID NO 74
<211> LENGTH: 22
<212> TYPE: RNA
<213> ORGANISM: Artificial Sequence
<220> FEATURE:
<223> OTHER INFORMATION: siTACE antisens siRNA

<400> SEQUENCE: 74
uuccauaaac cuuuaaaucc ug                                                22

<210> SEQ ID NO 75
<211> LENGTH: 21
<212> TYPE: DNA
<213> ORGANISM: Artificial Sequence
<220> FEATURE:
<223> OTHER INFORMATION: siADAM10 sens siRNA

<400> SEQUENCE: 75
gaaugguaga acaaggugat t                                                 21

<210> SEQ ID NO 76
<211> LENGTH: 21
<212> TYPE: DNA
<213> ORGANISM: Artificial Sequence
<220> FEATURE:
<223> OTHER INFORMATION: siADAM10 antisens siRNA

<400> SEQUENCE: 76
ucaccuuguu cuaccauucc a                                                 21

<210> SEQ ID NO 77
<211> LENGTH: 23
<212> TYPE: DNA
<213> ORGANISM: Artificial Sequence
<220> FEATURE:
<223> OTHER INFORMATION: siMT1MMP sens siRNA

<400> SEQUENCE: 77
gcgaugaagu cuucacuuad tdt                                               23
```

<210> SEQ ID NO 78
<211> LENGTH: 19
<212> TYPE: DNA
<213> ORGANISM: Artificial Sequence
<220> FEATURE:
<223> OTHER INFORMATION: siMT1MMP antisens siRNA

<400> SEQUENCE: 78
uaagugaaga cuucaucgc                                                    19

<210> SEQ ID NO 79
<211> LENGTH: 25
<212> TYPE: DNA
<213> ORGANISM: Artificial Sequence
<220> FEATURE:
<223> OTHER INFORMATION: sishCD146 sens siRNA

<400> SEQUENCE: 79
caggagaugg agagaaauac aucga                                             25

<210> SEQ ID NO 80
<211> LENGTH: 25
<212> TYPE: DNA
<213> ORGANISM: Artificial Sequence
<220> FEATURE:
<223> OTHER INFORMATION: sishCD146 antisens siRNA

<400> SEQUENCE: 80
ucgauguauu ucucuccauc uccug                                             25

<210> SEQ ID NO 81
<211> LENGTH: 25
<212> TYPE: DNA
<213> ORGANISM: Artificial Sequence
<220> FEATURE:
<223> OTHER INFORMATION: silgCD146 sens siRNA

<400> SEQUENCE: 81
cccgucucgu aagaccgaac uugua                                             25

<210> SEQ ID NO 82
<211> LENGTH: 25
<212> TYPE: DNA
<213> ORGANISM: Artificial Sequence
<220> FEATURE:
<223> OTHER INFORMATION: silgCD146 antisens siRNA

<400> SEQUENCE: 82
uacaaguucg gucuuacgag acggg                                             25

<210> SEQ ID NO 83
<211> LENGTH: 25
<212> TYPE: DNA
<213> ORGANISM: Artificial Sequence
<220> FEATURE:
<223> OTHER INFORMATION: siI10-sCD146 sens siRNA

<400> SEQUENCE: 83
cccucccucu ggguagagac caggu                                             25

<210> SEQ ID NO 84
<211> LENGTH: 25
<212> TYPE: DNA
<213> ORGANISM: Artificial Sequence
<220> FEATURE:

<223> OTHER INFORMATION: siI10-sCD146 antisens siRNA

<400> SEQUENCE: 84
accuggucuc uacccagagg gaggg                                              25

<210> SEQ ID NO 85
<211> LENGTH: 25
<212> TYPE: DNA
<213> ORGANISM: Artificial Sequence
<220> FEATURE:
<223> OTHER INFORMATION: siI5-13-sCD146 sens siRNA

<400> SEQUENCE: 85
uggacaucua gacggcugcu cguuu                                              25

<210> SEQ ID NO 86
<211> LENGTH: 25
<212> TYPE: DNA
<213> ORGANISM: Artificial Sequence
<220> FEATURE:
<223> OTHER INFORMATION: siI5-13-sCD146 antisens siRNA

<400> SEQUENCE: 86
aaacgagcag ccgucuagau gucca                                              25

<210> SEQ ID NO 87
<211> LENGTH: 8
<212> TYPE: PRT
<213> ORGANISM: Artificial Sequence
<220> FEATURE:
<223> OTHER INFORMATION: 26D12-7 CDR1

<400> SEQUENCE: 87

Gly Tyr Thr Phe Thr Ser His Phe
1               5

<210> SEQ ID NO 88
<211> LENGTH: 8
<212> TYPE: PRT
<213> ORGANISM: Artificial Sequence
<220> FEATURE:
<223> OTHER INFORMATION: 26D12-7 CDR2

<400> SEQUENCE: 88

Ile Phe Pro Gly Ser Gly Asp Thr
1               5

<210> SEQ ID NO 89
<211> LENGTH: 6
<212> TYPE: PRT
<213> ORGANISM: Artificial Sequence
<220> FEATURE:
<223> OTHER INFORMATION: 26D12-7 CDR3

<400> SEQUENCE: 89

Ala Arg Thr Trp Ala Tyr
1               5

<210> SEQ ID NO 90
<211> LENGTH: 11
<212> TYPE: PRT
<213> ORGANISM: Artificial Sequence
<220> FEATURE:
<223> OTHER INFORMATION: 26D12-7 CDR4

<400> SEQUENCE: 90

```
Gln Ser Leu Leu Tyr Ser Asp Gly Lys Thr Tyr
1               5                   10
```

<210> SEQ ID NO 91
<211> LENGTH: 9
<212> TYPE: PRT
<213> ORGANISM: Artificial Sequence
<220> FEATURE:
<223> OTHER INFORMATION: 26D12-7 CDR6

<400> SEQUENCE: 91

```
Ala Gln Thr Thr His Phe Pro Leu Thr
1               5
```

<210> SEQ ID NO 92
<211> LENGTH: 113
<212> TYPE: PRT
<213> ORGANISM: Artificial Sequence
<220> FEATURE:
<223> OTHER INFORMATION: 26D12-7 variable heavy chain

<400> SEQUENCE: 92

```
Gln Val Gln Leu Gln Gln Ser Gly Ala Glu Leu Val Lys Pro Gly Ser
1               5                   10                  15

Ser Val Lys Ile Ser Cys Lys Ala Ser Gly Tyr Thr Phe Thr Ser His
                20                  25                  30

Phe Val His Trp Ile Lys Gln Gln Pro Gly Asn Gly Leu Glu Trp Ile
            35                  40                  45

Gly Trp Ile Phe Pro Gly Ser Gly Asp Thr Glu Tyr Asn Gln Lys Phe
50                  55                  60

Asn Gly Lys Ala Thr Leu Thr Ala Asp Lys Ser Ser Ser Thr Ala Tyr
65                  70                  75                  80

Met Gln Leu Asn Ser Leu Thr Ser Glu Asp Ser Ala Val Tyr Phe Cys
                85                  90                  95

Ala Arg Thr Trp Ala Tyr Trp Gly Gln Gly Thr Leu Val Thr Val Ser
            100                 105                 110

Ser
```

<210> SEQ ID NO 93
<211> LENGTH: 112
<212> TYPE: PRT
<213> ORGANISM: Artificial Sequence
<220> FEATURE:
<223> OTHER INFORMATION: 26D12-7 light variable chain

<400> SEQUENCE: 93

```
Asp Val Val Met Thr Gln Thr Pro Pro Ser Leu Ser Val Ala Ile Gly
1               5                   10                  15

Gln Ser Val Ser Ile Ser Cys Lys Ser Ser Gln Ser Leu Leu Tyr Ser
                20                  25                  30

Asp Gly Lys Thr Tyr Leu His Trp Leu Leu Gln Ser Ser Gly Arg Ser
            35                  40                  45

Pro Lys Arg Leu Ile Tyr Gln Val Ser Asn Leu Asp Ser Gly Val Pro
50                  55                  60

Asp Arg Phe Ser Gly Thr Gly Ser Gln Lys Asp Phe Thr Leu Lys Ile
65                  70                  75                  80

Ser Arg Val Glu Ala Lys Asp Leu Gly Val Tyr Tyr Cys Ala Gln Thr
                85                  90                  95

Thr His Phe Pro Leu Thr Phe Gly Ser Gly Thr Lys Leu Glu Ile Lys
            100                 105                 110
```

```
<210> SEQ ID NO 94
<211> LENGTH: 8
<212> TYPE: PRT
<213> ORGANISM: Artificial Sequence
<220> FEATURE:
<223> OTHER INFORMATION: 2B9-4 CDR1

<400> SEQUENCE: 94

Gly Phe Thr Phe Ser Asp Tyr Gly
1               5

<210> SEQ ID NO 95
<211> LENGTH: 8
<212> TYPE: PRT
<213> ORGANISM: Artificial Sequence
<220> FEATURE:
<223> OTHER INFORMATION: 2B9-4 CDR2

<400> SEQUENCE: 95

Ile Tyr Tyr Asp Ser Ser Lys Met
1               5

<210> SEQ ID NO 96
<211> LENGTH: 7
<212> TYPE: PRT
<213> ORGANISM: Artificial Sequence
<220> FEATURE:
<223> OTHER INFORMATION: 2B9-4 CDR3

<400> SEQUENCE: 96

Ala Ala Phe Gln Phe Asp Tyr
1               5

<210> SEQ ID NO 97
<211> LENGTH: 6
<212> TYPE: PRT
<213> ORGANISM: Artificial Sequence
<220> FEATURE:
<223> OTHER INFORMATION: 2B9-4 CDR4

<400> SEQUENCE: 97

Gln Gly Ile Ser Thr Ser
1               5

<210> SEQ ID NO 98
<211> LENGTH: 9
<212> TYPE: PRT
<213> ORGANISM: Artificial Sequence
<220> FEATURE:
<223> OTHER INFORMATION: 2B9-4 CDR6

<400> SEQUENCE: 98

Gln Gln Ser Tyr Asn Leu Pro Tyr Thr
1               5

<210> SEQ ID NO 99
<211> LENGTH: 114
<212> TYPE: PRT
<213> ORGANISM: Artificial Sequence
<220> FEATURE:
<223> OTHER INFORMATION: 2B9-4 variable heavy chain

<400> SEQUENCE: 99

Glu Val Lys Leu Val Glu Ser Gly Gly Gly Leu Val Gln Pro Gly Asn
1               5                   10                  15
```

```
Ser Leu Thr Leu Ser Cys Val Ala Ser Gly Phe Thr Phe Ser Asp Tyr
            20                  25                  30

Gly Met His Trp Ile Arg Gln Ala Pro Glu Lys Gly Leu Glu Trp Ile
        35                  40                  45

Ala Met Ile Tyr Tyr Asp Ser Ser Lys Met Tyr Tyr Ala Asp Thr Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Ser Glu Asp Thr Ala Met Tyr Tyr Cys
                85                  90                  95

Ala Ala Phe Gln Phe Asp Tyr Trp Gly Gln Gly Val Met Val Thr Val
            100                 105                 110

Ser Ser

<210> SEQ ID NO 100
<211> LENGTH: 107
<212> TYPE: PRT
<213> ORGANISM: Artificial Sequence
<220> FEATURE:
<223> OTHER INFORMATION: 2B9-4 variable light chain

<400> SEQUENCE: 100

Asp Ile Val Leu Thr Gln Ser Pro Ala Thr Leu Ser Val Thr Pro Gly
1               5                   10                  15

Glu Ser Val Ser Leu Ser Cys Arg Ala Ser Gln Gly Ile Ser Thr Ser
            20                  25                  30

Ile Tyr Trp Tyr Gln Gln Lys Ser Asn Glu Ser Pro Arg Leu Leu Ile
        35                  40                  45

Lys Phe Ala Ser Gln Ser Ile Ser Gly Ile Pro Ser Arg Phe Ser Gly
    50                  55                  60

Ser Gly Ser Gly Thr Asp Phe Thr Leu Ser Ile Asn Arg Val Glu Ser
65                  70                  75                  80

Glu Asp Phe Ser Val Tyr Tyr Cys Gln Gln Ser Tyr Asn Leu Pro Tyr
                85                  90                  95

Thr Phe Gly Ala Gly Thr Lys Leu Glu Leu Lys
            100                 105

<210> SEQ ID NO 101
<211> LENGTH: 14
<212> TYPE: PRT
<213> ORGANISM: Artificial Sequence
<220> FEATURE:
<223> OTHER INFORMATION: Peptide

<400> SEQUENCE: 101

Tyr Leu Asp Gly Pro Leu Pro Thr Pro Val Asp Asn Pro Arg
1               5                   10

<210> SEQ ID NO 102
<211> LENGTH: 18
<212> TYPE: PRT
<213> ORGANISM: Artificial Sequence
<220> FEATURE:
<223> OTHER INFORMATION: Peptide

<400> SEQUENCE: 102

Arg Asp Gln Val Thr Pro Ser Gly Val Val Phe Lys Leu Phe Asp Lys
1               5                   10                  15

Lys Pro
```